US010900960B2

(12) United States Patent
De Buck

(10) Patent No.: US 10,900,960 B2
(45) Date of Patent: Jan. 26, 2021

(54) ALLOSTERIC SPLIT TREHALASE BIOSENSOR

(71) Applicant: Creative Protein Solutions Inc., Calgary (CA)

(72) Inventor: Jeroen De Buck, Calgary (CA)

(73) Assignee: Creative Protein Solutions Inc., Calgary (CA)

(*) Notice: Subject to any disclaimer, the term of this patent is extended or adjusted under 35 U.S.C. 154(b) by 0 days.

(21) Appl. No.: 16/289,357

(22) Filed: Feb. 28, 2019

(65) Prior Publication Data

US 2019/0257824 A1    Aug. 22, 2019

Related U.S. Application Data

(63) Continuation of application No. PCT/CA2017/051033, filed on Sep. 1, 2017.

(60) Provisional application No. 62/383,107, filed on Sep. 2, 2016.

(51) Int. Cl.
| | |
|---|---|
| G01N 33/535 | (2006.01) |
| C07K 16/26 | (2006.01) |
| C12N 9/24 | (2006.01) |
| C12Q 1/00 | (2006.01) |
| C12Q 1/34 | (2006.01) |
| C12Q 1/54 | (2006.01) |
| G01N 33/542 | (2006.01) |

(52) U.S. Cl.
CPC ............ *G01N 33/535* (2013.01); *C07K 16/26* (2013.01); *C12N 9/2402* (2013.01); *C12Q 1/006* (2013.01); *C12Q 1/007* (2013.01); *C12Q 1/34* (2013.01); *C12Q 1/54* (2013.01); *G01N 33/542* (2013.01); *C12Y 302/01028* (2013.01); *G01N 2333/924* (2013.01)

(58) Field of Classification Search
None
See application file for complete search history.

(56) References Cited

U.S. PATENT DOCUMENTS

2008/0248463 A1    10/2008   Weiss et al.

FOREIGN PATENT DOCUMENTS

WO    2016/065415    5/2016

OTHER PUBLICATIONS

De Buck, Jeroen, "Turning the glucose sensor into a versatile point-of-care platform for the detection of a wide range of biological analytes", 6th International Conference and Exhibition on Biosensors & Bioelectronics, https:/www.omicsonline/org/speaker/jeroen-de-buck-associate-professor-university-of-calgary-canada/, Sep. 22-23, 2016.

Guo, Zhong , et al., "Engineered PQQ-Glucose Dehydrogenase as a Universal Biosensor Platform", Journal of the American Chemical Society, vol. 138, 2016, 10108-10111.

Stains, Cliff I., et al., "A General Approach for Receptor and Antibody-Targeted Detection of Native Proteins utilizing Split-Luciferase Reassembly", ACS Chem. Biol., vol. 5, No. 10, Oct. 15, 2010, 943-952.

Antonelli, M. L., et al., "Construction, assembling and application of a trehalase-GOD enzyme electrode system", Biosensors and Bioelectronics, vol. 24, 2009, 1382-1388.

Drikic, Marija , et al., "Detecting total immunoglobulins in diverse animal species with a novel split enzymatic assay", BMC Veterinary Research, vol. 15, No. 374, 2019, 1-8.

Drikic, Marija , et al., "Determining the IgG concentrations in bovine colostrum and calf sera with a novel enzymatic assay", Journal of Animal Science and Biotechnology, vol. 9, No. 69, 2018, 1-9.

Drikic, Marija , et al., "Split trehalase as a versatile reporter for a wide range of biological analytes", Biotechnology and Bioengineering, vol. 115, 2018, 1128-1136.

*Primary Examiner* — Kagnew H Gebreyesus
(74) *Attorney, Agent, or Firm* — Peacock Law P.C.; Janeen Vilven

(57) ABSTRACT

The present disclosure relates to a method referred to herein as the "split trehalase assay biosensor" (also referred to herein as "STIGA") is based on the use of engineered *E. coli* trehalase to detect analytes such as antibodies in a sample. The trehalase is engineered in a way such that the enzyme is split into two inactive fragments (N-terminal fragment H and C-terminal fragment A) with antigens fused to both fragments. When bivalent antibodies react specifically with the fused antigens, two inactive trehalase fragments are brought in close proximity to restore the activity of trehalase. The restored trehalase will hydrolyze trehalose into two glucose molecules which can be measured using existing glucose detection methods such as glucometer, Benedict's reagent, or ACCU-CHEK AVIVA® glucose test strips.

8 Claims, 34 Drawing Sheets
Specification includes a Sequence Listing.

| Tre A | 6H-C | C-6H | 6H-N | N-6H | N-6H + 6H-C | 6H-N + C-6H | N-6H + C-6H | 6H-N + 6H-C |

| TreAN-pG | TreAN-pA | TreAN-pL |
|---|---|---|
|  |  |  |
| TreAC-pG | TreAC-pA | TreAC-pL |
|  |  |  |

ALLOSTERIC SPLIT TREHALASE BIOSENSOR

CROSS-REFERENCE TO RELATED APPLICATIONS

This application is a continuation application of International Patent Application No. PCT/CA2017/051033, entitled "ALLOSTERIC SPLIT TREHALASE BIOSENSOR", filed on Sep. 1, 2017 and claims priority to and the benefit of the filing of U.S. Provisional Patent Application No. 62/383,107, entitled "ALLOSTERIC SPLIT TREHALASE BIOSENSOR", filed on Sep. 1, 2016, and the specification and claims thereof are incorporated herein by reference.

STATEMENT REGARDING FEDERALLY SPONSORED RESEARCH OR DEVELOPMENT

Not Applicable.

THE NAMES OF PARTIES TO A JOINT RESEARCH AGREEMENT

Not Applicable.

INCORPORATION BY REFERENCE OF MATERIAL SUBMITTED ON A COMPACT DISC

Not Applicable.

STATEMENT REGARDING PRIOR DISCLOSURES BY THE INVENTOR OR A JOINT INVENTOR

Not Applicable.

SEQUENCE LISTING

The instant application contains a SEQUENCE LISTING which has been submitted electronically in ASCII format and is hereby incorporated by reference in its entirety. The ASCII copy, created on Apr. 16, 2019 is 236 Kbytes in size and is named "sequence listing_ST25041619".

BACKGROUND OF THE INVENTION

Field of the Invention (Technical Field)

TECHNICAL FIELD

The present disclosure generally relates to biosensors. More particularly, the present disclosure pertains to biosensors for detection of antibodies that are reactive with bacteria, viruses, fungi, parasites, irritants, and polypeptides, and to biosensors for detection of other biological analytes.

BACKGROUND

Although mobile and wearable technology are omnipresent, the promise to sense and report a variety of meaningful health related signals to the user and play an integral role in the health care system has not been achieved. Many biosensor devices have been developed (optical, electrical, electrochemical and mass-based). However, only a few have made it into clinical practice or into daily use. The main reasons for this are their poor performance in clinical samples (blood, urine, saliva, sputum), insufficient sensitivity or specificity, expensive supporting equipment, or high cost of production.

SUMMARY

The present disclosure generally relates to a split enzyme assay for detection of selected analytes in a sample. Disclosed herein are compositions, biosensors, kits and methods relating to splitting a selected enzyme into two fragments, separately binding the fragments to one or more complexing domain(s), and then contacting the complexed fragments with a biological sample that potentially contains a target analyte. If the target analyte is present in the biological sample, the analyte will bind to the two enzyme fragments thereby restoring the functionality of the split enzyme.

According to one aspect, the restored enzyme functionality can be detected with an electrode measuring electrostatic charges produced as a result of enzyme activity.

According to another aspect, the restored enzyme functionality can be detected by adding a suitable substrate, and then colorimetrically measuring substrate catabolism.

According to one embodiment, the present disclosure relates to compositions, biosensors, kits and methods relating to splitting of a trehalase enzyme for use in the present split enzyme assays, referred to herein as a "split trehalase assay biosensor" and alternatively as a "split TreA assay", and based on the use of engineered Escherichia coli trehalase to detect analytes in a biological sample. The trehalase is engineered in a way such that the enzyme is split into two inactive fragments (N-terminal fragment H and C-terminal fragment A) with antigens fused to both fragments. When bivalent antibodies react specifically with the fused antigens, two inactive trehalase fragments are brought in close proximity to restore the activity of trehalase. Alternatively, any other mechanism that brings the trehalase fragments in close proximity under specific conditions will restore the activity of trehalase. The restored trehalase will hydrolyze trehalose into two glucose molecules which can be measured using existing glucose detection methods such as glucometers, test strips, enzyme assays, Benedict's reagent, and the like.

BRIEF DESCRIPTION OF THE DRAWINGS

The present disclosure will be described in conjunction with reference to the following drawings in which.

Figure 8:
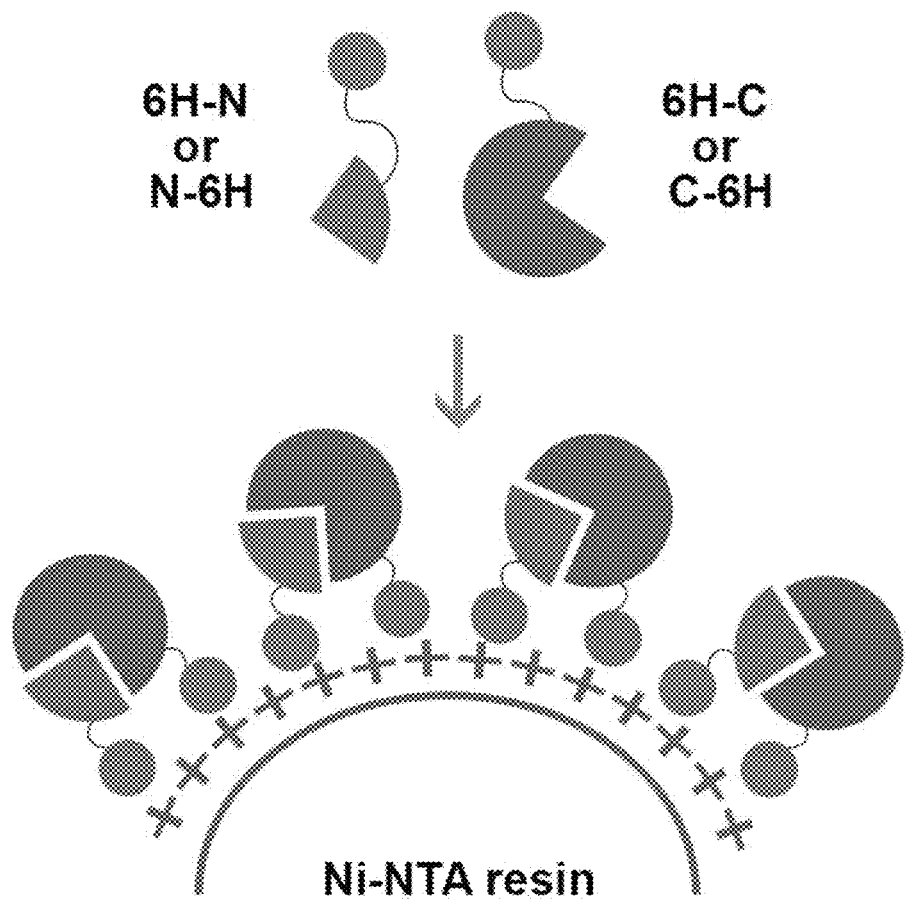
Figure 9A:
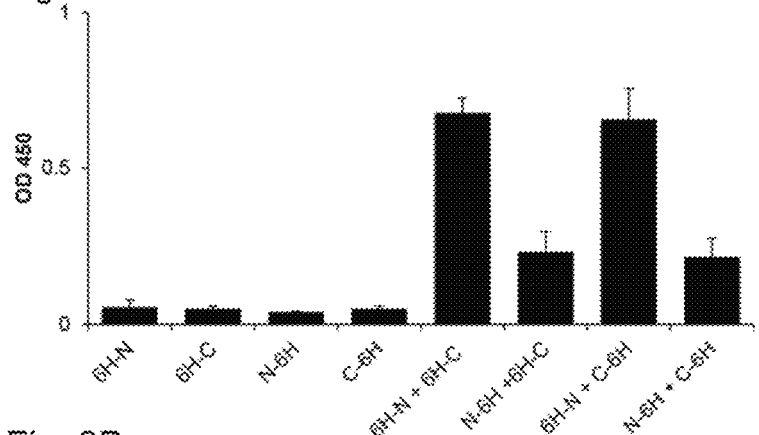
Figure 9B:
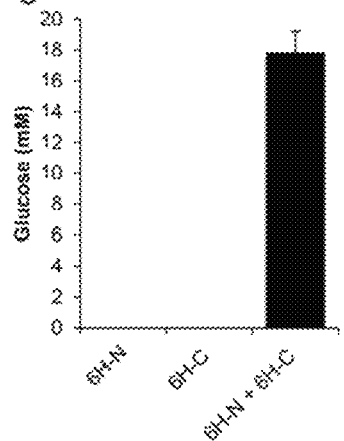
Figure 9C:
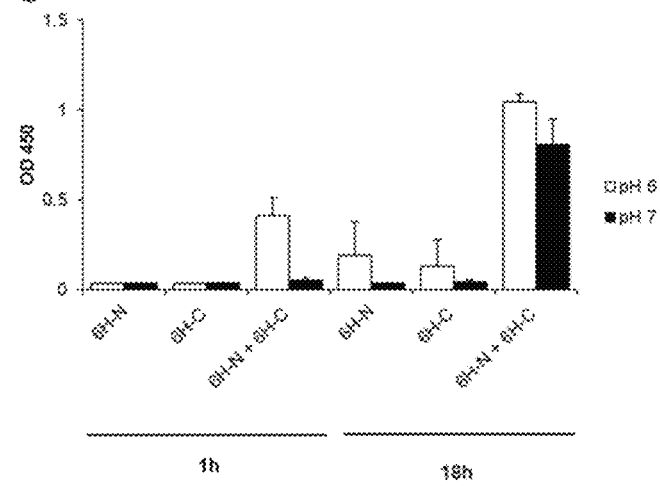
Figure 10:
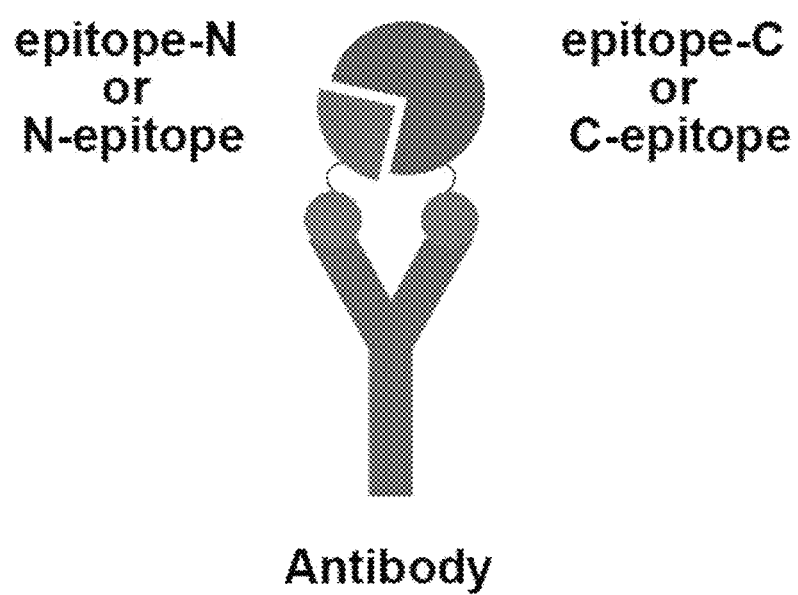
Figure 11A:
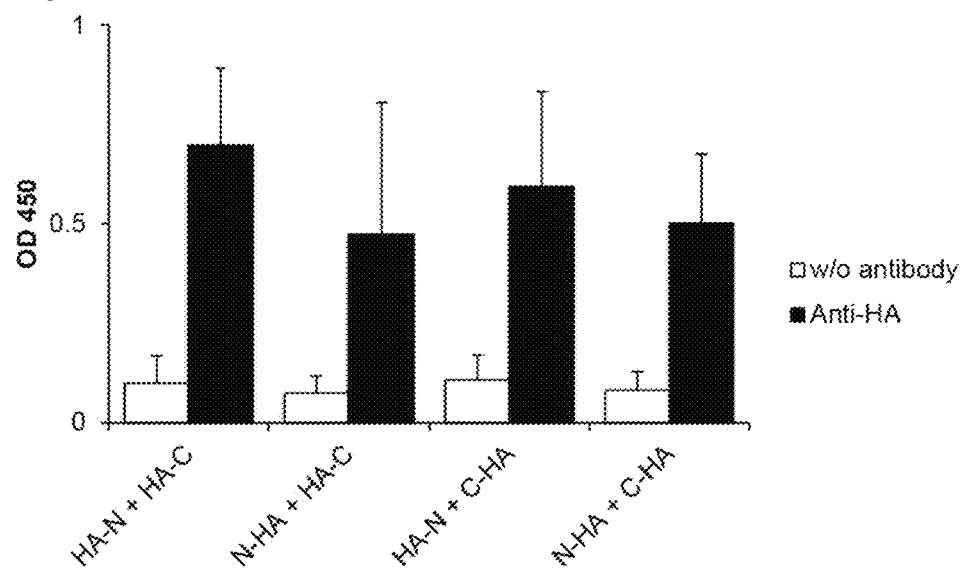
Figure 11B:
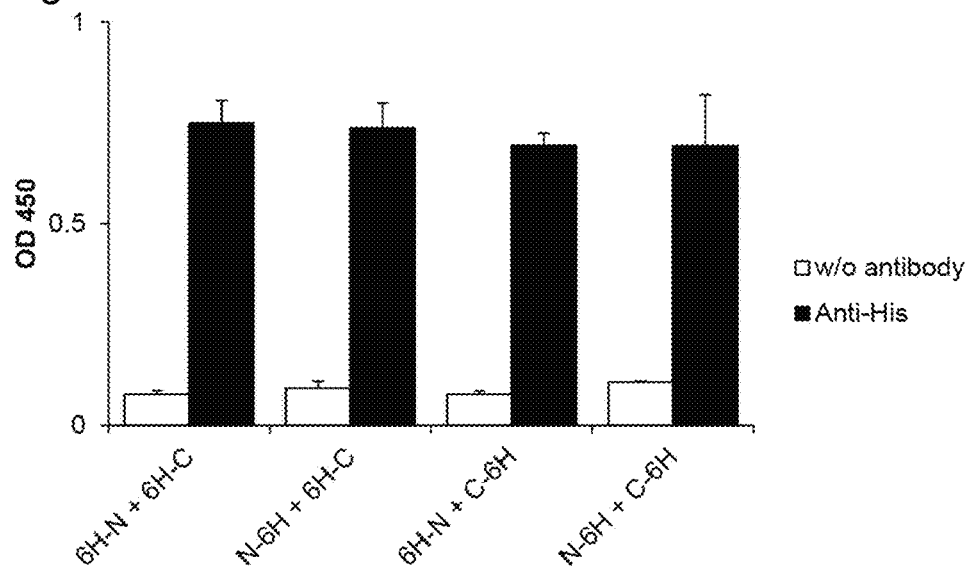
Figure 12A:
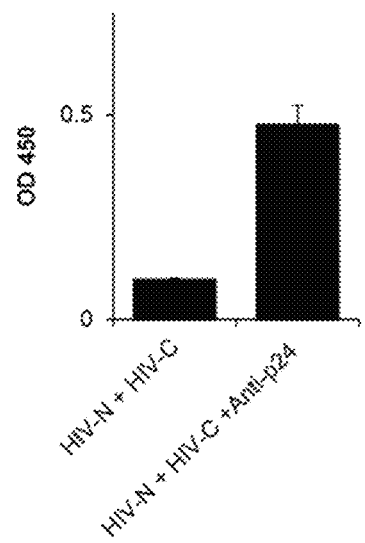
Figure 12B:
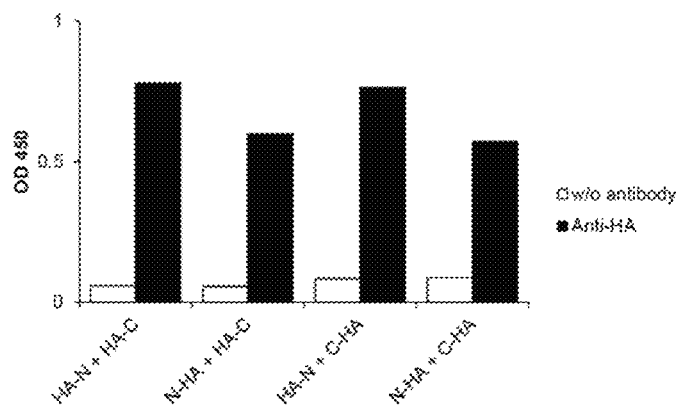
Figure 25A:
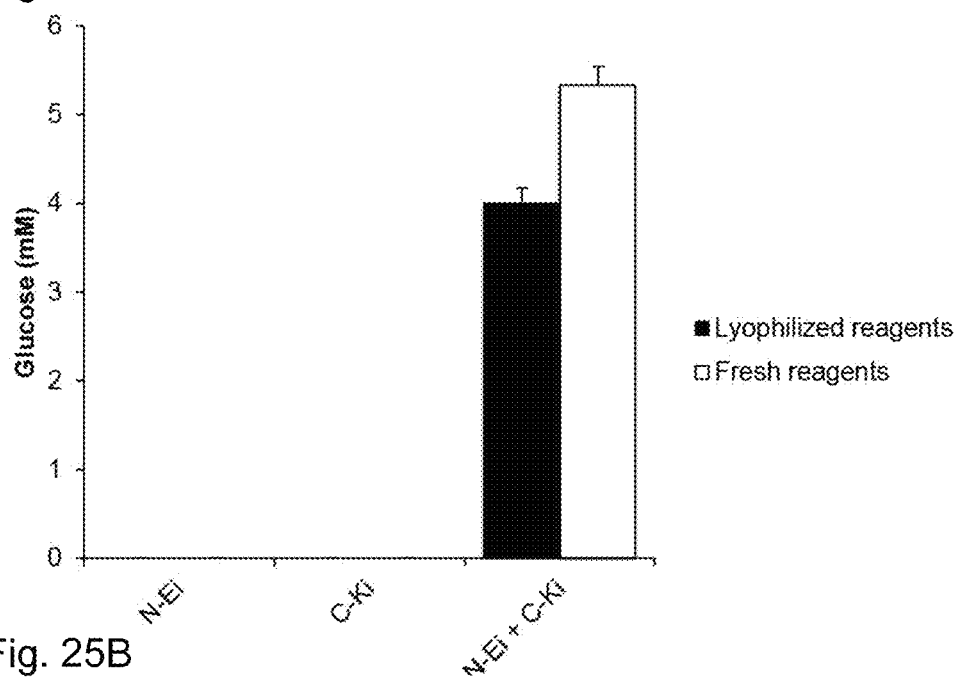
Figure 25B:
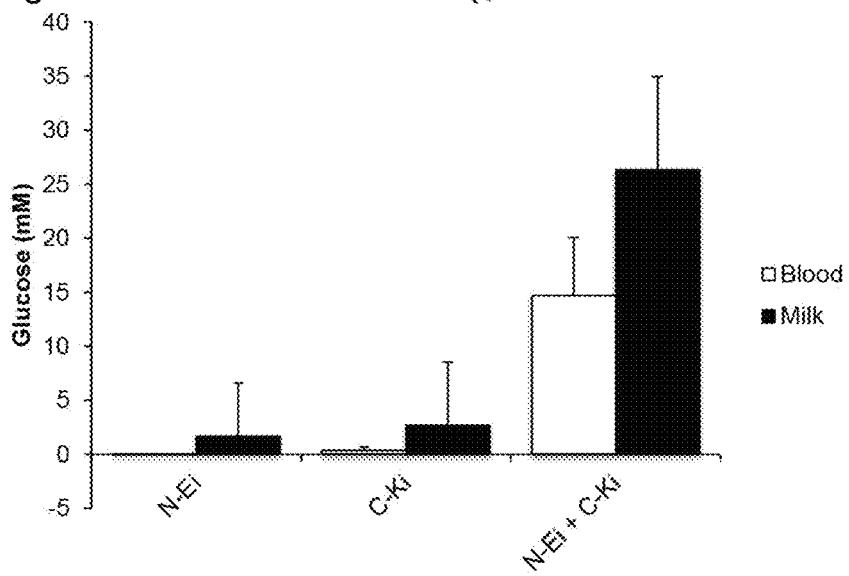
Figure 26:
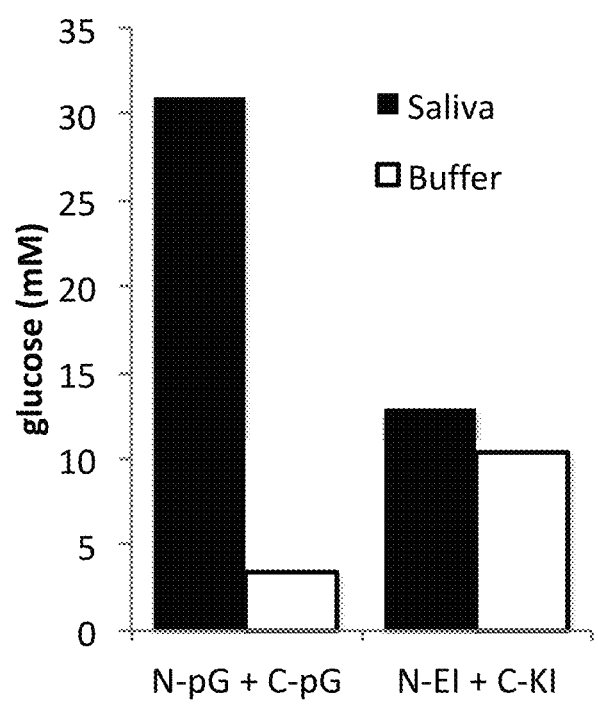
Figure 27A:
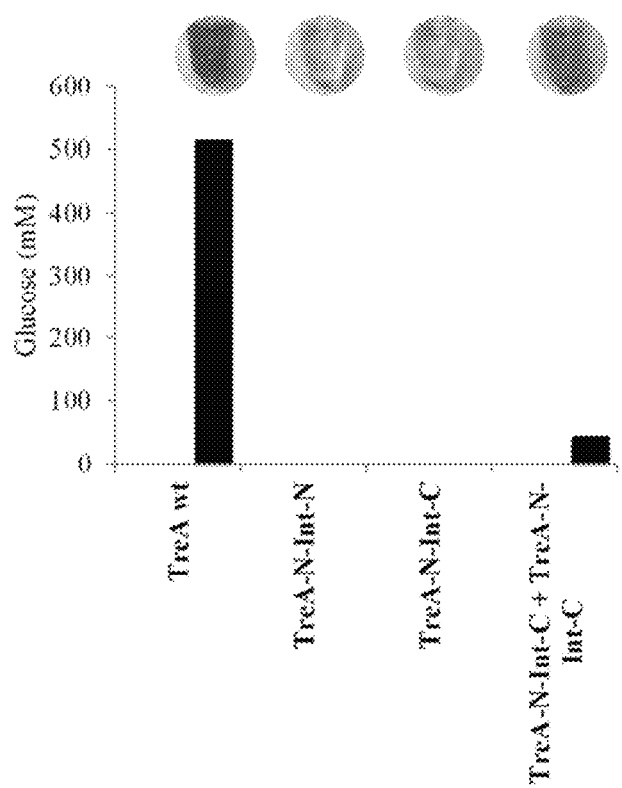
Figure 27B:
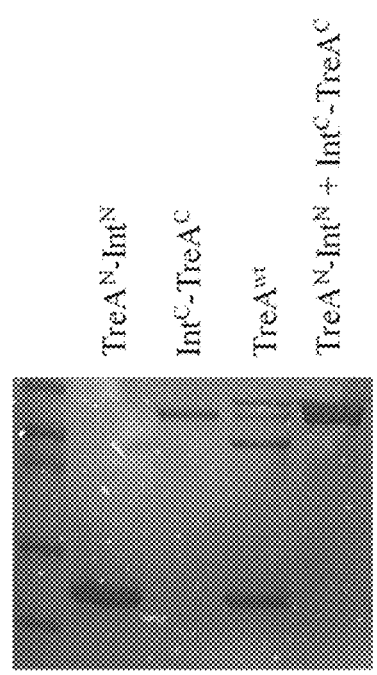
Figure 28:
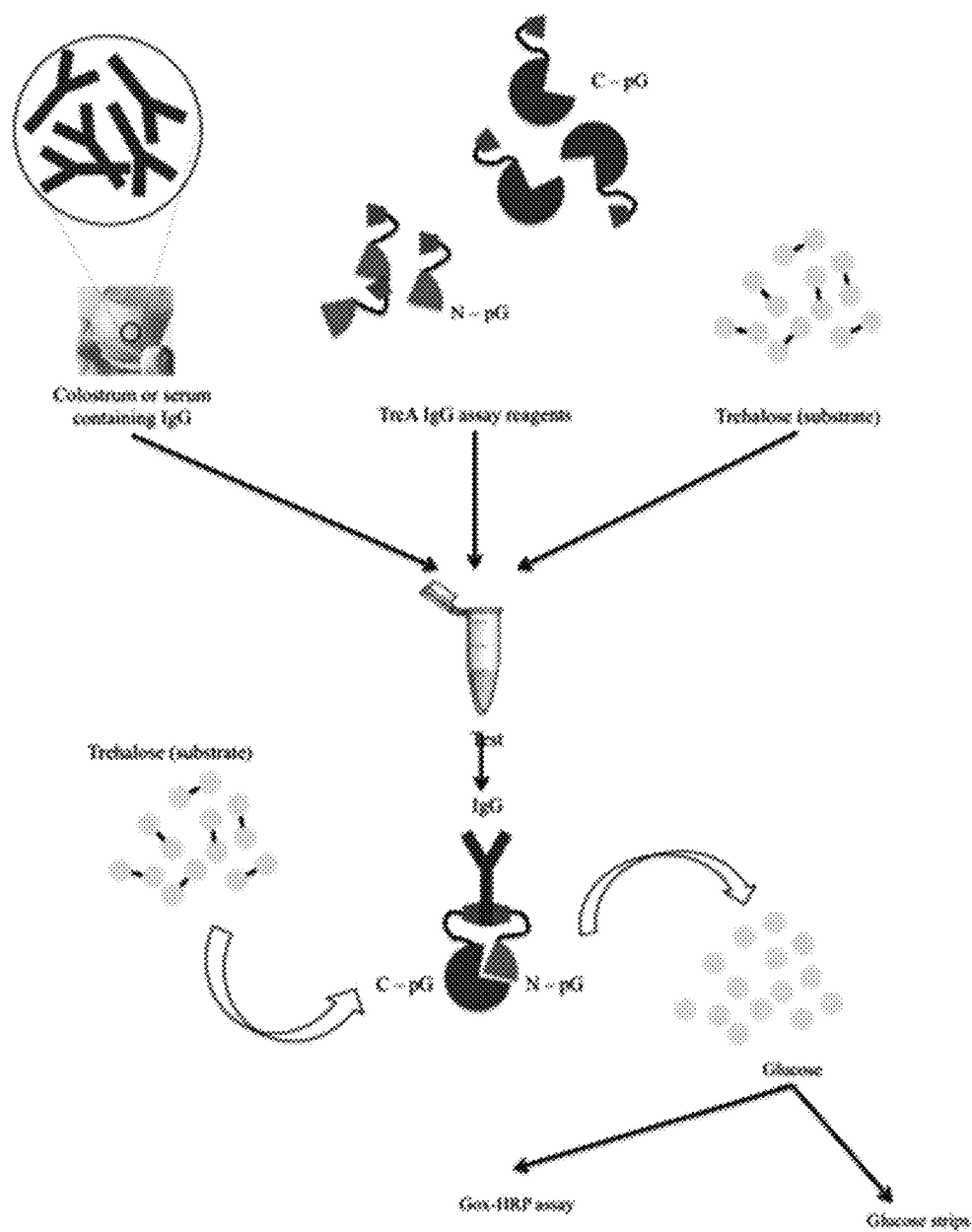
Figure 29:
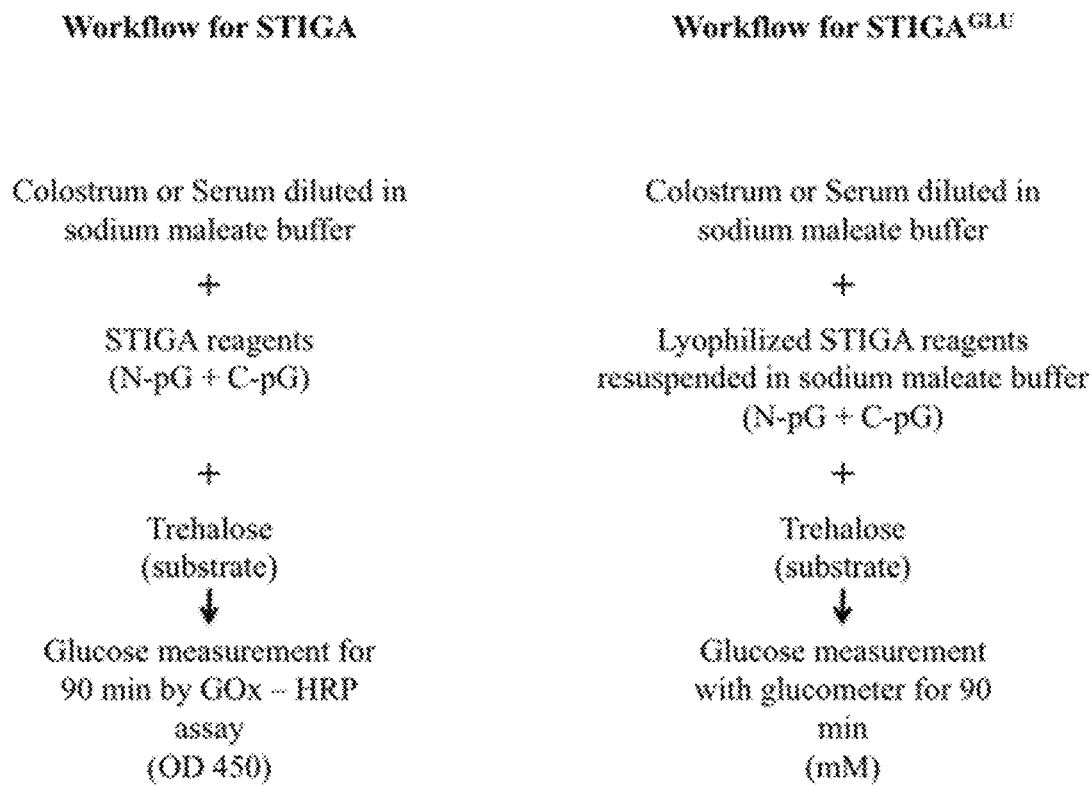
Figure 30A:
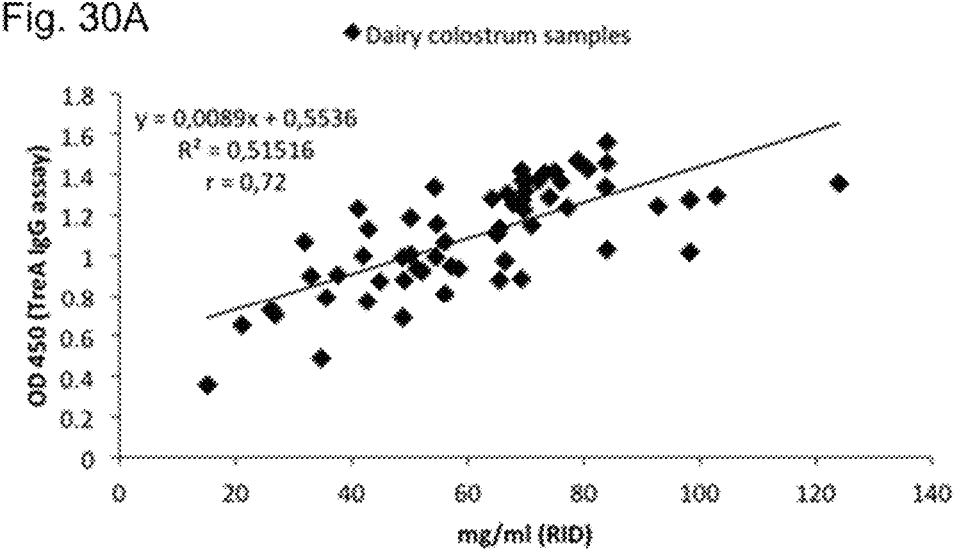
Figure 30B:
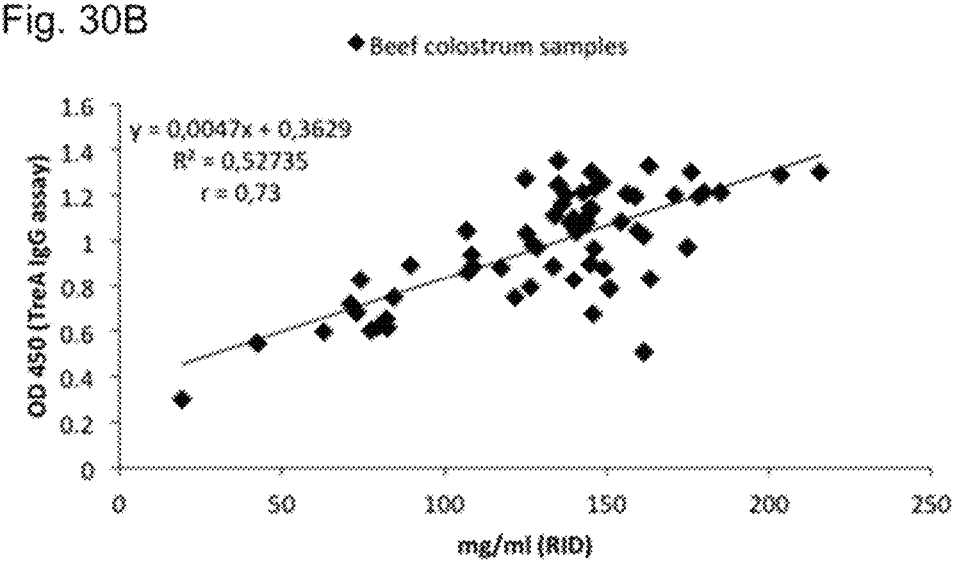
Figure 31A:
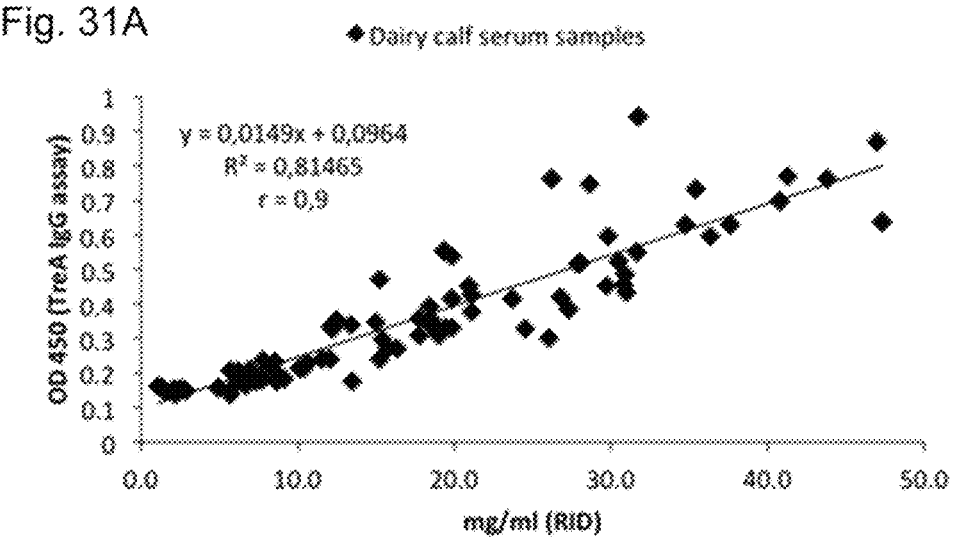
Figure 31B:
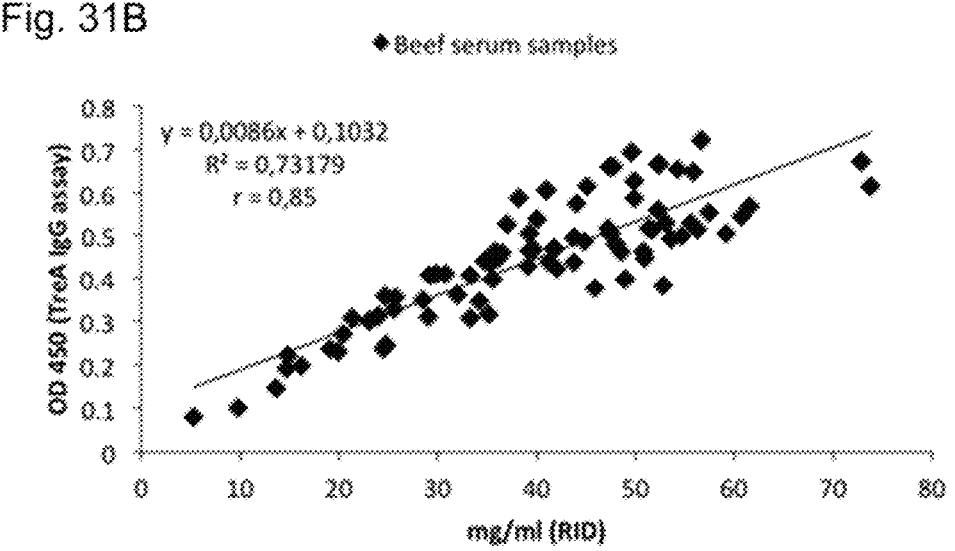
Figure 32A:
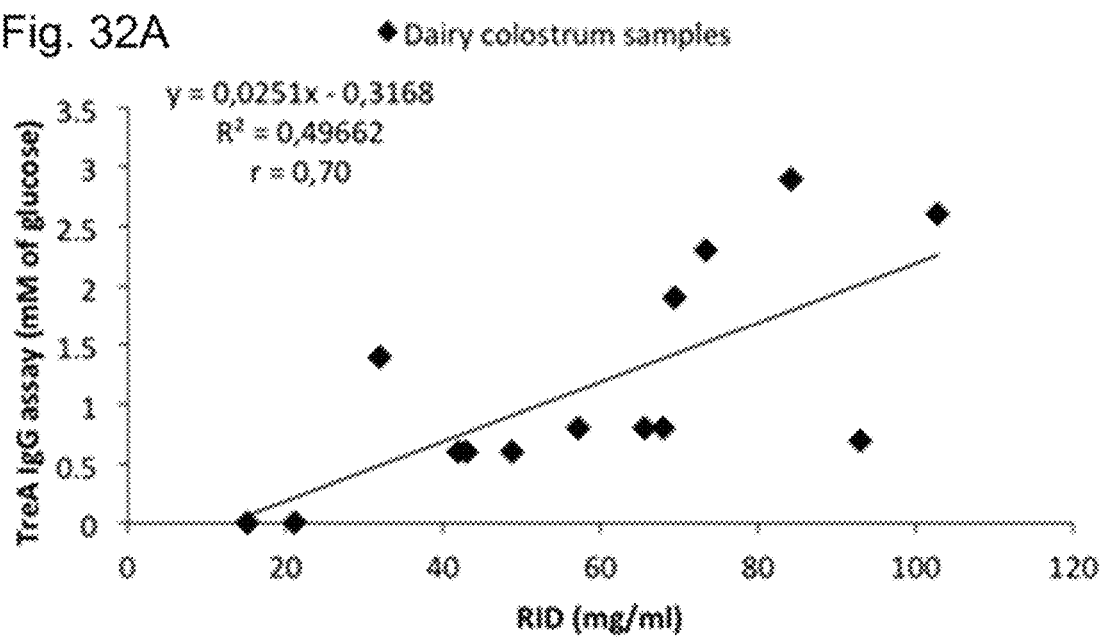
Figure 32B:
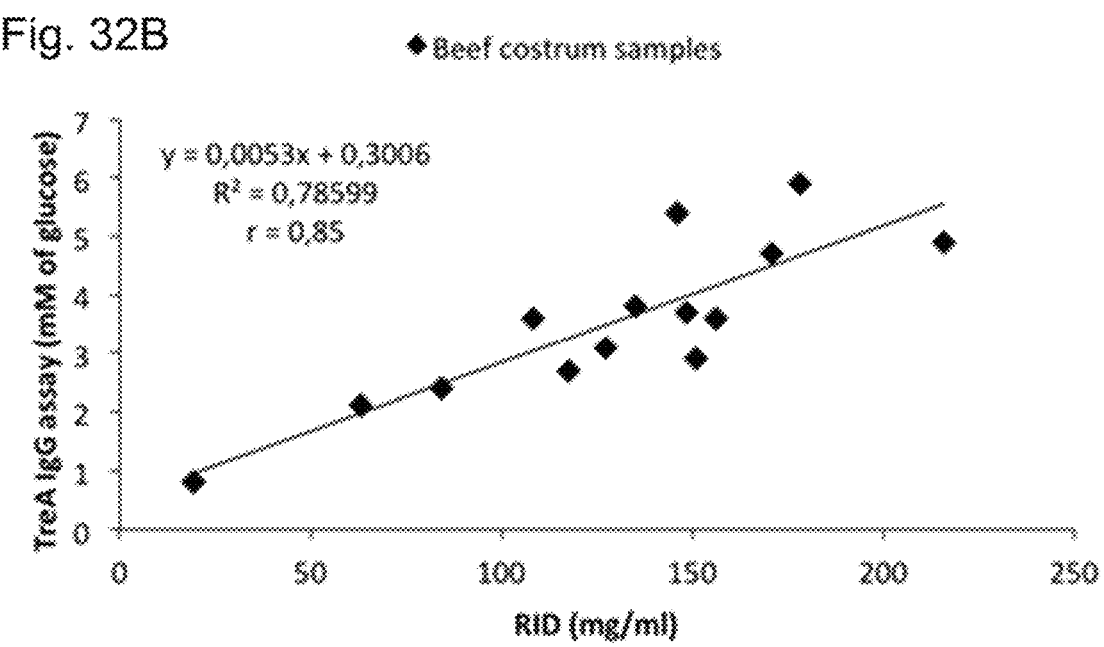
Figure 33A:
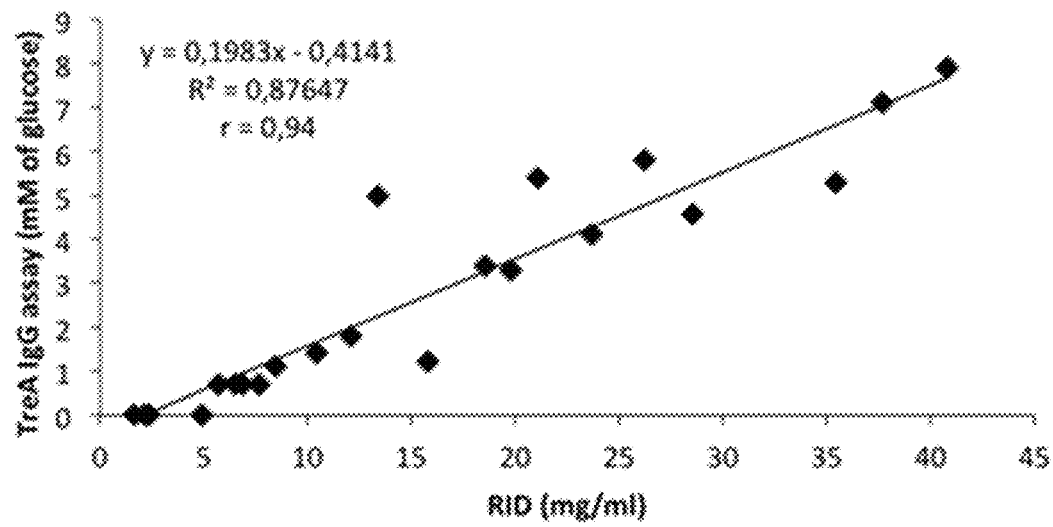
Figure 33B:
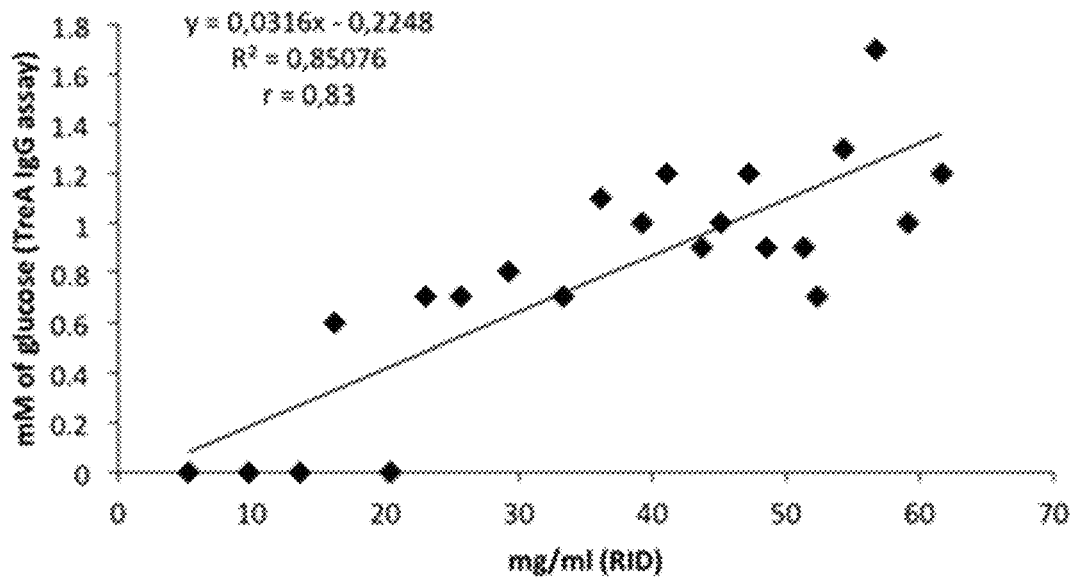
Figure 34A:
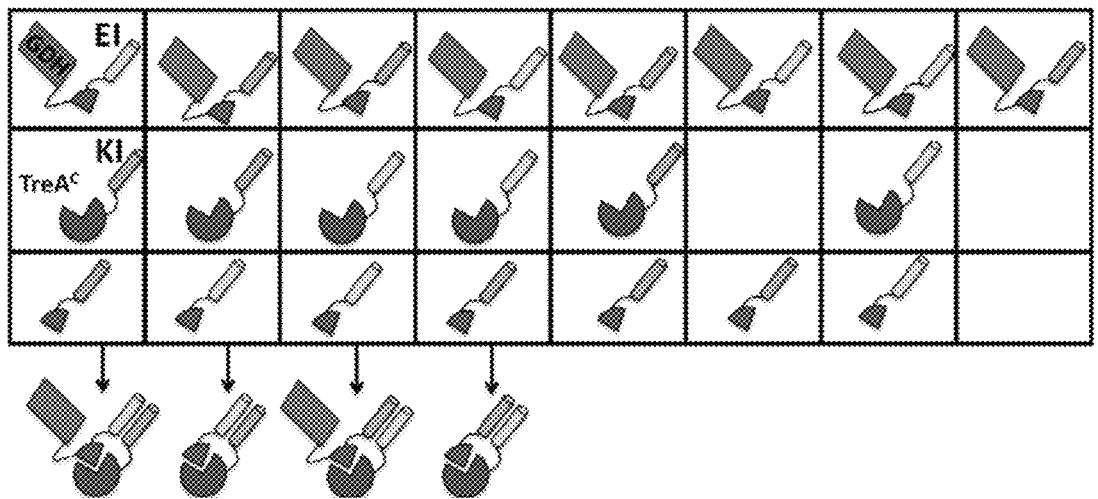
Figure 34B:
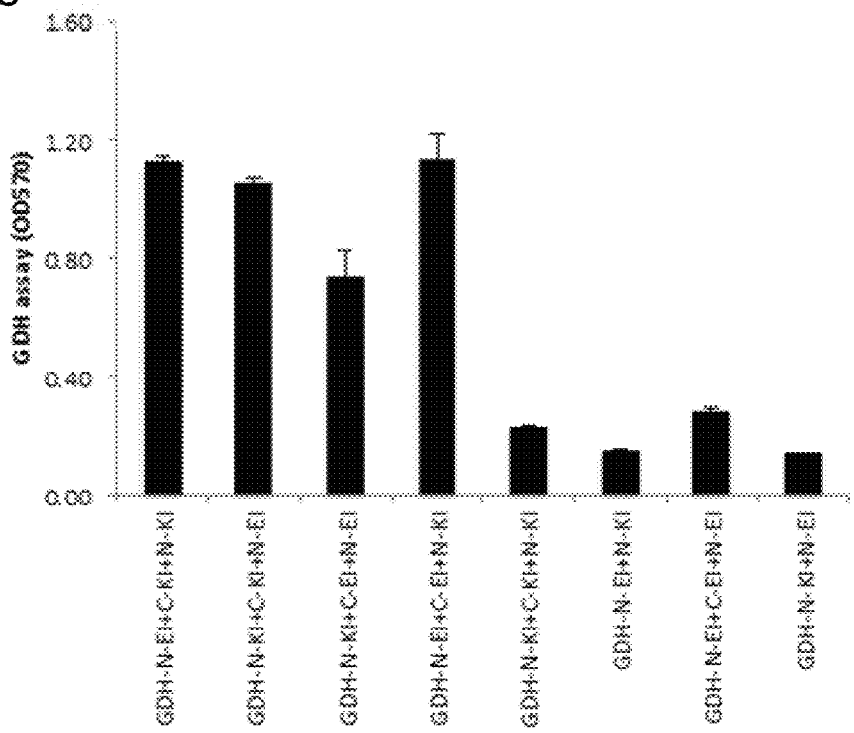

FIG. 8 is a schematic representation of an example of a complementation of split TreA on Ni-NTA resin with the N-terminal fragment TreA$^N$ (red), C-terminal TreA$^C$ (blue), HIS tag (green) and the Ni-NTA resin (violet). Recombinant TreA$^C$ and TreA$^N$ fragments, HIS-tagged at N or C terminus, were immobilised on Ni-NTA resin, either separately or together (n=3) (SEQ ID NOs: 20, 21, 22, 23);

FIG. 9A is a chart showing trehalase activity and the resulting glucose concentration in complementations prepared as shown in FIG. 8 measured by GOx-HRP assay after 30 min, FIG. 9B is a chart showing trehalase activity and the resulting glucose concentration measured by ACCU-CHEK AVIVA® glucose strips after 30 min, and FIG. 9C is a chart showing trehalase activity of HIS-tagged TreA$^C$ and TreA$^N$ fragments were immobilised on Ni-NTA resin, either separately or together at pH 6 or at pH 7 after 5 min, using the GOx-HRP assay (SEQ ID NOs: 20, 21, 22, 23);

FIG. 10 is a schematic representation of an example of a complementation of split TreA induced by antibodies with the N-terminal fragment TreA$^N$ (red), C-terminal TreA$^C$ (blue), peptide antigens (green), and cognate antibodies (violet) (SEQ ID NOs: 20, 21, 22, 23, 24, 25, 26, 27);

FIG. 11A is a chart showing trehalase activity after incubation of HA-tagged TreA$^C$ and TreA$^N$ fragments (SEQ ID NOs: 24, 25, 26, 27) with or without anti-HA monoclonal antibodies using the GOx-HRP assay in complementations prepared as shown in FIG. 10, and FIG. 11B is a chart showing Trehalase activity after incubation of HIS-tagged TreA$^C$ and TreA$^N$ fragments (SEQ ID NOs: 20, 21, 22, 23) with or without anti-HIS monoclonal antibodies using the Anti-HIS assay;

FIG. 12A is a chart showing trehalase activity after incubation of TreA$^C$ and TreA$^N$ fragments fused to HIV capsid protein p24 (HIV) (SEQ ID NOs: 30, 31) with or without anti-HIV (p24) rabbit antiserum using the Anti-HIV assay in complementations prepared as shown in FIG. 10, and FIG. 12B is a chart comparing the measurement of glucose detection using the GOx-HRP assay, a glucometer and Benedict's reagent (SEQ ID NO 24, 25, 26, 27);

FIG. 13A is a chart showing the sensitivity of the TreA split Ab detection assay demonstrated by incubating TreA$^C$ fragment and TreA$^N$ fragment carrying HA tags (SEQ ID NOs: 24, 26) with decreasing amounts of Anti-HA tag mAb or without.(n=3)(glucose levels were measured by the GOx-HRP assay every 5 minutes for 1 h), FIG. 13B is a chart showing the time response of TreA spilt detection assay with and without anti-HA (n=3), and FIG. 13C is a chart showing the specificity of the TreA split Ab detection assay demonstrated by incubating HIS-tagged TreA$^N$ and TreA$^C$ fragments (SEQ ID NOs: 21, 23) with anti-HIS tag mAb, anti-HA mAb or without antibodies (n=3)(glucose concentration was measured by GOx-HRP assay performed for 30 min);

FIG. 14 is a chart showing the sensitivity of a 3-enzyme assay (3EA) for detection of a series of concentrations of human IgGs quantified by complementation of split TreA fragments fused to protein G (SEQ ID NOs: 28, 29) wherein glucose oxidase, horse radish peroxidase, and O-dianisidine convert the de novo produced glucose by the complemented TreA into a colorimetric signal detectable at 450 nm OD;

FIG. 15 is a schematic representation of an example of complementations of split TreA induced throughout interaction with different antibody regions (variable (antigen binding) and constant region) with the N-terminal fragment TreA$^N$ (red), C-terminal TreA$^C$ (blue), antigen (green), protein G (pG) (green) and analyte (violet) (SEQ ID NOs: 25, 27, 28, 29);

FIG. 16A is a chart showing trehalase activity after incubation of TreA$^N$ and TreA$^C$ fragments either both fused to HA-tag or one fused to Protein G and the other to HA-tag in the presence of cognate monoclonal antibodies (n=3) in complementations prepared as shown in FIG. 15 (SEQ ID NOs: 25, 27, 28, 29), and FIG. 16B is a chart showing trehalase activity after incubation of TreA$^N$ and TreA$^C$ fragments both fused to Protein G in the presence bovine IgGs (SEQ ID NOs: 28, 29);

FIG. 17A is a schematic illustration showing the affinity of protein G (pG), protein A (pA) and protein L (pL) for regions within immunoglobulins, and FIG. 17B is a schematic illustration of TreA fragment fusions with pG, pA, and pL (SEQ ID NOs: 28, 29, 32, 33, 34, 35);

FIG. 18A is a chart showing complementation of split TreA fusions by IgG over time, and FIG. 18B is a chart showing detection of human IgG, IgM or IgA (40 nM) with TreA fragments (TreA$^N$ and TreAC) fused to protein G (pG), protein A (pA), or protein L (pL). The 3EA assay was used to detect de novo glucose production by the complemented TreA (SEQ ID NOs: 28, 29, 32, 33, 34, 35);

FIG. 19A is a schematic representation of an example of a split TreA complementation occurring on a pathogen's surface with the N-terminal fragment TreA$^N$ (red), C-terminal TreA$^C$ (blue), sensors (green), analyte (violet), and FIG. 19B is a chart showing trehalase activity after incubation of TreA$^C$ and TreA$^N$ fragments fused with *S. aureus* specific binding peptides (SAbp) in the presence of *S. aureus, S. epidermidis* or in the absence of bacteria (n=3) is a schematic representation of the STIGA detection mechanism used to estimate/determine the quantity of IgGs in samples (SEQ ID NOs: 40, 41, 42, 43);

FIG. 20 is a chart showing showing detection of *Mycobacterium avium* subsp. *paratuberculosis* (MAP) whole bacterial cells with an exemplary split TreA detection assay with incorporated MAP specific binding peptide (Mp3) (SEQ ID NOs: 44, 45, 46, 47);

FIG. 21 is a chart showing showing detection of *Listeria monocytogenes* whole bacterial cells with an exemplary split TreA detection assay with cognate incorporated variable fragment (scFv) specific for *L. monocytogenes* ActA (SEQ ID NOs: 49, 50);

FIG. 22 is a chart showing showing detection of small analytes ATP by monitoring trehalase activity when TreA C fragment and TreA N fragment with C terminal fusions with ATPase subunit FOF1 ε are incubated with 10 mM of ATP or GTP in the presence of 0.25 M trehalose (SEQ ID NOs: 51, 52);

FIG. 23 is a schematic representation of an example of a split TreA complementation split TreA complementation occurring upon protein-protein interaction and protein aggregation with the N-terminal fragment TreA$^N$ (red), C-terminal TreA$^C$ (blue), leucine zippers or recombinant PrP (green) (SEQ ID NOs: 53, 54, 55, 56, 58, 59);

FIG. 24A is a chart showing trehalase activity after co-incubation of TreA$^C$ and TreA$^N$ fragments fused to complementary leucine zippers (Ei; Ki) (n=3) (SEQ ID NOs: 53, 54, 55, 56), and FIG. 24B is a chart showing trehalase activity after aggregation of TreA$^C$ and TreA$^N$ fragments fused to PrP induced by co-dialysis (n=3) (SEQ ID NOs: 58, 59, 20, 22);

FIG. 25A is a chart showing trehalase activity after incubation of lyophilized TreA$^N$ and TreA$^C$ fragments fused to complementary leucine zippers (Ki+Ei), resuspended in acidified bovine blood or milk (pH 6) (n=3) (glucose concentration was measured with ACCU-AVIVA® glucose strips after 3 h of incubation, residual glucose detected in both blood and milk was subtracted from measured signals), and FIG. 25B is a chart showing complementation of lyophilized TreA$^N$ and TreA$^C$ carrying complementary leucine zippers (Ki+Ei) fragments compared to fresh preparation (n=3). Glucose concentration was measured with ACCU-AVIVA® glucose strips after 1 h of incubation) (SEQ ID NOs: 55, 56);

FIG. 26 is a chart showing trehalase activity after incubation of lyophilized TreA$^N$ and TreA$^C$ fragments fused to either protein G or complementary leucine zippers (Ki+Ei), resuspended in pure saliva (glucose concentration was measured with ACCU-AVIVA® glucose strips after 2 h) (SEQ ID NOs: 55, 56);

FIG. 27A is a chart showing trehalase activity after complementation of fusions of split trehalase and split inteins fragments and excision of the intein and ligation of the trehalase fragments, and FIG. 27B is a SDS-PAGE gel showing intein and ligation of the trehalase fragments of a biodetector according to an embodiment of the present disclosure (SEQ ID NOs: 17, 61, 62);

FIG. 28 is a schematic representation of the STIGA detection mechanism used to estimate/determine the quantity of IgGs in samples (SEQ ID NOs: 28, 29);

FIG. 29 is a schematic representation of the methods used for the STIGA and the STIGA$^{GLU}$ assays (SEQ ID NOs: 28, 29);

FIG. 30A is a scatter plot comparing IgG concentration measured by STIGA (OD 450) and by RID (ml/mg) in dairy colostrum (n=60) and FIG. 30B is a scatter plot comparing IgG concentration measured by STIGA (OD 450) and by RID (ml/mg) in beef colostrum (n=64) (SEQ ID NOs: 28, 29);

FIG. 31A is a scatter plot comparing IgG concentration determined by RID (mg/ml) and by STIGA (OD 450) in dairy calf sera (n=83), and FIG. 31B a scatter plot comparing IgG concentration determined by RID (mg/ml) and by STIGA (OD 450) in beef calf sera (n=84) (SEQ ID NOs: 28, 29);

FIG. 32A is a scatter plot of IgG concentration measured by TreA IgG assay (mM of glucose measured with a glucometer) and concentration determined by RID (mg/ml) for dairy colostrum samples (n=14), and FIG. 32B is a scatter plot of IgG concentration measured by TreA IgG assay and by RID for beef colostrum samples (n=14) (SEQ ID NOs: 28, 29);

FIG. 33A is a scatter plot of IgG concentration measured by TreA IgG assay and by RID for dairy calf serum samples (n=22), and FIG. 33B is a scatter plot of IgG concentration measured by TreA IgG assay and by RID for beef calf serum samples (n=22) (SEQ ID NOs: 28, 29); and FIG. 34A is a schematic representation of complementation of split TreA fragments fused to heterodimerizing peptides (El and Kl) whereby one fragment is also fused to glucose dehydrogenase (GDH) and generation of a colorimetric signal by GDH wherein different combinations of TreA fragments and peptides are combined to demonstrate that the complementation occurs only when complementary heterodimerizing peptides are fused to the correct fragments, and FIG. 34B shows a corresponding colorimetric assay (570 nm OD) using 1-methoxy-5-methylphenazinium methyl sulfate (mPMS) as the mediator, thiazolyl blue tetrazolium bromide (MTT) as the substrate, and pyrroloquinoline quinone (PQQ) as co-factor, to convert the de novo glucose produced by the complemented TreA into the colorimetric signals (SEQ ID NOs: 53, 54, 55, 71, 72).

DETAILED DESCRIPTION

The embodiments of the present disclosure generally relate to protein/enzyme fragment complementation assays which are routinely used to identify protein-protein interactions. In complementation assay, protein/enzyme is split into two fragments and reconstituted non-covalently to restore activity by other interacting proteins that are fused to fragments. Some examples of split proteins are luciferase, beta-lactamase, Gal4, beta-galactosidase, GFP and ubiquitin.

The efficacy of split trehalase assay biosensor disclosed herein is based on the following parameters: 1) split trehalase can restore its activity when its two fragments are brought together in close proximity; 2) either fragment alone does not possess enzymatic activity; 3) two fragments co-incubated together do not possess enzymatic activity without the specific complexing analyte; 4) only antibodies specific to fused antigens or other specific analytes interacting with the cognate fused (poly)peptides are capable of restoring enzymatic activity of trehalase; 5) there is no or very low level of endogenous trehalase activity in the biological sample to be tested.

Some aspects of the present disclosure pertain to splitting trehalase into N-terminal and C-terminal fragments and to fuse antigens, e.g. His-tag, HA-tag, or antigenic protein P24 to the end(s) of each fragment. The aspects of the present disclosure include the scheme of incorporating the antigens into the trehalase fragments. It investigates the position effects of the antigens with regard to the N-terminal or C-terminal of the fragments on the restored enzymatic activity.

Some aspects of the present disclosure pertain to expressing recombinant trehalase fragments in the E. coli strain BL-21 (DE3) knock-out for endogenous TreA gene (Bl-21 ΔTreA) and purifying recombinant fragments using Ni-NTA columns. The assay is performed in a test tube by combining N-terminal and C-terminal fragments in a solution containing trehalose. A method to eliminate glucose present in the biological sample before the enzyme is activated is also within the scope of the present disclosure.

Another aspect of the present disclosure pertains to fusing one of the antigen-trehalase fragments (i.e. N-terminal) to glucose oxidase or glucose dehydrogenase. This design allows the glucose generated by restored trehalase to be quickly converted to a signal that can be detected photospectrometrically or electrochemically.

For the successful creation of a split-reporter protein, several criteria must be met. Each protein fragment by itself should not exhibit any activity, the affinity of the fragments in the absence of attached interacting proteins should be negligible, and ideally the reassembled split-protein must provide an easily measurable read out.

The present disclosure pertains to split biosensor-linked immunodetector biosensors that are solution-based, homogenous, "mix and read" that rely on recognition of antibodies and other analytes coupled with enzymatic gain.

The biosensors disclosed herein include, but are not limited to, enzymes that can be split into two independent folding domains, which by themselves have little or no detectable activity, nor sufficient affinity for their complementary partner to lead to automatic complementation. if the latter is not naturally the case, it could still be accomplished by re-engineering residues at the interacting surfaces of the split fragments. This ensures a good signal-to-noise ratio. However, once brought together by the affinity of the detector for its analyte, activity is restored. Because of the enzymatic turn-over of a measurable product, this assay provides gain (amplification) to the signal associated with the presence of the targeted analyte.

This disclosure outlines many advantages to bio-detection: sensitivity, specificity, simplicity, use of simple (existing) readers, homogenous, compatibility with biological samples types and matrices, "mix and read" format. The solution-based, dual-recognition, split-enzyme linked detector systems will have broad applications where highly specific, sensitive, inexpensive and portable detection of specific biological agents or substances are required. For example, for detecting analytes in a 'field' setting.

The biosensors disclosed herein may detect the presence of antibodies that are reactive with bacteria, viruses, fungi, irritants, and proteins.

The biosensors disclosed herein may also detect other target entities found in biological samples, for example, a cell, protein, peptide, hormone, cytokine, chemokine, nucleic acid, a virus, a bacterium, an organic molecule, a lipid, a fatty acid, a carbohydrate, a drug, an element, a toxin, a chemical, a metabolite, or a complex comprising two or more of any of the aforementioned items.

The target entities may be present in biological samples collected from animals or human individuals if the individuals are positive for the conditions being tested. Such target entities may be, for example markers of the condition, or they may be the actual toxin, drug, or pathogen being sought. Accordingly, the target entities (or components of the target entity) may be, for example, a nucleic acid, a ribonucleic acid, a polypeptide, a carbohydrate, a protein, a peptide, an amino acid, a hormone, a steroid, a vitamin, an ion, a metabolite, a chemical, an element, a derivative, an analogue, a polysaccharide, a lipid, a fatty acid, a lipopolysaccharide, a glycoprotein, a lipoprotein, a nucleoprotein, an oligonucleotide, an antibody, an immunoglobulin, a coagulation factor, a peptide hormone, a protein hormone, a non-peptide hormone, an interleukin, an interferon, a cytokine, a chemokine, a cell, a cell-surface molecule, a microorganism, a small organic molecule, a virion, a bacterium, a toxin, a drug, a cell membrane, a membrane fraction, a protein complex, an antigen, a hapten, a receptor, a macromolecule, or a molecular complex comprising two or more of any of the aforementioned items.

Many biosensor devices have been developed, for example, optical, electrical, electrochemical and mass-based. However, only a few have made it into clinical practice or into home use. The main reasons for this are their poor performance in clinical samples (blood, urine, saliva, sputum), insufficient sensitivity or specificity, expensive supporting equipment, or high cost of production. Regardless, the markets are ready to adopt "Anything-Anywhere-Anytime-Anyone" biosensors if such biosensors meet certain expectations.

In order to fulfill the 'Anyone' requirement, a candidate biosensor should be extremely user-friendly (even for unskilled users), require non-invasive samples (e.g. pin-prick of blood, tears or saliva) and minimal sample handling. Moreover, the biosensor should be quantitative and easily interface with mobile technology and thereby be compatible with emerging telehealth-based health care. To satisfy the 'Anywhere' requirement, a candidate biosensor must not require expensive equipment, must require no or minimal sample processing, and must be robust and portable. To satisfy the 'Anytime' requirement, a candidate biosensor should be accessible, cheap and fast, and devoid of a need for a transport chain. To satisfy the 'Anything' requirement, a candidate biosensor should be sensitive, specific and versatile. However, most biosensors currently available are optimized for a specific analyte or group of analytes, which restricts their applicability and broad adoption.

The most successful class of biosensor currently available on the market that meets the first three 'A' requirements, is glucometers used to monitor blood glucose concentrations. Currently available glucometers comprise a glucose-specific oxido-reductase (glucose oxidase or dehydrogenase) and an electrochemical transducer that converts enzyme activity into an electrochemical signal. A technology that makes use of this existing biosensor but adds versatility (i.e., 'Anything') by increasing the type of analytes that can be analysed, would have important advantages. The split Trehalase biosensors disclosed herein satisfy the 'A' requirements.

For successful creation of a split-reporter protein, several criteria must be met. Each fragment by itself should not exhibit activity, the affinity of the fragments in the absence of fused interacting proteins should be negligible, and the re-assembled split-protein must provide an easily measurable output. Despite its deceptive simplicity, identification of potential split proteins and their appropriate dissection sites is limited. Currently, there are a finite number of reported split proteins available for consideration, i.e., luciferase, fluorescent proteins, beta-lactamase, proteases, and the like.

Herein is disclosed a versatile detection platform based on the protein complementation principle that is able to detect a wide range of types of analytes. At the core of this platform is a glycolytic enzyme trehalase (TreA) localized in the periplasmic space of *E. coli* that catalyzes hydrolysis of trehalose into two glucose molecules. Production of glucose can be easily detected by a glucometer whereas the output signal from other split enzymes are less compatible with existing detectors and with detection in biofluids of humans and animals, e.g. fluorescence or luminescence from GFP or luciferase. Glucose detection has a quick and easy read-out with proven compatibility with complex samples without additional handling or processing.

Figure 1:
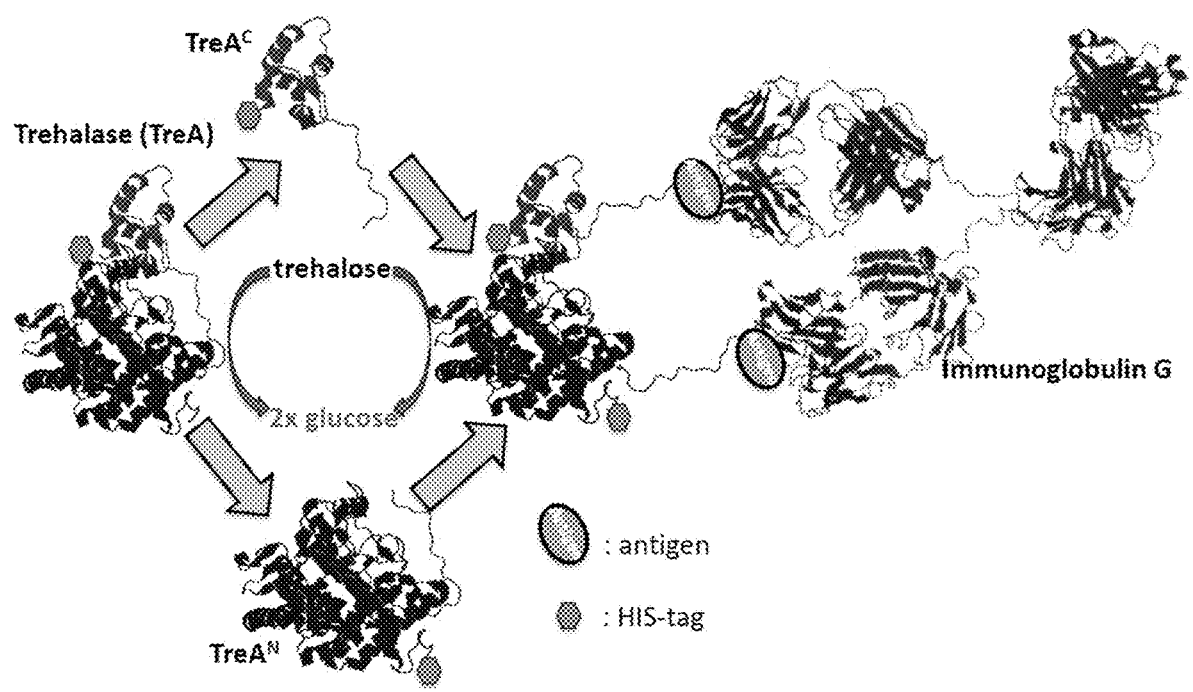
FIG. 1 shows a schematic illustration of the split TreA assay disclosed herein applied to the detection of antibodies.
Figure 2:
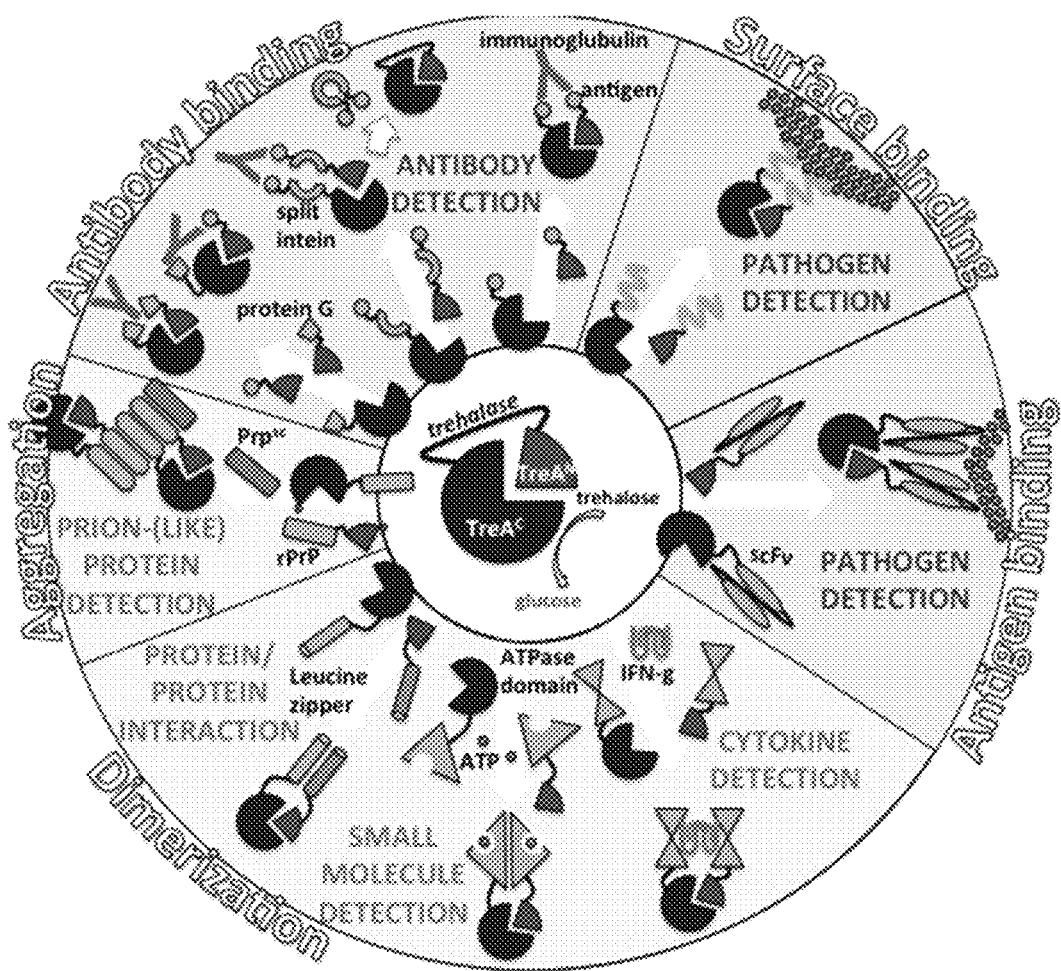
FIG. 2 is a schematic representation of the different embodiments of split TreA assays disclosed herein.
Figure 3:
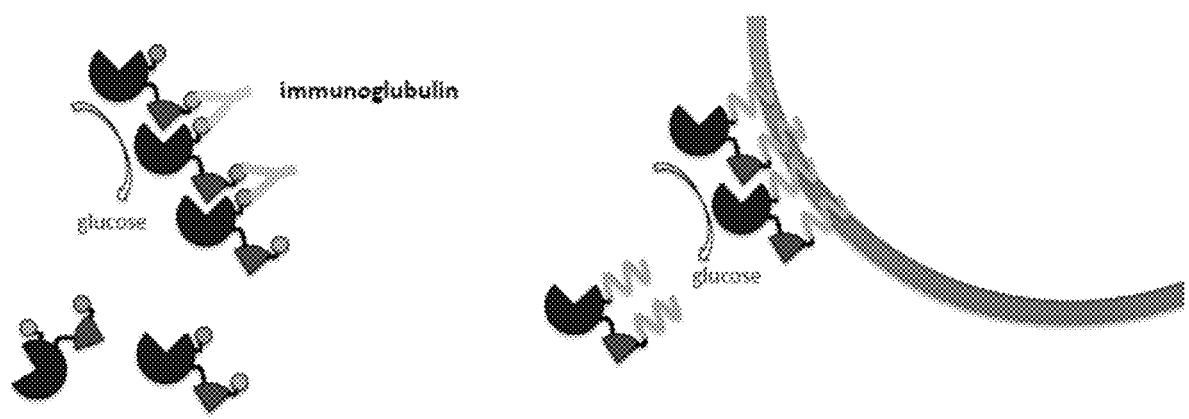
FIG. 3 is a schematic representation of the alternative frame folding of TreA domains (SEQ ID NOs: 76, 77, 78) applied to detect antibodies and bacterial cells.

Trehalase has a bimodular structure with a connecting flexible linker, not unlike luciferase. Consequently, TreA, split at the site of this liker into two non-functional fragments, can be fused to sensor domains specific for an analyte of interest. The interaction/bond between analyte and sensor triggers complementation of two TreA fragments, which leads to activation of the enzyme. Suitable biosensors for detection of a wide variety of analytes, including antibodies, bacteria, viruses, small molecules, hormones, cytokines and prion-(like) protein based on various mechanisms to mediate complementation of reporter fragments, such as bivalent binding of antibodies, protein dimerization, protein aggregation, surface binding by using peptide aptamers, single chain fragment variables (scFv), antigens, receptor proteins and recombinant prion-like proteins as fusion partners to the reporter enzyme, are shown in FIGS. 1 and 2. Also, shown are complementation of TreA fragments by heterodimerizing coiled-coil peptides (leucine zipper) and the reconstitution of TreA by split intein fragments fused to split TreA fragments.

The present disclosure relates to a method for detection of analytes in biological samples with an engineered enzyme, for example the periplasmic trehalase of *E. coli* (TreA) that is split into two domains and thereby rendered inactive, and having sensor polypeptides fused to both fragments. These polypeptides interact in the presence of the analyte and thereby bring the TreA fragments into close enough proximity such that protein complementation is induced. Accordingly, the present disclosure pertains to a replacement of a naturally occurring linker connecting the two domains with a conditional linker, whereby the conditional linker only materializes through when an analyte is present. The conditional linker comprise non-covalent or covalent bonds. In the case that the conditional linker comprises covalent bonds, split inteins may be used as the conditional linkers.

According to a first embodiment of the present disclosure, different interaction mechanisms enable this 'complementation by a proximity' mechanism, thereby enabling detection of a variety of analytes using different fusion partners (i.e., sensor (poly)peptides). Firstly, antibodies are bivalent and when each of both binding sites binds with a corresponding antigen fused to the trehalase fragments, the fragments are kept in close enough proximity to restore the activity of the trehalase. The restoration of trehalase activity leads to hydrolysis of trehalose into two glucose molecules, an activity that is not present in either trehalase fragment alone or in combined trehalase fragments without the presence of a complexing antibody (FIG. 1).

According to a second embodiment of the present disclosure, peptide aptamers enable binding of TreA fragments onto a surface, for example a bacterial surface or the surface of a Ni-NTA resin bead, in close enough proximity for protein complementation to occur. Other examples of this mechanism include for example, peptides that specifically bind to bacterial cell envelopes, cell membranes, cell walls, viral particles, parasite surfaces, parasite cuticles, and the like.

According to a third embodiment of the present disclosure, single-chain fragment variables (i.e., antibody derivatives) with specificity for a bacterial surface protein, may be fused to bind TreA fragments close enough together to initiate protein complementation.

Figure 6:
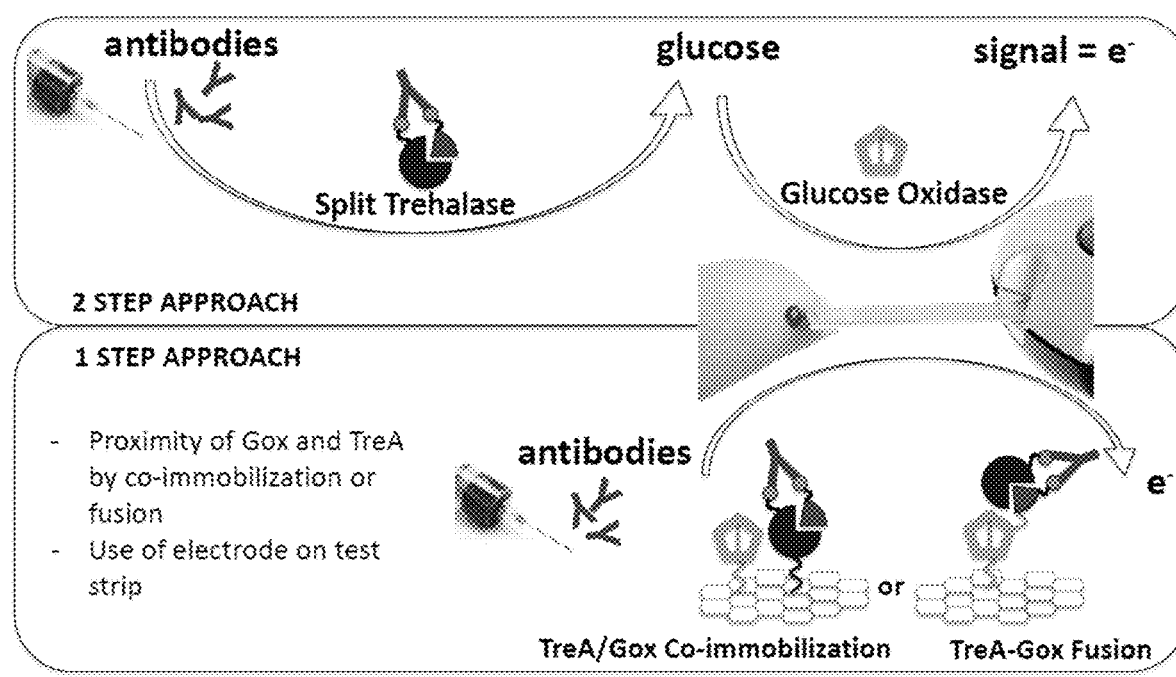
FIG. 6 is a schematic representation of two approaches for conversion of antibodies into a signals detectable with an exemplary trehalase biosensor according to an embodiment of the present disclosure.

According to a fourth embodiment of the present disclosure, proteins that dimerize in the presence of specific small molecules such as ATP and estradiol, may be used to detect the presence. Similarly, protein G or protein A may be fused to the TreA fragments to thereby bind both heavy chains of IgG molecules, and can thereby complement the trehalase activity. Additionally, heterodimerizing peptides fused to TreA fragments may complement enzymatic activity as would other pairs of (poly)peptides that have affinities for each other.

According to a fifth embodiment of the present disclosure, TreA fragments may be fused to recombinant proteins that have a tendency to aggregate. Co-aggregation of such fusion proteins may facilitate bringing the TreA fragments lose enough together to restore the trehalase enzyme activity. Recombinant prion proteins may be incorporated to detect infectious prion proteins by the induction of misfolding and fibril formation in the recombinant prion proteins.

It is known that trehalase may be engineered so that the N-terminal fragment is relocated and fused to the end of the protein (FIG. 3; also known as alternative frame folding (AFF)) with a linker that does not allow the correct bimodular conformation of the enzyme to occur thereby ensuring that this protein is not functional on its own (e.g., SEQ ID NOs: 76, 77). Two different antigens are fused to the N-terminus and C-terminus of this protein. These fusion proteins are produced in pairs whereby the same antigen is fused to the opposite terminus of the protein resulting in the ability of antibodies for either antigen to link the proteins together thereby complementing a N-fragment and a C-fragment of trehalase, and thereby activating glycoside hydrolase activity. If both antigen-specific antibodies are present, the formation of fibrils are possible with activation of trehalase activity. Fusing the same antigen to both ends of one protein is avoided because otherwise, a portion of binding antibodies will bind with both binding sites on a single fusion protein without restoring protein function. This AFF strategy can also be followed to construct a single bacterial surface-recognizing protein (SEQ ID NO: 78), for example, for *Staphylococcus aureus* by including peptide SA5-1 (SEQ ID NO: 38; FIG. 3).

Trehalase may be modified and engineered as outlined in some of the embodiments disclosed herein. The fragments of trehalase may be produced recombinantly and purified. The signal peptide may be eliminated from the N-terminal fragment, and the naturally existing linker between both domains may be duplicated and kept in both fragments at their original positions. His-tags may fused to all termini, sometimes with the inclusion of a small number of amino acids. Restriction enzymes sites may be added to the termini to allow cloning and subsequent insertion or deletion of peptides.

According to one aspect of the present disclosure, the compositions, biosensors, kits, and methods disclosed herein may be modified for use in the detection the presence of antibodies and other analytes in a solution or in a biological sample for example such as a fluid from animal or human exemplified by blood, serum, milk, sweat, semen, ejaculate, mucus, tears, saliva, plasma, secretions of the genitourinary tract, lymph fluid, urine, white blood cells, sputum, pleural fluid, ascites, sputum, pus, excrement, peritoneal fluid, cerebrospinal fluid, pleural fluid, pericardial fluid, amniotic fluid, synovial fluid, interstitial fluid, or any combination of such fluids, or any derivations of such fluids. Such biological samples are also referred to herein as "biofluids".

The compositions, biosensors, kits, and methods disclosed herein may utilize a split enzyme biosensor in which same (poly)peptide is fused to both fragments of the split enzyme. This antigen may a peptide or a polypeptide or a protein fragment or a protein domain or an entire protein. The antigen may be fused by incorporating the coding DNA sequence in the gene for the split enzyme fragment that is in turn, produced recombinantly in a cell expression system, for example a yeast cell expression system, a plant cell expression system, a fungal cell expression system, a mammalian cell expression system, or a bacterial cell expression system.

According to one embodiment of the present disclosure, both fragments of the enzyme portion of the sensors may be combined to form a biologically active enzyme when the fused antigens bind to a bivalent-complementing immunoglobulin. Such bivalent-complementing immunoglobulin may be of any isotype for example IgA, IgG, IgM, and the like. According to some aspects, the interaction of fusion partners with a selected analyte may also result in complementation of the fragments.

When trehalase enzymes are used, the production of a reducing sugar (glucose) from a non-reducing sugar (trehalose) may be detected. Also, the resulting product, i.e. glucose, may be detected by known methods that use glucose-oxidase functionalized glucometers or alternatively, with glucose-dehydrogenase functionalized glucometers.

The embodiments of the present disclosure are based on the selection of an enzyme that can create a signal that is measurable in biological samples using known measuring methods and devices for example, glucometers. In essence, the methods disclosed herein convert the presence of the analyte into a signal, for example glucose, for which quick, practical, mobile and individual user methods and devices have been developed. According to one aspect, a 2-step method according to the present disclosure may be used with conventional glucometer strips to measure glucose produced by the split trehalase (FIG. 6). According to another aspect, a 1-step method according to the present disclosure condenses the two enzymatic functions by co-immobilization of split trehalase and glucose oxidase onto electrode-containing test strips (FIG. 6). According to another aspect, a 1-step method according to the present disclosure condenses the two enzymatic functions by fusion of split trehalase and glucose oxidase onto electrode-containing test strips (FIG. 6).

This is in contrast with known methods whereby the output i.e. a measurable signal, is less compatible with existing detectors and with its detection in fluid samples from humans and animals, for example fluorescence or luminescence from Green fluorescent Protein (GFP) or luciferase, because these signals are quenched by components naturally present in these biological samples.

Colorimetric substrates of some split reporter proteins (beta-lactamase/nitrocefin or Centa) and beta-galactosidase (x-gal) are also difficult to quantify in a POC device (i.e., a point-of-care device) and don't provide good sensitivity or dynamic range. Some split enzymes only function as a selection marker and therefore require a cellular application, such as Trp1 wherein cells grow on a medium lacking tryptophan (i.e., a positive selection), or grow in the presence of antibiotics (beta-lactamase) lactamase (i.e., a negative selection).

Glucose detection is a quick and easy to read-out in POC devices, and has proven compatibility with live complex samples such as blood, serum, milk, and the like, without the requirements for additional handling and processing.

The compositions, biosensors, kits, and methods disclosed herein designed to provide an individual with an opportunity to perform all the steps of the method without the assistance of a health care professional. Accordingly, the individual can collect the sample themselves, manipulate components to allow contact of the sample with a solution comprising the reagents for a detection assay and then use a POC device such as a glucometer to show the results in as a digitized value or a quantitation value. Alternatively, other methods or reagents such as Benedict's reagent, may be used to detect glucose. The results generated with the assays disclosed herein, may be digitized for wireless transmission to smart phones or other such smart devices, and additionally, could be transmitted to a subject's health care professional.

This disclosure pertains to an antibody detection system that does not require the use of secondary antibodies or antibody binding proteins such as Protein A, Protein G, Protein L, or any hybrid or fusion of these proteins, except for production of the monovalent variant disclosed herein which relies on the incorporation of antibody-binding proteins. Neither does the present antibody detection system require additional conjugated enzymes. This disclosure also pertains to antibody detection systems that do not require any rinse steps, thereby providing a significant advantage in Point-of-Care methods.

Additionally, the production of glucose can be detected by the growth of microorganisms on a selected carbon source. This may be done in minimal media (MM) with a selected defined carbon source. In the case of trehalose as the substrate, this would require the use of trehalase-negative cells. This may be achieved by naturally trehalase-deficient organisms or by use of organisms in which one of the one or more the multiple genes coding for trehalases have been knocked-out (KO).

Disclosed herein is a TreA KO strain created and used to express all of the TreA constructs disclosed herein, in order to minimize or eliminate any background activity by native TreA that may be present in *E. coli*.

As an additional feature of the present disclosure, the gain of the method may be enhanced by combination with an additional enzyme such as glucose oxidase or glucose dehydrogenase, to convert the initial enzyme into another analyte that can be detected in a variety of ways.

This disclosure also relates to the fusion of one of the trehalase fragments functionalized with an antigen or a peptide or another molecule to glucose oxidase or glucose dehydrogenase. When this glucose oxidase fused to a trehalase fragment is complemented with the other trehalase fragments, antibodies, or any other complexing or immobilizing analytes, the hydrolysis activity of trehalase will be restored whereby the resulting glucose molecule may be taken up by the glucose oxidase domain. This may result in a faster assay because only a very localized concentration of glucose needs to be formed for the glucose oxidase to generate a signal that may be captured photospectrometrically or electrochemically with a glucometer, or alternatively, by capturing the electrons. Immobilization of the glucose oxidase/trehalase complex onto an electrode may provide a composition for sensitive and quick detection of the analyte. Alternatively, the fusion between GOX or GDH may established by intein protein ligation technology or other suitable biochemical ways.

Figure 5:
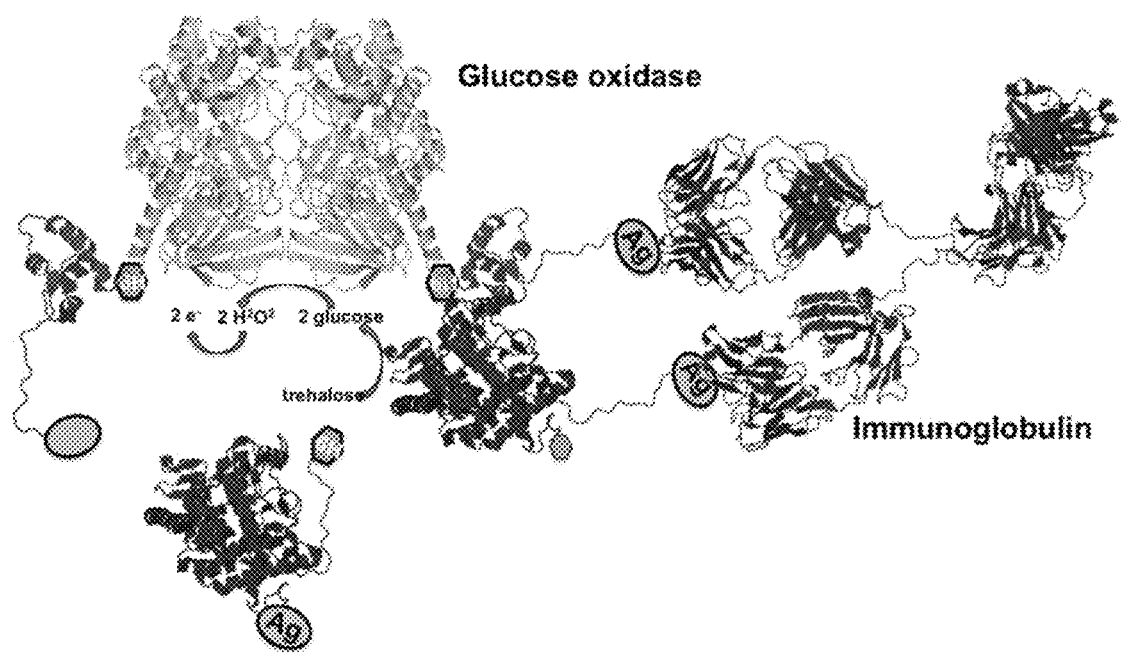
FIG. 5 is a schematic representation of an exemplary fusion of a glucose oxidase molecule with $TreA^N$ (SEQ ID NOs: 28, 79)

Important to note is the fact that glucose oxidase and glucose dehydrogenase typically form dimers, and therefore, a complex comprising two glucose oxidases, two trehalases and, for example, two IgG can be formed (FIG. 5).

The present disclosure also pertains to the discovery of the effect and impact of the locations of the antigens with regard to the N-terminal or C-terminal of the fragments. Antigens may be added in either of the four combinations whereby one combination leads to 2 N-terminal antigens, a second combination leads to 2 C-terminal antigens and the remaining two combinations each lead to a C- and N-terminal antigen. However, the binding of antigen specific antibodies or its capacity to restore the functionality of the trehalase, is variable among the different combinations. For small antigenic peptides, it might be favorable for recognition by corresponding antibodies to be fused at the same terminus on both fragments in order to have identical presentations and conformations.

Also for other applications, (poly)peptides may be fused to either terminus of the fragments to achieve complementation of the fragments in interactions with a selected analyte (for example, binding to a bacterial surface). In some applications, the fusion order is determined by the structure of the fusion partner. For example, prion proteins can only be fused at the N-terminus.

Due to the fact that trehalase is an enzyme, signal amplification may be achieved with methods and compositions according to this disclosure, with more and more signal being produced over time with every specific antibody activating a trehalase protein. Periplasmic trehalase has a Vmax of 66 μmol/min/mg, pH optimum of 5-6. For trehalase, this amplification is intensified because every catalytic reaction generates not one, but two glucose molecules. Trehalases with higher activity from different sources could replace the periplasmic trehalase of *E. coli*.

The present disclosure also pertains to the linking of non-peptide molecules to the trehalase fragments with covalent or non-covalent bonds. The covalent bonds may be achieved by protein chemistry as explained below. In some cases, this might require an insertion of specific amino acids into the sequence, especially at the termini, or it might require the fusion of a peptide that can be modified by protein chemistry to bind to the desired molecules. Examples of such molecules are lipids, carbohydrates, glycolipids, or combinations of these. These molecules might be antigens, epitopes, or enable dimerization in the presence of a specific analyte, or immobilize the fragments to a surface.

Figure 4:
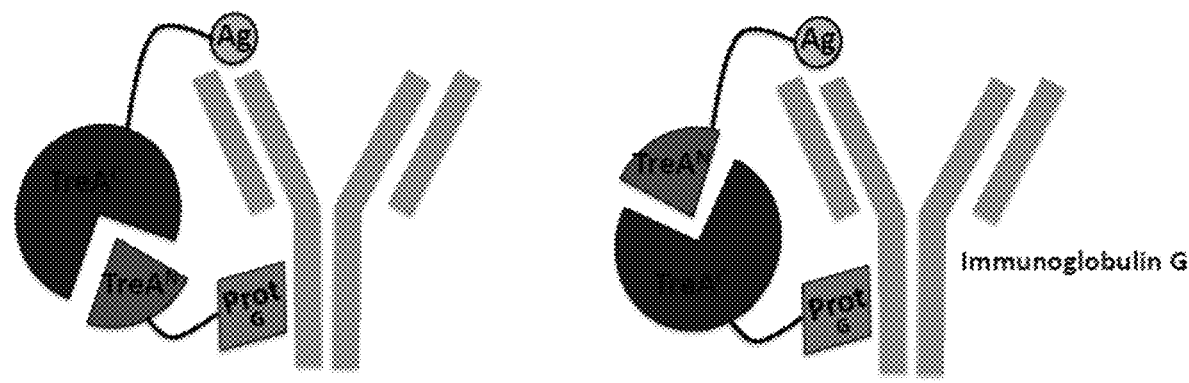
FIG. 4 is a schematic representation of a split TreA monovalent antibody sensor (SEQ ID NOs: 25, 26, 28, 29) according to one embodiment of the present disclosure.

The present disclosure also pertains to compositions, biosensors, kits, and methods wherein one trehalase fragment is fused to an immunoglobulin heavy chain binding molecule (e.g. protein A or G or A/G or L) and the other fragment is fused to the antigen (FIG. 4). In this case, the bivalent nature of immunoglobulins is not utilized. However, complementation on two sides of the immunoglobulin is possible.

Previously several split proteins and enzymes have been produced. The specific properties of the split enzymes often limit their use to specific applications. Split trehalase offers advantages to a variety of applications not yet found in the existing list of split proteins or not yet found in this combination.

TreA does not require cofactors, including metals, or specific cations or anions.

TreA has high activity at a neutral pH, the pH of most relevant biological samples for the detection of antibodies, although its optimum is around pH 5-6.

TreA is highly active at room temperature, i.e. 20-25° C.

TreA's product, glucose, can be measured directly in complex biological samples such as blood without any additional sample preparation, as demonstrated by the applications of the glucometers.

Split TreA has the advantage of not resulting in self-complementation between the fragments without a linking molecule or bond. Self-complementation as seen in split beta-galactosidase (lacZ) largely eliminates the possibility of conditional complementation.

Furthermore, split trehalase fragments do not have any residual activity on their own or in combination without a specific complexing analyte. This is in contrast to split GFP or the beta-galactosidase complementation reaction whereby relatively low concentrations of both fragments will lead to fluorescence or enzymatic activity, respectively. This makes for a method whereby the background signal is minimal or non-existent.

The existence as dimers of some split proteins or candidate split proteins can also be an important consideration or sometimes disadvantage (e.g. PCNA).

A more practical advantage of using trehalase is that the trehalase molecular structure is relatively easy to fold and refold. Furthermore, it appears that the split fragments fold correctly independently of each other. In other proteins, refolding only happens at the complementation stage (for example, GFP, split inteins, DnaE), likely putting restrictions on the physicochemical properties of the reaction solution.

TreA has absolute substrate specificity for trehalose.

Positive signal: Split trehalase provides one of the only antibody detection systems where a positive signal is created, in contrast to several other methods where a reduction of enzymatic activity indicates the presence of specific antibodies. In said previous methods, steric hindrance or inhibition by conformational changes by binding of antibodies to antigens fused to the enzyme are achieved leading to reductions in activity. Methods that are based on decreasing of activity are typically less sensitive.

It is known that trehalase activity is non-existent or extremely low in most biological samples from vertebrates. Only two trehalose hydrolyzing activities are present in vertebrates with the exception of fecal matter that might have trehalose originating from fecal-associated microbiota. These activities in humans display precise locations, often acting as intrinsic glycoproteins of the microvillus intestinal mucosa and renal brush-border membranes linked by a GPI-anchor, as shown by their selective solubilization by phospholipase C. This dual enzymatic activity points to a strict control and rapid degradation of the trehalose ingested in the diet, preventing it from being accumulated even in transitory or low levels. Intestinal trehalase is in all probability, the sole enzyme responsible for the hydrolysis of ingested trehalose (mushrooms and honey among other foods, are rich in the non-reducing disaccharide). Notably, intestinal trehalase is never released into the bloodstream and is tightly attached to the external surface of the microvilli of enterocytes, resisting all proteolytic treatments. As a result, if the split trehalase methods are applied in biological samples derived from animals, then all the measurable trehalase activity results from the presence of the analyte and corresponding activation of the biosensor. This freedom or low level of trehalase activity in biological samples is in contrast with the high activity of other potential reporter enzymes such as catalases of peroxidases.

Elimination of background glucose: Another advantage is that all free glucose present in biological samples can be quickly, efficiently and completely be eliminated before the de novo production of glucose is initiated. This elimination of glucose can be done by chemical or enzymatic methods, including the use of metaperiodate and glucose oxidase or glucose dehydrogenase. hi other cases de novo generated glucose will be distinguished from background glucose by measuring differential glucose concentrations or by measuring rate of increase of the glucose concentration.

Also of importance is the naturally low concentration of glucose in milk including breast milk (for example, about 0.331 mM). In some applications of the compositions and methods disclosed herein, it may be possible to disregard this initial low concentration glucose and measure de novo produced glucose by the specific antibodies or analytes being detected. In other applications, it may be necessary to eliminate the initial levels of glucose present in samples before use of the compositions and methods disclosed herein.

Unless otherwise defined, all technical and scientific terms used herein have the same meaning as commonly understood by one of ordinary skill in the art to which this invention belongs. In order that the invention herein described may be fully understood, the following terms and definitions are provided herein.

The word "comprise" or variations such as "comprises" or "comprising" will be understood to imply the inclusion of a stated integer or groups of integers but not the exclusion of any other integer or group of integers.

The term "nucleic acid" used herein refers to a polymeric compound comprised of covalently linked subunits called nucleotides. Nucleic acid includes polyribonucleic acid (RNA) and polydeoxyribonucleic acid (DNA), both of which may be single-stranded or double-stranded. DNA includes cDNA, genomic DNA, synthetic DNA, and semi-synthetic DNA.

The term "gene" used herein refers to an assembly of nucleotides that encode a polypeptide, and includes cDNA and genomic DNA nucleic acids.

The term "recombinant DNA molecule" used herein refers to a DNA molecule that has undergone a molecular biological manipulation.

The term "vector" used herein refers to any means for the transfer of a nucleic acid into a host cell. A vector may be a replicon to which another DNA segment may be attached so as to bring about the replication of the attached segment. A "replicon" is any genetic element (e.g., plasmid, phage, cosmid, chromosome, virus) that functions as an autonomous unit of DNA replication in vivo, i.e., capable of replication under its own control. The term "vector" includes plasmids, liposomes, electrically charged lipids (cytofectins), DNA-protein complexes, and biopolymers. In addition to a nucleic acid, a vector may also contain one or more regulatory regions, and/or selectable markers useful in selecting, measuring, and monitoring nucleic acid transfer results (transfer to which tissues, duration of expression, etc.).

The term "cloning vector" used herein refers to a replicon, such as plasmid, phage or cosmid, to which another DNA segment may be attached so as to bring about the replication of the attached segment. Cloning vectors may be capable of replication in one cell type, and expression in another ("shuttle vector").

A cell has been "transfected" by exogenous or heterologous DNA when such DNA has been introduced inside the cell. A cell has been "transformed" by exogenous or heterologous DNA when the transfected DNA effects a phenotypic change. The transforming DNA can be integrated (covalently linked) into chromosomal DNA making up the genome of the cell.

The term "nucleic acid molecule" used herein refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules"), or any phosphoester anologs thereof, such as phosphorothioates and thioesters, in either single stranded form, or a double-stranded helix. Double stranded DNA-DNA, DNA-RNA and RNA-RNA helices are possible. The term nucleic acid molecule, and in particular DNA or RNA molecule, refers only to the primary and secondary structure of the molecule, and does not limit it to any particular tertiary forms.

Modification of a genetic and/or chemical nature is understood to mean any mutation, substitution, deletion, addition and/or modification of one or more residues. Such derivatives may be generated for various purposes, such as in particular that of enhancing its production levels, that of increasing and/or modifying its activity, or that of conferring new pharmacokinetic and/or biological properties on it. Among the derivatives resulting from an addition, there may be mentioned, for example, the chimeric nucleic acid sequences comprising an additional heterologous part linked to one end, for example of the hybrid construct type consisting of a cDNA with which one or more introns would be associated.

The term "promoter sequence" used herein refers to a DNA regulatory region capable of binding RNA polymerase in a cell and initiating transcription of a downstream (3' direction) coding sequence. For purposes of defining the present invention, the promoter sequence is fuseded at its 3' terminus by the transcription initiation site and extends upstream (5' direction) to include the minimum number of bases or elements necessary to initiate transcription at levels detectable above background.

A coding sequence is "under the control" of transcriptional and translational control sequences in a cell when RNA polymerase transcribes the coding sequence into mRNA, which is then trans-RNA spliced (if the coding sequence contains introns) and translated into the protein encoded by the coding sequence.

The term "homologous" in all its grammatical forms and spelling variations refers to the relationship between proteins that possess a "common evolutionary origin," including homologous proteins from different species. Such proteins (and their encoding genes) have sequence homology, as reflected by their high degree of sequence similarity. This homology is greater than about 75%, greater than about 80%, greater than about 85%. In some cases the homology will be greater than about 90% to 95% or 98%.

"Amino acid sequence homology" is understood to include both amino acid sequence identity and similarity. Homologous sequences share identical and/or similar amino acid residues, where similar residues are conservative substitutions for, or "allowed point mutations" of, corresponding amino acid residues in an aligned reference sequence. Thus, a candidate polypeptide sequence that shares 70% amino acid homology with a reference sequence is one in which any 70% of the aligned residues are either identical to, or are conservative substitutions of, the corresponding residues in a reference sequence.

The term "polypeptide" used herein refers to a polymeric compound comprised of covalently linked amino acid residues. Amino acids are classified into seven groups on the basis of the side chain R: (1) aliphatic side chains, (2) side chains containing a hydroxylic (OH) group, (3) side chains containing sulfur atoms, (4) side chains containing an acidic or amide group, (5) side chains containing a basic group, (6) side chains containing an aromatic ring, and (7) proline, an imino acid in which the side chain is fused to the amino group. A polypeptide of the invention preferably comprises at least about 14 amino acids.

The term "protein" used herein refers to a polypeptide which plays a structural or functional role in a living cell.

The term "corresponding to" is used herein to refer to similar or homologous sequences, whether the exact position is identical or different from the molecule to which the similarity or homology is measured. A nucleic acid or amino acid sequence alignment may include spaces. Thus, the term "corresponding to" refers to the sequence similarity, and not the numbering of the amino acid residues or nucleotide bases.

The term "derivative" used herein refers to a product comprising, for example, modifications at the level of the primary structure, such as deletions of one or more residues, substitutions of one or more residues, and/or modifications at the level of one or more residues. The number of residues affected by the modifications may be, for example, from 1, 2 or 3 to 10, 20, or 30 residues. The term derivative also comprises the molecules comprising additional internal or terminal parts, of a peptide nature or otherwise. They may be in particular active parts, markers, amino acids, such as methionine at position −1. The term derivative also comprises the molecules comprising modifications at the level of the tertiary structure (N-terminal end, and the like). The term derivative also comprises sequences homologous to the sequence considered, derived from other cellular sources, and in particular from cells of human origin, or from other organisms, and possessing activity of the same type or of substantially similar type. Such homologous sequences may be obtained by hybridization experiments. The hybridizations may be performed based on nucleic acid libraries, using, as probe, the native sequence or a fragment thereof, under conventional stringency conditions or preferably under high stringency conditions.

The term "analyte" as used herein means any one of a nucleic acid, a ribonucleic add, a polypeptide, a carbohydrate, a protein, a peptide, an amino acid, a hormone, a steroid, a vitamin, an ion, a metabolite, a chemical, an element, a derivative, an analogue, a polysaccharide, a lipid, a fatty acid, a lipopolysaccharide, a glycoprotein, a lipoprotein, a nucleoprotein, an oligonucleotide, an antibody, an immunoglobulin, a coagulation factor, a peptide hormone, a protein hormone, a non-peptide hormone, an interleukin, an interferon, a cytokine, a chemokine, a bacterial cell, an eukaryotic cell, a plant cell, a fungal cell, a protozoan cell, a cell-surface molecule, a microorganism, a small organic molecule, a virion, a bacterium, a toxin, a drug, a cell membrane, a membrane fraction, a protein complex, an antigen, a hapten, a receptor, a macromolecule, or a molecular complex comprising two or more of any of the aforementioned items.

The term "biological sample" as used herein means a sample collected from a mammalian subject and may include any one of blood, serum, milk, sweat, semen, ejaculate, mucus, tears, saliva, plasma, secretions of the genito-urinary tract, lymph fluid, urine, white blood cells, pleural fluid, ascites, sputum, peritoneal fluid, cerebrospinal fluid, pleural fluid, pericardial fluid, amniotic fluid, synovial fluid, interstitial fluid, and any combinations or mixtures of the aforementioned items. It is to be noted that the term "biofluid" may be used in place of the term "biological sample"

The term "complexing domain" used herein refers to a conserved stable part of a given protein sequence and structure that can evolve, function, and exist independently of the rest of the protein chain, and in particlar, to a selected protein sequence to which a fragment of a split enzyme can be fused. Examples of suitable "complexing domains" for bonding with split enzyme fragments disclosed herein include proteins, enzymes, peptide antigens, lipoprotein antigens, glycoprotein antigens, small molecule antigens, heterodimerizing proteins, homodimerizing proteins, antibody-binding proteins, aggregating proteins, antibodies, antibody derivatives, antibody mimics, antibody variants, aptamers, DNA oligomers, PNA oligomers, and the like.

The phrases "close enough proximity" and "close proximity" as used herein are descriptive of conditions wherein two fragments from a split enzyme that are separately fused to one or more complexing domains, are brought together in a suspension or solution or fluid mixture so that interactions may occur between the two fragments (also known as "complementation") such that split enzyme functionality is restored. These phrases may also be used to refer to two fragments from a split enzyme wherein each fragment is fused to a complexing domain, and one of the fragment-complexing domain structures physically immobilized is in close enough proximity to an oxidoreductase (glucose oxidase or glucose reductase) such that chemical transfer may occur between the the complemented enzyme and the oxidoreductase thereby enabling signal transduction. These phrases may also be used to refer to one of the fragments from a split enzyme that is fused to a complexing domain and an oxidoreductase, whereby the oxidoreductase is fused to a surface or an electrode, and there is electron transfer to this surface or electrode.

The term "biosensor" as used herein refers to a device or apparatus that my be used to detect an analyte in biological sample wherein the biosensor is provided with both fragments of a split enzyme wherein each fragment is separately fused to a complexing domain. When contacted by the biological sample, the analyte will be captured by binding to either immobilized or non-immobilized enzyme fragments thereby restoring enzyme function which may then be detected, for example, with an electrical assay that measures electron transfer. Alternatively, a suitable enzyme substrate may be added to the biosensor after it has been contacted by the biological sample, to detect and measure the production of one or more breakdown products by the restored enzyme activity, wherein the detection of the breakdown product may be one of a colorimetric assay, a fluorometric assay, and a luminescent assay.

According to one aspect, a suitable biosensor may comprise a paper strip or a plastic strip or polymeric strip or other like strip onto which have been immobilized fragments from a selected split enzyme wherein the fragments have been fused to one or more complexing domains. Such biosensors may be referred to herein as a "test strip" and/or a "biosensor test strip". In one example, such a biosensor strip may be contacted with a biological sample after which, a suitable substrate may contacted with biostrip resulting in the formation of one or more substrate breakdown products that may be detected with a colorimetric assay, a fluorometric assay, or a luminescent assay. In another example, the biosensor test strip may additionally comprise an electrode exteding along one surface of the strip to which, fragments from a selected split enzyme fused to one or more complexing domains, have been immobolized. Contacting such a biosensor with biological sample will result in electron transfer between the enzyme fragments that is measurable with a suitable instrument.

According to another aspect, a suitable biosensor is a composition comprising two or more components wherein a first component is fluid mixture of one of the two types of fragments from a split enzyme, fused to a complexing domain, and the second component is a fluid mixture of other of the two types of fragments from a split enzyme, fused to a complexing domain. The two components are mixed together with a biological sample after which, electron transfer within the mixture may be measured with a suitable instrument. Alternatively, a suitable substrate may be added to the mixture, and after a selected period of time, the presence and quantity of substrate breakdown products may be measured with a colorimetric assay or a fluorometric assay or and a luminescent assay.

According to one aspect, kits according to the present disclosure may comprise, for example, one or more biosensor test strips. Such kits may additionally comprise a selected enzyme substrate. Such kits may additionally comprise one or more enzyme assay reagents for addition individually or in mixtures, to the test strips for use in certain types of colorimetric assays known to those skilled in these arts. Optionally, the kits may comprise one or more biosensor test strips that have an electrode extending along one or more surfaces of the test strip.

According to another aspect, kits according to the present disclosure may comprise one or more biosensors having at least two components wherein the first components is a fluid mixture of one of the two types of fragments from a split enzyme, fused to a complexing domain, and the second component is a fluid mixture of other of the two types of fragments from a split enzyme, fused to a complexing domain. The two components may be mixed together with a biological sample after which, electron transfer within the mixture may be measured with a suitable instrument. Alternatively, a suitable enzyme substrate may be added to the mixture of components and biological sample, and after a selected period of time, the presence and quantity of substrate breakdown products may be measured with a colorimetric assay or a fluorometric assay or and a luminescent assay. It is an option for such kits to additionally comprise a component that contains the selected enzyme substrate. It is also an option for such kits to additionally comprise one or more enzyme assay reagents mixing with the mixture of components and biological sample and/or with the mixture of components, biological sample, and selected enzym substrate. All of the above mixtures of the components with the biological sample can be assayed directly in one of a colorimetric assay, a fluorometric assay, and a luminescent assay. Alternatively, any of the above mixtures of the components with the biological sample can be transferred to a test strip for further analysis.

EXAMPLES

Example 1

1.1 Materials

Monoclonal antibodies (anti-HIS-tag mAb and anti-HA-tag tag mAb; 1 mg/ml) were purchased from MBL Corporation, whereas rabbit polyclonal anti-HIV p24 polyclonal serum was purchased from Abcam (ab63913), and bovine IgG (12.8 mg/ml) was purchased from Sigma-Aldrich.

1.2 Bacterial Strains

All plasmid manipulations and amplifications were performed in *E. coli* strain DH5α (New England Biolabs) whereas protein expression was done in a TreA knock-out of *E. coli* strain BL-21 (DE3) (NEB), named BL-21ΔTreA, constructed by targeted chromosomal gene knockout system using red recombinase as taught by Murphy (2011, *Targeted chromosomal gene knockout using PCR fragments*. Methods Mol. Biol. 765:27-42). The entire TreA gene was replaced with Tn5 (aph) type II (kanamycin resistance) using the following primers: (i) forward: 5'-TATGGACAGC-AAGCGAACCG-3' (SEQ ID NO: 1) and (ii) reverse: 5'-TCAGAAGAACTCGTCAAGAAG-3' (SEQ ID NO: 2). *S. aureus* and *S. uberis* isolates were provided by the Canadian Bovine Mastitis Milk Quality Research Network (CBMQRN). All strains were grown in LB broth at 37° C.

1.3 Plasmids

The gene for periplasmic Trehalase (TreA) was amplified from *E. coli* strain BL-21. During PCR amplification, the secretion peptide was replaced with a HIS-tag, and NcoI and AvrII restriction sites were introduced at 5' and 3' ends of the gene, respectively, to clone the amplified fragment in pET-Duet vector (Novagen). Primer sequences used for generation of all constructs are shown in Table 1.

TABLE 1

Primers used in this study

| Construct | Primer | Sequence |
| --- | --- | --- |
| pETDuet-HIS-TreA | HIS-TreAFatg-F | TATACCATGGCACACCATCACCATCACCATGAAGAAACACCG GTAACACCACA (SEQ ID NO: 3) |
| | TreARtaa-R | TATACCTAGGTTAAGGTGTGGGTTGTGCCTCT (SEQ ID NO: 4) |
| pETDuet-HIS-N-ter | HIS-TreAFatg-F | TATACCATGGCACACCATCACCATCACCATGAAGAAACACCG GTAACACCACA (SEQ ID NO: 3) |
| | TreA-BamHI-N-R | TAATTCCTAGGTCAGGATCCCGGAACATATTTCTCGCCTTC (SEQ ID NO: 5) |
| pETDuet-N-ter-HIS | TreAFatg-F | TATACCATGGAAGAAACACCGGTAACACCA (SEQ ID NO: 6) |
| | TreA-TruncN-R | TAATTCCTAGGTCAATGGTGATGGTGATGGTGCGGAACATAT TTCTCGCCTTC (SEQ ID NO: 7) |
| pETDuet-HIS-C-ter | TreA-TruncC-F | TAATTCCATGGCACACCATCACCATCACCATAATTTCACCCTG CCGAAAG (SEQ ID NO: 8) |
| | TreARtaa-R | TATACCTAGGTTAAGGTGTGGGTTGTGCCTCT (SEQ ID NO: 4) |
| pETDuet-C-ter-HIS | TreA-SalI-C-F | TAATTCCATGGCAGTCGACAATTTCACCCTGCCGAAAG (SEQ ID NO: 9) |
| | TreA-HIS-R | TATACCTAGGTTAATGGTGATGGTGATGGTGAGGTGTGGGT TGTGCCTCT (SEQ ID NO: 10) |
| pETDuet-HA-N-ter | HA-TreA-N-F | TATACCATGGCATACCCATACGATGTTCCAGATTACGCTGTCG ACGAAGAAACACCGGTAACA (SEQ ID NO: 11) |
| | TreA-TruncN-R | TAATTCCTAGGTCAATGGTGATGGTGATGGTGCGGAACATAT TTCTCGCCTTC (SEQ ID NO: 7) |
| pETDuet-N-ter-HA | HIS-TreAFatg-F | TATACCATGGCACACCATCACCATCACCATGAAGAAACACCG GTAACACCACA (SEQ ID NO: 3) |
| | TreA-N-HA-R | TATACCTAGGTCAAGCGTAATCTGGAACATCGTATGGGTAGG ATCCCGGAACATATTTCTCGCC (SEQ ID NO: 12) |
| pETDuet-HA-C-ter | HA-TreA-C-F | TATACCATGGCATACCCATACGATGTTCCAGATTACGCTGTCG ACAATTTCACCCTGCCGAAA (SEQ ID NO: 13) |
| | TreA-HIS-R | TATACCTAGGTTAATGGTGATGGTGATGGTGAGGTGTGGGT TGTGCCTCT (SEQ ID NO: 10) |

TABLE 1-continued

Primers used in this study

| Construct | Primer | Sequence |
|---|---|---|
| pETDuet-C-ter-HA | TreA-TruncC-F | TAATTCCATGGCACACCATCACCATCACCATAATTTCACCCTG CCGAAAG (SEQ ID NO: 8) |
| | TreA-C-HA-R | TATACCTAGGTCAAGCGTAATCTGGAACATCGTATGGGTAGG ATCCAGGTGTGGGTTGTGCCTC (SEQ ID NO: 12) |

Coding sequences for HIV p24 (AC: KJ925006.1) were synthetized using GeneArt (Thermo Fisher Scientific). The coding sequences for Protein G (TYKLI LNGKTLKGET-TTEAVDAATAEKVFKQYANDNGVDGEVVTYDAAT-KTFT V TE; SEQ ID NO: 14), Protein A (TADNKFNKE-QQNAFYEILHLPNLNEEQRN GFIQSLKDDPSQSANL-LAEAKKLNDAQAPKA) (SEQ ID NO:15) and Protein L (AMEEVTIKANLIFANGSTQTAEFKGTFEKATSEAYA-YADTLKKDNGEVVTVDV ADKGYTLNIKFAG) (SEQ ID NO:16) were incorporated as oligonucleotides linkers. All coding sequences introduced at the N-terminus of fragments were cloned between NcoI and SalI restriction sites, whereas coding sequences introduced at C-terminus were cloned between BamHI and AvrII.

It is to be noted that the amino acid sequence of trehalase (TreA) with a HIS-tag at the N-terminus is shown as SEQ ID NO 17. Variants with the HIS-tag at the C-terminus or at both termini, code for SEQ ID NOs: 18 and 19 respectively. TreA N (66 aa long) and C terminal (456 aa long) fragments tagged with the HIS or HA tag at the N- or C-terminals, were generated using the same strategy.

1.4 Protein Expression, HIS-Tag Purification and Buffer Exchange

Proteins were expressed in BL-21ΔTreA by induction with 0.5 mM of isopropyl-β-D-thiogalactoside (IPTG) (UBP Bio) for 3 h at 37° C. Bacterial lysates were prepared by harvesting 10 ml of induced bacterial colonies at 3,000×g at 4° C. for 10 min. Pellets were washed with PBS, re-suspended in 800 µl of 6M guanidinium buffer (6M Guanidinium-HCl; 25 mM Imidazole; PBS 1×) and sonicated using five 5-s bursts (total of 30 s). Protein fragments were purified on Ni-NTA columns (Fisher Thermo Scientific) according to the manufacturer's instructions. Briefly, proteins were fused on columns of equilibrated Ni-NTA resin in the presence of 6 M guanidinium buffer (6 M guanidinium-HCl; 25 mM imidazole; PBS 1×), refolded on column during washing steps with wash buffer (25 mM imidazole; PBS 1×) containing gradually decreasing guanidinium-HCl concentrations (6, 4, 3, 2, and 0 M, respectively) and eluted in elution buffer (250 mM imidazole; PBS 1×).

Subsequently, samples were dialyzed against 1 L of sodium maleate buffer (50 mM, pH 6) or PBS (pH 7) with SNAKESKIN® dialysis tubing (SNAKESKIN is a registered trademark of Pierce Chemical Company Corp., Rockford, Ill., USA) at 7 kDa MWKO for 24 h at 25° C. to remove imidazole.

Bacterial lysates and purified proteins were separated on 10% SDS-page (Bis-Tris Acrylamide gel) and stained with Bio-Safe Coomassie blue G-250 (Bio-Rad).

1.5 Complementation Assays

Protein concentration was determined with a QUBIT® protein assay kit (QUBIT is a registered trademark of Molecular Probes Inc., Eugene, Oreg., USA). Antibody complementation assays and Ni-NTA complementation assays were performed in sodium maleate buffer (50 mM, pH 6). Antibodies were detected in 1:1 molar ratios with reagents.

All assays were performed with 5 µg of the TreAc fragment, whereas the concentration of TreA$^N$ fragment was adjusted for every assay (to maintain a 1 to 1 molar ratio). Assays were performed in 60 µl of final volume. Assays were incubated with 0.25 M solution of trehalose (Sigma) at 25° C. for at pH 6 for 1 h or O/N at pH 7, as specified for each experiment.

Glucose concentrations were measured with ACCU-CHEK AVIVA® glucometer strips (ACCU-CHEK AVIVA is a registered trademark of Roche Diagnostics GmbH, Mannheim, Fed. Rep. Germany), a Benedict's reagent (Sigma) assay, or with a colorimetric enzymatic assay using glucose oxidase (0.26 U/mL; Sigma), horseradish peroxidase (0.2 U/mL; Sigma), and o-Dianisidine (0.5 mM; Sigma) in sodium maleate buffer (50 mM, pH 6). Absorbance (OD) was measured after 30 min (Ni-NTA, anti-HIS, anti-HA and Intein assays), after 1 h for Anti-HIV antibody assay, or 10 min (all other assays) of incubation at 450 nm of wavelength using an ENSPIRE® spectrophotometer (ENSPIRE is a registered trademark of PerkinElmer Singapore PTE Ltd., Singapore, Singapore) and Benedict's reagent assay (Sigma).

1.6 Lyophilisation of Proteins

Proteins were mixed in 1 to 1 weight ratio with BSA and, frozen at −80° C. for 30 min and then lyophilized O/N at −85° C. and 12 mT. Proteins were re-suspended in acidified sample (blood or milk). Samples were acidified by addition of 10 mg of citric acid, 61 mg of sodium citrate and 0.189 g of trehalose.

1.7 Biosensor Design

Figure 7:
FIG. 7 is a micrograph showing glucose production, using Benedict's reagent, by $TreA^C$ and $TreA^N$ fragments that were purified separately and incubated with the substrate/ trehalose separately and together (blue: no detectable glucose levels; orange: detectable glucose levels) (SEQ ID NOs: 20, 21, 22, 23)
Figure 7:
Figure 7:
Figure 7:
Figure 7:
Figure 7:
Figure 7:
Figure 7:
Figure 7:

First, TreA (lacking a leader sequence) was split into two fragments: (i) 66 aa N-terminal (TreA$^N$), and (ii) 456 aa C-terminal (TreA$^C$). The fragmentation point of TreA was placed into a 12 aa long region that was unresolved in a published crystal structure (PDB: 2JF4). TreA$^N$ and TreA$^C$ were expressed and purified separately. Neither fragment had any detectable enzymatic activity during 24 h of incubation with substrate, nor was there evidence of self-assembly (resulting in trehalase activity) when incubated together (FIG. 7).

Conditional reassembly of fragments was tested by fusing HIS-tags to TreA$^N$ and TreA$^C$ (SEQ ID NOs: 20, 21, 22, 23) and immobilizating them separately or together on Ni-NTA resin columns (FIG. 8). Co-immobilization of fragments on resin beads was sufficient to induce complementation, regardless of the N or C terminal position of the HIS-tag on either fragment (FIGS. 9A, 9B, 9C). Trehalose was only hydrolysed when TreA$^N$ and TreA$^C$ fragments were fused together on a column, whereas no glucose was detected when two fragments were separately fused on a column. Elution of co-immobilized TreA fragments from the column abolished trehalase activity in the elution, confirming transient complementation.

In accordance with known optimal pH of TreA, the Ni-NTA resin complementation assay reacted faster at pH 6 then at pH 7, producing comparable amounts of glucose (output signal) in 1 h at pH 6 and 18 h at pH 7 (FIG. 9A). Therefore, analyte detection assays were performed at pH 6 (unless the sensor that was incorporated into a detection assay required a neutral pH for proper function).

1.8 Antibody Detection

Antibody-dependent complementation of split TreA was demonstrated with anti-HIS and anti-HA monoclonal antibodies and anti-HIV (anti-p24) polyclonal serum as illustrated in FIG. 10.

Incubation of HA-tagged TreA$^N$ and TreA$^C$ fragments (SEQ ID NOs: 24, 25, 26, 27) with anti-HA mAb or HIS-tagged TreA$^N$ and TreA$^C$ fragments (SEQ ID NO and SEQ ID NOs: 21, 22, 23, 24) with anti-HIS mAb induced complementation and subsequent trehalase activity, measured as glucose production (FIGS. 11A, 11B). The location of the HIS-tag antigen on either N or C-terminus only had minor impact on trehalase activity.

Figure 13A:
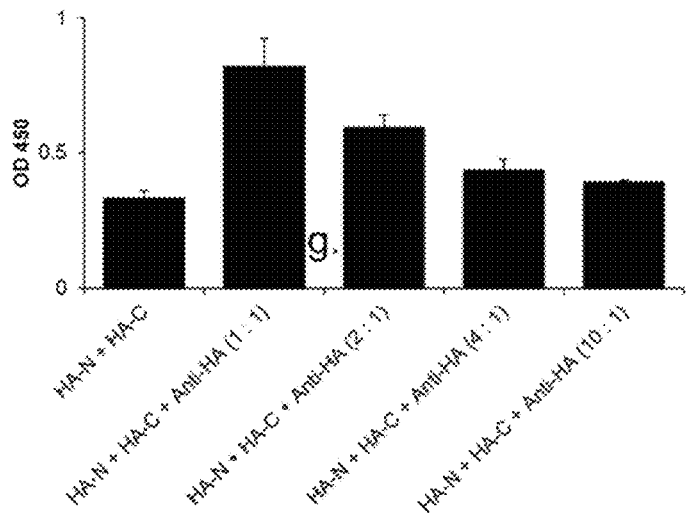
Figure 13B:
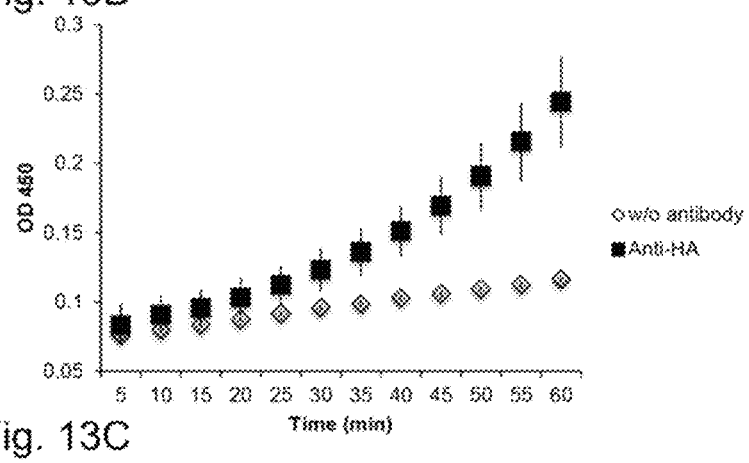

Glucose production after complementation of TreA$^N$ and TreA$^C$ fragments carrying the HA-tag (SEQ ID NOs: 25, 26, 27, 28) with anti-HA mAb was measured in comparison by GOx/HRP (3EA assay) or Benedict's reagent or glucometer strips (FIG. 12B). The time response of the anti-HA specific TreA detection assay was followed for 1 h. The assay was incubated with or without Anti-HA, and glucose concentrations were measured every 5 min and the increase of glucose concentration was detected after 25 min (FIG. 13B).

Next, experimental sensitivity of antibody-mediated complementation was examined. Complementation of HA tagged TreA fragments was induced with decreasing concentrations of anti-HA mAb. Output glucose signal decreased proportionally with the analyte, with complementation detected even when the concentration of anti-HA was decreased 5-fold (FIG. 13A).

Figure 14:
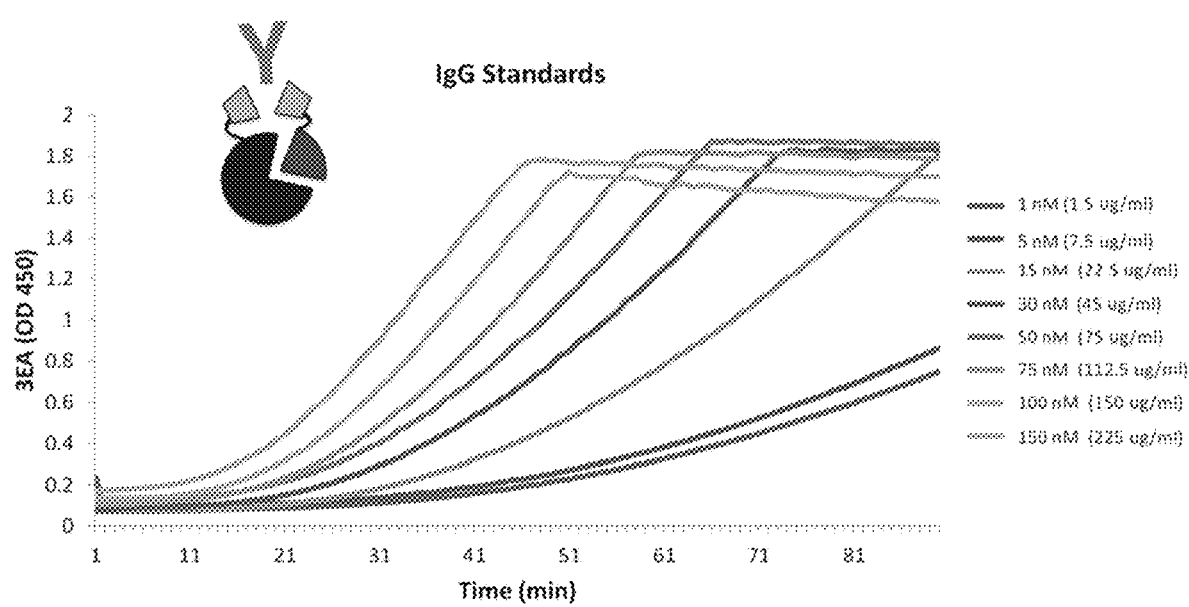

Experimental sensitivity was also demonstrated in an experiment where decreasing amounts of total bovine immunoglobulin G was detected with the TreA fragments fused to protein G (SEQ ID NOs: 28, 29). Colorimetric signals as generated by the GOx, HRP and O-dianisidine reagents as measures of glucose, were proportional with the concentrations of IgG in the samples (FIG. 14).

Figure 13C:
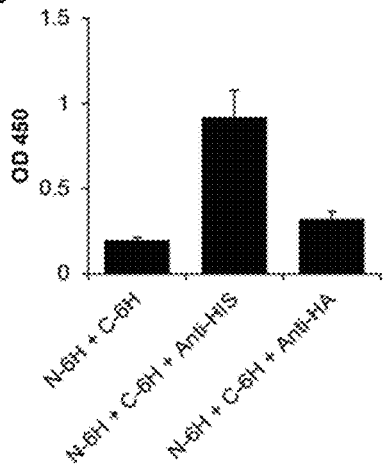

Specificity of antibody-mediated complementation was tested by incubating HIS-tagged fusions of TreA$^N$ and TreA$^C$ with non-cognate anti-HA mAbs next to cognate anti-HIS mAbs. Anti-HA mAb were unable to complement HIS-tagged TreA fragments, whereas anti-HIS mAb resulted in glucose production (FIG. 13C).

A complete antigenic protein, non-assembling mutant of HIV capsid protein p24, was fused to both TreA$^N$ and TreA$^C$ (SEQ ID NOs: 30, 31) to investigate complementation by antibodies in a non-purified rabbit polyclonal hyper-immune antiserum. Increased glucose concentrations were detected only in the presence of anti-p24 serum (FIG. 12A).

Figure 15:
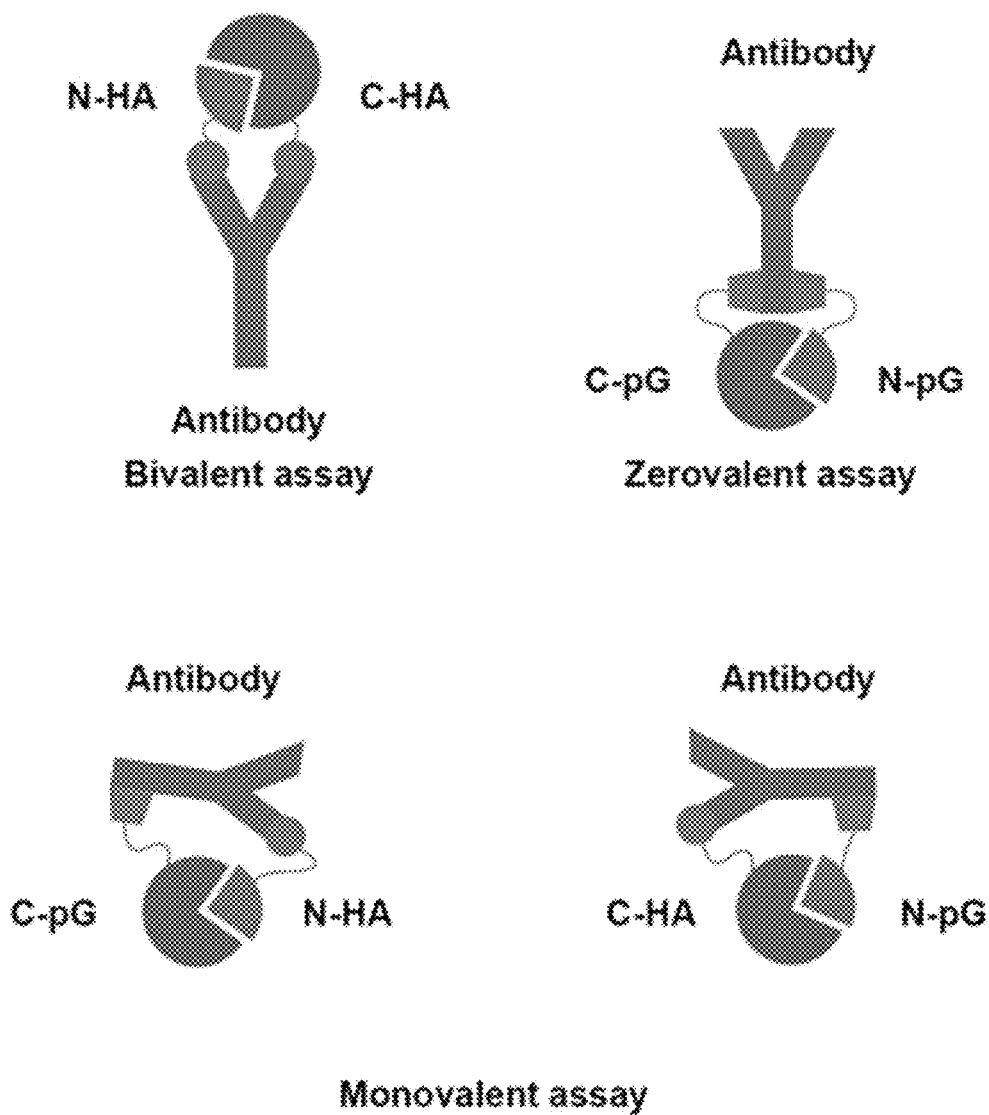
Figure 16A:
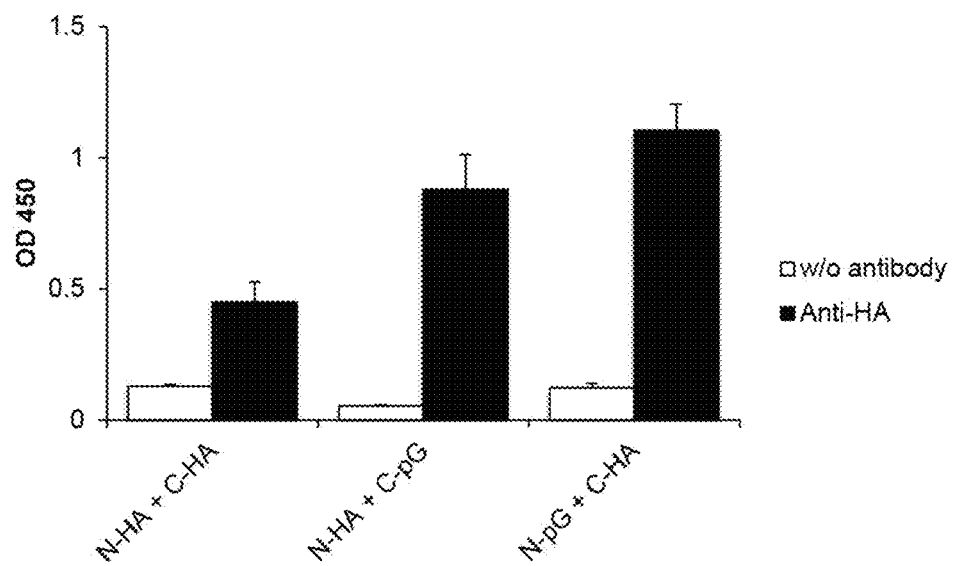
Figure 16B:
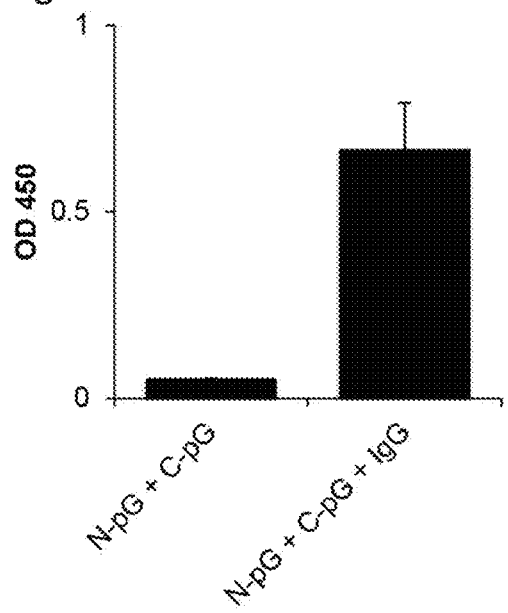

1.9 Detection of Antibodies through Interactions with their Variable and Constant Regions Fusions of TreA were engineered to recognise and detect various regions of antibodies (FIG. 15). Protein G (pG), a virulence factor expressed in streptococcal bacteria that binds to constant regions (Fc) of IgGs, was introduced as a sensor into TreA fusions. Combinations of TreA fragment fusions carrying protein G and HA tag (monovalent assay), Protein G only (zerovalent assay) or HA tags only (bivalent assay) were used to detect anti-HA mAb in antigen-specific or antigen non-specific manners (FIG. 16A). Fusions of TreA carrying only protein G were inefficient in detecting anti-HA mAb raised in mouse cells, although when bovine IgG were used as an analyte, dimerization was more efficient (FIG. 16B), indicating a species difference in capacity of IgG to bind two molecules of protein G.

Figure 17A:
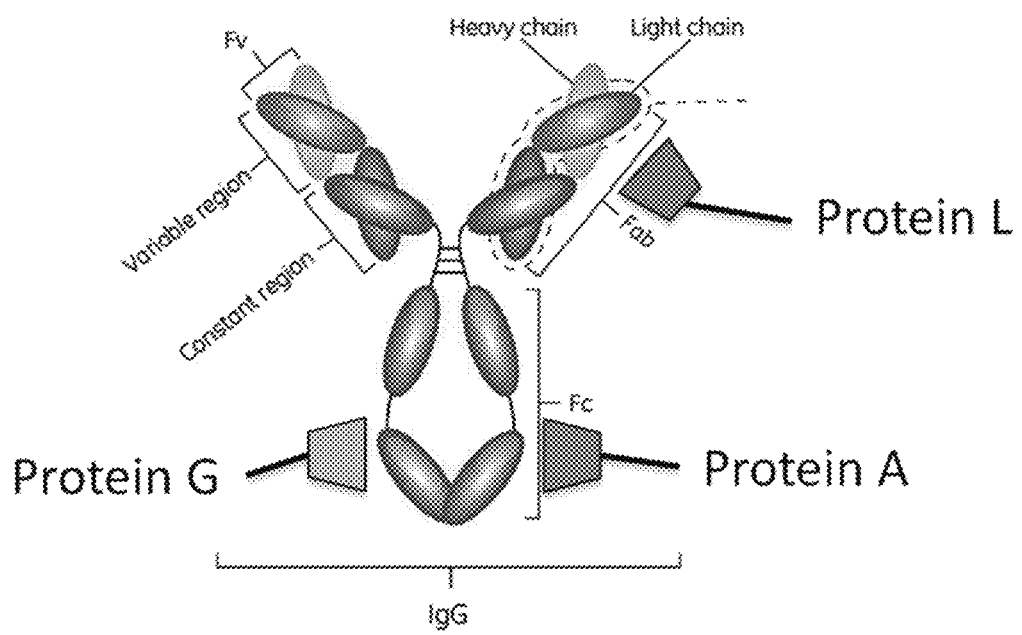
Figure 17B:
Figure 17B:
Figure 17B:
Figure 17B:
Figure 17B:
Figure 17B:
Figure 18A:
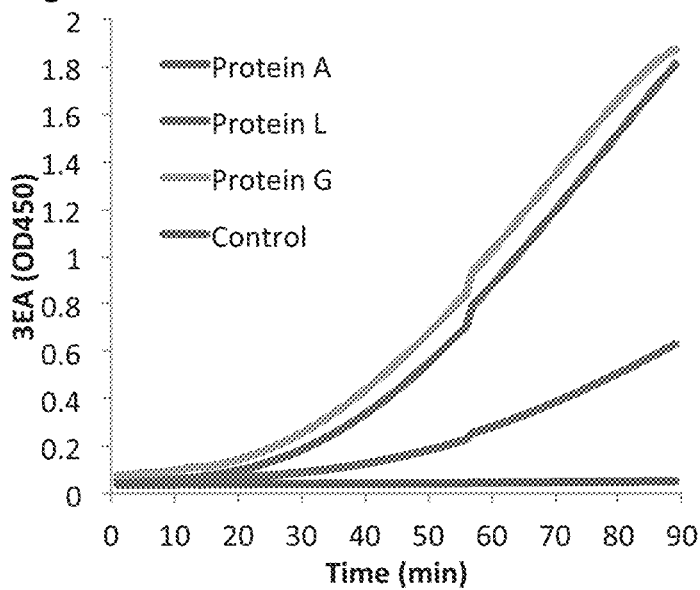
Figure 18B:
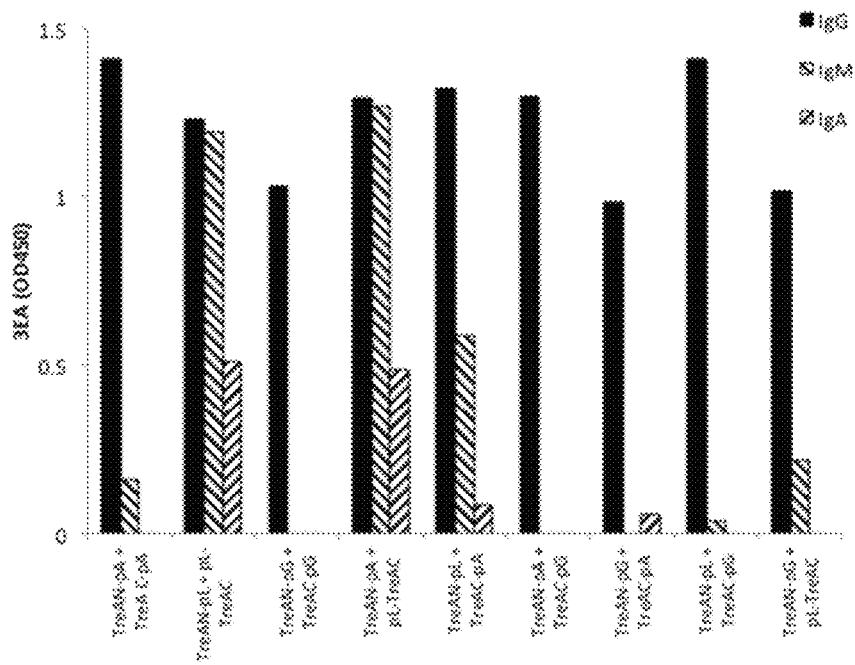

The IgG binding domain of Protein A (pA), a virulence factor expressed by staphylococcal bacteria that binds to the constant regions of (Fc) of IgGs, and the immunoglobulin binding domain of Protein L (pL), a virulence factor of *Peptostreptococcus magnus* that binds to the light chains of IgG, IgA and IgM, were also introduced as sensors into TreA fusions (FIGS. 17A, 17B). Combinations of TreA fragment fusions carrying pG (SEQ ID NOs: 28, 29), pA (SEQ ID NOs: 32-33), or pL (SEQ ID NOs: 34, 35), in all possible combinations, were used to detect IgG, IgM, and IgA (FIGS. 18A, 18B).

The biosensor platform tested novel split enzyme reporters by fusing polyhistidine tags (HIS) to the TreA fragment termini and immobilizing them onto a continuous binding surface of Ni-NTA resin beads. The biosensor platform disclosed herein efficiently detected monoclonal antibodies as well as polyclonal antibodies present in non-purified serum by fusing either peptide epitopes or whole-protein antigens to the split enzyme fragments. A positive signal (increased glucose concentrations) was detected in <30 min at room temperature with the GOx-HRP assay and with glucose strips, only when the bioreagents were interacting with cognate antibody. Successful conversion of the presence of antigen-specific antibody into a glucose signal (measured with a conventional glucometer) enables this biosensor platform to monitor host humoral immune responses (e.g. in response to an infection).

By incorporating immunoglobulin binding proteins that recognize the constant regions of immunoglobulins, the TreA platform detects total immunoglobulin concentrations. In addition, immunoglobulin binding protein and antigen fusions were combined to detect antigen-specific antibodies in a manner that required only one TreA fragment to be modified to result in the new test disclosed herein, which can be used to simplify antigen screening.

The biosensor platform tested novel split enzyme reporters by fusing polyhistidine tags (HIS) to the TreA fragment termini and immobilizing them on a continuous binding surface of Ni-NTA resin beads. The biosensor platform disclosed herein efficiently detected monoclonal antibodies as well as polyclonal antibodies present in non-purified serum by fusing either peptide epitopes or whole-protein antigens to the split enzyme fragments. A positive signal (increased glucose concentrations) was detected in <30 min at room temperature with the GOx-HRP assay and with glucose strips, only when the bioreagents were interacting with cognate antibody. Successful conversion of the presence of antigen-specific antibody into a glucose signal (measured with a conventional glucometer) enables this biosensor platform to monitor host humoral immune responses (e.g. in response to an infection).

By incorporating immunoglobulin binding proteins that recognize the constant regions of immunoglobulins, the TreA platform detects total immunoglobulin concentrations. In addition, immunoglobulin binding protein and antigen fusions were combined to detect antigen-specific antibodies in a manner that required only one TreA fragment to be modified to result in the new test disclosed herein, which can be used to simplify antigen screening.

Exmaple 2

2.1 Bacterial Strains

All plasmid manipulations and amplifications were carried out as disclosed in Example 1. *Staphylococcus aureus* and *Streptococcus uberis* strains were kindly provided by the Canadian Bovine Mastitis Milk Quality Research Network. *Listeria monocytogenes* strains NF-924, NF-1166, NF-1177 were kindly provided by Dr. Nancy Freitag, University of Illinois. All strains were grown in LB broth except *L. monocytogenes*, which were grown in BHI broth at 37° C. overnight.

2.2 Plasmids

Plasmids were constructed as disclosed in Example 1.

The coding sequence for bankvole PrP (residues 23 to 230; Accession No. AF367624) was synthetized using GeneArt (Thermo Fisher Scientific). The coding sequences for *S. aureus* binding peptide SA5-1 (VPHNPGLISLQG; SEQ ID NO: 36), for *Mycobacterium avium* subsp. *paratuberculosis* peptide Mp3 (NYVIHDVPRHPA; SEQ ID NO: 37), the complementary coiled-coil peptides with the leucine zipper motifs Ei (EIAALEKEIAALEKENAALEWE-IAALEK; SEQ ID NO: 38), Ki (KIAALKEKIAALKEK-NAALKWKIAALKE; SEQ ID NO: 39), Protein G (TYKLILNGKTLKGETTTEAVDAATAEKVFKQY-ANDNGVDGEVVTYDAATKTFT V TE; SEQ ID NO: 14), Protein A (TADNKFNKEQQNAFYEILHLPNLNEEQRN GFIQSLKDDPSQSANLLAEAKKLNDAQAPKA; SEQ ID NO: 15) and Protein L (AMEEVTIKANLIFANGSTQ-TAEFKGTFEKATSEAYAYADTLKKDNGEVVTVDV ADKGYTLNIKFAG; SEQ ID NO: 16) were incorporated as oligonucleotides linkers. All coding sequences introduced at the N-terminus of fragments were cloned between NcoI and SalI restriction sites, whereas coding sequences introduced at C-terminus were cloned between BamHI and AvrII.

2.3 Protein Expression, HIS-Tag Purification and Buffer Exchange

Proteins were expressed and purified as disclosed in Example 1.

For protein aggregation assays, rPrP fusions (rPrP-TreA (SEQ ID NO 44), rPrP-TreA$^N$ (SEQ ID NO 45) and rPrP-TreA$^C$ (SEQ ID NO 46)) were purified separately on Ni-NTA columns under denaturing conditions, then mixed (1 to 1 ratio) and co-dialyzed against 1 L of 10 mM sodium phosphate (pH 5.8) with SNAKESKIN® dialysis tubing at 7 kDa MWKO for 24 h at 25° C. to remove the denaturing agent. After dialysis, samples were centrifuged (10,000×g for 10 min) to separate precipitated and soluble proteins. Supernatant was discarded and the pellet washed with PBS and re-suspended in 0.25 M trehalose.

2.4 Complementation Assays

Complementation assays were carried out as disclosed in Example 1.

Bacterial complementation assays were performed in PBS (pH 7). For this, 0.2 ml of bacterial culture grown overnight was pelleted (OD$_{600nm}$=1.2), washed 3 times with PBS, re-suspended in 10 µl of PBS (pH 7) and added to protein fragments.

For protein aggregation assays, rPrP fusions (rPrP-TreA$^N$ and rPrP-TreA$^C$, SEQ ID NOs: 45, 46) were purified separately on Ni-NTA columns under denaturing conditions, then mixed (1:1 ratio) and co-dialyzed against 1 L of 10 mM sodium phosphate (pH 5.8) with SNAKESKIN® dialysis tubing at 7 kDa MWKO for 24 h at 25° C. to remove the denaturing agent. After dialysis, samples were centrifuged (10,000×g for 10 min) to separate precipitated and soluble proteins. Supernatant was discarded and the pellet washed with PBS and re-suspended in 0.25 M trehalose.

Glucose concentrations were measured as disclosed in example 1.

2.5 Direct Whole-Pathogen Detection

Figure 19A:
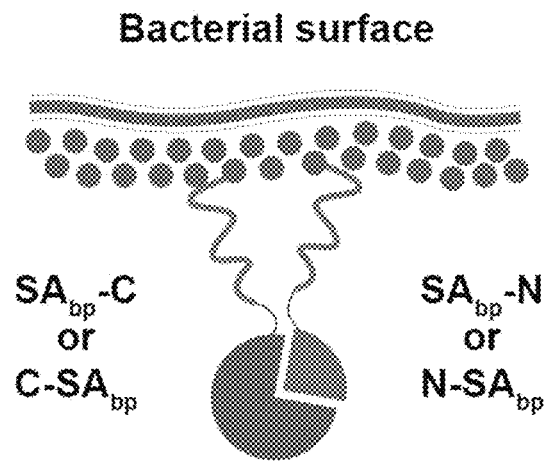
Figure 19B:
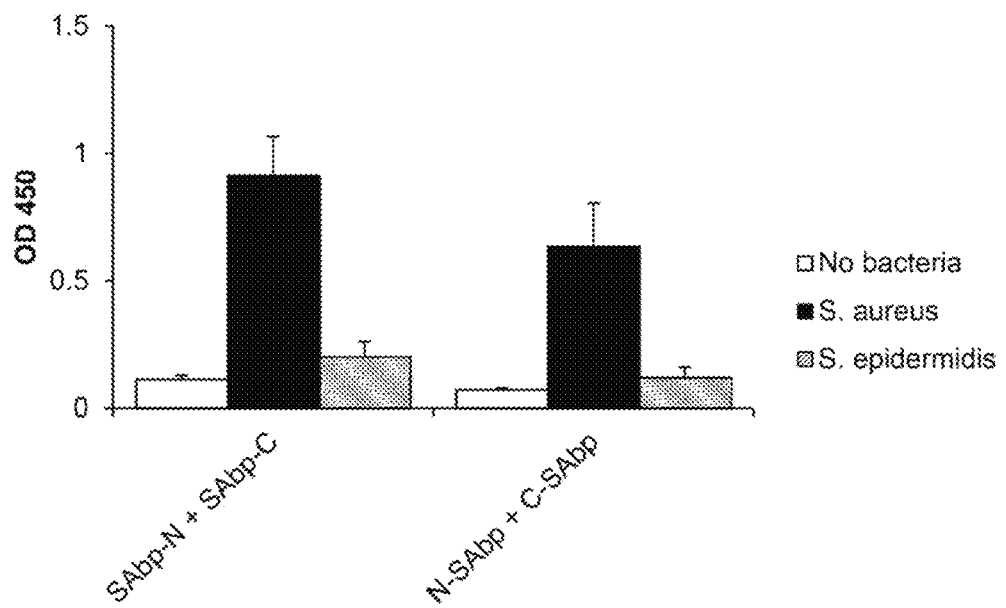

Split TreA was applied to detect intact bacterial cells by incorporating peptide aptamers (FIG. 19A). Specifically, *S. aureus* surface binding peptides were placed at the N or C terminals of TreA$^N$ and TreA$^C$ fragments (SEQ ID NOs: 40, 41, 42, 43). Resulting TreA fusions were incubated with *S. aureus* or *S. epidermidis*. Trehalase complementation and a subsequent glucose increase was only detected when TreA fragments were incubated with *S. aureus*, whereas glucose concentrations were low when fusions were incubated with *S. epidermidis* (FIG. 19B). Trehalase activity was higher when the peptide aptamer was fused to the N-terminus of both TreA fragments.

Figure 20:
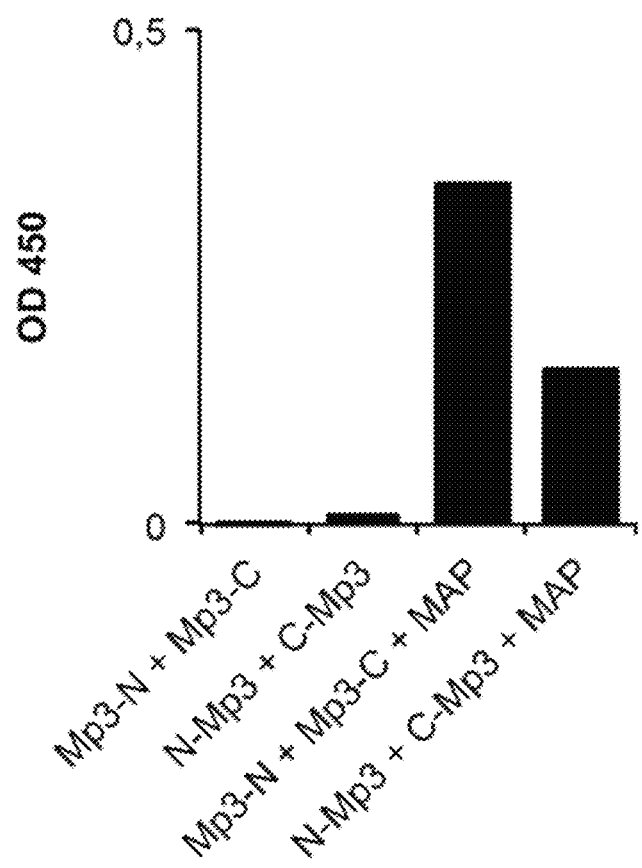

*Mycobacterium avium* subsp. *paratuberculosis* (MAP) binding peptide (Mp3) were also placed at the N or C terminals of TreA$^N$ and TreA$^C$ fragments (SEQ ID NOs: 44, 45, 46, 47). Resulting TreA fusions were incubated with MAP. Trehalase complementation and a subsequent glucose increase indicated the detection of MAP cells regardless of fusion of the peptide aptamers to the N or C terminus of the TreA fragments (FIG. 20).

Figure 21:
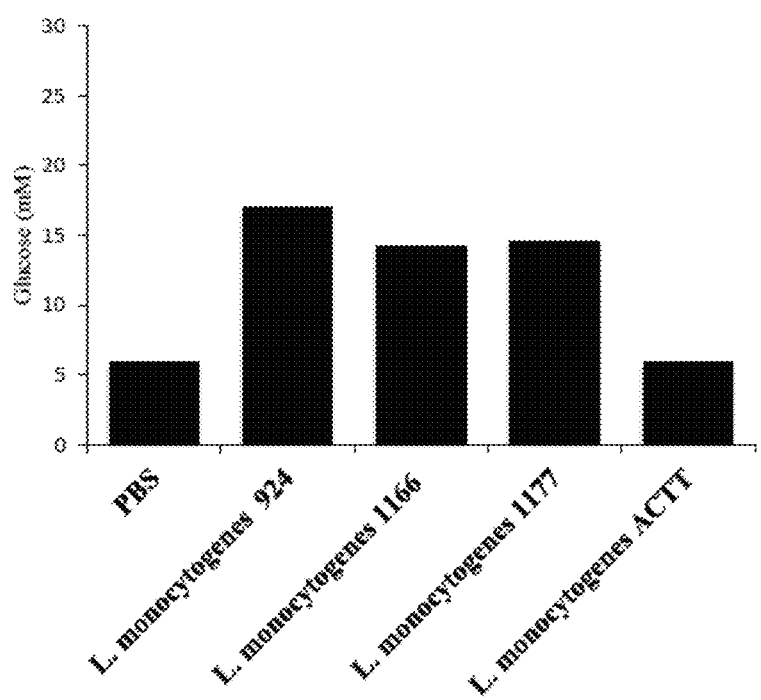

Single-chain variable fragment (scFv), an antibody mimic that specifically recognizes ActA, a virulence factor expressed on the surface of *L. monocytogenes*, was fused to Tre, TreA$^N$ and TreA$^C$ (SEQ ID NOs: 48, 49, 50). ActA-overexpressing *L. monocytogenes* mutants (924, 1166, 1177) were used for comparison with wild type *L. monocytogenes* (ATCC) which expresses very low levels up to 200-fold less) of ActA when grown extracellularly. Glucose production corresponded with expected levels of ActA expression on the bacterial cell surface (FIG. 21).

2.6 Small Molecule Detection

Figure 22:
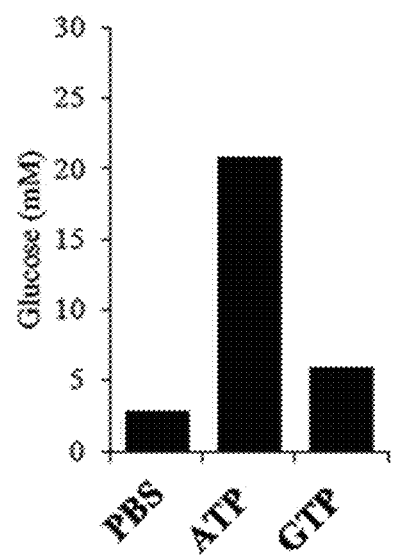

Small molecules that are known to dimerize their receptor proteins, such as ATP and estradiol, were used to complement the split TreA reporter. TreA$^N$ and TreA$^C$ were fused to ATPase subunit FOF1 ε from *Bacillus* PS3 (SEQ ID NOs: 51, 52). Protein preparations were incubated in equimolar concentration with 10 mM of ATP or 10 mM of GTP in presence of 10 mM of MgCl$_2$. Glucose production was observed in presence of ATP as expected in contrast to a PBS control. A more modest production was also observed in the presence of GTP (FIG. 22).

2.7 Protein-Protein Interaction and Protein Aggregation Detection

Figure 23:
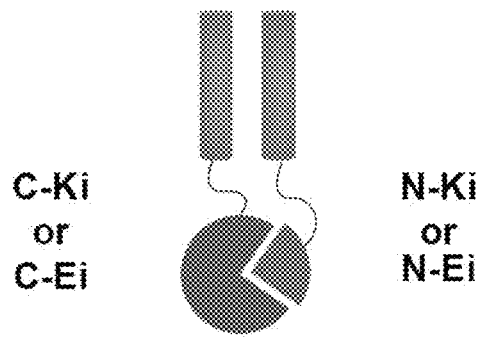
Figure 23:
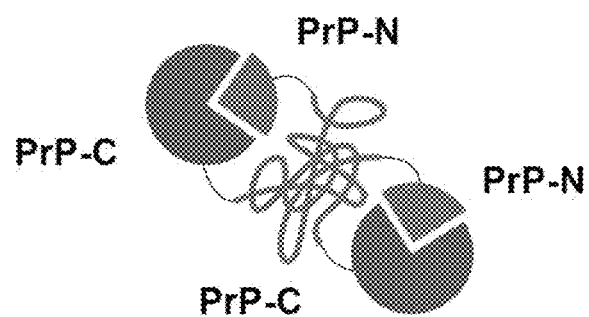
Figure 24A:
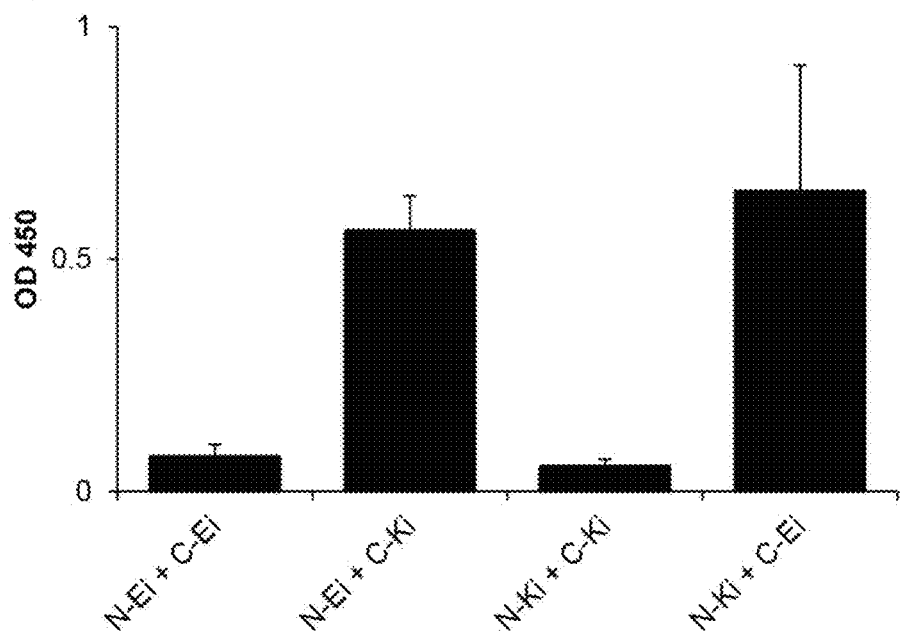

The TreA detection assay was also used to detect protein-protein interactions and protein aggregation (FIG. 23). As an example of the former, complementary coiled-coil peptides with the leucine zipper motifs Ei (SEQ ID NO: 38) and Ki (SEQ ID NO: 39) were used to induce TreA complementation. TreA$^N$ and TreA$^C$ with complementary heterodimzerizing peptides Kl and El or non-complementary zippers (Ei+Ei and Ki+Ki) (SEQ ID NOs: 53, 54, 56) were assayed for TreA complementation. Only combinations with complementary leucine zippers (Ki+Ei) increased glucose concentrations, whereas other combinations did not (FIG. 24A).

Leucine zipper TreA fusions were used as models to investigate sample matrix effects on TreA complementation assays and to explore the possibility of the bio-reagents to withstand lyophilisation and subsequent resolubization (i.e., assess stability for long-term shelf life). The TreA$^N$-Ei and TreA$^C$-Ki fusions were purified and lyophilized separately in the presence of substrate. Next, fusions were re-suspended in whole bovine blood or bovine milk (acidified to pH 6 by addition of citric acid/sodium citrate powder). Glucose concentrations were measured over 3 h; the glucose signal doubled in samples containing complementary fusions, demonstrating that neither lyophilisation nor the presence of blood or milk inhibited TreA complementation (FIGS. 25A, 25B).

Leucine zipper TreA fusions were also tested in pure saliva samples by desolving lyophilized assay reagents in saliva. The comparison with a buffer control demonstrates that the assay reagents are equally active in saliva as in buffer (FIG. 26). Similarly, lyophilized protein G TreA fusions described in more detail in Example 1, were also reconstituted in saliva to detect the presence of IgG in saliva in comparison with buffer which did not contain antibodies (FIG. 26).

Figure 24B:
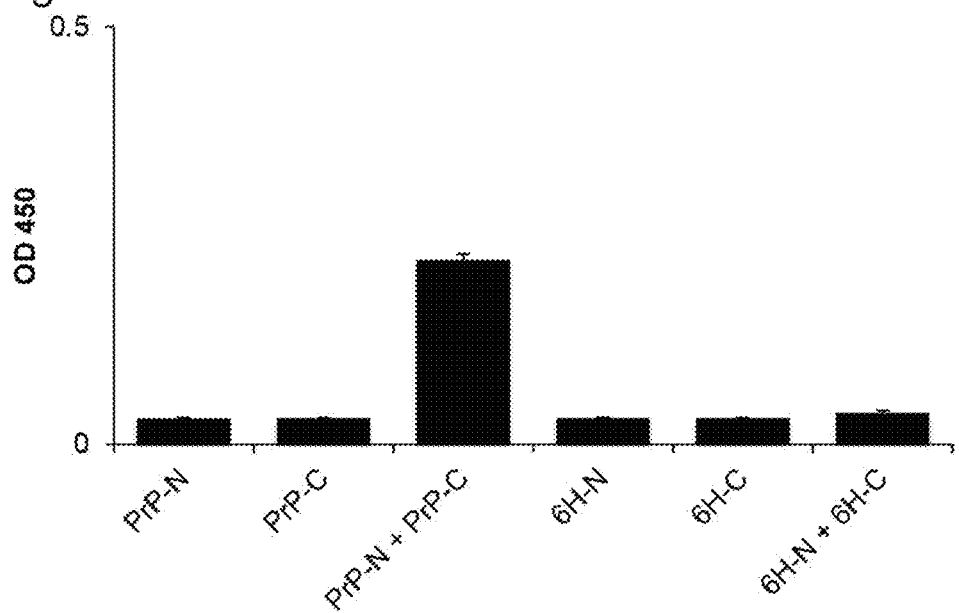

Furthermore, Tre, TreA$^N$ and TreA$^C$ were fused N-terminally to recombinant bank vole prion protein (rPrPc) (SEQ ID Nos: 57, 58, 59), which forms aggregates spontaneously under specific conditions. The rPrP-dependent aggregation was induced by co-dialysis of TreA$^N$ and TreA$^C$ fusions, and protein aggregates were isolated from soluble fusion proteins and incubated with substrate. Glucose production was detected only when the TreA$^N$ and TreA$^C$ rPrP fusions were co-aggregated, but not when they aggregated separately (FIG. 24B). Furthermore, HIS-tagged TreA fusions showed no evidence of aggregation under the same conditions.

2.8 Complementation of TreA by Inteins

Split inteins were used to induce the complementation of TreA. Inteins are protein elements placed inside host proteins (i.e., exteins) that are able to self-excise from the extein when activated. During the excision, inteins catalyze the restoration of the peptide bond between two terminals of the original host protein, which leads to restoration of the extein and activation of its function. The CWE residues that needed to be introduced to flank the N-terminus of the C-terminal extein were also introduced in the linker region of the complete TreA protein and this scar was demonstrated not to abolish the trehalase activity in the recombinant protein (SEQ ID NO: 60). Trehalase activity was detected after mixing TreA$^N$ and TreA$^C$ fusions with split DnaE inteins (SEQ ID NOs: 61, 62) (FIG. 27A) and successful intein excision and TreA ligation was verified on SDS page (FIG. 27B).

This example discloses a versatile biosensor platform and demonstrates that this platform can be used to detect various types of molecules, for example antibodies (as demonstrated in Example 1), small molecules (ATP), whole pathogens and inter-molecule interactions (protein-protein binding and protein aggregation). Cytokines (e.g. interferon gamma) and hormones (e.g. estradiol) could also be detected with sensor proteins that dimerize in the presence with these molecules, for example with human estradiol receptor or bovine interferon-gamma receptor (SEQ ID NOs: 63, 64, 65, 66). The biosensor platform is based on split enzyme complementation of an *E. coli* glycolytic enzyme trehalase (TreA) that hydrolyses trehalose into two molecules of glucose, which can be easily detected with commercially available glucometers. Glucose detection is compatible with clinical samples and does not need additional handling or processing. In contrast, the output signals generated by many other approaches are less compatible with existing detectors and with detection in biofluids from humans or animals (e.g. fluorescence or luminescence from GFP or luciferase).

This biosensor platform was adapted to detect whole bacterial cells, protein-protein interactions and protein aggregation, simply by replacing the sensor component with protein elements specific to the analyte of interest. Fusions of TreA fragments with small peptide aptamers specific to components present on bacterial surface or single chain fragment variables (antibody derivative) specific for surface antigen enabled detection of bacterial cells (e.g. *S. aureus* and *Listeria monocytogenes*). Heterodimerizing leucine zippers and PrP were used as models to demonstrate that this platform can be applied to monitor protein-protein interactions or protein aggregation, respectively.

To summarize, disclosed herein are the implementation of dimerization and complexation strategies to complement a split enzyme to monitor various types of analytes and interactions in parallel. Also disclosed herein are complementation strategies never before combined with split reporter enzymes, for example surface binding and protein aggregation (e.g., prion protein; PrP) and amyloid β (SEQ ID NOs: 67, 68, 69). In addition, heterodimerizing peptides were used to investigate effects of clinical sample composition. It was noteworthy that that TreA complementation was not severely impacted by the composition of real life/clinical samples, in contrast to some other reporters (e.g. GFP and Luciferase).

Example 3

3.1 Materials

Purified Bovine IgG (12.8 mg/ml) used for standard curves was purchased from Sigma-Aldrich. Plasmids used in this example were prepared as described in Examples 1 and 2. In short, the gene coding for *E. coli* glycolytic enzyme TreA was split in 2 fragments, TreA N (66 aa long) and TreA C (456 aa long) through PCR amplification. Each fragment was fused C terminally to Protein G (residues: 270-324; AC: P19909) and cloned in pETDuet expression vector (Novagen, Canada) using NcoI and AvrII restriction sites.

3.2 Protein Purification and Lyophilisation

Proteins were recombinantly expressed in BL-21 ΔTreA strain and purified on Ni-NTA resin following the methods disclosed in Example 1. Briefly, recombinant cultures were induced with 0.5 mM of IPTG and harvested after 3 h at 37° C. Bacterial pellets with recombinant proteins were resuspended in 6M guanidinium buffer, sonicated and loaded on equilibrated Ni-NTA resin. Proteins were refolded on resin during washing steps containing gradually decreasing guanidinium-HCl concentrations and eluted in Elution buffer containing 250 mM of Imidazole. Finally, samples were dialyzed against 1 L of sodium maleate buffer (50 mM, pH 6) with SNAKESKIN® dialysis tubing for 24 h at 25° C. and protein concentration was determined with a QUBIT® assay. Lyophilized reagents were prepared by mixing the proteins in 1:1 weight ratio with BSA, frozen in microtiter plate wells at −80° C. and then lyophilized O/N at −85° C. and 12 mT.

3.3 Split Trehalase Immunoglobulin G Assay (STIGA)

Glucose quantification was done in two ways in this example. First, glucose measurements used for statistical analysis were collected with a GOx-HRP colorimetric assay based on based on glucose oxidase (0.1 mg/mL), horse radish proxidase (0.2 U/mL), and O-dianisidine (0.5 mM) in sodium maleate buffer (50 mM) (FIG. 28). Second, STIGA quantification assays were performed in two ways (FIG. 29). The STIGA assays are based on the *E. coli* glycolytic enzyme, trehalase (TreA) that converts trehalose into glucose. TreA is split in two non-functional fragments i.e., (i) TreA N (N), and (ii) TreA C (C). Both functional fragments were fused C-terminally to Protein G (pG) originating from Lancefield group C and D streptococci, thereby resulting in the recombinant fusion proteins N-pG and C-pG (SEQ ID NO 28, 29). Protein G binds specifically to constant region of IgG (Fc) and consequently acts as a sensor for immunoglobulins (IgGs) independently of their affinity/antigen binding specificity. When the two fusions are incubated with samples containing IgGs (e.g. colostrum or serum), the two fusion proteins will bind to the Fc of IgG thereby leading to the dimerization and re-activation of the TreA enzyme. Re-activated TreA will produce glucose in the presence of trehalose.

GOx-HRP colorimetric STIGA: Colostrum and calf serum samples were diluted in sodium maleate buffer (50 mM, pH 6) (dairy colostrum 1:2,000; beef colostrum 1:4,000; dairy and beef calf serum 1:1,000). STIGA was performed with 20 µg of C-pG and 5.2 µg of N-pG (1:1 molar ratio) for colostrum or 10 µg of C-pG and 2.6 µg of N-pG for serum in sodium maleate buffer with 250 mM of trehalose (Sigma) in final volume of 150 µl. The glucose concentration was measured with a colorimetric enzymatic assay based on glucose oxidase (0.1 mg/mL), horseradish peroxidase (0.2 U/mL), and O-dianisidine (0.5 mM) in sodium maleate buffer (50 mM, pH 6). Absorbance (OD) was measured every minute for 90 min in an ENSPIRE® multimode plate reader at 450 nm (Perkin Elmer).

Glucose strips based STIGA (STIGA$^{GLU}$): This assay was performed with lyophilized protein preparations. Lyophilized proteins were resuspended in 150 µl of Sodium-maleate buffer with 250 mM of trehalose containing the same colostrum or serum dilution used in previous assay. Glucose production was measured by ACCU-CHEK AVIVA® Blood Glucose Meter every 30 min for a total of 90 min.

3.4 Sample Collection

Dairy colostrum (n=60) and serum samples (n=83) were randomly selected from previously collected samples. Briefly, colostrum samples were collected from 13 farms in central Alberta between February and July of 2012. Samples were collected by the farm owners, frozen at −20° C. and transported to the University of Calgary where they were stored at −80° C. Blood samples were collected at the same time from bull calves and heifer calves that were more than 24 h old and 8 days or less of age. The samples were stored on ice, transported to the University of Calgary where the serum was harvested by centrifugation at 1,800×g at 4° C. for 25 min. Serum samples were stored at −80° C. as well. Beef colostrum (n=64) and serum samples (n=84) were collected during calving seasons during 2013 through 2015 from two large commercial cow-calf operations in Alberta. IgG concentrations of all the samples were determined by Prairie Diagnostic Laboratories (University of Saskatchewan, Saskatoon, SK) by RID.

3.5 Statistical Analysis

Pearson correlation coefficient was used to establish association between IgG concentration measured with STIGA detection assay and RID. Sensitivity, specificity, positive and negative predicted values and accuracy were calculated using RID as the gold standard.

3.6 Detection of IgGs in Bovine Colostrum

The IgG contents of dairy (n=60) and beef (n=64) colostrum samples were determined with the colorimetric STIGA. Obtained OD values corresponding to IgG levels were then correlated with IgG concentrations determined previously by RID analysis. The correlation coefficient for dairy colostrum was 0.72 (FIG. 30A), whereas for beef colostrum, the correlation coefficient was 0.73 (FIG. 30B).

With 50 mg/ml set as a threshold for adequate quality dairy colostrum, STIGA had the highest sensitivity (64.7%) and specificity (93%) when an OD of 0.9 was used as the cut-off (Table 2). Dairy samples had a 71.4% chance of being truly poor quality (=positive predictive value (PPV)) and 84.8% chance of being truly adequate (=negative predictive value (NPV)). STIGA identified 23% of analyzed colostrum samples to be of poor quality whereas RID identified 28.3% of samples of poor quality.

With a threshold set at 100 mg/ml for beef colostrum, STIGA reached its highest sensitivity (83.3%) and specificity (90.3%) when an OD of 0.8 was used as the cut-off value (Table 2). At this cut-off value, the beef colostrum sample had 66.7% PPV and a 95.92% NPV. STIGA identified 23.4% of colostrum samples of poor quality whereas according to RID 18.75% of samples were of poor quality 3.7 Detection of IgGs in Calf Serum Dairy (n=83) and beef (n=84) calf sera were analyzed for their IgG concentration by STIGA. The IgG concentrations in these sera were measured previously by RID analysis. Correlation of the IgG concentrations determined by RID with OD values obtained by STIGA was 0.72 for dairy samples (FIG. 31A) and 0.85 for beef samples (FIG. 31B).

TABLE 2

Accuracy, sensitivity (Se), specificity (Sp), positive predictive value (PPV) and negative predictive value (NPV) calculated for OD cut points obtained with STIGA compared with 50 mg/mL IgG for dairy colostrum and 100 mg/mL of beef colostrum determined by RID

|  | Cut point (OD 450) | Accuracy (%) | Se (%) | Sp (%) | PPV (%) | NPV (%) |
|---|---|---|---|---|---|---|
| Dairy colostrum | 0.6 | 75.0 | 11.8 | 100.0 | 100.0 | 74.1 |
|  | 0.7 | 78.3 | 23.5 | 100.0 | 100.0 | 76.8 |
|  | 0.8 | 85.0 | 47.1 | 100.0 | 100.0 | 82.7 |
|  | 0.9 | 85.0 | 64.7 | 93.0 | 78.6 | 87.0 |
|  | 1.0 | 78.3 | 76.5 | 79.1 | 59.1 | 89.5 |
|  | 1.1 | 75.0 | 88.2 | 69.8 | 53.6 | 93.8 |
|  | 1.2 | 68.3 | 94.1 | 58.1 | 47.1 | 96.2 |
| Beef colostrum | 0.6 | 84.4 | 25.0 | 98.1 | 75.0 | 85.0 |
|  | 0.7 | 90.6 | 66.7 | 96.2 | 80.0 | 92.6 |
|  | 0.8 | 89.1 | 83.3 | 90.4 | 66.7 | 95.9 |
|  | 0.9 | 79.7 | 100.0 | 75.0 | 48.0 | 100.0 |
|  | 1.0 | 71.9 | 100.0 | 65.4 | 40.0 | 100.0 |
|  | 1.1 | 53.1 | 100.0 | 42.3 | 28.6 | 100.0 |
|  | 1.2 | 42.2 | 100.0 | 28.8 | 24.5 | 100.0 |

With thresholds for FPS set at 10 mg/ml for dairy calves and 24 mg/ml for beef calves, STIGA reached its highest sensitivity (88.9%) and specificity (85.7%) at an OD of 0.6 (Table 3) in dairy calf serum samples whereas in beef calf sera, the highest sensitivity (69.2%) and specificity (97.2%) were reached at an OD of 0.3 (Table 3). In dairy and beef calf serum samples, STIGA had 75% and 81.8% chance, respectively, of truly indicating FPS whereas it had 94% and 94.5% chance, respectively, of truly showing that the calf received enough immunoglobulins. FTP was diagnosed in 38.5% of dairy calf serum samples and 13% of beef calf serum samples by STIGA as compared to 32.5% and 15.5% respectively diagnosed by RID.

TABLE 3

Accuracy, sensitivity (Se), specificity (Sp), positive predictive value (PPV), and negative predictive value (NPV) calculated for OD cut points obtained with STIGA compared with 10 mg/mL IgG for dairy calf sera and 24 mg/mL for beef calf sera determined by RID.

|  | Cut point (OD 450) | Accuracy (%) | Se (%) | Sp (%) | PPV (%) | NPV (%) |
|---|---|---|---|---|---|---|
| Dairy calf sera | 0.2 | 91.6 | 77.8 | 98.2 | 95.5 | 90.2 |
|  | 0.3 | 86.7 | 100.0 | 80.4 | 71.1 | 100.0 |
|  | 0.4 | 67.5 | 100.0 | 51.8 | 50.0 | 100.0 |

TABLE 3-continued

Accuracy, sensitivity (Se), specificity (Sp), positive predictive value (PPV), and negative predictive value (NPV) calculated for OD cut points obtained with STIGA compared with 10 mg/mL IgG for dairy calf sera and 24 mg/mL for beef calf sera determined by RID.

|  | Cut point (OD 450) | Accuracy (%) | Se (%) | Sp (%) | PPV (%) | NPV (%) |
|---|---|---|---|---|---|---|
|  | 0.5 | 55.4 | 100.0 | 33.9 | 42.2 | 100.0 |
|  | 0.6 | 45.8 | 100.0 | 19.6 | 37.5 | 100.0 |
|  | 0.7 | 41.0 | 100.0 | 12.5 | 35.5 | 100.0 |
|  | 0.8 | 34.9 | 100.0 | 3.6 | 33.3 | 100.0 |
| Beef | 0.1 | 85.7 | 7.7 | 100.0 | 100.0 | 85.5 |
| calf sera | 0.2 | 90.5 | 38.5 | 100.0 | 100.0 | 102.9 |
|  | 0.3 | 92.9 | 69.2 | 97.2 | 81.8 | 94.5 |
|  | 0.4 | 83.9 | 100.0 | 91.5 | 46.4 | 116.1 |
|  | 0.5 | 52.4 | 100.0 | 43.7 | 24.5 | 100.0 |
|  | 0.6 | 31.0 | 100.0 | 18.3 | 18.3 | 100.0 |
|  | 0.7 | 16.7 | 100.0 | 1.4 | 15.7 | 100.0 |

3.8 Detection of IgGs by STIGA using a Glucometer (STIGA$^{glu}$)

In order to develop STIGA for future on-farm use, a smaller sample set for each test group (dairy colostrum n=14; beef colostrum n=14; dairy calf sera n=18 and beef calf sera n=18) was analyzed with lyophilized STIGA bioreagents, and the produced glucose was measured with a common glucometer. The correlation coefficients between RID determined IgG concentrations and glucose levels were 0.7 for dairy colostrum (FIG. 32A), 0.85 for beef colostrum (FIG. 32B), 0.94 for dairy calf sera (FIG. 33A), and 0.83 for beef calf sera (FIG. 33B).

Example 4

4.1 Bacterial Strains

All plasmid manipulations and amplifications were performed as disclosed in Example 1.

4.2 Plasmids

Coding sequences for PQQ-GDH from *Alcinetobacter calcoaceticus* (PDB: 1CQ1) was synthetized using GeneArt (Thermo Fisher Scientific). This sequence plus a sequence for a short flexible linker and a His-tag were introduced at the N-terminus of the TreA$^N$ fragment (or TreA SEQ ID NO: 70) that was either fused with leucine zipper peptides E1 or K1 (SEQ ID NOs: 71, 72), were cloned between NcoI and SalI restriction sites.

4.3 Protein Expression, HIS-Tag Purification and Buffer Exchange

Protein expression and purification were carried out as disclosed in Example 1.

4.4 Complementation and Colorimetric Assays

Protein concentration was determined with a QUBIT® protein assay kit. Complementation of TreA fragments fused to leucine zipper peptides (SEQ ID NOs: 55, 56) was measured by a GDH assay. Complementation of the TreA fragments leads to trehalase activity and consequently glucose production. The glucose is hydrolysed by the fused GDH which leads to a colorimetric detection in the presence of the GDH assay reagents (3.0 mM 1-methoxy-5-methylphenazinium methyl sulfate, 6.6 mM Thiazolyl Blue Tetrazolium Bromide, 1 mM Pyrroloquinoline quinone or Methoxatin disodium salt (PQQ), 25 mM CaCl2, 10% Triton-100, 1 M Trehalose, 200 mM sodium maleate (pH 6.0). The reaction was read at OD at 570 nm every 1 min for 90 minutes.

4.5. Complementation of TreA Fragments Fused to GDH

Complementation of the TreA fragments fused to heterodimerizing peptides E1 and K1 where GDH was fused to one of the complementing interaction partners (SEQ ID NOs: 71, 72), was compared with combinations where GDH was fused to TreA$^N$ that did not engage in complementation (FIG. 34A). Care was taken that the stoichiometry of the reaction was identical in all the samples. First of all, it was shown that GDH can be used to measure the activity of complemented split TreA with specific GDH colorimetric reagents. It was shown that the fusion of GDH did not interfere with the activity of either GDH or the complemented split TreA (FIG. 34B).

It is to be noted that the heterodimerizing peptides in the above disclosed fusions with TreA fragments and GDH, may be changed out for other analyte sensing domains such as pG, pA or pL (SEQ ID NOs: 73, 74, 75) to detect immunoglobulins. In fact, all analyte sensors could be incorporated into the GDH assays disclosed herein.

SEQUENCES:

SEQ ID NO: 1: Forward primer for preparation of the Tn5
(aph) type II (kanamycin resistance) replacement for the entire TreA gene
TATGGACAGCAAGCGAACCG SEQ ID NO: 2: Reverse primer for preparation of the Tn5
(aph) type II (kanamycin resistance) replacement for the entire TreA gene
TCAGAAGAACTCGTCAAGAAG SEQ ID NOs: 3-13: Primers shown in Table 1

SEQ ID NO: 14: Protein G
TYKLILNGKTLKGETTTEAVDAATAEKVFKQYANDNGVDGEWTYDAATKTFTV
TE SEQ ID NO: 15: Protein A
TADNKFNKEQQNAFYEILHLPNLNEEQRNGFIQSLKDDPSQSANLLAEAKKLN
DAQAPKA SEQ ID NO: 16: Protein L
AMEEVTIKANLIFANGSTQTAEFKGTFEKATSEAYAYADTLKKDNGEWTVDVA
DKGYTLNIKFAG SEQ ID NO: 17: HIS-TreA: N-terminally HIS-tagged TreA (w/o
signal peptide)
MAHHHHHHEETPVTPQPPDILLGPLFNDVQNAKLFPDQKTFADAVPNSDPLM
ILADYRMQQNQSGFDLRHFVNVNFTLPKEGEKYVPPEGQSLREHIDGLWPVL

|             |
| ----------- |
| -continued  |
| SEQUENCES:  |

```
TRSTENTEKWDSLLPLPEPYVVPGGRFREVYYWDSYFTMLGLAESGHWDKV
ADMVANFAHEIDTYGHIPNGNRSYYLSRSQPPFFALMVELLAQHEGDAALKQ
YLPQMQKEYAYWMDGVENLQAGQQEKRVVKLQDGTLLNRYWDDRDTPRPE
SWVEDIATAKSNPNRPATEIYRDLRSAAASGWDFSSRWMDNPQQLNTLRTT
SIVPVDLNSLMFKMEKILARASKAAGDNAMANQYETLANARQKGIEKYLWND
QQGWYADYDLKSHKVRNQLTAAALFPLYVNAAAKDRANKMATATKTHLLQP
GGLNTTSVKSGQQWDAPNGWAPLQWVATEGLQNYGQKEVAMDISWHFLTN
VQHTYDREKKLVEKYDVSTTGTGGGGEYPLQDGFGWTNGVTLKMLDLICP
KEQPCDNVPATRPTVKSATTQPSTKEAQPTP

SEQ ID NO: 18: TreA-HIS: C-terminally HIS-tagged TreA (w/o
signal peptide)
MEETPVTPQPPDILLGPLFNDVQNAKLFPDQKTFADAVPNSDPLMILADYRMQ
QNQSGFDLRHFVNVNFTLPKEGEKYVPPEGQSLREHIDGLWPVLTRSTENTE
KWDSLLPLPEPYVVPGGRFREVYYWDSYFTMLGLAESGHWDKVADMVANF
AHEIDTYGHIPNGNRSYYLSRSQPPFFALMVELLAQHEGDAALKQYLPQMQK
EYAYWMDGVENLQAGQQEKRVVKLQDGTLLNRYWDDRDTPRPESWVEDIA
TAKSNPNRPATEIYRDLRSAAASGWDFSSRWMDNPQQLNTLRTTSIVPVDLN
SLMFKMEKILARASKAAGDNAMANQYETLANARQKGIEKYLWNDQQGWYAD
YDLKSHKVRNQLTAAALFPLYVNAAAKDRANKMATATKTHLLQPGGLNTTSV
KSGQQWDAPNGWAPLQWVATEGLQNYGQKEVAMDISWHFLTNVQHTYDR
EKKLVEKYDVSTTGTGGG
GGEYPLQDGFGWTNGVTLKMLDLICPKEQPCDNVPATRPTVKSATTQPSTKE
AQPTPHHHHHH SEQ ID NO: 19: HIS-TreA-HIS: N- and C- terminally HIS-tagged
TreA (w/o signal peptide)
MAHHHHHHEETPVTPQPPDILLGPLFNDVQNAKLFPDQKTFADAVPNSDPLM
ILADYRMQQNQSGFDLRHFVNVNFTLPKEGEKYVPPEGQSLREHIDGLWPVL
TRSTENTEKWDSLLPLPEPYVVPGGRFREVYYWDSYFTMLGLAESGHWDKV
ADMVANFAHEIDTYGHIPNGNRSYYLSRSQPPFFALMVELLAQHEGDAALKQ
YLPQMQKEYAYWMDGVENLQAGQQEKRVVKLQDGTLLNRYWDDRDTPRPE
SWVEDIATAKSNPNRPATEIYRDLRSAAASGWDFSSRWMDNPQQLNTLRTT
SIVPVDLNSLMFKMEKILARASKAAGDNAMANQYETLANARQKGIEKYLWND
QQGWYADYDLKSHKVRNQLTAAALFPLYVNAAAKDRANKMATATKTHLLQP
GGLNTTSVKSGQQWDAPNGWAPLQWVATEGLQNYGQKEVAMDISWHFLTN
VQHTYDREKKLVEKYDVSTTGTGGGGEYPLQDGFGWTNGVTLKMLDLICP
KEQPCDNVPATRPTVKSATTQPSTKEAQPTPHHHHHH SEQ ID NO: 20: HIS-TreAN: N-terminally HIS-tagged N-terminal
fragment of TreA (w/o signal peptide)
MAHHHHHHEETPVTPQPPDILLGPLFNDVQNAKLFPDQKTFADAVPNSDPLM
ILADYRMQQNQSGFDLRHFVNVNFTLPKEGEKYVPGS SEQ ID NO: 21: TreAN-HIS: C-terminally HIS-tagged N-terminal
fragment of TreA (w/o signal peptide)
MEETPVTPQPPDILLGPLFNDVQNAKLFPDQKTFADAVPNSDPLMILADYRMQ
QNQSGFDLRHFVNVNFTLPKEGEKYVPHHHHHH SEQ ID NO: 22: HIS-TreAC: N-terminally HIS-tagged C-terminal
fragment of TreA (w/o signal peptide)
MAHHHHHHNFTLPKEGEKYVPPEGQSLREHIDGLWPVLTRSTENTEKWDSL
LPLPEPYVVPGGRFREVYYWDSYFTMLGLAESGHWDKVADMVANFAHEIDT
YGHIPNGNRSYYLSRSQPPFFALMVELLAQHEGDAALKQYLPQMQKEYAYW
MDGVENLQAGQQEKRVVKLQDGTLLNRYWDDRDTPRPESWVEDIATAKSN
PNRPATEIYRDLRSAAASGWDFSSRWMDNPQQLNTLRTTSIVPVDLNSLMFK
MEKILARASKAAGDNAMANQYETLANARQKGIEKYLWNDQQGWYADYDLKS
HKVRNQLTAAALFPLYVNAAAKDRANKMATATKTHLLQPGGLNTTSVKSGQQ
WDAPNGWAPLQWVATEGLQNYGQKEVAMDISWHFLTNVQHTYDREKKLVE
KYDVSTTGTGGGGEYPLQDGFGWTNGVTLKMLDLICPKEQPCDNVPATRP
TVKSATTQPSTKEAQPTP SEQ ID NO: 23: TreAC-HIS: C-terminally HIS-tagged C-terminal
fragment of TreA (w/o signal peptide)
MAVNFTLPKEGEKYVPPEGQSLREHIDGLWPVLTRSTENTEKWDSLLPLPEP
YVVPGGRFREVYYWDSYFTMLGLAESGHWDKVADMVANFAHEIDTYGHIPN
GNRSYYLSRSQPPFFALMVELLAQHEGDAALKQYLPQMQKEYAYWMDGVE
NLQAGQQEKRVVKLQDGTLLNRYWDDRDTPRPESWVEDIATAKSNPNRPAT
EIYRDLRSAAASGWDFSSRWMDNPQQLNTLRTTSIVPVDLNSLMFKMEKILA
RASKAAGDNAMANQYETLANARQKGIEKYLWNDQQGWYADYDLKSHKVRN
QLTAAALFPLYVNAAAKDRANKMATATKTHLLQPGGLNTTSVKSGQQWDAP
NGWAPLQWVATEGLQNYGQKEVAMDISWHFLTNVQHTYDREKKLVEKYDV
STTGTGGGGEYPLQDGFGWTNGVTLKMLDLICPKEQPCDNVPATRPTVKS
ATTQPSTKEAQPTPHHHHHH SEQ ID NO: 24: HA-TreAN-HIS: N-terminally HA-tagged, C-
terminally HIS-tagged N-terminal fragment of TreA (w/o signal peptide)
```

-continued

SEQUENCES:

```
MAYPYDVPDYAVDEETPVTPQPPDILLGPLFNDVQNAKLFPDQKTFADAVPN
SDPLMILADYRMQQNQSGFDLRHFVNVNFTLPKEGEKYVPHHHHHH

SEQ ID NO: 25: HIS-TreAN-HA: N-terminally HIS-tagged, C-
terminally HA-tagged N-terminal fragment of TreA (w/o signal peptide)
MAHHHHHHEETPVTPQPPDILLGPLFNDVQNAKLFPDQKTFADAVPNSDPLM
ILADYRMQQNQSGFDLRHFVNVNFTLPKEGEKYVPGSYPYDVPDYA SEQ ID NO: 26: HA-TreAC-HIS: N-terminally HA-tagged, C-
terminally HIS-tagged C-terminal fragment of TreA
MAYPYDVPDYAVDNFTLPKEGEKYVPPEGQSLREHIDGLWPVLTRSTENTEK
WDSLLPLPEPYVVPGGRFREVYYWDSYFTMLGLAESGHWDKVADMVANFA
HEIDTYGHIPNGNRSYYLSRSQPPFFALMVELLAQHEGDAALKQYLPQMQKE
YAYWMDGVENLQAGQQEKRVVKLQDGTLLNRYWDDRDTPRPESWVEDIAT
AKSNPNRPATEIYRDLRSAAASGWDFSSRWMDNPQQLNTLRTTSIVPVDLNS
LMFKMEKILARASKAAGDNAMANQYETLANARQKGIEKYLWNDQQGWYADY
DLKSHKVRNQLTAAALFPLYVNAAAKDRANKMATATKTHLLQPGGLNTTSVK
SGQQWDAPNGWAPLQWVATEGLQNYGQKEVAMDISWHFLTNVQHTYDRE
KKLVEKYDVSTTGTGGG
GGEYPLQDGFGVVTNGVTLKMLDLICPKEQPCDNVPATRPTVKSATTQPSTKE
AQPTPHHHHHH SEQ ID NO: 27: HIS-TreAC-HA: N-terminally HIS-tagged, C-
terminally HA-tagged C-terminal fragment of TreA
MAHHHHHHNFTLPKEGEKYVPPEGQSLREHIDGLWPVLTRSTENTEKWDSL
LPLPEPYVVPGGRFREVYYWDSYFTMLGLAESGHWDKVADMVANFAHEIDT
YGHIPNGNRSYYLSRSQPPFFALMVELLAQHEGDAALKQYLPQMQKEYAYW
MDGVENLQAGQQEKRVVKLQDGTLLNRYWDDRDTPRPESWVEDIATAKSN
PNRPATEIYRDLRSAAASGWDFSSRWMDNPQQLNTLRTTSIVPVDLNSLMFK
MEKILARASKAAGDNAMANQYETLANARQKGIEKYLWNDQQGWYADYDLKS
HKVRNQLTAAALFPLYVNAAAKDRANKMATATKTHLLQPGGLNTTSVKSGQQ
WDAPNGWAPLQWVATEGLQNYGQKEVAMDISWHFLTNVQHTYDREKKLVE
KYDVSTTGTGGGGEYPLQDGFGVVTNGVTLKMLDLICPKEQPCDNVPATRP
TVKSATTQPSTKEAQPTPGSYPYDVPDYA SEQ ID NO: 28: HIS-TreAN-ProtG: N-terminally HIS-tagged N-
terminal fragment of TreA with C-terminal fusion with immunoglobulin binding
Domain B1 of protein G of Streptococcus
MAHHHHHHEETPVTPQPPDILLGPLFNDVQNAKLFPDQKTFADAVPNSDPLM
ILADYRMQQNQSGFDLRHFVNVNFTLPKEGEKYVPGSVPGS
TYKLILNGKTLKGETTTEAVDAATAEKVFKQYANDNGVDGEWTYDAATKTFTV
TE SEQ ID NO: 29: HIS-TreAC-ProtG: N-terminally HIS-tagged N-
terminal fragment of TreA with C-terminal fusion with immunoglobulin binding
Domain B1 of protein G of Streptococcus
MAHHHHHHNFTLPKEGEKYVPPEGQSLREHIDGLWPVLTRSTENTEKWDSL
LPLPEPYVVPGGRFREVYYWDSYFTMLGLAESGHWDKVADMVANFAHEIDT
YGHIPNGNRSYYLSRSQPPFFALMVELLAQHEGDAALKQYLPQMQKEYAYW
MDGVENLQAGQQEKRVVKLQDGTLLNRYWDDRDTPRPESWVEDIATAKSN
PNRPATEIYRDLRSAAASGWDFSSRWMDNPQQLNTLRTTSIVPVDLNSLMFK
MEKILARASKAAGDNAMANQYETLANARQKGIEKYLWNDQQGWYADYDLKS
HKVRNQLTAAALFPLYVNAAAKDRANKMATATKTHLLQPGGLNTTSVKSGQQ
WDAPNGWAPLQWVATEGLQNYGQKEVAMDISWHFLTNVQHTYDREKKLVE
KYDVSTTGTGGGGEYPLQDGFGWTNGVTLKMLDLICPKEQPCDNVPATRP
TVKSATTQPSTKEAQPTPGS
TYKLILNGKTLKGETTTEAVDAATAEKVFKQYANDNGVDGEWTYDAATKTFTV
TE SEQ ID NO: 30: HIVP24-TreAN-HIS: HIV capside protein P24
fused N-terminally to the N-terminal fragment of TreA (w/o signal peptide),
C-terminal HIS-tag
MEPIVQNIQGQMVHQAISPRTLNAWVKVVEEKAFSPEVIPMFSALSEGATPQD
LNTMLNTVGGHQAAMQMLKETINEEAAEWDRVHPVHAGPIAPGQMREPRGS
DIAGTTSTLQEQIGWMTNNPPIPVGEIYKRWIILGLNKIVRMYSPTSILDIRQGP
KEPFRDYVDRFYKTLRAEQASQEVKNAMTETLLVQNANPDCKTILKALGPAAT
LEEMMTACQGVGGPGHKARVLVDEETPVTPQPPDILLGPLFNDVQNAKLFPD
QKTFADAVPNSDPLMILADYRMQQNQSGFDLRHFVNVNFTLPKEGEKYVPH
HHHHH SEQ ID NO: 31: HIVP24-TreAC: HIV capside protein P24 fused
N-terminally to the C-terminal fragment of TreA, with C-terminal HIS-tag
MEPIVQNIQGQMVHQAISPRTLNAWVKVVEEKAFSPEVIPMFSALSEGATPQD
LNTMLNTVGGHQAAMQMLKETINEEAAEWDRVHPVHAGPIAPGQMREPRGS
DIAGTTSTLQEQIGWMTNNPPIPVGEIYKRWIILGLNKIVRMYSPTSILDIRQGP
KEPFRDYVDRFYKTLRAEQASQEVKNAMTETLLVQNANPDCKTILKALGPAAT
LEEMMTACQGVGGPGHKARVLVDNFTLPKEGEKYVPPEGQSLREHIDGLWP
```

SEQUENCES:

VLTRSTENTEKWDSLLPLPEPYVVPGGRFREVYYWDSYFTMLGLAESGHWD
KVADMVANFAHEIDTYGHIPNGNRSYYLSRSQPPFFALMVELLAQHEGDAAL
KQYLPQMQKEYAYWMDGVENLQAGQQEKRVVKLQDGTLLNRYWDDRDTP
RPESWVEDIATAKSNPNRPATEIYRDLRSAAASGWDFSSRWMDNPQQLNTL
RTTSIVPVDLNSLMFKMEKILARASKAAGDNAMANQYETLANARQKGIEKYLW
NDQQGWYADYDLKSHKVRNQLTAAALFPLYVNAAAKDRANKMATATKTHLL
QPGGLNTTSVKSGQQWDAPNGWAPLQWVATEGLQNYGQKEVAMDISWHF
LTNVQHTYDREKKLVEKYDVSTTGTGGGGGEYPLQDGFGWTNGVTLKMLDL
ICPKEQPCDNVPATRPTVKSATTQPSTKEAQPTPHHHHHH

SEQ ID NO 32: TreAN-pA: N-terminally HIS-tagged N-
terminus of TreA (w/o signal peptide) C-terminally fused with the
immunoglobulin binding domain of protein A
MAHHHHHHEETPVTPQPPDILLGPLFNDVQNAKLFPDQKTFADAVPNSDPLM
ILADYRMQQNQSGFDLRHFVNVNFTLPKEGEKYVPGSAMEEVTIKANLIFANG
STQTAEFKGTFEKATSEAYAYADTLKKDNGEWTVDVADKGYTLNIKFAG SEQ ID NO 33: TreAC-pA: N-terminally HIS-tagged C-
terminus of TreA (w/o signal peptide) C-terminally fused with the
immunoglobulin binding domain of protein A
MAHHHHHHNFTLPKEGEKYVPPEGQSLREHIDGLWPVLTRSTENTEKWDSL
LPLPEPYVVPGGRFREVYYWDSYFTMLGLAESGHWDKVADMVANFAHEIDT
YGHIPNGNRSYYLSRSQPPFFALMVELLAQHEGDAALKQYLPQMQKEYAYW
MDGVENLQAGQQEKRVVKLQDGTLLNRYWDDRDTPRPESWVEDIATAKSN
PNRPATEIYRDLRSAAASGWDFSSRWMDNPQQLNTLRTTSIVPVDLNSLMFK
MEKILARASKAAGDNAMANQYETLANARQKGVEKYLWNDQQGWYADYDLK
SHKVRNQLTAAALFPLYVNAAAKDRANKMATATKTHLLQPGGLNTTSVKSGQ
QWDAPNGWAPLQWVATEGLQNYGQKEVAMDISWHFLTNGQHTYDREKKLV
EKYDVSTTGTGGGGGEYPLQDGFGWTNGVTLKMLDLICPKEQPCDNVPATR
PTVKSATTQPSTKEAQPTPGSTADNKFNKEQQNAFYEILHLPNLNEEQRNGFI
QSLKDDPSQSANLLAEAKKLNDAQAPKA SEQ ID NO 34: TreAN-pL: N-terminally HIS-tagged N-
terminus of TreA (w/o signal peptide) C-terminally fused with the
immunoglobulin binding domain of protein L
MAHHHHHHEETPVTPQPPDILLGPLFNDVQNAKLFPDQKTFADAVPNSDPLM
ILADYRMQQNQSGFDLRHFVNVNFTLPKEGEKYVPGSTADNKFNKEQQNAF
YEILHLPNLNEEQRNGFIQSLKDDPSQSANLLAEAKKLNDAQAPKA SEQ ID NO 35: TreAC-pL: N-terminally HIS-tagged C-terminus of
TreA (w/o signal peptide) C-terminally fused with the immunoglobulin binding
domain of protein L
MAHHHHHHNFTLPKEGEKYVPPEGQSLREHIDGLWPVLTRSTENTEKWDSL
LPLPEPYVVPGGRFREVYYWDSYFTMLGLAESGHWDKVADMVANFAHEIDT
YGHIPNGNRSYYLSRSQPPFFALMVELLAQHEGDAALKQYLPQMQKEYAYW
MDGVENLQAGQQEKRVVKLQDGTLLNRYWDDRDTPRPESWVEDIATAKSN
PNRPATEIYRDLRSAAASGWDFSSRWMDNPQQLNTLRTTSIVPVDLNSLMFK
MEKILARASKAAGDNAMANQYETLANARQKGVEKYLWNDQQGWYADYDLK
SHKVRNQLTAAALFPLYVNAAAKDRANKMATATKTHLLQPGGLNTTSVKSGQ
QWDAPNGWAPLQWVATEGLQNYGQKEVAMDISWHFLTNGQHTYDREKKLV
EKYDVSTTGTGGGGGEYPLQDGFGWTNGVTLKMLDLICPKEQPCDNVPATR
PTVKSATTQPSTKEAQPTPGSAMEEVTIKANLIFANGSTQTAEFKGTFEKATS
EAYAYADTLKKDNGEWTVDVADKGYTLNIKFAG SEQ ID NO: 36: *Staphylococcus aureus* binding peptide SA5-1
VPHNPGLISLQG SEQ ID NO: 37: *Mycobacterium avium* subsp. *paratuberculosis*
binding peptide Mp3
NYVIHDVPRHPA SEQ ID NO: 38: complementary coiled-coil peptide with
leucine zipper motif Ei
EIAALEKEIAALEKENAALEWEIAALEK SEQ ID NO: 39: complementary coiled-coil peptide with
leucine zipper motif Ki
KIAALKEKIAALKEKNAALKWKIAALKE SEQ ID NO: 40: TreAN-SA: N-terminally HIS-tagged N-terminal
fragment of TreA with C-terminal fusion with *S. aureus* binding peptide
aptamer, SA5-1
MAHHHHHHEETPVTPQPPDILLGPLFNDVQNAKLFPDQKTFADAVPNSDPLM
ILADYRMQQNQSGFDLRHFVNVNFTLPKEGEKYVPGSVPHNPGLISLQG SEQ ID NO: 41: SA-TreAN: C-terminally HIS-tagged N-terminal
fragment of TreA with N-terminal fusion with *S. aureus* binding peptide -continued

SEQUENCES:

aptamer, SA5-1
MVPHNPGLISLQGVDEETPVTPQPPDILLGPLFNDVQNAKLFPDQKTFADAVP
NSDPLMILADYRMQQNQSGFDLRHFVNVNFTLPKEGEKYVPHHHHHH SEQ ID NO: 42: TreAC-SA: N-terminally HIS-tagged C-terminal
fragment of TreA with C-terminal fusion with S. aureus binding peptide
aptamer, SA5-1
MAHHHHHHNFTLPKEGEKYVPPEGQSLREHIDGLWPVLTRSTENTEKWDSL
LPLPEPYVVPGGRFREVYYWDSYFTMLGLAESGHWDKVADMVANFAHEIDT
YGHIPNGNRSYYLSRSQPPFFALMVELLAQHEGDAALKQYLPQMQKEYAYW
MDGVENLQAGQQEKRVVKLQDGTLLNRYWDDRDTPRPESWVEDIATAKSN
PNRPATEIYRDLRSAAASGWDFSSRWMDNPQQLNTLRTTSIVPVDLNSLMFK
MEKILARASKAAGDNAMANQYETLANARQKGIEKYLWNDQQGWYADYDLKS
HKVRNQLTAAALFPLYVNAAAKDRANKMATATKTHLLQPGGLNTTSVKSGQQ
WDAPNGWAPLQWVATEGLQNYGQKEVAMDISWHFLTNVQHTYDREKKLVE
KYDVSTTGTGGGGGEYPLQDGFGWTNGVTLKMLDLICPKEQPCDNVPATRP
TVKSATTQPSTKEAQPTPGSVPHNPGLISLQG SEQ ID NO: 43: SA-TreAC: C-terminally HIS-tagged C-terminal
fragment of TreA with N-terminal fusion with S. aureus binding peptide
aptamer, SA5-1
MVPHNPGLISLQGVDNFTLPKEGEKYVPPEGQSLREHIDGLWPVLTRSTENT
EKWDSLLPLPEPYVVPGGRFREVYYWDSYFTMLGLAESGHWDKVADMVAN
FAHEIDTYGHIPNGNRSYYLSRSQPPFFALMVELLAQHEGDAALKQYLPQMQ
KEYAYWMDGVENLQAGQQEKRVVKLQDGTLLNRYWDDRDTPRPESWVEDI
ATAKSNPNRPATEIYRDLRSAAASGWDFSSRWMDNPQQLNTLRTTSIVPVDL
NSLMFKMEKILARASKAAGDNAMANQYETLANARQKGIEKYLWNDQQGWYA
DYDLKSHKVRNQLTAAALFPLYVNAAAKDRANKMATATKTHLLQPGGLNTTS
VKSGQQWDAPNGWAPLQWVATEGLQNYGQKEVAMDISWHFLTNVQHTYD
REKKLVEKYDVSTTGTGGGGGEYPLQDGFGWTNGVTLKMLDLICPKEQPCD
NVPATRPTVKSATTQPSTKEAQPTPHHHHHH SEQ ID NO: 44: TreAN-Mp3: N-terminally HIS-tagged N-terminal
fragment of TreA with C-terminal fusion with M. avium subsp. paratuberculosis
binding peptide aptamer, Mp3
MAHHHHHHEETPVTPQPPDILLGPLFNDVQNAKLFPDQKTFADAVPNSDPLM
ILADYRMQQNQSGFDLRHFVNVNFTLPKEGEKYVPGSNYVIHDVPRHPA SEQ ID NO: 45: Mp3-TreAN: C-terminally HIS-tagged N-terminal
fragment of TreA with N-terminal fusion with M. avium subsp. paratuberculosis
binding peptide aptamer, Mp3
MGNYVIHDVPRHPAVDEETPVTPQPPDILLGPLFNDVQNAKLFPDQKTFADAV
PNSDPLMILADYRMQQNQSGFDLRHFVNVNFTLPKEGEKYVPHHHHHH SEQ ID NO: 46: TreAC-Mp3: N-terminally HIS-tagged C-terminal
fragment of TreA with C-terminal fusion with M. avium subsp. paratuberculosis
binding peptide aptamer, Mp3
MAHHHHHHNFTLPKEGEKYVPPEGQSLREHIDGLWPVLTRSTENTEKWDSL
LPLPEPYVVPGGRFREVYYWDSYFTMLGLAESGHWDKVADMVANFAHEIDT
YGHIPNGNRSYYLSRSQPPFFALMVELLAQHEGDAALKQYLPQMQKEYAYW
MDGVENLQAGQQEKRVVKLQDGTLLNRYWDDRDTPRPESWVEDIATAKSN
PNRPATEIYRDLRSAAASGWDFSSRWMDNPQQLNTLRTTSIVPVDLNSLMFK
MEKILARASKAAGDNAMANQYETLANARQKGIEKYLWNDQQGWYADYDLKS
HKVRNQLTAAALFPLYVNAAAKDRANKMATATKTHLLQPGGLNTTSVKSGQQ
WDAPNGWAPLQWVATEGLQNYGQKEVAMDISWHFLTNVQHTYDREKKLVE
KYDVSTTGTGGGGGEYPLQDGFGWTNGVTLKMLDLICPKEQPCDNVPATRP
TVKSATTQPSTKEAQPTPGSNYVIHDVPRHPA SEQ ID NO: 47: Mp3-TreAC: C-terminally HIS-tagged C-terminal
fragment of TreA with N-terminal fusion with M. avium subsp. paratuberculosis
binding peptide aptamer, Mp3
MGNYVIHDVPRHPAVDNFTLPKEGEKYVPPEGQSLREHIDGLWPVLTRSTEN
TEKWDSLLPLPEPYVVPGGRFREVYYWDSYFTMLGLAESGHWDKVADMVA
NFAHEIDTYGHIPNGNRSYYLSRSQPPFFALMVELLAQHEGDAALKQYLPQM
QKEYAYWMDGVENLQAGQQEKRVVKLQDGTLLNRYWDDRDTPRPESWVE
DIATAKSNPNRPATEIYRDLRSAAASGWDFSSRWMDNPQQLNTLRTTSIVPV
DLNSLMFKMEKILARASKAAGDNAMANQYETLANARQKGIEKYLWNDQQGW
YADYDLKSHKVRNQLTAAALFPLYVNAAAKDRANKMATATKTHLLQPGGLNT
TSVKSGQQWDAPNGWAPLQWVATEGLQNYGQKEVAMDISWHFLTNVQHTY
DREKKLVEKYDVSTTGTGGGGGEYPLQDGFGWTNGVTLKMLDLICPKEQPC
DNVPATRPTVKSATTQPSTKEAQPTPHHHHHH SEQ ID NO: 48: scFvLm-TreA-HIS: N-terminally HIS-tagged TreA
C-terminally fused with Listeria monocytogenes ActA protein specific single
chain fragment variable
MGKYLLPTAAAGLLLLAAQPAMAEVQLVESGGGVVQPGRSLRLSCAASGFAF
SSYGMHWVRQAPGKGLEWVAAISYDGSNKYYADSVKGRFTISRDNSKNTLY -continued

SEQUENCES:

```
LQMNSLRAEDTAVYYCARQADTKYFWGQGTLVTVSSGGGGSGGGGSGGSA
LSSELTQDPAVSVALGQTVRITCQGDSLRSYYASWYQQKPGQAPVLVIYGKN
NRPSGIPDRFSGSSSGNTASLTITGAQAEDEADYYCNSRDSSGNVFGGGTKL
TVLGAAAVDGGGSGGGSGGGETPVTPQPPDILLGPLFNDVQNAKLFPDQKT
FADAVPNSDPLMILADYRMQQNSGFDLRHFVNVNFTLPKEGEKYVPPEGQ
SLREHIDGLWPVLTRSTENTEKWDSLLPLPEPYVVPGGRFREVYYWDSYFTM
LGLAESGHWDKVADMVANFAHEIDTYGHIPNGNRSYYLSRSQPPFFALMVEL
LAQHEGDAALKQYLPQMQKEYAYWMDGVENLQAGQQEKRVVKLQDGTLLN
RYWDDRDTPRPESWVEDIATAKSNPNRPATEIYRDLRSAAASGWDFSSRWM
DNPQQLNTLRTTSIVPVDLNSLMFKMEKILARASKAAGDNAMANQYETLANA
RQKGIEKYLWNDQQGWYADYDLKSHKVRNQLTAAALFPLYVNAAAKDRANK
MATATKTHLLQPGGLNTTSVKSGQQWDAPNGWAPLQWVATEGLQNYGQKE
VAMDISWHFLTNVQHTYDREKKLVEKYDVSTTGTGGGGGEYPLQDGFGVVTN
GVTLKMLDLICPKEQPCDNVPATRPTVKSATTQPSTKEAQPTPHHHHHH
```

SEQ ID NO: 49: scFvLm-TreAN-HIS: N-terminally HIS-tagged N-
terminal fragment of TreA C-terminally fused with Listeria monocytogenes ActA
protein specific single chain fragment variable
```
MGKYLLPTAAAGLLLLAAQPAMAEVQLVESGGGWQPGRSLRLSCAASGFAF
SSYGMHWVRQAPGKGLEWVAAISYDGSNKYYADSVKGRFTIDNSKNTLY
LQMNSLRAEDTAVYYCARQADTKYFWGQGTLVTVSSGGGGSGGGGSGGSA
LSSELTQDPAVSVALGQTVRITCQGDSLRSYYASVVYQQKPGQAPVLVIYGKN
NRPSGIPDRFSGSSSGNTASLTITGAQAEDEADYYCNSRDSSGNVFGGGTKL
TVLGAAAVDEETPVTPQPPDILLGPLFNDVQNAKLFPDQKTFADAVPNSDPLM
ILADYRMQQNSGFDLRHFVNVNFTLPKEGEKYVPHHHHHH
```

SEQ ID NO: 50: scFvLm-TreAC-HIS: N-terminally HIS-tagged C-
terminal fragment of TreA C-terminally fused with Listeria monocytogenes ActA
protein specific single chain fragment variable
```
MGKYLLPTAAAGLLLLAAQPAMAEVQLVESGGGWQPGRSLRLSCAASGFAF
SSYGMHWVRQAPGKGLEWVAAISYDGSNKYYADSVKGRFTISRDNSKNTLY
LQMNSLRAEDTAVYYCARQADTKYFWGQGTLVTVSSGGGGSGGGGSGGSA
LSSELTQDPAVSVALGQTVRITCQGDSLRSYYASVVYQQKPGQAPVLVIYGKN
NRPSGIPDRFSGSSSGNTASLTITGAQAEDEADYYCNSRDSSGNVFGGGTKL
TVLGAAAVDNFTLPKEGEKYVPPEGQSLREHIDGLWPVLTRSTENTEKWDSL
LPLPEPYVVPGGRFREVYYWDSYFTMLGLAESGHWDKVADMVANFAHEIDT
YGHIPNGNRSYYLSRSQPPFFALMVELLAQHEGDAALKQYLPQMQKEYAYW
MDGVENLQAGQQEKRVVKLQDGTLLNRYWDDRDTPRPESWVEDIATAKSN
PNRPATEIYRDLRSAAASGWDFSSRWMDNPQQLNTLRTTSIVPVDLNSLMFK
MEKILARASKAAGDNAMANQYETLANARQKGIEKYLWNDQQGWYADYDLKS
HKVRNQLTAAALFPLYVNAAAKDRANKMATATKTHLLQPGGLNTTSVKSGQQ
WDAPNGWAPLQWVATEGLQNYGQKEVAMDISWHFLTNVQHTYDREKKLVE
KYDVSTTGTGGGGGEYPLQDGFGWTNGVTLKMLDLICPKEQPCDNVPATRP
TVKSATTQPSTKEAQPTPHHHHHH
```

SEQ ID NO: 51: HIS-TreAN-ATPase: N-terminally HIS-tagged N-
terminal fragment of TreA C-terminally fused with the ATP synthase epsilon
subunit of Geobacillus
```
MAHHHHHHEETPVTPQPPDILLGPLFNDVQNAKLFPDQKTFADAVPNSDPLM
ILADYRMQQNSGFDLRHFVNVNFTLPKEGEKYVPGSKTIHVSVVTPDGPVY
EDDVEMVSVKAKSGELGILPGHIPLVAPLEISAARLKKGGKTQYIAVSGGFLEV
RPDNVTILAQAAERAEDIDVLRAKARKSGRTPLQSQQDDIDFKRAELALKRAM
NRLSVAEMK
```

SEQ ID NO: 52: HIS-TreAC-ATPase: N-terminally HIS-tagged C-
terminal fragment of TreA C-terminally fused with the ATP synthase epsilon
subunit of Geobacillus
```
MAHHHHHHNFTLPKEGEKYVPPEGQSLREHIDGLWPVLTRSTENTEKWDSL
LPLPEPYVVPGGRFREVYYWDSYFTMLGLAESGHWDKVADMVANFAHE1DT
YGHIPNGNRSYYLSRSQPPFFALMVELLAQHEGDAALKQYLPQMQKEYAYW
MDGVENLQAGQQEKRVVKLQDGTLLNRYWDDRDTPRPESWVEDIATAKSN
PNRPATEIYRDLRSAAASGWDFSSRWMDNPQQLNTLRTTSIVPVDLNSLMFK
MEKILARASKAAGDNAMANQYETLANARQKGIEKYLWNDQQGWYADYDLKS
HKVRNQLTAAALFPLYVNAAAKDRANKMATATKTHLLQPGGLNTTSVKSGQQ
WDAPNGWAPLQWVATEGLQNYGQKEVAMDISWHFLTNVQHTYDREKKLVE
KYDVSTTGTGGGGGEYPLQDGFGWTNGVTLKMLDLICPKEQPCDNVPATRP
TVKSATTQPSTKEAQPTPGSKTIHVSVVTPDGPVYEDDVEMVSVKAKSGELGI
LPGHIPLVAPLEISAARLKKGGKTQYIAVSGGFLEVRPDNVTILAQAAERAEDID
VLRAKARKSGRTPLQSQQDDIDFKRAELALKRAMNRLSVAEMK
```

SEQ ID NO: 53: HIS-TreAN-KI: N-terminally HIS-tagged N-
terminal fragment of TreA with C-terminal fusion with leucine zipper 1
```
MAHHHHHHEETPVTPQPPDILLGPLFNDVQNAKLFPDQKTFADAVPNSDPLM
ILADYRMQQNSGFDLRHFVNVNFTLPKEGEKYVPGSVPGSKIAALKEKIAAL
KEKNAALKWKIAALKE
```

SEQ ID NO: 54: HIS-TreAC-EI: N-terminally HIS-tagged N-

SEQUENCES:

terminal fragment of TreA with C-terminal fusion leucine zipper 2
MAHHHHHHNFTLPKEGEKYVPPEGQSLREHIDGLWPVLTRSTENTEKWDSL
LPLPEPYVVPGGRFREVYYWDSYFTMLGLAESGHWDKVADMVANFAHEIDT
YGHIPNGNRSYYLSRSQPPFFALMVELLAQHEGDAALKQYLPQMQKEYAYW
MDGVENLQAGGQEKRVVKLQDGTLLNRYWDDRDTPRPESWVEDIATAKSN
PNRPATEIYRDLRSAAASGWDFSSRWMDNPQQLNTLRTTSIVPVDLNSLMFK
MEKILARASKAAGDNAMANQYETLANARQKGIEKYLWNDQQGWYADYDLKS
HKVRNQLTAAALFPLYVNAAAKDRANKMATATKTHLLQPGGLNTTSVKSGQQ
WDAPNGWAPLQWVATEGLQNYGQKEVAMDISWHFLTNVQHTYDREKKLVE
KYDVSTTGTGGGGGEYPLQDGFGWTNGVTLKMLDLICPKEQPCDNVPATRP
TVKSATTQPSTKEAQPTPGSEIAALEKEIAALEKENAALEWEIAALEK SEQ ID NO: 55: HIS-TreAN-EI: N-terminally HIS-tagged N-
terminal fragment of TreA with C-terminal fusion with leucine zipper 1
MAHHHHHHEETPVTPQPPDILLGPLFNDVQNAKLFPDQKTFADAVPNSDPLM
ILADYRMQQNQSGFDLRHFVNVNFTLPKEGEKYVPGSVPGSEIAALEKEIAAL
EKENAALEWEIAALEK SEQ ID NO: 56: HIS-TreAC-KI: N-terminally HIS-tagged N-
terminal fragment of TreA with C-terminal fusion leucine zipper 2
MAHHHHHHNFTLPKEGEKYVPPEGQSLREHIDGLWPVLTRSTENTEKWDSL
LPLPEPYVVPGGRFREVYYWDSYFTMLGLAESGHWDKVADMVANFAHEIDT
YGHIPNGNRSYYLSRSQPPFFALMVELLAQHEGDAALKQYLPQMQKEYAYW
MDGVENLQAGGQEKRVVKLQDGTLLNRYWDDRDTPRPESWVEDIATAKSN
PNRPATEIYRDLRSAAASGWDFSSRWMDNPQQLNTLRTTSIVPVDLNSLMFK
MEKILARASKAAGDNAMANQYETLANARQKGIEKYLWNDQQGWYADYDLKS
HKVRNQLTAAALFPLYVNAAAKDRANKMATATKTHLLQPGGLNTTSVKSGQQ
WDAPNGWAPLQWVATEGLQNYGQKEVAMDISWHFLTNVQHTYDREKKLVE
KYDVSTTGTGGGGGEYPLQDGFGWTNGVTLKMLDLICPKEQPCDNVPATRP
TVKSATTQPSTKEAQPTPGSKIAALKEKIAALKEKNAALKWKIAALKE SEQ ID NO: 57: rPrP-TreA-HIS: C-terminally HIS-tagged TreA N-
terminally fused with bank vole prion protein
MGKKRPKPGGWNTGGSRYPGQGSPGGNRYPPQGGGTWGQPHGGGWGQ
PHGGGWGQPHGGGWGQPHGGGWGQGGGTHNQWNKPSKPKTNMKHVAG
AAAAGAVVGGLGGYMLGSAMSRPMIHFGNDWEDRYYRENMNRYPNQVYYR
PVDQYNNQNNFVHDCVNITIKQHTVTTTTKGENFTETDVKMMERVVEQMCVT
QYQKESQAYYEGRSVDGGGSGGGSGGGETPVTPQPPDILLGPLFNDVQNA
KLFPDQKTFADAVPNSDPLMILADYRMQQNQSGFDLRHFVNVNFTLPKEGEK
YVPPEGQSLREHIDGLWPVLTRSTENTEKWDSLLPLPEPYVVPGGRFREVYY
WDSYFTMLGLAESGHWDKVADMVANFAHEIDTYGHIPNGNRSYYLSRSQPP
FFALMVELLAQHEGDAALKQYLPQMQKEYAYWMDGVENLQAGQQEKRVVK
LQDGTLLNRYWDDRDTPRPESWVEDIATAKSNPNRPATEIYRDLRSAAASG
WDFSSRWMDNPQQLNTLRTTSIVPVDLNSLMFKMEKILARASKAAGDNAMA
NQYETLANARQKGIEKYLWNDQQGWYADYDLKSHKVRNQLTAAALFPLYVN
AAAKDRANKMATATKTHLLQPGGLNTTSVKSGQQWDAPNGWAPLQWVATE
GLQNYGQKEVAMDISWHFLTNVQHTYDREKKLVEKYDVSTTGTGGGGGEYP
LQDGFGWTNGVTLKMLDLICPKEQPCDNVPATRPTVKSATTQPSTKEAQPTP
HHHHHH SEQ ID NO: 58: rPrP-TreAN-HIS: C-terminally HIS-tagged N-
terminal fragment of TreA N-terminally fused with bank vole prion protein
MGKKRPKPGGWNTGGSRYPGQGSPGGNRYPPQGGGTWGQPHGGGWGQ
PHGGGWGQPHGGGWGQPHGGGWGQGGGTHNQWNKPSKPKTNMKHVAG
AAAAGAVVGGLGGYMLGSAMSRPMIHFGNDWEDRYYRENMNRYPNQVYYR
PVDQYNNQNNFVHDCVNITIKQHTVTTTTKGENFTETDVKMMERVVEQMCVT
QYQKESQAYYEGRSVDGGGSGGGSGGGEETPVTPQPPDILLGPLFNDVQN
AKLFPDQKTFADAVPNSDPLMILADYRMQQNQSGFDLRHFVNVNFTLPKEGE
KYVPHHHHHH SEQ ID NO: 59: rPrP-TreAC-HIS: C-terminally HIS-tagged C-
terminal fragment of TreA N-terminally fused with bank vole prion protein
MGKKRPKPGGWNTGGSRYPGQGSPGGNRYPPQGGGTWGQPHGGGWGQ
PHGGGWGQPHGGGWGQPHGGGWGQGGGTHNQWNKPSKPKTNMKHVAG
AAAAGAVVGGLGGYMLGSAMSRPMIHFGNDWEDRYYRENMNRYPNQVYYR
PVDQYNNQNNFVHDCVNITIKQHTVTTTTKGENFTETDVKMMERVVEQMCVT
QYQKESQAYYEGRSVDNFTLPKEGEKYVPPEGQSLREHIDGLWPVLTRSTE
NTEKWDSLLPLPEPYVVPGGRFREVYYWDSYFTMLGLAESGHWDKVADMV
ANFAHEIDTYGHIPNGNRSYYLSRSQPPFFALMVELLAQHEGDAALKQYLPQ
MQKEYAYWMDGVENLQAGQQEKRVVKLQDGTLLNRYWDDRDTPRPESWV
EDIATAKSNPNRPATEIYRDLRSAAASGWDFSSRWMDNPQQLNTLRTTSIVP
VDLNSLMFKMEKILARASKAAGDNAMANQYETLANARQKGIEKYLWNDQQG
WYADYDLKSHKVRNQLTAAALFPLYVNAAAKDRANKMATATKTHLLQPGGLN
TTSVKSGQQWDAPNGWAPLQWVATEGLQNYGQKEVAMDISWHFLTNVQHT
YDREKKLVEKYDVSTTGTGGGGGEYPLQDGFGWTNGVTLKMLDLICPKEQP
CDNVPATRPTVKSATTQPSTKEAQPTPHHHHHH

SEQUENCES:

SEQ ID NO: 60: HIS-TreAcwE: N-terminally HIS-tagged TreA with OWE scar in linker region
MAHHHHHHEETPVTPQPPDILLGPLFNDVQNAKLFPDQKTFADAVPNSDPLM
ILADYRMQQNQSGFDLRHFVNVNFTLPKECWEKYVPPEGQSLREHIDGLWP
VLTRSTENTEKWDSLLPLPEPYVVPGGRFREVYYWDSYFTMLGLAESGHWD
KVADMVANFAHEIDTYGHIPNGNRSYYLSRSQPPFFALMVELLAQHEGDAAL
KQYLPQMQKEYAYWMDGVENLQAGQQEKRVVKLQDGTLLNRYWDDRDTP
RPESWVEDIATAKSNPNRPATEIYRDLRSAAASGWDFSSRWMDNPQQLNTL
RTTSIVPVDLNSLMFKMEKILARASKAAGDNAMANQYETLANARQKGIEKYLW
NDQQGWYADYDLKSHKVRNQLTAAALFPLYVNAAAKDRANKMATATKTHLL
QPGGLNTTSVKSGQQWDAPNGWAPLQWVATEGLQNYGQKEVAMDISWHF
LTNVQHTYDREKKLVEKYDVSTTGTGGGGGEYPLQDGFGWTNGVTLKMLDL
ICPKEQPCDNVPATRPTVKSATTQPSTKEAQPTP SEQ ID NO: 61: TreAN-IntN: N-terminally HIS-tagged N-terminal fragment of TreA N-terminally fused N-terminal fragment of the split intein DnaE of Nostoc punctiforme
MAHHHHHHEETPVTPQPPDILLGPLFNDVQNAKLFPDQKTFADAVPNSDPLM
ILADYRMQQNQSGFDLRHFVNVNFTLPKECLSYETEILTVEYGLLPIGKIVEKRI
ECTVYSVDNNGNIYTQPVAQWHDRGEQEVFEYCLEDGSLIRATKDHKFMTV
DGQMLPIDEIFERELDLMRVDNLPNGSGGKL SEQ ID NO: 62: IntC-TreAC: C-terminally HIS-tagged C-terminal fragment of TreA N-terminally fused C-terminal fragment of the split intein DnaE of Nostoc punctiforme
MAASGGTSIKIATRKYLGKQNVYDIGVERDHNFALKNGFIASNCWEKYVPPEG
QSLREHIDGLWPVLTRSTENTEKWDSLLPLPEPYVVPGGRFREVYYWDSYFT
MLGLAESGHWDKVADMVANFAHEIDTYGHIPNGNRSYYLSRSQPPFFALMVE
LLAQHEGDAALKQYLPQMQKEYAYWMDGVENLQAGQQEKRVVKLQDGTLL
NRYWDDRDTPRPESWVEDIATAKSNPNRPATEIYRDLRSAAASGWDFSSRW
MDNPQQLNTLRTTSIVPVDLNSLMFKMEKILARASKAAGDNAMANQYETLAN
ARQKGIEKYLWNDQQGWYADYDLKSHKVRNQLTAAALFPLYVNAAAKDRAN
KMATATKTHLLQPGGLNTTSVKSGQQWDAPNGWAPLQWVATEGLQNYGQK
EVAMDISWHFLTNVQHTYDREKKLVEKYDVSTTGTGGGGGEYPLQDGFGWT
NGVTLKMLDLICPKEQPCDNVPATRPTVKSATTQPSTKEAQPTPHHHHHH SEQ ID NO: 63: ER-TreAN-HIS: C-terminally HIS-tagged N-terminal fragment of TreA N-terminally fused with human estradiol receptor fragment
MGKRSKKNSLALSLTADQMVSALLDAEPPILYSEYDPTRPFSEASMMGLLTNL
ADRELVHMINWAKRVPGFVDLTLHDQVHLLESAWLEILMIGLVWRSMEHPGK
LLFAPNLLLDRNQGKSVEGMVEIFDMLLATSSRFRMMNLQGEEFVCLKSIILLN
SGVYTFLSSTLKSLEEKDHIHRVLDKITDTLIHLMAKAGLTLQQQHQRLAQLLLI
LSHIRHMSNKGMEHLYSMKSKNGGSGVDEETPVTPQPPDILLGPLFNDVQNA
KLFPDQKTFADAVPNSDPLMILADYRMQQNQSGFDLRHFVNVNFTLPKEGEK
YVPHHHHHH SEQ ID NO: 64: ER-TreAC-HIS: C-terminally HIS-tagged C-terminal fragment of TreA N-terminally fused with human estradiol receptor fragment
MGKRSKKNSLALSLTADQMVSALLDAEPPILYSEYDPTRPFSEASMMGLLTNL
ADRELVHMINWAKRVPGFVDLTLHDQVHLLESAWLEILMIGLVWRSMEHPGK
LLFAPNLLLDRNQGKSVEGMVEIFDMLLATSSRFRMMNLQGEEFVCLKSIILLN
SGVYTFLSSTLKSLEEKDHIHRVLDKITDTLIHLMAKAGLTLQQQHQRLAQLLLI
LSHIRHMSNKGMEHLYSMKSKNGGSGVDNFTLPKEGEKYVPPEGQSLREHI
DGLWPVLTRSTENTEKWDSLLPLPEPYVPGGRFREVYYWDSYFTMLGLAE
SGHWDKVADMVANFAHEIDTYGHIPNGNRSYYLSRSQPPFFALMVELLAQHE
GDAALKQYLPQMQKEYAYWMDGVENLQAGQQEKRVVKLQDGTLLNRYWD
DRDTPRPESWVEDIATAKSNPNRPATEIYRDLRSAAASGWDFSSRWMDNPQ
QLNTLRTTSIVPVDLNSLMFKMEKILARASKAAGDNAMANQYETLANARQKGI
EKYLWNDQQGWYADYDLKSHKVRNQLTAAALFPLYVNAAAKDRANKMATAT
KTHLLQPGGLNTTSVKSGQQWDAPNGWAPLQWVATEGLQNYGQKEVAMDI
SWHFLTNVQHTYDREKKLVEKYDVSTTGTGGGGGEYPLQDGFGWTNGVTL
KMLDLICPKEQPCDNVPATRPTVKSATTQPSTKEAQPTPHHHHHH SEQ ID NO: 65: IFNGRA-TreAN-HIS: C-terminally HIS-tagged N-terminal fragment of TreA N-terminally fused with bovine interferon-gamma receptor A fragment
MASAIPGLSSVPPPTNVTIQAYNLNTVIFWDYPVILQSPMFTVQVMNYEDGKW
IDACNTSDHSCNIFSVINDPSSSVWGRVKVRVGQEESVYAQSKEFILCKEGKV
GPPKLGIRKKENQIIVDIFHPLITVNGKEPEAMYDDENTCYTFTYSVFVSINRSE
TTDKMYTKEEDCNETQCFLNIPVSSLNSQYCVSAEGVSELWAVTTEKSDELCI
TFSVDEETPVTPQPPDILLGPLFNDVQNAKLFPDQKTFADAVPNSDPLMILAD
YRMQQNQSGFDLRHFVNVNFTLPKEGEKYVPHHHHHH SEQ ID NO: 66: IFNGRA-TreAC-HIS: C-terminally HIS-tagged C-terminal fragment of TreA N-terminally fused with bovine interferon-gamma receptor A fragment
MASAIPGLSSVPPPTNVTIQAYNLNTVIFWDYPVILQSPMFTVQVMNYEDGKW
IDACNTSDHSCNIFSVINDPSSSVWGRVKVRVGQEESVYAQSKEFILCKEGKV
GPPKLGIRKKENQIIVDIFHPLITVNGKEPEAMYDDENTCYTFTYSVFVSINRSE
TTDKMYTKEEDCNETQCFLNIPVSSLNSQYCVSAEGVSELWAVTTEKSDELCI
TFSVDNFTLPKEGEKYVPPEGQSLREHIDGLWPVLTRSTENTEKWDSLLPLP
EPYVVPGGRFREVYYWDSYFTMLGLAESGHWDKVADMVANFAHEIDTYGHI
PNGNRSYYLSRSQPPFFALMVELLAQHEGDAALKQYLPQMQKEYAYWMDG
VENLQAGQQEKRVVKLQDGTLLNRYWDDRDTPRPESWVEDIATAKSNPNRP
ATEIYRDLRSAAASGWDFSSRWMDNPQQLNTLRTTSIVPVDLNSLMFKMEKIL
ARASKAAGDNAMANQYETLANARQKGIEKYLWNDQQGWYADYDLKSHKVR
NQLTAAALFPLYVNAAAKDRANKMATATKTHLLQPGGLNTTSVKSGQQWDA
PNGWAPLQWVATEGLQNYGQKEVAMDISWHFLTNVQHTYDREKKLVEKYD
VSTTGTGGGGEYPLQDGFGWTNGVTLKMLDLICPKEQPCDNVPATRPTVK
SATTQPSTKEAQPTPHHHHHH SEQ ID NO 67: Ab-TreA-HIS: C-terminally HIS-tagged TreA with
N-terminal fusion with Amyloid beta p42 peptide
MDAEFRHDSGYEVHHQKLVFFAEDVGSNKGAIIGLMVGGVVIAVDGGGSGG
GSGGGGETPVTPQPPDILLGPLFNDVQNAKLFPDQKTFADAVPNSDPLMILADY
RMQQNQSGFDLRHFVNVNFTLPKEGEKYVPPEGQSLREHIDGLWPVLTRST
ENTEKWDSLLPLPEPYVVPGGRFREVYYWDSYFTMLGLAESGHWDKVADM
VANFAHEIDTYGHIPNGNRSYYLSRSQPPFFALMVELLAQHEGDAALKQYLPQ
MQKEYAYWMDGVENLQAGQQEKRVVKLQDGTLLNRYWDDRDTPRPESWV
EDIATAKSNPNRPATEIYRDLRSAAASGWDFSSRWMDNPQQLNTLRTTSIVP
VDLNSLMFKMEKILARASKAAGDNAMANQYETLANARQKGIEKYLWNDQQG
WYADYDLKSHKVRNQLTAAALFPLYVNAAAKDRANKMATATKTHLLQPGGLN
TTSVKSGQQWDAPNGWAPLQWVATEGLQNYGQKEVAMDISWHFLTNVQHT
YDREKKLVEKYDVSTTGTGGGGEYPLQDGFGVVTNGVTLKMLDLICPKEQP
CDNVPATRPTVKSATTQPSTKEAQPTPHHHHHH SEQ ID NO 68: Ab-TreAN-HIS: C-terminally HIS-tagged N-
terminal fragment of TreA with N-terminal fusion with Amyloid beta p42 peptide
MDAEFRHDSGYEVHHQKLVFFAEDVGSNKGAIIGLMVGGVVIAVDEETPVTP
QPPDILLGPLFNDVQNAKLFPDQKTFADAVPNSDPLMILADYRMQQNQSGFD
LRHFVNVNFTLPKEGEKYVPHHHHHH SEQ ID NO 69: Ab-TreAC-HIS: C-terminally HIS-tagged C-
terminal fragment of TreA with N-terminal fusion with Amyloid beta p42 peptide
MDAEFRHDSGYEVHHQKLVFFAEDVGSNKGAIIGLMVGGVVIAVDNFTLPKE
GEKYVPPEGQSLREHIDGLWPVLTRSTENTEKWDSLLPLPEPYVVPGGRFRE
VYYWDSYFTMLGLAESGHWDKVADMVANFAHEIDTYGHIPNGNRSYYLSRS
QPPFFALMVELLAQHEGDAALKQYLPQMQKEYAYWMDGVENLQAGQQEKR
VVKLQDGTLLNRYWDDRDTPRPESWVEDIATAKSNPNRPATEIYRDLRSAAA
SGWDFSSRWMDNPQQLNTLRTTSIVPVDLNSLMFKMEKILARASKAAGDNA
MANQYETLANARQKGIEKYLWNDQQGWYADYDLKSHKVRNQLTAAALFPLY
VNAAAKDRANKMATATKTHLLQPGGLNTTSVKSGQQWDAPNGWAPLQWVA
TEGLQNYGQKEVAMDISWHFLTNVQHTYDREKKLVEKYDVSTTGTGGGGE
YPLQDGFGWTNGVTLKMLDLICPKEQPCDNVPATRPTVKSATTQPSTKEAQP
TPHHHHHH SEQ ID NO 70: GDH-HIS-TreA: Glucose dehydrogenase N-
terminally fused to the TreA (w/o signal peptide) with flexible linker and
HIS-tag in between GDH and TreA
MAGKYLLPTAAAGLLLLAAQPAMADVPLTPSQFAKAKSENFDKKVILSNLNKP
HALLWGPDNQIWLTERATGKILRVNPESGSVKTVFQVPEIVNDADGQNGLLG
FAFHPRFKNNPYIYISGTFKNPKSTDKELPNQTIIRRYTYKKKTDTLEKPVDLLA
GLPSSKDHQGGRLVIGPDQKIYYTIGDQGRNQFAGLFLPNQAQHTPTQQELN
GKDYHTYMGKVLRLNLDGSIPKDNPSFNGVVSHIYTLGHRNPQGLAFTPNGK
LLQSDHGPNSDDEINLIVKGGNYGWPNVAGYKDDSGYAYANYSAAANKSIKD
LAQNGLKVAAGVPVTKESEWTGKNFVPPLKTLYTVQDTYNYNDPTCGEVTYI
CWPSVAPSSAYVYKGGKKAITGWENTLLVPSLKRGVIFRIKFDPTYSTTYDDA
VPMFKSNNRYRDVIASPDGNVLYVLTDTAGNPVQKDDGSPTNTLENPGSLIK
FTYKAKGGKGGSGGSSYAHHHHHHEETPVTPQPPDILLGPLFNDVQNAKLFP
DQKTFADAVPNSDPLMILADYRMQQNQSGFDLRHFVNVNFTLPKEGEKYVPP
EGQSLREHIDGLWPVLTRSTENTEKWDSLLPLPEPYVVPGGRFREVYYWDS
YFTMLGLAESGHWDKVADMVANFAHEIDTYGHIPNGNRSYYLSRSQPPFFAL
MVELLAQHEGDAALKQYLPQMQKEYAYWMDGVENLQAGQQEKRVVKLQDG
TLLNRYWDDRDTPRPESWVEDIATAKSNPNRPATEIYRDLRSAAASGWDFSS
RWMDNPQQLNTLRTTSIVPVDLNSLMFKMEKILARASKAAGDNAMANQYETL
ANARQKGIEKYLWNDQQGWYADYDLKSHKVRNQLTAAALFPLYVNAAAKDR
ANKMATATKTHLLQPGGLNTTSVKSGQQWDAPNGWAPLQWVATEGLQNYG
QKEVAMDISWHFLTNVQHTYDREKKLVEKYDVSTTGTGGGGEYPLQDGFG
WTNGVTLKMLDLICPKEQPCDNVPATRPTVKSATTQPSTKEAQPTP SEQ ID NO 71: GDH-HIS-TreAN-EI: Glucose dehydrogenase N-
terminally, and leucine zipper peptide EI C-terminally fused to the N-terminal

SEQUENCES:

fragment of TreAN (w/o signal peptide), which with flexible linker and HIS-tag in between GDH and TreAN
MAGKYLLPTAAAGLLLLAAQPAMADVPLTPSQFAKAKSENFDKKVILSNLNKPHALLW
GPDNQIWLTERATGKILRVNPESGSVKTVFQVPEIVNDADGQNGLLGFAFHPRFKNN
PYIYISGTFKNPKSTDKELPNQTIIRRYTYKKKTDTLEKPVDLLAGLPSSKDHQGGRLVI
GPDQKIYYTIGDQGRNQFAGLFLPNQAQHTPTQQELNGKDYHTYMGKVLRLNLDGSI
PKDNPSFNGVVSHIYTLGHRNPQGLAFTPNGKLLQSDHGPNSDDEINLIVKGGNYGW
PNVAGYKDDSGYAYANYSAAANKSIKDLAQNGLKVAAGVPVTKESEWTGKNFVPPL
KTLYTVQDTYNYNDPTCGEVTYICWPSVAPSSAYVYKGGKKAITGWENTLLVPSLKR
GVIFRIKFDPTYSTTYDDAVPMFKSNNRYRDVIASPDGNVLYVLTDTAGNPVQKDDGS
PTNTLENPGSLIKFTYKAKGGKGGSGGSSYAHHHHHHEETPVTPQPPDILLGPLFND
VQNAKLFPDQKTFADAVPNSDPLMILADYRMQQNQSGFDLRHFVNVNFTLPKEGEK
YVPGSEIAALEKEIAALEKENAALEWEIAALEK SEQ ID NO 72: GDH-HIS-TreAN-KI: Glucose dehydrogenase N-
terminally, and leucine zipper peptide KI C-terminally fused to the N-terminal
fragment of TreAN (w/o signal peptide), which with flexible linker and HIS-tag
in between GDH and TreAN
MAGKYLLPTAAAGLLLLAAQPAMADVPLTPSQFAKAKSENFDKKVILSNLNKP
HALLWGPDNQIWLTERATGKILRVNPESGSVKTVFQVPEIVNDADGQNGLLG
FAFHPRFKNNPYIYISGTFKNPKSTDKELPNQTIIRRYTYKKKTDTLEKPVDLLA
GLPSSKDHQGGRLVIGPDQKIYYTIGDQGRNQFAGLFLPNQAQHTPTQQELN
GKDYHTYMGKVLRLNLDGSIPKDNPSFNGVVSHIYTLGHRNPQGLAFTPNGK
LLQSDHGPNSDDEINLIVKGGNYGWPNVAGYKDDSGYAYANYSAAANKSIKD
LAQNGLKVAAGVPVTKESEVVTGKNFVPPLKTLYTVQDTYNYNDPTCGEVTYI
CWPSVAPSSAYVYKGGKKAITGWENTLLVPSLKRGVIFRIKFDPTYSTTYDDA
VPMFKSNNRYRDVIASPDGNVLYVLTDTAGNPVQKDDGSPTNTLENPGSLIK
FTYKAKGGKGGSGGSSYAHHHHHHEETPVTPQPPDILLGPLFNDVQNAKLFP
DQKTFADAVPNSDPLMILADYRMQQNQSGFDLRHFVNVNFTLPKEGEKYVP
GSKIAALKEKIAALKEKNAALKWKIAALKE SEQ ID NO 73: GDH-HIS-TreAN-pG: Glucose
dehydrogenase N-terminally, and the immunoglobulin binding domain Domain
B1 of protein G C-terminally fused to the N-terminal fragment of TreAN (w/o
signal peptide), which with flexible linker and HIS-tag in between GDH and
TreAN
MAGKYLLPTAAAGLLLLAAQPAMADVPLTPSQFAKAKSENFDKKVILSNLNKP
HALLWGPDNQIWLTERATGKILRVNPESGSVKTVFQVPEIVNDADGQNGLLG
FAFHPRFKNNPYIYISGTFKNPKSTDKELPNQTIIRRYTYKKKTDTLEKPVDLLA
GLPSSKDHQGGRLVIGPDQKIYYTIGDQGRNQFAGLFLPNQAQHTPTQQELN
GKDYHTYMGKVLRLNLDGSIPKDNPSFNGVVSHIYTLGHRNPQGLAFTPNGK
LLQSDHGPNSDDEINLIVKGGNYGWPNVAGYKDDSGYAYANYSAAANKSIKD
LAQNGLKVAAGVPVTKESEWTGKNFVPPLKTLYTVQDTYNYNDPTCGEVTYI
CWPSVAPSSAYVYKGGKKAITGWENTLLVPSLKRGVIFRIKFDPTYSTTYDDA
VPMFKSNNRYRDVIASPDGNVLYVLTDTAGNPVQKDDGSPTNTLENPGSLIK
FTYKAKGGKGGSGGSSYAHHHHHHEETPVTPQPPDILLGPLFNDVQNAKLFP
DQKTFADAVPNSDPLMILADYRMQQNQSGFDLRHFVNVNFTLPKEGEKYVP
GSTYKLILNGKTLKGETTTEAVDAATAEKVFKQYANDNGVDGEWTYDAATKT
FTVTE SEQ ID NO 74: GDH-HIS-TreAN-pA: Glucose
dehydrogenase N-terminally, and the immunoglobulin binding domain Domain
B1 of protein G C-terminally fused to the N-terminal fragment of TreAN (w/o
signal peptide), which with flexible linker and HIS-tag in between GDH and
TreAN
MADVPLTPSQFAKAKSENFDKKVILSNLNKPHALLWGPDNQIWLTERATGKIL
RVNPESGSVKTVFQVPEIVNDADGQNGLLGFAFHPRFKNNPYIYISGTFKNPK
STDKELPNQTIIRRYTYKKKTDTLEKPVDLLAGLPSSKDHQGGRLVIGPDQKIY
YTIGDQGRNQFAGLFLPNQAQHTPTQQELNGKDYHTYMGKVLRLNLDGSIPK
DNPSFNGVVSHIYTLGHRNPQGLAFTPNGKLLQSDHGPNSDDEINLIVKGGN
YGWPNVAGYKDDSGYAYANYSAAANKSIKDLAQNGLKVAAGVPVTKESEVVT
GKNFVPPLKTLYTVQDTYNYNDPTCGEVTYICWPSVAPSSAYVYKGGKKAIT
GWENTLLVPSLKRGVIFRIKFDPTYSTTYDDAVPMFKSNNRYRDVIASPDGNV
LYVLTDTAGNPVQKDDGSPTNTLENPGSLIKFTYKAKGGKGGSGGSSYAHHH
HHHEETPVTPQPPDILLGPLFNDVQNAKLFPDQKTFADAVPNSDPLMILADYR
MQQNQSGFDLRHFVNVNFTLPKEGEKYVPGSTADNKFNKEQQNAFYEILHLP
NLNEEQRNGFIQSLKDDPSQSANLLAEAKKLNDAQAPKA SEQ ID NO 75: GDH-HIS-TreAN-pL: Glucose
dehydrogenase N-terminally, and the immunoglobulin binding domain B1 of
protein G C-terminally fused to the N-terminal fragment of TreAN (w/o signal
peptide), which with flexible linker and HIS-tag in between GDH and TreAN
MAGKYLLPTAAAGLLLLAAQPAMADVPLTPSQFAKAKSENFDKKVILSNLNKP
HALLWGPDNQIWLTERATGKILRVNPESGSVKTVFQVPEIVNDADGQNGLLG
FAFHPRFKNNPYIYISGTFKNPKSTDKELPNQTIIRRYTYKKKTDTLEKPVDLLA
GLPSSKDHQGGRLVIGPDQKIYYTIGDQGRNQFAGLFLPNQAQHTPTQQELN
GKDYHTYMGKVLRLNLDGSIPKDNPSFNGVVSHIYTLGHRNPQGLAFTPNGK -continued

SEQUENCES:

```
LLQSDHGPNSDDEINLIVKGGNYGWPNVAGYKDDSGYAYANYSAAANKSIKD
LAQNGLKVAAGVPVTKESEVVTGKNFVPPLKTLYTVQDTYNYNDPTCGEVTYI
CWPSVAPSSAYVYKGGKKAITGWENTLLVPSLKRGVIFRIKFDPTYSTTYDDA
VPMFKSNNRYRDVIASPDGNVLYVLTDTAGNPVQKDDGSPTNTLENPGSLIK
FTYKAKGGKGGSGGSSYAHHHHHHEETPVTPQPPDILLGPLFNDVQNAKLFP
DQKTFADAVPNSDPLMILADYRMQQNQSGFDLRHFVNVNFTLPKEGEKYVP
GSAMEEVTIKANLIFANGSTQTAEFKGTFEKATSEAYAYADTLKKDNGEVVTVD
VADKGYTLNIKFAG
```

SEQ ID NO: 76: HIS-TreAC-TreAN-HA: N-terminally HIS-tagged,
C-terminally HA-tagged fusion of the N-terminal and C-terminal fragments of
TreA in alternative frame folded format

```
MAHHHHHHNFTLPKEGEKYVPPEGQSLREHIDGSYFTMLGLAESGHWDKVA
DMVANFAHEIDTYGHIPNGNRSYYLSRSQPPFFALMVELLAQHEGDAALKQY
LPQMQKEYAYWMDGVRPESWVEDIATAKSNPNRPATEIYRDLRSAAASGWD
FSSRWMDNPQQLNTLRTTSIVPVDLNSLMFKMEKILARASKAAGDNAMANQY
ETLANARQKGIEKYLWNDQQGWYADYDLKSHKVRNQLTAAALFPLYVNAAA
KDRANKMATATKTHLLQPGGLNTTSVKSGQQWDAPNGWAPLQWVATEGLQ
NYGQKEVAMDISWHFLTNVQHTYDREKKLVEKYDVSTTGTGGGGEYPLQD
GFGWTNGVTLKMLDLICPKEQPEFEETPVTPQPPDILLGPLFNDVQNAKLFPD
QKTFADAVPNSDPLMILADYRMQQNQSGFDLRHFVNVNFTLPKEGEKYVPG
SYPYDVPDYA
```

SEQ ID NO: 77: HA-TreAC-TreAN-HIS: N-terminally HA-tagged,
C-terminally HIS-tagged fusion of the N-terminal and C-terminal fragments of
TreA in alternative frame folded format

```
MAYPYDVPDYAVDNFTLPKEGEKYVPPEGQSLREHIDGLWPVLTRSTENTEK
WDSLLPLPEPYVVPGGRFREVYYWDSYFTMLGLAESGHWDKVADMVANFA
HEIDTYGHIPNGNRSYYLSRSQPPFFALMVELLAQHEGDAALKQYLPQMQKE
YAYWMDGVENLQAGQQEKRVVKLQDGTLLNRYWDDRDTPRPESWVEDIAT
AKSNPNRPATEIYRDLRSAAASGWDFSSRWMDNPQQLNTLRTTSIVPVDLNS
LMFKMEKILARASKAAGDNAMANQYETLANARQKGIEKYLWNDQQGWYADY
DLKSHKVRNQLTAAALFPLYVNAAAKDRANKMATATKTHLLQPGGLNTTSVK
SGQQWDAPNGWAPLQWVATEGLQNYGQKEVAMDISWHFLTNVQHTYDRE
KKLVEKYDVSTTGTGGGGEYPLQDGFGVVTNGVTLKMLDLICPKEQPEFEE
TPVTPQPPDILLGPLFNDVQNAKLFPDQKTFADAVPNSDPLMILADYRMQQN
QSGFDLRHFVNVNFTLPKEGEKYVPHHHHHH
```

SEQ ID NO: 78: SA-TreAC-HIS-TreAN-SA: N-terminal and C-
terminal fragments of TreA in alternative frame folded format with N-terminal
and C-terminal fusion with S. aureus binding peptide aptamer and a HIS-tag
between both fragments

```
MVPHNPGLISLQGVDNFTLPKEGEKYVPPEGQSLREHIDGLWPVLTRSTENT
EKWDSLLPLPEPYVVPGGRFREVYYWDSYFTMLGLAESGHWDKVADMVAN
FAHEIDTYGHIPNGNRSYYLSRSQPPFFALMVELLAQHEGDAALKQYLPQMQ
KEYAYWMDGVENLQAGQQEKRVVKLQDGTLLNRYWDDRDTPRPESWVEDI
ATAKSNPNRPATEIYRDLRSAAASGWDFSSRWMDNPQQLNTLRTTSIVPVDL
NSLMFKMEKILARASKAAGDNAMANQYETLANARQKGIEKYLWNDQQGWYA
DYDLKSHKVRNQLTAAALFPLYVNAAAKDRANKMATATKTHLLQPGGLNTTS
VKSGQQWDAPNGWAPLQWVATEGLQNYGQKEVAMDISWHFLTNVQHTYD
REKKLVEKYDVSTTGTGGGGEYPLQDGFGVVTNGVTLKMLDLICPHHHHHH
EFEETPVTPEETPVTPQPPDILLGPLFNDVQNAKLFPDQKTFADAVPNSDPLM
ILADYRMQQNQSGFDLRHFVNVNFTLPKEGEKYVPGSVPHNPGLISLQG
```

SEQ ID NO: 79: GOx-HIS-TreAN-HA: Signal Peptide of
Aspergillus oryzae fused to glucose oxidase of Aspergillus niger with linker
containing HIS-tag to fused to N-terminal fragment of TreA fused to the HA tag

```
MMVAWWSLFLYGLQVAAPALASNGIEASLLTDPRDVSGRTVDYIIAGGGLTGL
TTAARLTENPNISVLVIESGSYESDRGPIIEDLNAYGDIFGSSVDHAYETVELAT
NNQTALIRSGNGLGGSTLVNGGTWTRPHKAQVDSWETVFGNEGWNWDNVA
AYSLQAERARAPNAKQIAAGHYFNASCHGVNGTVHAGPRDTGDDYSPIVKAL
MSAVEDRGVPTKKDFGCGDPHGVSMFPNTLHEDQVRSDAAREWLLPNYQR
PNLQVLTGQYVGKVLLSQNGTTPRAVGVEFGTHKGNTHNVYAKHEVLLAAG
SAVSPTILEYSGIGMKSILEPLGIDTVVDLPVGLNLQDQTTATVRSRITSAGAG
QGQAAWFATFNETFGDYSEKAHELLNTKLEQWAEEAVARGGFHNTTALLIQY
ENYRDWIVNHNVAYSELFLDTAGVASFDVWDLLPFTRGYVHILDKDPYLHHFA
YDPQYFLNELDLLGQAAATQLARNISNSGAMQTYFAGETIPGDNLAYDADLSA
WTEYIPYHFRPNYHGVGTCSMMPKEMGGWDNAARVYGVQGLRVIDGSIPP
TQMSSHVMTVFYAMALKISDAILEDYASMQKGKGGSGGSSYAHHHHHHEET
PVTPQPPDILLGPLFNDVQNAKLFPDQKTFADAVPNSDPLMILADYRMQQNQ
SGFDLRHFVNVNFTLPKEGEKYVPGSYPYDVPDYA
```

The preceding examples can be repeated with similar success by substituting the generically or specifically described reactants and/or operating conditions of this invention for those used in the preceding examples.

Note that in the specification and claims, "about" or "approximately" means within twenty percent (20%) of the numerical amount cited.

Although the invention has been described in detail with particular reference to these embodiments, other embodiments can achieve the same results. Variations and modifications of the present invention will be obvious to those skilled in the art and it is intended to cover in the appended claims all such modifications and equivalents. The entire disclosures of all references, applications, patents, and publications cited above are hereby incorporated by reference.

SEQUENCE LISTING

```
<160> NUMBER OF SEQ ID NOS: 79

<210> SEQ ID NO 1
<211> LENGTH: 20
<212> TYPE: DNA
<213> ORGANISM: Artificial sequence
<220> FEATURE:
<223> OTHER INFORMATION: synthetic oligonucleotide

<400> SEQUENCE: 1
tatggacagc aagcgaaccg                                                     20

<210> SEQ ID NO 2
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 2
tcagaagaac tcgtcaagaa g                                                   21

<210> SEQ ID NO 3
<211> LENGTH: 53
<212> TYPE: DNA
<213> ORGANISM: Artificial Sequence
<220> FEATURE:
<223> OTHER INFORMATION: synthetic oligonucleotide

<400> SEQUENCE: 3
tataccatgg cacaccatca ccatcaccat gaagaaacac cggtaacacc aca               53

<210> SEQ ID NO 4
<211> LENGTH: 32
<212> TYPE: DNA
<213> ORGANISM: Artificial sequence
<220> FEATURE:
<223> OTHER INFORMATION: synthetic oligonucleotide

<400> SEQUENCE: 4
tatacctagg ttaaggtgtg ggttgtgcct ct                                       32

<210> SEQ ID NO 5
<211> LENGTH: 41
<212> TYPE: DNA
<213> ORGANISM: Artificial Sequence
<220> FEATURE:
<223> OTHER INFORMATION: synthetic oligonucleotide

<400> SEQUENCE: 5
taattcctag gtcaggatcc cggaacatat ttctcgcctt c                             41

<210> SEQ ID NO 6
<211> LENGTH: 30
<212> TYPE: DNA
<213> ORGANISM: Artificial Sequence
```

```
<220> FEATURE:
<223> OTHER INFORMATION: sythetic oligonucleotide

<400> SEQUENCE: 6
tataccatgg aagaaacacc ggtaacacca                                30

<210> SEQ ID NO 7
<211> LENGTH: 53
<212> TYPE: DNA
<213> ORGANISM: Artificial Sequence
<220> FEATURE:
<223> OTHER INFORMATION: synthetic oligonucleotide

<400> SEQUENCE: 7
taattcctag gtcaatggtg atggtgatgg tgcggaacat atttctcgcc ttc       53

<210> SEQ ID NO 8
<211> LENGTH: 50
<212> TYPE: DNA
<213> ORGANISM: Artificial Sequence
<220> FEATURE:
<223> OTHER INFORMATION: synthetic oligonucleotide

<400> SEQUENCE: 8
taattccatg gcacaccatc accatcacca taatttcacc ctgccgaaag           50

<210> SEQ ID NO 9
<211> LENGTH: 38
<212> TYPE: DNA
<213> ORGANISM: Artificial Sequence
<220> FEATURE:
<223> OTHER INFORMATION: synthetic oligonucleotide

<400> SEQUENCE: 9
taattccatg gcagtcgaca atttcaccct gccgaaag                        38

<210> SEQ ID NO 10
<211> LENGTH: 50
<212> TYPE: DNA
<213> ORGANISM: Artificial Sequence
<220> FEATURE:
<223> OTHER INFORMATION: synthetic oligonucleotide

<400> SEQUENCE: 10
tatacctagg ttaatggtga tggtgatggt gaggtgtggg ttgtgcctct           50

<210> SEQ ID NO 11
<211> LENGTH: 63
<212> TYPE: DNA
<213> ORGANISM: Artificial Sequence
<220> FEATURE:
<223> OTHER INFORMATION: synthetic oligonucleotide

<400> SEQUENCE: 11
tataccatgg catacccata cgatgttcca gattacgctg tcgacgaaga aacaccggta    60
aca                                                             63

<210> SEQ ID NO 12
<211> LENGTH: 64
<212> TYPE: DNA
<213> ORGANISM: Artificial Sequence
<220> FEATURE:
<223> OTHER INFORMATION: synthetic oligonucleotide

<400> SEQUENCE: 12
```

```
tatacctagg tcaagcgtaa tctggaacat cgtatgggta ggatcccgga acatatttct    60
cgcc                                                                64
```

<210> SEQ ID NO 13
<211> LENGTH: 63
<212> TYPE: DNA
<213> ORGANISM: Artificial Sequence
<220> FEATURE:
<223> OTHER INFORMATION: synthetic oligonucleotide

<400> SEQUENCE: 13

```
tataccatgg catacccata cgatgttcca gattacgctg tcgacaattt cacccctgccg   60 aaa                                                                  63
```

<210> SEQ ID NO 14
<211> LENGTH: 55
<212> TYPE: PRT
<213> ORGANISM: Artificial Sequence
<220> FEATURE:
<223> OTHER INFORMATION: Protein G

<400> SEQUENCE: 14

```
Thr Tyr Lys Leu Ile Leu Asn Gly Lys Thr Leu Lys Gly Glu Thr Thr
1               5                   10                  15

Thr Glu Ala Val Asp Ala Ala Thr Ala Glu Lys Val Phe Lys Gln Tyr
            20                  25                  30

Ala Asn Asp Asn Gly Val Asp Gly Glu Trp Thr Tyr Asp Ala Ala Thr
        35                  40                  45

Lys Thr Phe Thr Val Thr Glu
    50                  55
```

<210> SEQ ID NO 15
<211> LENGTH: 60
<212> TYPE: PRT
<213> ORGANISM: Artificial Sequence
<220> FEATURE:
<223> OTHER INFORMATION: Protein A

<400> SEQUENCE: 15

```
Thr Ala Asp Asn Lys Phe Asn Lys Glu Gln Gln Asn Ala Phe Tyr Glu
1               5                   10                  15

Ile Leu His Leu Pro Asn Leu Asn Glu Glu Gln Arg Asn Gly Phe Ile
            20                  25                  30

Gln Ser Leu Lys Asp Asp Pro Ser Gln Ser Ala Asn Leu Leu Ala Glu
        35                  40                  45

Ala Lys Lys Leu Asn Asp Ala Gln Ala Pro Lys Ala
    50                  55                  60
```

<210> SEQ ID NO 16
<211> LENGTH: 65
<212> TYPE: PRT
<213> ORGANISM: Artificial Sequence
<220> FEATURE:
<223> OTHER INFORMATION: Protein L

<400> SEQUENCE: 16

```
Ala Met Glu Glu Val Thr Ile Lys Ala Asn Leu Ile Phe Ala Asn Gly
1               5                   10                  15

Ser Thr Gln Thr Ala Glu Phe Lys Gly Thr Phe Glu Lys Ala Thr Ser
            20                  25                  30

Glu Ala Tyr Ala Tyr Ala Asp Thr Leu Lys Lys Asp Asn Gly Glu Trp
```

```
                35                  40                  45
Thr Val Asp Val Ala Asp Lys Gly Tyr Thr Leu Asn Ile Lys Phe Ala
 50                  55                  60
Gly
 65

<210> SEQ ID NO 17
<211> LENGTH: 543
<212> TYPE: PRT
<213> ORGANISM: Artificial Sequence
<220> FEATURE:
<223> OTHER INFORMATION: HIS-TreA: N-terminally HIS-tagged TreA (w/o
      signal peptide)

<400> SEQUENCE: 17

Met Ala His His His His His His Glu Glu Thr Pro Val Thr Pro Gln
  1               5                  10                  15

Pro Pro Asp Ile Leu Leu Gly Pro Leu Phe Asn Asp Val Gln Asn Ala
                 20                  25                  30

Lys Leu Phe Pro Asp Gln Lys Thr Phe Ala Asp Ala Val Pro Asn Ser
             35                  40                  45

Asp Pro Leu Met Ile Leu Ala Asp Tyr Arg Met Gln Gln Asn Gln Ser
 50                  55                  60

Gly Phe Asp Leu Arg His Phe Val Asn Val Asn Phe Thr Leu Pro Lys
 65                  70                  75                  80

Glu Gly Glu Lys Tyr Val Pro Pro Gly Gln Ser Leu Arg Glu His
                 85                  90                  95

Ile Asp Gly Leu Trp Pro Val Leu Thr Arg Ser Thr Glu Asn Thr Glu
                100                 105                 110

Lys Trp Asp Ser Leu Leu Pro Leu Pro Glu Pro Tyr Val Val Pro Gly
            115                 120                 125

Gly Arg Phe Arg Glu Val Tyr Tyr Trp Asp Ser Tyr Phe Thr Met Leu
130                 135                 140

Gly Leu Ala Glu Ser Gly His Trp Asp Lys Val Ala Asp Met Val Ala
145                 150                 155                 160

Asn Phe Ala His Glu Ile Asp Thr Tyr Gly His Ile Pro Asn Gly Asn
                165                 170                 175

Arg Ser Tyr Tyr Leu Ser Arg Ser Gln Pro Pro Phe Phe Ala Leu Met
                180                 185                 190

Val Glu Leu Leu Ala Gln His Glu Gly Asp Ala Ala Leu Lys Gln Tyr
            195                 200                 205

Leu Pro Gln Met Gln Lys Glu Tyr Ala Tyr Trp Met Asp Gly Val Glu
210                 215                 220

Asn Leu Gln Ala Gly Gln Gln Glu Lys Arg Val Val Lys Leu Gln Asp
225                 230                 235                 240

Gly Thr Leu Leu Asn Arg Tyr Trp Asp Asp Arg Asp Thr Pro Arg Pro
                245                 250                 255

Glu Ser Trp Val Glu Asp Ile Ala Thr Ala Lys Ser Asn Pro Asn Arg
            260                 265                 270

Pro Ala Thr Glu Ile Tyr Arg Asp Leu Arg Ser Ala Ala Ala Ser Gly
            275                 280                 285

Trp Asp Phe Ser Ser Arg Trp Met Asp Asn Pro Gln Gln Leu Asn Thr
290                 295                 300

Leu Arg Thr Thr Ser Ile Val Pro Val Asp Leu Asn Ser Leu Met Phe
305                 310                 315                 320
```

Lys Met Glu Lys Ile Leu Ala Arg Ala Ser Lys Ala Gly Asp Asn
            325                 330                 335

Ala Met Ala Asn Gln Tyr Glu Thr Leu Ala Asn Ala Arg Gln Lys Gly
            340                 345                 350

Ile Glu Lys Tyr Leu Trp Asn Asp Gln Gln Gly Trp Tyr Ala Asp Tyr
            355                 360                 365

Asp Leu Lys Ser His Lys Val Arg Asn Gln Leu Thr Ala Ala Leu
    370                 375                 380

Phe Pro Leu Tyr Val Asn Ala Ala Lys Asp Arg Ala Asn Lys Met
385                 390                 395                 400

Ala Thr Ala Thr Lys Thr His Leu Leu Gln Pro Gly Gly Leu Asn Thr
            405                 410                 415

Thr Ser Val Lys Ser Gly Gln Gln Trp Asp Ala Pro Asn Gly Trp Ala
            420                 425                 430

Pro Leu Gln Trp Val Ala Thr Glu Gly Leu Gln Asn Tyr Gly Gln Lys
            435                 440                 445

Glu Val Ala Met Asp Ile Ser Trp His Phe Leu Thr Asn Val Gln His
            450                 455                 460

Thr Tyr Asp Arg Glu Lys Lys Leu Val Glu Lys Tyr Asp Val Ser Thr
465                 470                 475                 480

Thr Gly Thr Gly Gly Gly Gly Glu Tyr Pro Leu Gln Asp Gly Phe
            485                 490                 495

Gly Trp Thr Asn Gly Val Thr Leu Lys Met Leu Asp Leu Ile Cys Pro
            500                 505                 510

Lys Glu Gln Pro Cys Asp Asn Val Pro Ala Thr Arg Pro Thr Val Lys
            515                 520                 525

Ser Ala Thr Thr Gln Pro Ser Thr Lys Glu Ala Gln Pro Thr Pro
            530                 535                 540

<210> SEQ ID NO 18
<211> LENGTH: 542
<212> TYPE: PRT
<213> ORGANISM: Artificial Sequence
<220> FEATURE:
<223> OTHER INFORMATION: TreA-HIS: C-terminally HIS-tagged TreA (w/o
      signal peptide)

<400> SEQUENCE: 18

Met Glu Glu Thr Pro Val Thr Pro Gln Pro Pro Asp Ile Leu Leu Gly
1               5                   10                  15

Pro Leu Phe Asn Asp Val Gln Asn Ala Lys Leu Phe Pro Asp Gln Lys
            20                  25                  30

Thr Phe Ala Asp Ala Val Pro Asn Ser Asp Pro Leu Met Ile Leu Ala
            35                  40                  45

Asp Tyr Arg Met Gln Gln Asn Gln Ser Gly Phe Asp Leu Arg His Phe
    50                  55                  60

Val Asn Val Asn Phe Thr Leu Pro Lys Glu Gly Glu Lys Tyr Val Pro
65                  70                  75                  80

Pro Glu Gly Gln Ser Leu Arg Glu His Ile Asp Gly Leu Trp Pro Val
            85                  90                  95

Leu Thr Arg Ser Thr Glu Asn Thr Glu Lys Trp Asp Ser Leu Leu Pro
            100                 105                 110

Leu Pro Glu Pro Tyr Val Val Pro Gly Gly Arg Phe Arg Glu Val Tyr
            115                 120                 125

Tyr Trp Asp Ser Tyr Phe Thr Met Leu Gly Leu Ala Glu Ser Gly His
    130                 135                 140

```
Trp Asp Lys Val Ala Asp Met Val Ala Asn Phe Ala His Glu Ile Asp
145                 150                 155                 160

Thr Tyr Gly His Ile Pro Asn Gly Asn Arg Ser Tyr Tyr Leu Ser Arg
            165                 170                 175

Ser Gln Pro Pro Phe Phe Ala Leu Met Val Glu Leu Leu Ala Gln His
        180                 185                 190

Glu Gly Asp Ala Ala Leu Lys Gln Tyr Leu Pro Gln Met Gln Lys Glu
            195                 200                 205

Tyr Ala Tyr Trp Met Asp Gly Val Glu Asn Leu Gln Ala Gly Gln Gln
210                 215                 220

Glu Lys Arg Val Val Lys Leu Gln Asp Gly Thr Leu Leu Asn Arg Tyr
225                 230                 235                 240

Trp Asp Asp Arg Asp Thr Pro Arg Pro Glu Ser Trp Val Glu Asp Ile
                245                 250                 255

Ala Thr Ala Lys Ser Asn Pro Asn Arg Pro Ala Thr Glu Ile Tyr Arg
            260                 265                 270

Asp Leu Arg Ser Ala Ala Ala Ser Gly Trp Asp Phe Ser Ser Arg Trp
        275                 280                 285

Met Asp Asn Pro Gln Gln Leu Asn Thr Leu Arg Thr Thr Ser Ile Val
290                 295                 300

Pro Val Asp Leu Asn Ser Leu Met Phe Lys Met Glu Lys Ile Leu Ala
305                 310                 315                 320

Arg Ala Ser Lys Ala Ala Gly Asp Asn Ala Met Ala Asn Gln Tyr Glu
                325                 330                 335

Thr Leu Ala Asn Ala Arg Gln Lys Gly Ile Glu Lys Tyr Leu Trp Asn
            340                 345                 350

Asp Gln Gln Gly Trp Tyr Ala Asp Tyr Asp Leu Lys Ser His Lys Val
        355                 360                 365

Arg Asn Gln Leu Thr Ala Ala Leu Phe Pro Leu Tyr Val Asn Ala
370                 375                 380

Ala Ala Lys Asp Arg Ala Asn Lys Met Ala Thr Ala Thr Lys Thr His
385                 390                 395                 400

Leu Leu Gln Pro Gly Gly Leu Asn Thr Thr Ser Val Lys Ser Gly Gln
                405                 410                 415

Gln Trp Asp Ala Pro Asn Gly Trp Ala Pro Leu Gln Trp Val Ala Thr
            420                 425                 430

Glu Gly Leu Gln Asn Tyr Gly Gln Lys Glu Val Ala Met Asp Ile Ser
        435                 440                 445

Trp His Phe Leu Thr Asn Val Gln His Thr Tyr Asp Arg Glu Lys Lys
450                 455                 460

Leu Val Glu Lys Tyr Asp Val Ser Thr Gly Thr Gly Gly Gly Gly
465                 470                 475                 480

Gly Glu Tyr Pro Leu Gln Asp Gly Phe Gly Trp Thr Asn Gly Val Thr
                485                 490                 495

Leu Lys Met Leu Asp Leu Ile Cys Pro Lys Glu Gln Pro Cys Asp Asn
            500                 505                 510

Val Pro Ala Thr Arg Pro Thr Val Lys Ser Ala Thr Thr Gln Pro Ser
        515                 520                 525

Thr Lys Glu Ala Gln Pro Thr Pro His His His His His
530                 535                 540

<210> SEQ ID NO 19
<211> LENGTH: 549
```

<212> TYPE: PRT
<213> ORGANISM: Artificial Sequence
<220> FEATURE:
<223> OTHER INFORMATION: HIS-TreA-HIS: N- and C- terminally HIS-tagged
    TreA (w/o signal peptide)

<400> SEQUENCE: 19

```
Met Ala His His His His His His Glu Glu Thr Pro Val Thr Pro Gln
1               5                   10                  15

Pro Pro Asp Ile Leu Leu Gly Pro Leu Phe Asn Asp Val Gln Asn Ala
            20                  25                  30

Lys Leu Phe Pro Asp Gln Lys Thr Phe Ala Asp Ala Val Pro Asn Ser
        35                  40                  45

Asp Pro Leu Met Ile Leu Ala Asp Tyr Arg Met Gln Gln Asn Gln Ser
    50                  55                  60

Gly Phe Asp Leu Arg His Phe Val Asn Val Asn Phe Thr Leu Pro Lys
65                  70                  75                  80

Glu Gly Glu Lys Tyr Val Pro Pro Glu Gly Gln Ser Leu Arg Glu His
                85                  90                  95

Ile Asp Gly Leu Trp Pro Val Leu Thr Arg Ser Thr Glu Asn Thr Glu
            100                 105                 110

Lys Trp Asp Ser Leu Leu Pro Leu Pro Glu Pro Tyr Val Val Pro Gly
        115                 120                 125

Gly Arg Phe Arg Glu Val Tyr Tyr Trp Asp Ser Tyr Phe Thr Met Leu
130                 135                 140

Gly Leu Ala Glu Ser Gly His Trp Asp Lys Val Ala Asp Met Val Ala
145                 150                 155                 160

Asn Phe Ala His Glu Ile Asp Thr Tyr Gly His Ile Pro Asn Gly Asn
                165                 170                 175

Arg Ser Tyr Tyr Leu Ser Arg Ser Gln Pro Pro Phe Phe Ala Leu Met
            180                 185                 190

Val Glu Leu Leu Ala Gln His Glu Gly Asp Ala Ala Leu Lys Gln Tyr
        195                 200                 205

Leu Pro Gln Met Gln Lys Glu Tyr Ala Tyr Trp Met Asp Gly Val Glu
    210                 215                 220

Asn Leu Gln Ala Gly Gln Gln Glu Lys Arg Val Val Lys Leu Gln Asp
225                 230                 235                 240

Gly Thr Leu Leu Asn Arg Tyr Trp Asp Asp Arg Asp Thr Pro Arg Pro
                245                 250                 255

Glu Ser Trp Val Glu Asp Ile Ala Thr Ala Lys Ser Asn Pro Asn Arg
            260                 265                 270

Pro Ala Thr Glu Ile Tyr Arg Asp Leu Arg Ser Ala Ala Ala Ser Gly
        275                 280                 285

Trp Asp Phe Ser Ser Arg Trp Met Asp Asn Pro Gln Gln Leu Asn Thr
    290                 295                 300

Leu Arg Thr Thr Ser Ile Val Pro Val Asp Leu Asn Ser Leu Met Phe
305                 310                 315                 320

Lys Met Glu Lys Ile Leu Ala Arg Ala Ser Lys Ala Ala Gly Asp Asn
                325                 330                 335

Ala Met Ala Asn Gln Tyr Glu Thr Leu Ala Asn Ala Arg Gln Lys Gly
            340                 345                 350

Ile Glu Lys Tyr Leu Trp Asn Asp Gln Gln Gly Trp Tyr Ala Asp Tyr
        355                 360                 365

Asp Leu Lys Ser His Lys Val Arg Asn Gln Leu Thr Ala Ala Ala Leu
    370                 375                 380
```

```
Phe Pro Leu Tyr Val Asn Ala Ala Lys Asp Arg Ala Asn Lys Met
385                 390                 395                 400

Ala Thr Ala Thr Lys Thr His Leu Leu Gln Pro Gly Gly Leu Asn Thr
            405                 410                 415

Thr Ser Val Lys Ser Gly Gln Gln Trp Asp Ala Pro Asn Gly Trp Ala
        420                 425                 430

Pro Leu Gln Trp Val Ala Thr Glu Gly Leu Gln Asn Tyr Gly Gln Lys
            435                 440                 445

Glu Val Ala Met Asp Ile Ser Trp His Phe Leu Thr Asn Val Gln His
        450                 455                 460

Thr Tyr Asp Arg Glu Lys Lys Leu Val Glu Lys Tyr Val Ser Thr
465                 470                 475                 480

Thr Gly Thr Gly Gly Gly Gly Glu Tyr Pro Leu Gln Asp Gly Phe
            485                 490                 495

Gly Trp Thr Asn Gly Val Thr Leu Lys Met Leu Asp Leu Ile Cys Pro
            500                 505                 510

Lys Glu Gln Pro Cys Asp Asn Val Pro Ala Thr Arg Pro Thr Val Lys
        515                 520                 525

Ser Ala Thr Thr Gln Pro Ser Thr Lys Glu Ala Gln Pro Thr Pro His
    530                 535                 540

His His His His His
545

<210> SEQ ID NO 20
<211> LENGTH: 89
<212> TYPE: PRT
<213> ORGANISM: Artificial Sequence
<220> FEATURE:
<223> OTHER INFORMATION: HIS-TreAN: N-terminally HIS-tagged N-terminal
      fragment of TreA (w/o signal peptide)

<400> SEQUENCE: 20

Met Ala His His His His His His Glu Glu Thr Pro Val Thr Pro Gln
1               5                   10                  15

Pro Pro Asp Ile Leu Leu Gly Pro Leu Phe Asn Asp Val Gln Asn Ala
            20                  25                  30

Lys Leu Phe Pro Asp Gln Lys Thr Phe Ala Asp Ala Val Pro Asn Ser
        35                  40                  45

Asp Pro Leu Met Ile Leu Ala Asp Tyr Arg Met Gln Gln Asn Gln Ser
    50                  55                  60

Gly Phe Asp Leu Arg His Phe Val Asn Val Asn Phe Thr Leu Pro Lys
65                  70                  75                  80

Glu Gly Glu Lys Tyr Val Pro Gly Ser
                85

<210> SEQ ID NO 21
<211> LENGTH: 86
<212> TYPE: PRT
<213> ORGANISM: Artificial Sequence
<220> FEATURE:
<223> OTHER INFORMATION: TreAN-HIS: C-terminally HIS-tagged N-terminal
      fragment of TreA (w/o signal peptide)

<400> SEQUENCE: 21

Met Glu Glu Thr Pro Val Thr Pro Gln Pro Pro Asp Ile Leu Leu Gly
1               5                   10                  15

Pro Leu Phe Asn Asp Val Gln Asn Ala Lys Leu Phe Pro Asp Gln Lys
            20                  25                  30
```

Thr Phe Ala Asp Ala Val Pro Asn Ser Asp Pro Leu Met Ile Leu Ala
                35                  40                  45

Asp Tyr Arg Met Gln Gln Asn Gln Ser Gly Phe Asp Leu Arg His Phe
        50                  55                  60

Val Asn Val Asn Phe Thr Leu Pro Lys Glu Gly Glu Lys Tyr Val Pro
 65                  70                  75                  80

His His His His His His
                85

<210> SEQ ID NO 22
<211> LENGTH: 477
<212> TYPE: PRT
<213> ORGANISM: Artificial Sequence
<220> FEATURE:
<223> OTHER INFORMATION: HIS-TreAC: N-terminally HIS-tagged C-terminal
      fragment of TreA (w/o signal peptide)

<400> SEQUENCE: 22

Met Ala His His His His His Asn Phe Thr Leu Pro Lys Glu Gly
 1               5                  10                  15

Glu Lys Tyr Val Pro Pro Glu Gly Gln Ser Leu Arg Glu His Ile Asp
                20                  25                  30

Gly Leu Trp Pro Val Leu Thr Arg Ser Thr Glu Asn Thr Glu Lys Trp
            35                  40                  45

Asp Ser Leu Leu Pro Leu Pro Glu Pro Tyr Val Val Pro Gly Gly Arg
        50                  55                  60

Phe Arg Glu Val Tyr Tyr Trp Asp Ser Tyr Phe Thr Met Leu Gly Leu
 65                  70                  75                  80

Ala Glu Ser Gly His Trp Asp Lys Val Ala Asp Met Val Ala Asn Phe
                85                  90                  95

Ala His Glu Ile Asp Thr Tyr Gly His Ile Pro Asn Gly Asn Arg Ser
               100                 105                 110

Tyr Tyr Leu Ser Arg Ser Gln Pro Pro Phe Phe Ala Leu Met Val Glu
            115                 120                 125

Leu Leu Ala Gln His Glu Gly Asp Ala Ala Leu Lys Gln Tyr Leu Pro
        130                 135                 140

Gln Met Gln Lys Glu Tyr Ala Tyr Trp Met Asp Gly Val Glu Asn Leu
145                 150                 155                 160

Gln Ala Gly Gln Gln Glu Lys Arg Val Val Lys Leu Gln Asp Gly Thr
                165                 170                 175

Leu Leu Asn Arg Tyr Trp Asp Asp Arg Asp Thr Pro Arg Pro Glu Ser
            180                 185                 190

Trp Val Glu Asp Ile Ala Thr Ala Lys Ser Asn Pro Asn Arg Pro Ala
        195                 200                 205

Thr Glu Ile Tyr Arg Asp Leu Arg Ser Ala Ala Ser Gly Trp Asp
        210                 215                 220

Phe Ser Ser Arg Trp Met Asp Asn Pro Gln Gln Leu Asn Thr Leu Arg
225                 230                 235                 240

Thr Thr Ser Ile Val Pro Val Asp Leu Asn Ser Leu Met Phe Lys Met
                245                 250                 255

Glu Lys Ile Leu Ala Arg Ala Ser Lys Ala Ala Gly Asp Asn Ala Met
            260                 265                 270

Ala Asn Gln Tyr Glu Thr Leu Ala Asn Ala Arg Gln Lys Gly Ile Glu
        275                 280                 285

Lys Tyr Leu Trp Asn Asp Gln Gln Gly Trp Tyr Ala Asp Tyr Asp Leu

```
            290                 295                 300
Lys Ser His Lys Val Arg Asn Gln Leu Thr Ala Ala Ala Leu Phe Pro
305                 310                 315                 320

Leu Tyr Val Asn Ala Ala Lys Asp Arg Ala Asn Lys Met Ala Thr
                325                 330                 335

Ala Thr Lys Thr His Leu Leu Gln Pro Gly Gly Leu Asn Thr Thr Ser
            340                 345                 350

Val Lys Ser Gly Gln Gln Trp Asp Ala Pro Asn Gly Trp Ala Pro Leu
            355                 360                 365

Gln Trp Val Ala Thr Glu Gly Leu Gln Asn Tyr Gly Gln Lys Glu Val
        370                 375                 380

Ala Met Asp Ile Ser Trp His Phe Leu Thr Asn Val Gln His Thr Tyr
385                 390                 395                 400

Asp Arg Glu Lys Lys Leu Val Glu Lys Tyr Asp Val Ser Thr Thr Gly
                405                 410                 415

Thr Gly Gly Gly Gly Glu Tyr Pro Leu Gln Asp Gly Phe Gly Trp
            420                 425                 430

Thr Asn Gly Val Thr Leu Lys Met Leu Asp Leu Ile Cys Pro Lys Glu
            435                 440                 445

Gln Pro Cys Asp Asn Val Pro Ala Thr Arg Pro Thr Val Lys Ser Ala
        450                 455                 460

Thr Thr Gln Pro Ser Thr Lys Glu Ala Gln Pro Thr Pro
465                 470                 475

<210> SEQ ID NO 23
<211> LENGTH: 478
<212> TYPE: PRT
<213> ORGANISM: Artificial Sequence
<220> FEATURE:
<223> OTHER INFORMATION: TreAC-HIS: C-terminally HIS-tagged C-terminal
      fragment of TreA (w/o signal peptide)

<400> SEQUENCE: 23

Met Ala Val Asn Phe Thr Leu Pro Lys Glu Gly Glu Lys Tyr Val Pro
1               5                   10                  15

Pro Glu Gly Gln Ser Leu Arg Glu His Ile Asp Gly Leu Trp Pro Val
            20                  25                  30

Leu Thr Arg Ser Thr Glu Asn Thr Glu Lys Trp Asp Ser Leu Leu Pro
        35                  40                  45

Leu Pro Glu Pro Tyr Val Val Pro Gly Gly Arg Phe Arg Glu Val Tyr
    50                  55                  60

Tyr Trp Asp Ser Tyr Phe Thr Met Leu Gly Leu Ala Glu Ser Gly His
65                  70                  75                  80

Trp Asp Lys Val Ala Asp Met Val Ala Asn Phe Ala His Glu Ile Asp
                85                  90                  95

Thr Tyr Gly His Ile Pro Asn Gly Asn Arg Ser Tyr Tyr Leu Ser Arg
            100                 105                 110

Ser Gln Pro Pro Phe Phe Ala Leu Met Val Glu Leu Leu Ala Gln His
        115                 120                 125

Glu Gly Asp Ala Ala Leu Lys Gln Tyr Leu Pro Gln Met Gln Lys Glu
    130                 135                 140

Tyr Ala Tyr Trp Met Asp Gly Val Glu Asn Leu Gln Ala Gly Gln Gln
145                 150                 155                 160

Glu Lys Arg Val Val Lys Leu Gln Asp Gly Thr Leu Leu Asn Arg Tyr
                165                 170                 175
```

-continued

```
Trp Asp Asp Arg Asp Thr Pro Arg Pro Glu Ser Trp Val Glu Asp Ile
            180                 185                 190

Ala Thr Ala Lys Ser Asn Pro Asn Arg Pro Ala Thr Glu Ile Tyr Arg
        195                 200                 205

Asp Leu Arg Ser Ala Ala Ala Ser Gly Trp Asp Phe Ser Ser Arg Trp
    210                 215                 220

Met Asp Asn Pro Gln Gln Leu Asn Thr Leu Arg Thr Thr Ser Ile Val
225                 230                 235                 240

Pro Val Asp Leu Asn Ser Leu Met Phe Lys Met Glu Lys Ile Leu Ala
                245                 250                 255

Arg Ala Ser Lys Ala Ala Gly Asp Asn Ala Met Ala Asn Gln Tyr Glu
            260                 265                 270

Thr Leu Ala Asn Ala Arg Gln Lys Gly Ile Glu Lys Tyr Leu Trp Asn
        275                 280                 285

Asp Gln Gln Gly Trp Tyr Ala Asp Tyr Asp Leu Lys Ser His Lys Val
    290                 295                 300

Arg Asn Gln Leu Thr Ala Ala Ala Leu Phe Pro Leu Tyr Val Asn Ala
305                 310                 315                 320

Ala Ala Lys Asp Arg Ala Asn Lys Met Ala Thr Ala Thr Lys Thr His
                325                 330                 335

Leu Leu Gln Pro Gly Gly Leu Asn Thr Thr Ser Val Lys Ser Gly Gln
            340                 345                 350

Gln Trp Asp Ala Pro Asn Gly Trp Ala Pro Leu Gln Trp Val Ala Thr
        355                 360                 365

Glu Gly Leu Gln Asn Tyr Gly Gln Lys Glu Val Ala Met Asp Ile Ser
    370                 375                 380

Trp His Phe Leu Thr Asn Val Gln His Thr Tyr Asp Arg Glu Lys Lys
385                 390                 395                 400

Leu Val Glu Lys Tyr Asp Val Ser Thr Thr Gly Thr Gly Gly Gly Gly
                405                 410                 415

Gly Glu Tyr Pro Leu Gln Asp Gly Phe Gly Trp Thr Asn Gly Val Thr
            420                 425                 430

Leu Lys Met Leu Asp Leu Ile Cys Pro Lys Glu Gln Pro Cys Asp Asn
        435                 440                 445

Val Pro Ala Thr Arg Pro Thr Val Lys Ser Ala Thr Thr Gln Pro Ser
    450                 455                 460

Thr Lys Glu Ala Gln Pro Thr Pro His His His His His His
465                 470                 475
```

<210> SEQ ID NO 24
<211> LENGTH: 98
<212> TYPE: PRT
<213> ORGANISM: Artificial Sequence
<220> FEATURE:
<223> OTHER INFORMATION: HA-TreAN-HIS: N-terminally HA-tagged, C-terminally HIS-tagged N-terminal fragment of TreA (w/o signal peptide)

<400> SEQUENCE: 24

```
Met Ala Tyr Pro Tyr Asp Val Pro Asp Tyr Ala Val Asp Glu Glu Thr
1               5                   10                  15

Pro Val Thr Pro Gln Pro Pro Asp Ile Leu Leu Gly Pro Leu Phe Asn
            20                  25                  30

Asp Val Gln Asn Ala Lys Leu Phe Pro Asp Gln Lys Thr Phe Ala Asp
        35                  40                  45

Ala Val Pro Asn Ser Asp Pro Leu Met Ile Leu Ala Asp Tyr Arg Met
```

```
                    50                  55                  60

Gln Gln Asn Gln Ser Gly Phe Asp Leu Arg His Phe Val Asn Val Asn
 65                  70                  75                  80

Phe Thr Leu Pro Lys Glu Gly Glu Lys Tyr Val Pro His His His His
                     85                  90                  95

His His
```

<210> SEQ ID NO 25
<211> LENGTH: 98
<212> TYPE: PRT
<213> ORGANISM: Artificial Sequence
<220> FEATURE:
<223> OTHER INFORMATION: HIS-TreAN-HA: N-terminally HIS-tagged, C-
      terminally HA-tagged N-terminal fragment of TreA (w/o signal
      peptide)

<400> SEQUENCE: 25

```
Met Ala His His His His His Glu Glu Thr Pro Val Thr Pro Gln
 1               5                  10                  15

Pro Pro Asp Ile Leu Leu Gly Pro Leu Phe Asn Asp Val Gln Asn Ala
                    20                  25                  30

Lys Leu Phe Pro Asp Gln Lys Thr Phe Ala Asp Ala Val Pro Asn Ser
                35                  40                  45

Asp Pro Leu Met Ile Leu Ala Asp Tyr Arg Met Gln Gln Asn Gln Ser
 50                  55                  60

Gly Phe Asp Leu Arg His Phe Val Asn Val Asn Phe Thr Leu Pro Lys
 65                  70                  75                  80

Glu Gly Glu Lys Tyr Val Pro Gly Ser Tyr Pro Tyr Asp Val Pro Asp
                    85                  90                  95

Tyr Ala
```

<210> SEQ ID NO 26
<211> LENGTH: 488
<212> TYPE: PRT
<213> ORGANISM: Artificial Sequence
<220> FEATURE:
<223> OTHER INFORMATION: HA-TreAC-HIS: N-terminally HA-tagged, C-
      terminally HIS-tagged C-terminal fragment of TreA

<400> SEQUENCE: 26

```
Met Ala Tyr Pro Tyr Asp Val Pro Asp Tyr Ala Val Asp Asn Phe Thr
 1               5                  10                  15

Leu Pro Lys Glu Gly Glu Lys Tyr Val Pro Pro Glu Gly Gln Ser Leu
                    20                  25                  30

Arg Glu His Ile Asp Gly Leu Trp Pro Val Leu Thr Arg Ser Thr Glu
                35                  40                  45

Asn Thr Glu Lys Trp Asp Ser Leu Leu Pro Leu Glu Pro Tyr Val
 50                  55                  60

Val Pro Gly Gly Arg Phe Arg Glu Val Tyr Tyr Trp Asp Ser Tyr Phe
 65                  70                  75                  80

Thr Met Leu Gly Leu Ala Glu Ser Gly His Trp Asp Lys Val Ala Asp
                85                  90                  95

Met Val Ala Asn Phe Ala His Glu Ile Asp Thr Tyr Gly His Ile Pro
                100                 105                 110

Asn Gly Asn Arg Ser Tyr Tyr Leu Ser Arg Ser Gln Pro Pro Phe Phe
                115                 120                 125

Ala Leu Met Val Glu Leu Leu Ala Gln His Glu Gly Asp Ala Ala Leu
                130                 135                 140
```

Lys Gln Tyr Leu Pro Gln Met Gln Lys Glu Tyr Ala Tyr Trp Met Asp
145                 150                 155                 160

Gly Val Glu Asn Leu Gln Ala Gly Gln Gln Glu Lys Arg Val Val Lys
            165                 170                 175

Leu Gln Asp Gly Thr Leu Leu Asn Arg Tyr Trp Asp Asp Arg Asp Thr
        180                 185                 190

Pro Arg Pro Glu Ser Trp Val Glu Asp Ile Ala Thr Ala Lys Ser Asn
    195                 200                 205

Pro Asn Arg Pro Ala Thr Glu Ile Tyr Arg Asp Leu Arg Ser Ala Ala
210                 215                 220

Ala Ser Gly Trp Asp Phe Ser Arg Trp Met Asp Asn Pro Gln Gln
225                 230                 235                 240

Leu Asn Thr Leu Arg Thr Thr Ser Ile Val Pro Val Asp Leu Asn Ser
                245                 250                 255

Leu Met Phe Lys Met Glu Lys Ile Leu Ala Arg Ala Ser Lys Ala Ala
            260                 265                 270

Gly Asp Asn Ala Met Ala Asn Gln Tyr Glu Thr Leu Ala Asn Ala Arg
        275                 280                 285

Gln Lys Gly Ile Glu Lys Tyr Leu Trp Asn Asp Gln Gln Gly Trp Tyr
    290                 295                 300

Ala Asp Tyr Asp Leu Lys Ser His Lys Val Arg Asn Gln Leu Thr Ala
305                 310                 315                 320

Ala Ala Leu Phe Pro Leu Tyr Val Asn Ala Ala Lys Asp Arg Ala
                325                 330                 335

Asn Lys Met Ala Thr Ala Thr Lys Thr His Leu Leu Gln Pro Gly Gly
            340                 345                 350

Leu Asn Thr Thr Ser Val Lys Ser Gly Gln Gln Trp Asp Ala Pro Asn
        355                 360                 365

Gly Trp Ala Pro Leu Gln Trp Val Ala Thr Glu Gly Leu Gln Asn Tyr
370                 375                 380

Gly Gln Lys Glu Val Ala Met Asp Ile Ser Trp His Phe Leu Thr Asn
385                 390                 395                 400

Val Gln His Thr Tyr Asp Arg Glu Lys Lys Leu Val Glu Lys Tyr Asp
                405                 410                 415

Val Ser Thr Thr Gly Thr Gly Gly Gly Gly Glu Tyr Pro Leu Gln
            420                 425                 430

Asp Gly Phe Gly Trp Thr Asn Gly Val Thr Leu Lys Met Leu Asp Leu
        435                 440                 445

Ile Cys Pro Lys Glu Gln Pro Cys Asp Asn Val Pro Ala Thr Arg Pro
    450                 455                 460

Thr Val Lys Ser Ala Thr Thr Gln Pro Ser Thr Lys Glu Ala Gln Pro
465                 470                 475                 480

Thr Pro His His His His His His
                485

<210> SEQ ID NO 27
<211> LENGTH: 488
<212> TYPE: PRT
<213> ORGANISM: Artificial Sequence
<220> FEATURE:
<223> OTHER INFORMATION: HIS-TreAC-HA: N-terminally HIS-tagged, C-
      terminally HA-tagged C-terminal fragment of TreA

<400> SEQUENCE: 27

Met Ala His His His His His His Asn Phe Thr Leu Pro Lys Glu Gly

-continued

```
1               5                   10                  15
Glu Lys Tyr Val Pro Pro Glu Gly Gln Ser Leu Arg Glu His Ile Asp
                20                  25                  30

Gly Leu Trp Pro Val Leu Thr Arg Ser Thr Glu Asn Thr Glu Lys Trp
                35                  40                  45

Asp Ser Leu Leu Pro Leu Pro Glu Pro Tyr Val Val Pro Gly Gly Arg
                50                  55                  60

Phe Arg Glu Val Tyr Tyr Trp Asp Ser Tyr Phe Thr Met Leu Gly Leu
65                  70                  75                  80

Ala Glu Ser Gly His Trp Asp Lys Val Ala Asp Met Val Ala Asn Phe
                85                  90                  95

Ala His Glu Ile Asp Thr Tyr Gly His Ile Pro Asn Gly Asn Arg Ser
                100                 105                 110

Tyr Tyr Leu Ser Arg Ser Gln Pro Pro Phe Phe Ala Leu Met Val Glu
                115                 120                 125

Leu Leu Ala Gln His Glu Gly Asp Ala Ala Leu Lys Gln Tyr Leu Pro
130                 135                 140

Gln Met Gln Lys Glu Tyr Ala Tyr Trp Met Asp Gly Val Glu Asn Leu
145                 150                 155                 160

Gln Ala Gly Gln Gln Glu Lys Arg Val Val Lys Leu Gln Asp Gly Thr
                165                 170                 175

Leu Leu Asn Arg Tyr Trp Asp Asp Arg Asp Thr Pro Arg Pro Glu Ser
                180                 185                 190

Trp Val Glu Asp Ile Ala Thr Ala Lys Ser Asn Pro Asn Arg Pro Ala
                195                 200                 205

Thr Glu Ile Tyr Arg Asp Leu Arg Ser Ala Ala Ser Gly Trp Asp
                210                 215                 220

Phe Ser Ser Arg Trp Met Asp Asn Pro Gln Gln Leu Asn Thr Leu Arg
225                 230                 235                 240

Thr Thr Ser Ile Val Pro Val Asp Leu Asn Ser Leu Met Phe Lys Met
                245                 250                 255

Glu Lys Ile Leu Ala Arg Ala Ser Lys Ala Ala Gly Asp Asn Ala Met
                260                 265                 270

Ala Asn Gln Tyr Glu Thr Leu Ala Asn Ala Arg Gln Lys Gly Ile Glu
                275                 280                 285

Lys Tyr Leu Trp Asn Asp Gln Gln Gly Trp Tyr Ala Asp Tyr Asp Leu
                290                 295                 300

Lys Ser His Lys Val Arg Asn Gln Leu Thr Ala Ala Ala Leu Phe Pro
305                 310                 315                 320

Leu Tyr Val Asn Ala Ala Ala Lys Asp Arg Ala Asn Lys Met Ala Thr
                325                 330                 335

Ala Thr Lys Thr His Leu Leu Gln Pro Gly Gly Leu Asn Thr Thr Ser
                340                 345                 350

Val Lys Ser Gly Gln Gln Trp Asp Ala Pro Asn Gly Trp Ala Pro Leu
                355                 360                 365

Gln Trp Val Ala Thr Glu Gly Leu Gln Asn Tyr Gly Gln Lys Glu Val
370                 375                 380

Ala Met Asp Ile Ser Trp His Phe Leu Thr Asn Val Gln His Thr Tyr
385                 390                 395                 400

Asp Arg Glu Lys Lys Leu Val Glu Lys Tyr Asp Val Ser Thr Thr Gly
                405                 410                 415

Thr Gly Gly Gly Gly Glu Tyr Pro Leu Gln Asp Gly Phe Gly Trp
                420                 425                 430
```

```
Thr Asn Gly Val Thr Leu Lys Met Leu Asp Leu Ile Cys Pro Lys Glu
            435                 440                 445

Gln Pro Cys Asp Asn Val Pro Ala Thr Arg Pro Thr Val Lys Ser Ala
    450                 455                 460

Thr Thr Gln Pro Ser Thr Lys Glu Ala Gln Pro Thr Pro Gly Ser Tyr
465                 470                 475                 480

Pro Tyr Asp Val Pro Asp Tyr Ala
                485

<210> SEQ ID NO 28
<211> LENGTH: 148
<212> TYPE: PRT
<213> ORGANISM: Artificial Sequence
<220> FEATURE:
<223> OTHER INFORMATION: HIS-TreAN-ProtG: N-terminally HIS-tagged N-
      terminal fragment of TreA with C-terminal fusion with
      immunoglobulin binding Domain B1 of protein G of Streptococcus

<400> SEQUENCE: 28

Met Ala His His His His His His Glu Glu Thr Pro Val Thr Pro Gln
1               5                   10                  15

Pro Pro Asp Ile Leu Leu Gly Pro Leu Phe Asn Asp Val Gln Asn Ala
            20                  25                  30

Lys Leu Phe Pro Asp Gln Lys Thr Phe Ala Asp Ala Val Pro Asn Ser
        35                  40                  45

Asp Pro Leu Met Ile Leu Ala Asp Tyr Arg Met Gln Gln Asn Gln Ser
    50                  55                  60

Gly Phe Asp Leu Arg His Phe Val Asn Val Asn Phe Thr Leu Pro Lys
65                  70                  75                  80

Glu Gly Glu Lys Tyr Val Pro Gly Ser Val Pro Gly Ser Thr Tyr Lys
                85                  90                  95

Leu Ile Leu Asn Gly Lys Thr Leu Lys Gly Glu Thr Thr Thr Glu Ala
            100                 105                 110

Val Asp Ala Ala Thr Ala Glu Lys Val Phe Lys Gln Tyr Ala Asn Asp
        115                 120                 125

Asn Gly Val Asp Gly Glu Trp Thr Tyr Asp Ala Ala Thr Lys Thr Phe
    130                 135                 140

Thr Val Thr Glu
145

<210> SEQ ID NO 29
<211> LENGTH: 534
<212> TYPE: PRT
<213> ORGANISM: Artificial Sequence
<220> FEATURE:
<223> OTHER INFORMATION: HIS-TreAN-ProtG: N-terminally HIS-tagged N-
      terminal fragment of TreA with C-terminal fusion with
      immunoglobulin binding Domain B1 of protein G of Streptococcus

<400> SEQUENCE: 29

Met Ala His His His His His His Asn Phe Thr Leu Pro Lys Glu Gly
1               5                   10                  15

Glu Lys Tyr Val Pro Pro Glu Gly Gln Ser Leu Arg Glu His Ile Asp
            20                  25                  30

Gly Leu Trp Pro Val Leu Thr Arg Ser Thr Glu Asn Thr Glu Lys Trp
        35                  40                  45

Asp Ser Leu Leu Pro Leu Pro Glu Pro Tyr Val Val Pro Gly Gly Arg
    50                  55                  60
```

```
Phe Arg Glu Val Tyr Tyr Trp Asp Ser Tyr Phe Thr Met Leu Gly Leu
 65                  70                  75                  80

Ala Glu Ser Gly His Trp Asp Lys Val Ala Asp Met Val Ala Asn Phe
                 85                  90                  95

Ala His Glu Ile Asp Thr Tyr Gly His Ile Pro Asn Gly Asn Arg Ser
            100                 105                 110

Tyr Tyr Leu Ser Arg Ser Gln Pro Pro Phe Phe Ala Leu Met Val Glu
        115                 120                 125

Leu Leu Ala Gln His Glu Gly Asp Ala Ala Leu Lys Gln Tyr Leu Pro
    130                 135                 140

Gln Met Gln Lys Glu Tyr Ala Tyr Trp Met Asp Gly Val Glu Asn Leu
145                 150                 155                 160

Gln Ala Gly Gln Gln Glu Lys Arg Val Val Lys Leu Gln Asp Gly Thr
                165                 170                 175

Leu Leu Asn Arg Tyr Trp Asp Asp Arg Asp Thr Pro Arg Pro Glu Ser
            180                 185                 190

Trp Val Glu Asp Ile Ala Thr Ala Lys Ser Asn Pro Asn Arg Pro Ala
        195                 200                 205

Thr Glu Ile Tyr Arg Asp Leu Arg Ser Ala Ala Ser Gly Trp Asp
    210                 215                 220

Phe Ser Ser Arg Trp Met Asp Asn Pro Gln Gln Leu Asn Thr Leu Arg
225                 230                 235                 240

Thr Thr Ser Ile Val Pro Val Asp Leu Asn Ser Leu Met Phe Lys Met
                245                 250                 255

Glu Lys Ile Leu Ala Arg Ala Ser Lys Ala Ala Gly Asp Asn Ala Met
            260                 265                 270

Ala Asn Gln Tyr Glu Thr Leu Ala Asn Ala Arg Gln Lys Gly Ile Glu
        275                 280                 285

Lys Tyr Leu Trp Asn Asp Gln Gln Gly Trp Tyr Ala Asp Tyr Asp Leu
    290                 295                 300

Lys Ser His Lys Val Arg Asn Gln Leu Thr Ala Ala Leu Phe Pro
305                 310                 315                 320

Leu Tyr Val Asn Ala Ala Ala Lys Asp Arg Ala Asn Lys Met Ala Thr
                325                 330                 335

Ala Thr Lys Thr His Leu Leu Gln Pro Gly Gly Leu Asn Thr Thr Ser
            340                 345                 350

Val Lys Ser Gly Gln Gln Trp Asp Ala Pro Asn Gly Trp Ala Pro Leu
        355                 360                 365

Gln Trp Val Ala Thr Glu Gly Leu Gln Asn Tyr Gly Gln Lys Glu Val
    370                 375                 380

Ala Met Asp Ile Ser Trp His Phe Leu Thr Asn Val Gln His Thr Tyr
385                 390                 395                 400

Asp Arg Glu Lys Lys Leu Val Glu Lys Tyr Asp Val Ser Thr Thr Gly
                405                 410                 415

Thr Gly Gly Gly Gly Glu Tyr Pro Leu Gln Asp Gly Phe Gly Trp
            420                 425                 430

Thr Asn Gly Val Thr Leu Lys Met Leu Asp Leu Ile Cys Pro Lys Glu
        435                 440                 445

Gln Pro Cys Asp Asn Val Pro Ala Thr Arg Pro Thr Val Lys Ser Ala
    450                 455                 460

Thr Thr Gln Pro Ser Thr Lys Glu Ala Gln Pro Thr Pro Gly Ser Thr
465                 470                 475                 480

Tyr Lys Leu Ile Leu Asn Gly Lys Thr Leu Lys Gly Glu Thr Thr Thr
```

485                 490                 495
Glu Ala Val Asp Ala Ala Thr Ala Glu Lys Val Phe Lys Gln Tyr Ala
            500                 505                 510

Asn Asp Asn Gly Val Asp Gly Glu Trp Thr Tyr Asp Ala Ala Thr Lys
            515                 520                 525

Thr Phe Thr Val Thr Glu
            530

<210> SEQ ID NO 30
<211> LENGTH: 320
<212> TYPE: PRT
<213> ORGANISM: Artificial Sequence
<220> FEATURE:
<223> OTHER INFORMATION: HIVP24-TreAN-HIS:  HIV capside protein P24
      fused N-terminally to the N-terminal fragment of TreA (w/o signal
      peptide), C-terminal HIS-tag

<400> SEQUENCE: 30

Met Glu Pro Ile Val Gln Asn Ile Gln Gly Gln Met Val His Gln Ala
1               5                   10                  15

Ile Ser Pro Arg Thr Leu Asn Ala Trp Val Lys Val Val Glu Glu Lys
            20                  25                  30

Ala Phe Ser Pro Glu Val Ile Pro Met Phe Ser Ala Leu Ser Glu Gly
        35                  40                  45

Ala Thr Pro Gln Asp Leu Asn Thr Met Leu Asn Thr Val Gly Gly His
    50                  55                  60

Gln Ala Ala Met Gln Met Leu Lys Glu Thr Ile Asn Glu Glu Ala Ala
65                  70                  75                  80

Glu Trp Asp Arg Val His Pro Val His Ala Gly Pro Ile Ala Pro Gly
                85                  90                  95

Gln Met Arg Glu Pro Arg Gly Ser Asp Ile Ala Gly Thr Thr Ser Thr
            100                 105                 110

Leu Gln Glu Gln Ile Gly Trp Met Thr Asn Asn Pro Pro Ile Pro Val
        115                 120                 125

Gly Glu Ile Tyr Lys Arg Trp Ile Ile Leu Gly Leu Asn Lys Ile Val
    130                 135                 140

Arg Met Tyr Ser Pro Thr Ser Ile Leu Asp Ile Arg Gln Gly Pro Lys
145                 150                 155                 160

Glu Pro Phe Arg Asp Tyr Val Asp Arg Phe Tyr Lys Thr Leu Arg Ala
                165                 170                 175

Glu Gln Ala Ser Gln Glu Val Lys Asn Ala Met Thr Glu Thr Leu Leu
            180                 185                 190

Val Gln Asn Ala Asn Pro Asp Cys Lys Thr Ile Leu Lys Ala Leu Gly
        195                 200                 205

Pro Ala Ala Thr Leu Glu Glu Met Met Thr Ala Cys Gln Gly Val Gly
    210                 215                 220

Gly Pro Gly His Lys Ala Arg Val Leu Val Asp Glu Glu Thr Pro Val
225                 230                 235                 240

Thr Pro Gln Pro Pro Asp Ile Leu Leu Gly Pro Leu Phe Asn Asp Val
                245                 250                 255

Gln Asn Ala Lys Leu Phe Pro Asp Gln Lys Thr Phe Ala Asp Ala Val
            260                 265                 270

Pro Asn Ser Asp Pro Leu Met Ile Leu Ala Asp Tyr Arg Met Gln Gln
        275                 280                 285

Asn Gln Ser Gly Phe Asp Leu Arg His Phe Val Asn Val Asn Phe Thr
    290                 295                 300

```
Leu Pro Lys Glu Gly Glu Lys Tyr Val Pro His His His His His
305                 310                 315                 320
```

<210> SEQ ID NO 31
<211> LENGTH: 710
<212> TYPE: PRT
<213> ORGANISM: Artificial Sequenced
<220> FEATURE:
<223> OTHER INFORMATION: HIVP24-TreAC: HIV capside protein P24 fused N-
      terminally to the C-terminal fragment of TreA, with C-terminal
      HIS-tag

<400> SEQUENCE: 31

```
Met Glu Pro Ile Val Gln Asn Ile Gln Gly Gln Met Val His Gln Ala
1               5                   10                  15

Ile Ser Pro Arg Thr Leu Asn Ala Trp Val Lys Val Val Glu Glu Lys
            20                  25                  30

Ala Phe Ser Pro Glu Val Ile Pro Met Phe Ser Ala Leu Ser Glu Gly
        35                  40                  45

Ala Thr Pro Gln Asp Leu Asn Thr Met Leu Asn Thr Val Gly Gly His
    50                  55                  60

Gln Ala Ala Met Gln Met Leu Lys Glu Thr Ile Asn Glu Glu Ala Ala
65                  70                  75                  80

Glu Trp Asp Arg Val His Pro Val His Ala Gly Pro Ile Ala Pro Gly
                85                  90                  95

Gln Met Arg Glu Pro Arg Gly Ser Asp Ile Ala Gly Thr Thr Ser Thr
            100                 105                 110

Leu Gln Glu Gln Ile Gly Trp Met Thr Asn Asn Pro Pro Ile Pro Val
        115                 120                 125

Gly Glu Ile Tyr Lys Arg Trp Ile Ile Leu Gly Leu Asn Lys Ile Val
    130                 135                 140

Arg Met Tyr Ser Pro Thr Ser Ile Leu Asp Ile Arg Gln Gly Pro Lys
145                 150                 155                 160

Glu Pro Phe Arg Asp Tyr Val Asp Arg Phe Tyr Lys Thr Leu Arg Ala
                165                 170                 175

Glu Gln Ala Ser Gln Glu Val Lys Asn Ala Met Thr Glu Thr Leu Leu
            180                 185                 190

Val Gln Asn Ala Asn Pro Asp Cys Lys Thr Ile Leu Lys Ala Leu Gly
        195                 200                 205

Pro Ala Ala Thr Leu Glu Glu Met Met Thr Ala Cys Gln Gly Val Gly
    210                 215                 220

Gly Pro Gly His Lys Ala Arg Val Leu Val Asp Asn Phe Thr Leu Pro
225                 230                 235                 240

Lys Glu Gly Glu Lys Tyr Val Pro Pro Glu Gly Gln Ser Leu Arg Glu
                245                 250                 255

His Ile Asp Gly Leu Trp Pro Val Leu Thr Arg Ser Thr Glu Asn Thr
            260                 265                 270

Glu Lys Trp Asp Ser Leu Leu Pro Leu Pro Glu Pro Tyr Val Val Pro
        275                 280                 285

Gly Gly Arg Phe Arg Glu Val Tyr Tyr Trp Asp Ser Tyr Phe Thr Met
    290                 295                 300

Leu Gly Leu Ala Glu Ser Gly His Trp Asp Lys Val Ala Asp Met Val
305                 310                 315                 320

Ala Asn Phe Ala His Glu Ile Asp Thr Tyr Gly His Ile Pro Asn Gly
                325                 330                 335
```

-continued

Asn Arg Ser Tyr Tyr Leu Ser Arg Ser Gln Pro Pro Phe Phe Ala Leu
            340                 345                 350

Met Val Glu Leu Leu Ala Gln His Glu Gly Asp Ala Ala Leu Lys Gln
        355                 360                 365

Tyr Leu Pro Gln Met Gln Lys Glu Tyr Ala Tyr Trp Met Asp Gly Val
    370                 375                 380

Glu Asn Leu Gln Ala Gly Gln Gln Glu Lys Arg Val Val Lys Leu Gln
385                 390                 395                 400

Asp Gly Thr Leu Leu Asn Arg Tyr Trp Asp Asp Arg Asp Thr Pro Arg
                405                 410                 415

Pro Glu Ser Trp Val Glu Asp Ile Ala Thr Ala Lys Ser Asn Pro Asn
            420                 425                 430

Arg Pro Ala Thr Glu Ile Tyr Arg Asp Leu Arg Ser Ala Ala Ala Ser
        435                 440                 445

Gly Trp Asp Phe Ser Ser Arg Trp Met Asp Asn Pro Gln Gln Leu Asn
    450                 455                 460

Thr Leu Arg Thr Thr Ser Ile Val Pro Val Asp Leu Asn Ser Leu Met
465                 470                 475                 480

Phe Lys Met Glu Lys Ile Leu Ala Arg Ala Ser Lys Ala Ala Gly Asp
                485                 490                 495

Asn Ala Met Ala Asn Gln Tyr Glu Thr Leu Ala Asn Ala Arg Gln Lys
            500                 505                 510

Gly Ile Glu Lys Tyr Leu Trp Asn Asp Gln Gln Gly Trp Tyr Ala Asp
        515                 520                 525

Tyr Asp Leu Lys Ser His Lys Val Arg Asn Gln Leu Thr Ala Ala Ala
    530                 535                 540

Leu Phe Pro Leu Tyr Val Asn Ala Ala Ala Lys Asp Arg Ala Asn Lys
545                 550                 555                 560

Met Ala Thr Ala Thr Lys Thr His Leu Leu Gln Pro Gly Gly Leu Asn
                565                 570                 575

Thr Thr Ser Val Lys Ser Gly Gln Gln Trp Asp Ala Pro Asn Gly Trp
            580                 585                 590

Ala Pro Leu Gln Trp Val Ala Thr Glu Gly Leu Gln Asn Tyr Gly Gln
        595                 600                 605

Lys Glu Val Ala Met Asp Ile Ser Trp His Phe Leu Thr Asn Val Gln
    610                 615                 620

His Thr Tyr Asp Arg Glu Lys Lys Leu Val Glu Lys Tyr Asp Val Ser
625                 630                 635                 640

Thr Thr Gly Thr Gly Gly Gly Gly Glu Tyr Pro Leu Gln Asp Gly
                645                 650                 655

Phe Gly Trp Thr Asn Gly Val Thr Leu Lys Met Leu Asp Leu Ile Cys
            660                 665                 670

Pro Lys Glu Gln Pro Cys Asp Asn Val Pro Ala Thr Arg Pro Thr Val
        675                 680                 685

Lys Ser Ala Thr Thr Gln Pro Ser Thr Lys Glu Ala Gln Pro Thr Pro
    690                 695                 700

His His His His His His
705                 710

<210> SEQ ID NO 32
<211> LENGTH: 154
<212> TYPE: PRT
<213> ORGANISM: Artificial Sequence
<220> FEATURE:
<223> OTHER INFORMATION: TreAN-pA: N-terminally HIS-tagged N-terminus of TreA (w/o signal peptide) C-terminally fused with the
immunoglobulin binding domain of protein A

<400> SEQUENCE: 32

```
Met Ala His His His His His Glu Glu Thr Pro Val Thr Pro Gln
1               5                   10                  15

Pro Pro Asp Ile Leu Leu Gly Pro Leu Phe Asn Asp Val Gln Asn Ala
                20                  25                  30

Lys Leu Phe Pro Asp Gln Lys Thr Phe Ala Asp Ala Val Pro Asn Ser
                35                  40                  45

Asp Pro Leu Met Ile Leu Ala Asp Tyr Arg Met Gln Gln Asn Gln Ser
            50                  55                  60

Gly Phe Asp Leu Arg His Phe Val Asn Val Asn Phe Thr Leu Pro Lys
65                  70                  75                  80

Glu Gly Glu Lys Tyr Val Pro Gly Ser Ala Met Glu Glu Val Thr Ile
                85                  90                  95

Lys Ala Asn Leu Ile Phe Ala Asn Gly Ser Thr Gln Thr Ala Glu Phe
                100                 105                 110

Lys Gly Thr Phe Glu Lys Ala Thr Ser Glu Ala Tyr Ala Tyr Ala Asp
                115                 120                 125

Thr Leu Lys Lys Asp Asn Gly Glu Trp Thr Val Asp Val Ala Asp Lys
            130                 135                 140

Gly Tyr Thr Leu Asn Ile Lys Phe Ala Gly
145                 150
```

<210> SEQ ID NO 33
<211> LENGTH: 539
<212> TYPE: PRT
<213> ORGANISM: Artificial Sequence
<220> FEATURE:
<223> OTHER INFORMATION: TreAC-pA: N-terminally HIS-tagged C-terminus of
    TreA (w/o signal peptide) C-terminally fused with the
    immunoglobulin binding domain of protein A

<400> SEQUENCE: 33

```
Met Ala His His His His His Asn Phe Thr Leu Pro Lys Glu Gly
1               5                   10                  15

Glu Lys Tyr Val Pro Pro Glu Gly Gln Ser Leu Arg Glu His Ile Asp
                20                  25                  30

Gly Leu Trp Pro Val Leu Thr Arg Ser Thr Glu Asn Thr Glu Lys Trp
                35                  40                  45

Asp Ser Leu Leu Pro Leu Pro Glu Pro Tyr Val Val Pro Gly Gly Arg
            50                  55                  60

Phe Arg Glu Val Tyr Tyr Trp Asp Ser Tyr Phe Thr Met Leu Gly Leu
65                  70                  75                  80

Ala Glu Ser Gly His Trp Asp Lys Val Ala Asp Met Val Ala Asn Phe
                85                  90                  95

Ala His Glu Ile Asp Thr Tyr Gly His Ile Pro Asn Gly Asn Arg Ser
                100                 105                 110

Tyr Tyr Leu Ser Arg Ser Gln Pro Pro Phe Phe Ala Leu Met Val Glu
            115                 120                 125

Leu Leu Ala Gln His Glu Gly Asp Ala Ala Leu Lys Gln Tyr Leu Pro
            130                 135                 140

Gln Met Gln Lys Glu Tyr Ala Tyr Trp Met Asp Gly Val Glu Asn Leu
145                 150                 155                 160

Gln Ala Gly Gln Gln Glu Lys Arg Val Val Lys Leu Gln Asp Gly Thr
                165                 170                 175
```

```
Leu Leu Asn Arg Tyr Trp Asp Arg Asp Thr Pro Arg Pro Glu Ser
            180                 185                 190

Trp Val Glu Asp Ile Ala Thr Ala Lys Ser Asn Pro Asn Arg Pro Ala
        195                 200                 205

Thr Glu Ile Tyr Arg Asp Leu Arg Ser Ala Ala Ser Gly Trp Asp
    210                 215                 220

Phe Ser Ser Arg Trp Met Asp Asn Pro Gln Gln Leu Asn Thr Leu Arg
225                 230                 235                 240

Thr Thr Ser Ile Val Pro Val Asp Leu Asn Ser Leu Met Phe Lys Met
                245                 250                 255

Glu Lys Ile Leu Ala Arg Ala Ser Lys Ala Ala Gly Asp Asn Ala Met
            260                 265                 270

Ala Asn Gln Tyr Glu Thr Leu Ala Asn Ala Arg Gln Lys Gly Val Glu
        275                 280                 285

Lys Tyr Leu Trp Asn Asp Gln Gln Gly Trp Tyr Ala Asp Tyr Asp Leu
    290                 295                 300

Lys Ser His Lys Val Arg Asn Gln Leu Thr Ala Ala Leu Phe Pro
305                 310                 315                 320

Leu Tyr Val Asn Ala Ala Lys Asp Arg Ala Asn Lys Met Ala Thr
                325                 330                 335

Ala Thr Lys Thr His Leu Leu Gln Pro Gly Gly Leu Asn Thr Thr Ser
            340                 345                 350

Val Lys Ser Gly Gln Gln Trp Asp Ala Pro Asn Gly Trp Ala Pro Leu
        355                 360                 365

Gln Trp Val Ala Thr Glu Gly Leu Gln Asn Tyr Gly Gln Lys Glu Val
    370                 375                 380

Ala Met Asp Ile Ser Trp His Phe Leu Thr Asn Gly Gln His Thr Tyr
385                 390                 395                 400

Asp Arg Glu Lys Lys Leu Val Glu Lys Tyr Asp Val Ser Thr Thr Gly
                405                 410                 415

Thr Gly Gly Gly Gly Glu Tyr Pro Leu Gln Asp Gly Phe Gly Trp
            420                 425                 430

Thr Asn Gly Val Thr Leu Lys Met Leu Asp Leu Ile Cys Pro Lys Glu
        435                 440                 445

Gln Pro Cys Asp Asn Val Pro Ala Thr Arg Pro Thr Val Lys Ser Ala
    450                 455                 460

Thr Thr Gln Pro Ser Thr Lys Glu Ala Gln Pro Thr Pro Gly Ser Thr
465                 470                 475                 480

Ala Asp Asn Lys Phe Asn Lys Glu Gln Gln Asn Ala Phe Tyr Glu Ile
                485                 490                 495

Leu His Leu Pro Asn Leu Asn Glu Glu Gln Arg Asn Gly Phe Ile Gln
            500                 505                 510

Ser Leu Lys Asp Asp Pro Ser Gln Ser Ala Asn Leu Leu Ala Glu Ala
        515                 520                 525

Lys Lys Leu Asn Asp Ala Gln Ala Pro Lys Ala
    530                 535

<210> SEQ ID NO 34
<211> LENGTH: 149
<212> TYPE: PRT
<213> ORGANISM: Artificial Sequence
<220> FEATURE:
<223> OTHER INFORMATION: TreAN-pL: N-terminally HIS-tagged N-terminus of
      TreA (w/o signal peptide) C-terminally fused with the
      immunoglobulin binding domain of protein L
```

<400> SEQUENCE: 34

Met Ala His His His His His Glu Glu Thr Pro Val Thr Pro Gln
1               5                   10                  15

Pro Pro Asp Ile Leu Leu Gly Pro Leu Phe Asn Asp Val Gln Asn Ala
            20                  25                  30

Lys Leu Phe Pro Asp Gln Lys Thr Phe Ala Asp Ala Val Pro Asn Ser
                35                  40                  45

Asp Pro Leu Met Ile Leu Ala Asp Tyr Arg Met Gln Gln Asn Gln Ser
        50                  55                  60

Gly Phe Asp Leu Arg His Phe Val Asn Val Asn Phe Thr Leu Pro Lys
65                  70                  75                  80

Glu Gly Glu Lys Tyr Val Pro Gly Ser Thr Ala Asp Asn Lys Phe Asn
                85                  90                  95

Lys Glu Gln Gln Asn Ala Phe Tyr Glu Ile Leu His Leu Pro Asn Leu
            100                 105                 110

Asn Glu Glu Gln Arg Asn Gly Phe Ile Gln Ser Leu Lys Asp Asp Pro
        115                 120                 125

Ser Gln Ser Ala Asn Leu Leu Ala Glu Ala Lys Lys Leu Asn Asp Ala
    130                 135                 140

Gln Ala Pro Lys Ala
145

<210> SEQ ID NO 35
<211> LENGTH: 544
<212> TYPE: PRT
<213> ORGANISM: Artificial Sequence
<220> FEATURE:
<223> OTHER INFORMATION: TreAC-pL: N-terminally HIS-tagged C-terminus of
      TreA (w/o signal peptide) C-terminally fused with the
      immunoglobulin binding domain of protein L

<400> SEQUENCE: 35

Met Ala His His His His His Asn Phe Thr Leu Pro Lys Glu Gly
1               5                   10                  15

Glu Lys Tyr Val Pro Pro Glu Gly Gln Ser Leu Arg Glu His Ile Asp
            20                  25                  30

Gly Leu Trp Pro Val Leu Thr Arg Ser Thr Glu Asn Thr Glu Lys Trp
        35                  40                  45

Asp Ser Leu Leu Pro Leu Pro Glu Pro Tyr Val Val Pro Gly Gly Arg
    50                  55                  60

Phe Arg Glu Val Tyr Tyr Trp Asp Ser Tyr Phe Thr Met Leu Gly Leu
65                  70                  75                  80

Ala Glu Ser Gly His Trp Asp Lys Val Ala Asp Met Val Ala Asn Phe
                85                  90                  95

Ala His Glu Ile Asp Thr Tyr Gly His Ile Pro Asn Gly Asn Arg Ser
            100                 105                 110

Tyr Tyr Leu Ser Arg Ser Gln Pro Pro Phe Phe Ala Leu Met Val Glu
        115                 120                 125

Leu Leu Ala Gln His Glu Gly Asp Ala Ala Leu Lys Gln Tyr Leu Pro
    130                 135                 140

Gln Met Gln Lys Glu Tyr Ala Tyr Trp Met Asp Gly Val Glu Asn Leu
145                 150                 155                 160

Gln Ala Gly Gln Gln Glu Lys Arg Val Val Lys Leu Gln Asp Gly Thr
                165                 170                 175

Leu Leu Asn Arg Tyr Trp Asp Asp Arg Asp Thr Pro Arg Pro Glu Ser

```
                180                 185                 190
Trp Val Glu Asp Ile Ala Thr Ala Lys Ser Asn Pro Asn Arg Pro Ala
            195                 200                 205
Thr Glu Ile Tyr Arg Asp Leu Arg Ser Ala Ala Ser Gly Trp Asp
        210                 215                 220
Phe Ser Ser Arg Trp Met Asp Asn Pro Gln Gln Leu Asn Thr Leu Arg
225                 230                 235                 240
Thr Thr Ser Ile Val Pro Val Asp Leu Asn Ser Leu Met Phe Lys Met
                245                 250                 255
Glu Lys Ile Leu Ala Arg Ala Ser Lys Ala Ala Gly Asp Asn Ala Met
            260                 265                 270
Ala Asn Gln Tyr Glu Thr Leu Ala Asn Ala Arg Gln Lys Gly Val Glu
        275                 280                 285
Lys Tyr Leu Trp Asn Asp Gln Gln Gly Trp Tyr Ala Asp Tyr Asp Leu
            290                 295                 300
Lys Ser His Lys Val Arg Asn Gln Leu Thr Ala Ala Leu Phe Pro
305                 310                 315                 320
Leu Tyr Val Asn Ala Ala Lys Asp Arg Ala Asn Lys Met Ala Thr
                325                 330                 335
Ala Thr Lys Thr His Leu Leu Gln Pro Gly Gly Leu Asn Thr Thr Ser
            340                 345                 350
Val Lys Ser Gly Gln Gln Trp Asp Ala Pro Asn Gly Trp Ala Pro Leu
        355                 360                 365
Gln Trp Val Ala Thr Glu Gly Leu Gln Asn Tyr Gly Gln Lys Glu Val
    370                 375                 380
Ala Met Asp Ile Ser Trp His Phe Leu Thr Asn Gly Gln His Thr Tyr
385                 390                 395                 400
Asp Arg Glu Lys Lys Leu Val Glu Lys Tyr Asp Val Ser Thr Thr Gly
                405                 410                 415
Thr Gly Gly Gly Gly Glu Tyr Pro Leu Gln Asp Gly Phe Gly Trp
            420                 425                 430
Thr Asn Gly Val Thr Leu Lys Met Leu Asp Leu Ile Cys Pro Lys Glu
        435                 440                 445
Gln Pro Cys Asp Asn Val Pro Ala Thr Arg Pro Thr Val Lys Ser Ala
450                 455                 460
Thr Thr Gln Pro Ser Thr Lys Glu Ala Gln Pro Thr Pro Gly Ser Ala
465                 470                 475                 480
Met Glu Glu Val Thr Ile Lys Ala Asn Leu Ile Phe Ala Asn Gly Ser
                485                 490                 495
Thr Gln Thr Ala Glu Phe Lys Gly Thr Phe Glu Lys Ala Thr Ser Glu
            500                 505                 510
Ala Tyr Ala Tyr Ala Asp Thr Leu Lys Lys Asp Asn Gly Glu Trp Thr
        515                 520                 525
Val Asp Val Ala Asp Lys Gly Tyr Thr Leu Asn Ile Lys Phe Ala Gly
    530                 535                 540

<210> SEQ ID NO 36
<211> LENGTH: 12
<212> TYPE: PRT
<213> ORGANISM: Artificial Sequence
<220> FEATURE:
<223> OTHER INFORMATION: Staphylococcus aureus binding peptide SA5-1

<400> SEQUENCE: 36

Val Pro His Asn Pro Gly Leu Ile Ser Leu Gln Gly
```

<210> SEQ ID NO 37
<211> LENGTH: 12
<212> TYPE: PRT
<213> ORGANISM: Artificial Sequence
<220> FEATURE:
<223> OTHER INFORMATION: Mycobacterium avium subsp. paratuberculosis
      binding peptide Mp3

<400> SEQUENCE: 37

Asn Tyr Val Ile His Asp Val Pro Arg His Pro Ala
1               5                   10

<210> SEQ ID NO 38
<211> LENGTH: 28
<212> TYPE: PRT
<213> ORGANISM: Artificial Sequence
<220> FEATURE:
<223> OTHER INFORMATION: complementary coiled-coil peptide with leucine
      zipper motif Ei

<400> SEQUENCE: 38

Glu Ile Ala Ala Leu Glu Lys Glu Ile Ala Ala Leu Glu Lys Glu Asn
1               5                   10                  15

Ala Ala Leu Glu Trp Glu Ile Ala Ala Leu Glu Lys
            20                  25

<210> SEQ ID NO 39
<211> LENGTH: 28
<212> TYPE: PRT
<213> ORGANISM: Artificial Sequence
<220> FEATURE:
<223> OTHER INFORMATION: complementary coiled-coil peptide with leucine
      zipper motif Ki

<400> SEQUENCE: 39

Lys Ile Ala Ala Leu Lys Glu Lys Ile Ala Ala Leu Lys Glu Lys Asn
1               5                   10                  15

Ala Ala Leu Lys Trp Lys Ile Ala Ala Leu Lys Glu
            20                  25

<210> SEQ ID NO 40
<211> LENGTH: 101
<212> TYPE: PRT
<213> ORGANISM: Artificial Sequence
<220> FEATURE:
<223> OTHER INFORMATION: TreAN-SA: N-terminally HIS-tagged N-terminal
      fragment of TreA with C-terminal fusion with S. aureus binding
      peptide aptamer, SA5-1

<400> SEQUENCE: 40

Met Ala His His His His His His Glu Glu Thr Pro Val Thr Pro Gln
1               5                   10                  15

Pro Pro Asp Ile Leu Leu Gly Pro Leu Phe Asn Asp Val Gln Asn Ala
                20                  25                  30

Lys Leu Phe Pro Asp Gln Lys Thr Phe Ala Asp Ala Val Pro Asn Ser
        35                  40                  45

Asp Pro Leu Met Ile Leu Ala Asp Tyr Arg Met Gln Gln Asn Gln Ser
    50                  55                  60

Gly Phe Asp Leu Arg His Phe Val Asn Val Asn Phe Thr Leu Pro Lys
65                  70                  75                  80

Glu Gly Glu Lys Tyr Val Pro Gly Ser Val Pro His Asn Pro Gly Leu
                85                  90                  95

Ile Ser Leu Gln Gly
             100

<210> SEQ ID NO 41
<211> LENGTH: 100
<212> TYPE: PRT
<213> ORGANISM: Artificial Sequence
<220> FEATURE:
<223> OTHER INFORMATION: SA-TreAN: C-terminally HIS-tagged N-terminal
      fragment of TreA with N-terminal fusion with S. aureus binding
      peptide aptamer, SA5-1

<400> SEQUENCE: 41

Met Val Pro His Asn Pro Gly Leu Ile Ser Leu Gln Gly Val Asp Glu
1               5                   10                  15

Glu Thr Pro Val Thr Pro Gln Pro Pro Asp Ile Leu Leu Gly Pro Leu
            20                  25                  30

Phe Asn Asp Val Gln Asn Ala Lys Leu Phe Pro Asp Gln Lys Thr Phe
        35                  40                  45

Ala Asp Ala Val Pro Asn Ser Asp Pro Leu Met Ile Leu Ala Asp Tyr
    50                  55                  60

Arg Met Gln Gln Asn Gln Ser Gly Phe Asp Leu Arg His Phe Val Asn
65                  70                  75                  80

Val Asn Phe Thr Leu Pro Lys Glu Gly Glu Lys Tyr Val Pro His His
                85                  90                  95

His His His His
        100

<210> SEQ ID NO 42
<211> LENGTH: 491
<212> TYPE: PRT
<213> ORGANISM: Artificial Sequence
<220> FEATURE:
<223> OTHER INFORMATION: TreAC-SA: N-terminally HIS-tagged C-terminal
      fragment of TreA with C-terminal fusion with S. aureus binding
      peptide aptamer, SA5-1

<400> SEQUENCE: 42

Met Ala His His His His His His Asn Phe Thr Leu Pro Lys Glu Gly
1               5                   10                  15

Glu Lys Tyr Val Pro Pro Glu Gly Gln Ser Leu Arg Glu His Ile Asp
            20                  25                  30

Gly Leu Trp Pro Val Leu Thr Arg Ser Thr Glu Asn Thr Glu Lys Trp
        35                  40                  45

Asp Ser Leu Leu Pro Leu Pro Glu Pro Tyr Val Val Pro Gly Gly Arg
    50                  55                  60

Phe Arg Glu Val Tyr Tyr Trp Asp Ser Tyr Phe Thr Met Leu Gly Leu
65                  70                  75                  80

Ala Glu Ser Gly His Trp Asp Lys Val Ala Asp Met Val Ala Asn Phe
                85                  90                  95

Ala His Glu Ile Asp Thr Tyr Gly His Ile Pro Asn Gly Asn Arg Ser
            100                 105                 110

Tyr Tyr Leu Ser Arg Ser Gln Pro Pro Phe Phe Ala Leu Met Val Glu
        115                 120                 125

Leu Leu Ala Gln His Glu Gly Asp Ala Ala Leu Lys Gln Tyr Leu Pro
    130                 135                 140

Gln Met Gln Lys Glu Tyr Ala Tyr Trp Met Asp Gly Val Glu Asn Leu
145                 150                 155                 160

```
Gln Ala Gly Gln Gln Glu Lys Arg Val Val Lys Leu Gln Asp Gly Thr
                165                 170                 175

Leu Leu Asn Arg Tyr Trp Asp Asp Arg Asp Thr Pro Arg Pro Glu Ser
            180                 185                 190

Trp Val Glu Asp Ile Ala Thr Ala Lys Ser Asn Pro Asn Arg Pro Ala
        195                 200                 205

Thr Glu Ile Tyr Arg Asp Leu Arg Ser Ala Ala Ser Gly Trp Asp
    210                 215                 220

Phe Ser Ser Arg Trp Met Asp Asn Pro Gln Leu Asn Thr Leu Arg
225                 230                 235                 240

Thr Thr Ser Ile Val Pro Val Asp Leu Asn Ser Leu Met Phe Lys Met
                245                 250                 255

Glu Lys Ile Leu Ala Arg Ala Ser Lys Ala Ala Gly Asp Asn Ala Met
                260                 265                 270

Ala Asn Gln Tyr Glu Thr Leu Ala Asn Ala Arg Gln Lys Gly Ile Glu
            275                 280                 285

Lys Tyr Leu Trp Asn Asp Gln Gln Gly Trp Tyr Ala Asp Tyr Asp Leu
        290                 295                 300

Lys Ser His Lys Val Arg Asn Gln Leu Thr Ala Ala Leu Phe Pro
305                 310                 315                 320

Leu Tyr Val Asn Ala Ala Ala Lys Asp Arg Ala Asn Lys Met Ala Thr
                325                 330                 335

Ala Thr Lys Thr His Leu Leu Gln Pro Gly Gly Leu Asn Thr Thr Ser
            340                 345                 350

Val Lys Ser Gly Gln Gln Trp Asp Ala Pro Asn Gly Trp Ala Pro Leu
        355                 360                 365

Gln Trp Val Ala Thr Glu Gly Leu Gln Asn Tyr Gly Gln Lys Glu Val
    370                 375                 380

Ala Met Asp Ile Ser Trp His Phe Leu Thr Asn Val Gln His Thr Tyr
385                 390                 395                 400

Asp Arg Glu Lys Lys Leu Val Glu Lys Tyr Asp Val Ser Thr Thr Gly
                405                 410                 415

Thr Gly Gly Gly Gly Glu Tyr Pro Leu Gln Asp Gly Phe Gly Trp
            420                 425                 430

Thr Asn Gly Val Thr Leu Lys Met Leu Asp Leu Ile Cys Pro Lys Glu
        435                 440                 445

Gln Pro Cys Asp Asn Val Pro Ala Thr Arg Pro Thr Val Lys Ser Ala
    450                 455                 460

Thr Thr Gln Pro Ser Thr Lys Glu Ala Gln Pro Thr Pro Gly Ser Val
465                 470                 475                 480

Pro His Asn Pro Gly Leu Ile Ser Leu Gln Gly
                485                 490
```

<210> SEQ ID NO 43
<211> LENGTH: 490
<212> TYPE: PRT
<213> ORGANISM: Artificial Sequence
<220> FEATURE:
<223> OTHER INFORMATION: SA-TreAC: C-terminally HIS-tagged C-terminal
      fragment of TreA with N-terminal fusion with S. aureus binding
      peptide aptamer, SA5-1

<400> SEQUENCE: 43

```
Met Val Pro His Asn Pro Gly Leu Ile Ser Leu Gln Gly Val Asp Asn
1               5                   10                  15

Phe Thr Leu Pro Lys Glu Gly Glu Lys Tyr Val Pro Pro Glu Gly Gln
```

-continued

```
                20                  25                  30
Ser Leu Arg Glu His Ile Asp Gly Leu Trp Pro Val Leu Thr Arg Ser
            35                  40                  45
Thr Glu Asn Thr Glu Lys Trp Asp Ser Leu Leu Pro Leu Pro Glu Pro
        50                  55                  60
Tyr Val Val Pro Gly Arg Phe Arg Glu Val Tyr Trp Asp Ser
65                  70                  75                  80
Tyr Phe Thr Met Leu Gly Leu Ala Glu Ser Gly His Trp Asp Lys Val
                85                  90                  95
Ala Asp Met Val Ala Asn Phe Ala His Glu Ile Asp Thr Tyr Gly His
            100                 105                 110
Ile Pro Asn Gly Asn Arg Ser Tyr Tyr Leu Ser Arg Ser Gln Pro Pro
            115                 120                 125
Phe Phe Ala Leu Met Val Glu Leu Leu Ala Gln His Glu Gly Asp Ala
            130                 135                 140
Ala Leu Lys Gln Tyr Leu Pro Gln Met Gln Lys Glu Tyr Ala Tyr Trp
145                 150                 155                 160
Met Asp Gly Val Glu Asn Leu Gln Ala Gly Gln Gln Glu Lys Arg Val
                165                 170                 175
Val Lys Leu Gln Asp Gly Thr Leu Leu Asn Arg Tyr Trp Asp Asp Arg
            180                 185                 190
Asp Thr Pro Arg Pro Glu Ser Trp Val Glu Asp Ile Ala Thr Ala Lys
            195                 200                 205
Ser Asn Pro Asn Arg Pro Ala Thr Glu Ile Tyr Arg Asp Leu Arg Ser
            210                 215                 220
Ala Ala Ala Ser Gly Trp Asp Phe Ser Ser Arg Trp Met Asp Asn Pro
225                 230                 235                 240
Gln Gln Leu Asn Thr Leu Arg Thr Thr Ser Ile Val Pro Val Asp Leu
                245                 250                 255
Asn Ser Leu Met Phe Lys Met Glu Lys Ile Leu Ala Arg Ala Ser Lys
            260                 265                 270
Ala Ala Gly Asp Asn Ala Met Ala Asn Gln Tyr Glu Thr Leu Ala Asn
            275                 280                 285
Ala Arg Gln Lys Gly Ile Glu Lys Tyr Leu Trp Asn Asp Gln Gln Gly
            290                 295                 300
Trp Tyr Ala Asp Tyr Asp Leu Lys Ser His Lys Val Arg Asn Gln Leu
305                 310                 315                 320
Thr Ala Ala Ala Leu Phe Pro Leu Tyr Val Asn Ala Ala Ala Lys Asp
                325                 330                 335
Arg Ala Asn Lys Met Ala Thr Ala Thr Lys Thr His Leu Leu Gln Pro
            340                 345                 350
Gly Gly Leu Asn Thr Thr Ser Val Lys Ser Gly Gln Trp Asp Ala
            355                 360                 365
Pro Asn Gly Trp Ala Pro Leu Gln Trp Val Ala Thr Glu Gly Leu Gln
            370                 375                 380
Asn Tyr Gly Gln Lys Glu Val Ala Met Asp Ile Ser Trp His Phe Leu
385                 390                 395                 400
Thr Asn Val Gln His Thr Tyr Asp Arg Glu Lys Lys Leu Val Glu Lys
                405                 410                 415
Tyr Asp Val Ser Thr Thr Gly Thr Gly Gly Gly Gly Glu Tyr Pro
            420                 425                 430
Leu Gln Asp Gly Phe Gly Trp Thr Asn Gly Val Thr Leu Lys Met Leu
            435                 440                 445
```

```
Asp Leu Ile Cys Pro Lys Glu Gln Pro Cys Asp Asn Val Pro Ala Thr
        450                 455                 460
Arg Pro Thr Val Lys Ser Ala Thr Thr Gln Pro Ser Thr Lys Glu Ala
465                 470                 475                 480
Gln Pro Thr Pro His His His His His His
                485                 490
```

<210> SEQ ID NO 44
<211> LENGTH: 101
<212> TYPE: PRT
<213> ORGANISM: Artificial Sequence
<220> FEATURE:
<223> OTHER INFORMATION: TreAN-Mp3: N-terminally HIS-tagged N-terminal
      fragment of TreA with C-terminal fusion with M. avium subsp.
      paratuberculosis binding peptide aptamer, Mp3

<400> SEQUENCE: 44

```
Met Ala His His His His His His Glu Glu Thr Pro Val Thr Pro Gln
1               5                   10                  15
Pro Pro Asp Ile Leu Leu Gly Pro Leu Phe Asn Asp Val Gln Asn Ala
                20                  25                  30
Lys Leu Phe Pro Asp Gln Lys Thr Phe Ala Asp Ala Val Pro Asn Ser
            35                  40                  45
Asp Pro Leu Met Ile Leu Ala Asp Tyr Arg Met Gln Gln Asn Gln Ser
        50                  55                  60
Gly Phe Asp Leu Arg His Phe Val Asn Val Asn Phe Thr Leu Pro Lys
65                  70                  75                  80
Glu Gly Glu Lys Tyr Val Pro Gly Ser Asn Tyr Val Ile His Asp Val
                85                  90                  95
Pro Arg His Pro Ala
            100
```

<210> SEQ ID NO 45
<211> LENGTH: 101
<212> TYPE: PRT
<213> ORGANISM: Artificial Sequence
<220> FEATURE:
<223> OTHER INFORMATION: Mp3-TreAN: C-terminally HIS-tagged N-terminal
      fragment of TreA with N-terminal fusion with M. avium subsp.
      paratuberculosis binding peptide aptamer, Mp3

<400> SEQUENCE: 45

```
Met Gly Asn Tyr Val Ile His Asp Val Pro Arg His Pro Ala Val Asp
1               5                   10                  15
Glu Glu Thr Pro Val Thr Pro Gln Pro Pro Asp Ile Leu Leu Gly Pro
                20                  25                  30
Leu Phe Asn Asp Val Gln Asn Ala Lys Leu Phe Pro Asp Gln Lys Thr
            35                  40                  45
Phe Ala Asp Ala Val Pro Asn Ser Asp Pro Leu Met Ile Leu Ala Asp
        50                  55                  60
Tyr Arg Met Gln Gln Asn Gln Ser Gly Phe Asp Leu Arg His Phe Val
65                  70                  75                  80
Asn Val Asn Phe Thr Leu Pro Lys Glu Gly Glu Lys Tyr Val Pro His
                85                  90                  95
His His His His His
            100
```

<210> SEQ ID NO 46
<211> LENGTH: 491

<212> TYPE: PRT
<213> ORGANISM: Artificial Sequence
<220> FEATURE:
<223> OTHER INFORMATION: TreAC-Mp3: N-terminally HIS-tagged C-terminal
    fragment of TreA with C-terminal fusion with M. avium subsp.
    paratuberculosis binding peptide aptamer, Mp3

<400> SEQUENCE: 46

```
Met Ala His His His His His Asn Phe Thr Leu Pro Lys Glu Gly
1               5                   10                  15

Glu Lys Tyr Val Pro Pro Glu Gly Gln Ser Leu Arg Glu His Ile Asp
                20                  25                  30

Gly Leu Trp Pro Val Leu Thr Arg Ser Thr Glu Asn Thr Glu Lys Trp
            35                  40                  45

Asp Ser Leu Leu Pro Leu Pro Glu Pro Tyr Val Val Pro Gly Gly Arg
50                  55                  60

Phe Arg Glu Val Tyr Tyr Trp Asp Ser Tyr Phe Thr Met Leu Gly Leu
65                  70                  75                  80

Ala Glu Ser Gly His Trp Asp Lys Val Ala Asp Met Val Ala Asn Phe
                85                  90                  95

Ala His Glu Ile Asp Thr Tyr Gly His Ile Pro Asn Gly Asn Arg Ser
            100                 105                 110

Tyr Tyr Leu Ser Arg Ser Gln Pro Pro Phe Phe Ala Leu Met Val Glu
        115                 120                 125

Leu Leu Ala Gln His Glu Gly Asp Ala Ala Leu Lys Gln Tyr Leu Pro
130                 135                 140

Gln Met Gln Lys Glu Tyr Ala Tyr Trp Met Asp Gly Val Glu Asn Leu
145                 150                 155                 160

Gln Ala Gly Gln Gln Glu Lys Arg Val Val Lys Leu Gln Asp Gly Thr
                165                 170                 175

Leu Leu Asn Arg Tyr Trp Asp Asp Arg Asp Thr Pro Arg Pro Glu Ser
            180                 185                 190

Trp Val Glu Asp Ile Ala Thr Ala Lys Ser Asn Pro Asn Arg Pro Ala
        195                 200                 205

Thr Glu Ile Tyr Arg Asp Leu Arg Ser Ala Ala Ser Gly Trp Asp
210                 215                 220

Phe Ser Ser Arg Trp Met Asp Asn Pro Gln Gln Leu Asn Thr Leu Arg
225                 230                 235                 240

Thr Thr Ser Ile Val Pro Val Asp Leu Asn Ser Leu Met Phe Lys Met
                245                 250                 255

Glu Lys Ile Leu Ala Arg Ala Ser Lys Ala Ala Gly Asp Asn Ala Met
            260                 265                 270

Ala Asn Gln Tyr Glu Thr Leu Ala Asn Ala Arg Gln Lys Gly Ile Glu
        275                 280                 285

Lys Tyr Leu Trp Asn Asp Gln Gln Gly Trp Tyr Ala Asp Tyr Asp Leu
290                 295                 300

Lys Ser His Lys Val Arg Asn Gln Leu Thr Ala Ala Leu Phe Pro
305                 310                 315                 320

Leu Tyr Val Asn Ala Ala Ala Lys Asp Arg Ala Asn Lys Met Ala Thr
                325                 330                 335

Ala Thr Lys Thr His Leu Leu Gln Pro Gly Gly Leu Asn Thr Thr Ser
            340                 345                 350

Val Lys Ser Gly Gln Gln Trp Asp Ala Pro Asn Gly Trp Ala Pro Leu
        355                 360                 365

Gln Trp Val Ala Thr Glu Gly Leu Gln Asn Tyr Gly Gln Lys Glu Val
```

```
                    370                 375                 380
Ala Met Asp Ile Ser Trp His Phe Leu Thr Asn Val Gln His Thr Tyr
385                 390                 395                 400

Asp Arg Glu Lys Lys Leu Val Glu Lys Tyr Asp Val Ser Thr Thr Gly
                405                 410                 415

Thr Gly Gly Gly Gly Glu Tyr Pro Leu Gln Asp Gly Phe Gly Trp
            420                 425                 430

Thr Asn Gly Val Thr Leu Lys Met Leu Asp Leu Ile Cys Pro Lys Glu
            435                 440                 445

Gln Pro Cys Asp Asn Val Pro Ala Thr Arg Pro Thr Val Lys Ser Ala
450                 455                 460

Thr Thr Gln Pro Ser Thr Lys Glu Ala Gln Pro Thr Pro Gly Ser Asn
465                 470                 475                 480

Tyr Val Ile His Asp Val Pro Arg His Pro Ala
                485                 490

<210> SEQ ID NO 47
<211> LENGTH: 491
<212> TYPE: PRT
<213> ORGANISM: Artificial Sequence
<220> FEATURE:
<223> OTHER INFORMATION: Mp3-TreAC: C-terminally HIS-tagged C-terminal
      fragment of TreA with N-terminal fusion with M. avium subsp.
      paratuberculosis binding peptide aptamer, Mp3

<400> SEQUENCE: 47

Met Gly Asn Tyr Val Ile His Asp Val Pro Arg His Pro Ala Val Asp
1               5                   10                  15

Asn Phe Thr Leu Pro Lys Glu Gly Glu Lys Tyr Val Pro Pro Glu Gly
                20                  25                  30

Gln Ser Leu Arg Glu His Ile Asp Gly Leu Trp Pro Val Leu Thr Arg
            35                  40                  45

Ser Thr Glu Asn Thr Glu Lys Trp Asp Ser Leu Leu Pro Leu Pro Glu
50                  55                  60

Pro Tyr Val Val Pro Gly Gly Arg Phe Arg Glu Val Tyr Tyr Trp Asp
65                  70                  75                  80

Ser Tyr Phe Thr Met Leu Gly Leu Ala Glu Ser Gly His Trp Asp Lys
                85                  90                  95

Val Ala Asp Met Val Ala Asn Phe Ala His Glu Ile Thr Tyr Gly
            100                 105                 110

His Ile Pro Asn Gly Asn Arg Ser Tyr Tyr Leu Ser Arg Ser Gln Pro
        115                 120                 125

Pro Phe Phe Ala Leu Met Val Glu Leu Leu Ala Gln His Glu Gly Asp
    130                 135                 140

Ala Ala Leu Lys Gln Tyr Leu Pro Gln Met Gln Lys Glu Tyr Ala Tyr
145                 150                 155                 160

Trp Met Asp Gly Val Glu Asn Leu Gln Ala Gly Gln Gln Glu Lys Arg
                165                 170                 175

Val Val Lys Leu Gln Asp Gly Thr Leu Leu Asn Arg Tyr Trp Asp Asp
            180                 185                 190

Arg Asp Thr Pro Arg Pro Glu Ser Trp Val Glu Asp Ile Ala Thr Ala
        195                 200                 205

Lys Ser Asn Pro Asn Arg Pro Ala Thr Glu Ile Tyr Arg Asp Leu Arg
    210                 215                 220

Ser Ala Ala Ala Ser Gly Trp Asp Phe Ser Ser Arg Trp Met Asp Asn
225                 230                 235                 240
```

```
Pro Gln Gln Leu Asn Thr Leu Arg Thr Thr Ser Ile Val Pro Val Asp
                245                 250                 255

Leu Asn Ser Leu Met Phe Lys Met Glu Lys Ile Leu Ala Arg Ala Ser
            260                 265                 270

Lys Ala Ala Gly Asp Asn Ala Met Ala Asn Gln Tyr Glu Thr Leu Ala
        275                 280                 285

Asn Ala Arg Gln Lys Gly Ile Glu Lys Tyr Leu Trp Asn Asp Gln Gln
    290                 295                 300

Gly Trp Tyr Ala Asp Tyr Asp Leu Lys Ser His Lys Val Arg Asn Gln
305                 310                 315                 320

Leu Thr Ala Ala Ala Leu Phe Pro Leu Tyr Val Asn Ala Ala Ala Lys
                325                 330                 335

Asp Arg Ala Asn Lys Met Ala Thr Ala Thr Lys Thr His Leu Leu Gln
            340                 345                 350

Pro Gly Gly Leu Asn Thr Thr Ser Val Lys Ser Gly Gln Gln Trp Asp
        355                 360                 365

Ala Pro Asn Gly Trp Ala Pro Leu Gln Trp Val Ala Thr Glu Gly Leu
    370                 375                 380

Gln Asn Tyr Gly Gln Lys Glu Val Ala Met Asp Ile Ser Trp His Phe
385                 390                 395                 400

Leu Thr Asn Val Gln His Thr Tyr Asp Arg Glu Lys Lys Leu Val Glu
                405                 410                 415

Lys Tyr Asp Val Ser Thr Thr Gly Thr Gly Gly Gly Gly Gly Glu Tyr
            420                 425                 430

Pro Leu Gln Asp Gly Phe Gly Trp Thr Asn Gly Val Thr Leu Lys Met
        435                 440                 445

Leu Asp Leu Ile Cys Pro Lys Glu Gln Pro Cys Asp Asn Val Pro Ala
    450                 455                 460

Thr Arg Pro Thr Val Lys Ser Ala Thr Thr Gln Pro Ser Thr Lys Glu
465                 470                 475                 480

Ala Gln Pro Thr Pro His His His His His
                485                 490

<210> SEQ ID NO 48
<211> LENGTH: 817
<212> TYPE: PRT
<213> ORGANISM: Artificial Sequence
<220> FEATURE:
<223> OTHER INFORMATION: scFvLm-TreA-HIS: N-terminally HIS-tagged TreA
      C-terminally fused with Listeria monocytogenes ActA protein
      specific single chain fragment variable

<400> SEQUENCE: 48

Met Gly Lys Tyr Leu Leu Pro Thr Ala Ala Gly Leu Leu Leu
1               5                   10                  15

Ala Ala Gln Pro Ala Met Ala Glu Val Gln Leu Val Glu Ser Gly Gly
                20                  25                  30

Gly Val Val Gln Pro Gly Arg Ser Leu Arg Leu Ser Cys Ala Ala Ser
            35                  40                  45

Gly Phe Ala Phe Ser Ser Tyr Gly Met His Trp Val Arg Gln Ala Pro
        50                  55                  60

Gly Lys Gly Leu Glu Trp Val Ala Ala Ile Ser Tyr Asp Gly Ser Asn
65                  70                  75                  80

Lys Tyr Tyr Ala Asp Ser Val Lys Gly Arg Phe Thr Ile Ser Arg Asp
                85                  90                  95
```

-continued

```
Asn Ser Lys Asn Thr Leu Tyr Leu Gln Met Asn Ser Leu Arg Ala Glu
            100                 105                 110

Asp Thr Ala Val Tyr Tyr Cys Ala Arg Gln Ala Asp Thr Lys Tyr Phe
        115                 120                 125

Trp Gly Gln Gly Thr Leu Val Thr Val Ser Ser Gly Gly Gly Gly Ser
    130                 135                 140

Gly Gly Gly Gly Ser Gly Ser Ala Leu Ser Ser Glu Leu Thr Gln
145                 150                 155                 160

Asp Pro Ala Val Ser Val Ala Leu Gly Gln Thr Val Arg Ile Thr Cys
                165                 170                 175

Gln Gly Asp Ser Leu Arg Ser Tyr Tyr Ala Ser Trp Tyr Gln Gln Lys
            180                 185                 190

Pro Gly Gln Ala Pro Val Leu Val Ile Tyr Gly Lys Asn Asn Arg Pro
        195                 200                 205

Ser Gly Ile Pro Asp Arg Phe Ser Gly Ser Ser Ser Gly Asn Thr Ala
    210                 215                 220

Ser Leu Thr Ile Thr Gly Ala Gln Ala Glu Asp Glu Ala Asp Tyr Tyr
225                 230                 235                 240

Cys Asn Ser Arg Asp Ser Ser Gly Asn Val Phe Gly Gly Gly Thr Lys
                245                 250                 255

Leu Thr Val Leu Gly Ala Ala Ala Val Asp Gly Gly Gly Ser Gly Gly
            260                 265                 270

Gly Ser Gly Gly Gly Glu Thr Pro Val Thr Pro Gln Pro Pro Asp Ile
        275                 280                 285

Leu Leu Gly Pro Leu Phe Asn Asp Val Gln Asn Ala Lys Leu Phe Pro
    290                 295                 300

Asp Gln Lys Thr Phe Ala Asp Ala Val Pro Asn Ser Asp Pro Leu Met
305                 310                 315                 320

Ile Leu Ala Asp Tyr Arg Met Gln Gln Asn Gln Ser Gly Phe Asp Leu
                325                 330                 335

Arg His Phe Val Asn Val Asn Phe Thr Leu Pro Lys Glu Gly Glu Lys
            340                 345                 350

Tyr Val Pro Pro Glu Gly Gln Ser Leu Arg Glu His Ile Asp Gly Leu
        355                 360                 365

Trp Pro Val Leu Thr Arg Ser Thr Glu Asn Thr Glu Lys Trp Asp Ser
    370                 375                 380

Leu Leu Pro Leu Pro Glu Pro Tyr Val Val Pro Gly Gly Arg Phe Arg
385                 390                 395                 400

Glu Val Tyr Tyr Trp Asp Ser Tyr Phe Thr Met Leu Gly Leu Ala Glu
                405                 410                 415

Ser Gly His Trp Asp Lys Val Ala Asp Met Val Ala Asn Phe Ala His
            420                 425                 430

Glu Ile Asp Thr Tyr Gly His Ile Pro Asn Gly Asn Arg Ser Tyr Tyr
        435                 440                 445

Leu Ser Arg Ser Gln Pro Pro Phe Phe Ala Leu Met Val Glu Leu Leu
    450                 455                 460

Ala Gln His Glu Gly Asp Ala Ala Leu Lys Gln Tyr Leu Pro Gln Met
465                 470                 475                 480

Gln Lys Glu Tyr Ala Tyr Trp Met Asp Gly Val Glu Asn Leu Gln Ala
                485                 490                 495

Gly Gln Gln Glu Lys Arg Val Val Lys Leu Gln Asp Gly Thr Leu Leu
            500                 505                 510

Asn Arg Tyr Trp Asp Asp Arg Asp Thr Pro Arg Pro Glu Ser Trp Val
```

```
              515                 520                 525
Glu Asp Ile Ala Thr Ala Lys Ser Asn Pro Asn Arg Pro Ala Thr Glu
            530                 535                 540

Ile Tyr Arg Asp Leu Arg Ser Ala Ala Ala Ser Gly Trp Asp Phe Ser
545                 550                 555                 560

Ser Arg Trp Met Asp Asn Pro Gln Gln Leu Asn Thr Leu Arg Thr Thr
                565                 570                 575

Ser Ile Val Pro Val Asp Leu Asn Ser Leu Met Phe Lys Met Glu Lys
            580                 585                 590

Ile Leu Ala Arg Ala Ser Lys Ala Ala Gly Asp Asn Ala Met Ala Asn
595                 600                 605

Gln Tyr Glu Thr Leu Ala Asn Ala Arg Gln Lys Gly Ile Glu Lys Tyr
            610                 615                 620

Leu Trp Asn Asp Gln Gln Gly Trp Tyr Ala Asp Tyr Asp Leu Lys Ser
625                 630                 635                 640

His Lys Val Arg Asn Gln Leu Thr Ala Ala Leu Phe Pro Leu Tyr
                645                 650                 655

Val Asn Ala Ala Ala Lys Asp Arg Ala Asn Lys Met Ala Thr Ala Thr
            660                 665                 670

Lys Thr His Leu Leu Gln Pro Gly Gly Leu Asn Thr Thr Ser Val Lys
                675                 680                 685

Ser Gly Gln Gln Trp Asp Ala Pro Asn Gly Trp Ala Pro Leu Gln Trp
690                 695                 700

Val Ala Thr Glu Gly Leu Gln Asn Tyr Gly Gln Lys Glu Val Ala Met
705                 710                 715                 720

Asp Ile Ser Trp His Phe Leu Thr Asn Val Gln His Thr Tyr Asp Arg
                725                 730                 735

Glu Lys Lys Leu Val Glu Lys Tyr Asp Val Ser Thr Thr Gly Thr Gly
                740                 745                 750

Gly Gly Gly Gly Glu Tyr Pro Leu Gln Asp Gly Phe Gly Trp Thr Asn
            755                 760                 765

Gly Val Thr Leu Lys Met Leu Asp Leu Ile Cys Pro Lys Glu Gln Pro
770                 775                 780

Cys Asp Asn Val Pro Ala Thr Arg Pro Thr Val Lys Ser Ala Thr Thr
785                 790                 795                 800

Gln Pro Ser Thr Lys Glu Ala Gln Pro Thr Pro His His His His
                805                 810                 815

His

<210> SEQ ID NO 49
<211> LENGTH: 351
<212> TYPE: PRT
<213> ORGANISM: Artificial Sequence
<220> FEATURE:
<223> OTHER INFORMATION: scFvLm-TreAN-HIS: N-terminally HIS-tagged N-
      terminal fragment of TreA C-terminally fused with Listeria
      monocytogenes ActA protein specific single chain fragment variable

<400> SEQUENCE: 49

Met Gly Lys Tyr Leu Leu Pro Thr Ala Ala Gly Leu Leu Leu
1               5                   10                  15

Ala Ala Gln Pro Ala Met Ala Glu Val Gln Leu Val Glu Ser Gly Gly
            20                  25                  30

Gly Val Val Gln Pro Gly Arg Ser Leu Arg Leu Ser Cys Ala Ala Ser
            35                  40                  45
```

Gly Phe Ala Phe Ser Ser Tyr Gly Met His Trp Val Arg Gln Ala Pro
            50                  55                  60

Gly Lys Gly Leu Glu Trp Val Ala Ala Ile Ser Tyr Asp Gly Ser Asn
 65                  70                  75                  80

Lys Tyr Tyr Ala Asp Ser Val Lys Gly Arg Phe Thr Ile Ser Arg Asp
                 85                  90                  95

Asn Ser Lys Asn Thr Leu Tyr Leu Gln Met Asn Ser Leu Arg Ala Glu
            100                 105                 110

Asp Thr Ala Val Tyr Tyr Cys Ala Arg Gln Ala Asp Thr Lys Tyr Phe
            115                 120                 125

Trp Gly Gln Gly Thr Leu Val Thr Val Ser Ser Gly Gly Gly Gly Ser
130                 135                 140

Gly Gly Gly Gly Ser Gly Ser Ala Leu Ser Ser Glu Leu Thr Gln
145                 150                 155                 160

Asp Pro Ala Val Ser Val Ala Leu Gly Gln Thr Val Arg Ile Thr Cys
                165                 170                 175

Gln Gly Asp Ser Leu Arg Ser Tyr Tyr Ala Ser Trp Tyr Gln Gln Lys
            180                 185                 190

Pro Gly Gln Ala Pro Val Leu Val Ile Tyr Gly Lys Asn Asn Arg Pro
            195                 200                 205

Ser Gly Ile Pro Asp Arg Phe Ser Gly Ser Ser Ser Gly Asn Thr Ala
210                 215                 220

Ser Leu Thr Ile Thr Gly Ala Gln Ala Glu Asp Glu Ala Asp Tyr Tyr
225                 230                 235                 240

Cys Asn Ser Arg Asp Ser Ser Gly Asn Val Phe Gly Gly Gly Thr Lys
                245                 250                 255

Leu Thr Val Leu Gly Ala Ala Ala Val Asp Glu Glu Thr Pro Val Thr
            260                 265                 270

Pro Gln Pro Pro Asp Ile Leu Leu Gly Pro Leu Phe Asn Asp Val Gln
            275                 280                 285

Asn Ala Lys Leu Phe Pro Asp Gln Lys Thr Phe Ala Asp Ala Val Pro
            290                 295                 300

Asn Ser Asp Pro Leu Met Ile Leu Ala Asp Tyr Arg Met Gln Gln Asn
305                 310                 315                 320

Gln Ser Gly Phe Asp Leu Arg His Phe Val Asn Val Asn Phe Thr Leu
                325                 330                 335

Pro Lys Glu Gly Glu Lys Tyr Val Pro His His His His His His
            340                 345                 350

<210> SEQ ID NO 50
<211> LENGTH: 741
<212> TYPE: PRT
<213> ORGANISM: Artificial Sequence
<220> FEATURE:
<223> OTHER INFORMATION: scFvLm-TreAC-HIS: N-terminally HIS-tagged C-
      terminal fragment of TreA C-terminally fused with Listeria
      monocytogenes ActA protein specific single chain fragment variable

<400> SEQUENCE: 50

Met Gly Lys Tyr Leu Leu Pro Thr Ala Ala Ala Gly Leu Leu Leu Leu
 1               5                  10                  15

Ala Ala Gln Pro Ala Met Ala Glu Val Gln Leu Val Glu Ser Gly Gly
            20                  25                  30

Gly Val Val Gln Pro Gly Arg Ser Leu Arg Leu Ser Cys Ala Ala Ser
         35                  40                  45

Gly Phe Ala Phe Ser Ser Tyr Gly Met His Trp Val Arg Gln Ala Pro

```
            50                  55                  60
Gly Lys Gly Leu Glu Trp Val Ala Ala Ile Ser Tyr Asp Gly Ser Asn
 65                  70                  75                  80

Lys Tyr Tyr Ala Asp Ser Val Lys Gly Arg Phe Thr Ile Ser Arg Asp
                 85                  90                  95

Asn Ser Lys Asn Thr Leu Tyr Leu Gln Met Asn Ser Leu Arg Ala Glu
                100                 105                 110

Asp Thr Ala Val Tyr Tyr Cys Ala Arg Gln Ala Asp Thr Lys Tyr Phe
            115                 120                 125

Trp Gly Gln Gly Thr Leu Val Thr Val Ser Ser Gly Gly Gly Gly Ser
130                 135                 140

Gly Gly Gly Gly Ser Gly Ser Ala Leu Ser Ser Glu Leu Thr Gln
145                 150                 155                 160

Asp Pro Ala Val Ser Val Ala Leu Gly Gln Thr Val Arg Ile Thr Cys
                165                 170                 175

Gln Gly Asp Ser Leu Arg Ser Tyr Tyr Ala Ser Trp Tyr Gln Gln Lys
                180                 185                 190

Pro Gly Gln Ala Pro Val Leu Val Ile Tyr Gly Lys Asn Asn Arg Pro
                195                 200                 205

Ser Gly Ile Pro Asp Arg Phe Ser Gly Ser Ser Ser Gly Asn Thr Ala
                210                 215                 220

Ser Leu Thr Ile Thr Gly Ala Gln Ala Glu Asp Glu Ala Asp Tyr Tyr
225                 230                 235                 240

Cys Asn Ser Arg Asp Ser Ser Gly Asn Val Phe Gly Gly Gly Thr Lys
                245                 250                 255

Leu Thr Val Leu Gly Ala Ala Ala Val Asp Asn Phe Thr Leu Pro Lys
                260                 265                 270

Glu Gly Glu Lys Tyr Val Pro Pro Gly Gln Ser Leu Arg Glu His
                275                 280                 285

Ile Asp Gly Leu Trp Pro Val Leu Thr Arg Ser Thr Glu Asn Thr Glu
                290                 295                 300

Lys Trp Asp Ser Leu Leu Pro Leu Pro Glu Pro Tyr Val Val Pro Gly
305                 310                 315                 320

Gly Arg Phe Arg Glu Val Tyr Tyr Trp Asp Ser Tyr Phe Thr Met Leu
                325                 330                 335

Gly Leu Ala Glu Ser Gly His Trp Asp Lys Val Ala Asp Met Val Ala
                340                 345                 350

Asn Phe Ala His Glu Ile Asp Thr Tyr Gly His Ile Pro Asn Gly Asn
                355                 360                 365

Arg Ser Tyr Tyr Leu Ser Arg Ser Gln Pro Pro Phe Phe Ala Leu Met
                370                 375                 380

Val Glu Leu Leu Ala Gln His Glu Gly Asp Ala Ala Leu Lys Gln Tyr
385                 390                 395                 400

Leu Pro Gln Met Gln Lys Glu Tyr Ala Tyr Trp Met Asp Gly Val Glu
                405                 410                 415

Asn Leu Gln Ala Gly Gln Gln Glu Lys Arg Val Val Lys Leu Gln Asp
                420                 425                 430

Gly Thr Leu Leu Asn Arg Tyr Trp Asp Asp Arg Asp Thr Pro Arg Pro
                435                 440                 445

Glu Ser Trp Val Glu Asp Ile Ala Thr Ala Lys Ser Asn Pro Asn Arg
                450                 455                 460

Pro Ala Thr Glu Ile Tyr Arg Asp Leu Arg Ser Ala Ala Ala Ser Gly
465                 470                 475                 480
```

-continued

Trp Asp Phe Ser Ser Arg Trp Met Asp Asn Pro Gln Gln Leu Asn Thr
                485                 490                 495

Leu Arg Thr Thr Ser Ile Val Pro Val Asp Leu Asn Ser Leu Met Phe
            500                 505                 510

Lys Met Glu Lys Ile Leu Ala Arg Ala Ser Lys Ala Ala Gly Asp Asn
        515                 520                 525

Ala Met Ala Asn Gln Tyr Glu Thr Leu Ala Asn Ala Arg Gln Lys Gly
    530                 535                 540

Ile Glu Lys Tyr Leu Trp Asn Asp Gln Gln Gly Trp Tyr Ala Asp Tyr
545                 550                 555                 560

Asp Leu Lys Ser His Lys Val Arg Asn Gln Leu Thr Ala Ala Ala Leu
                565                 570                 575

Phe Pro Leu Tyr Val Asn Ala Ala Ala Lys Asp Arg Ala Asn Lys Met
            580                 585                 590

Ala Thr Ala Thr Lys Thr His Leu Leu Gln Pro Gly Gly Leu Asn Thr
        595                 600                 605

Thr Ser Val Lys Ser Gly Gln Gln Trp Asp Ala Pro Asn Gly Trp Ala
    610                 615                 620

Pro Leu Gln Trp Val Ala Thr Glu Gly Leu Gln Asn Tyr Gly Gln Lys
625                 630                 635                 640

Glu Val Ala Met Asp Ile Ser Trp His Phe Leu Thr Asn Val Gln His
                645                 650                 655

Thr Tyr Asp Arg Glu Lys Lys Leu Val Glu Lys Tyr Asp Val Ser Thr
            660                 665                 670

Thr Gly Thr Gly Gly Gly Gly Glu Tyr Pro Leu Gln Asp Gly Phe
        675                 680                 685

Gly Trp Thr Asn Gly Val Thr Leu Lys Met Leu Asp Leu Ile Cys Pro
    690                 695                 700

Lys Glu Gln Pro Cys Asp Asn Val Pro Ala Thr Arg Pro Thr Val Lys
705                 710                 715                 720

Ser Ala Thr Thr Gln Pro Ser Thr Lys Glu Ala Gln Pro Thr Pro His
                725                 730                 735

His His His His His
            740

<210> SEQ ID NO 51
<211> LENGTH: 220
<212> TYPE: PRT
<213> ORGANISM: Artificial Sequence
<220> FEATURE:
<223> OTHER INFORMATION: HIS-TreAN-ATPase: N-terminally HIS-tagged N-
      terminal fragment of TreA C-terminally fused with the ATP synthase
      epsilon subunit of Geobacillus

<400> SEQUENCE: 51

Met Ala His His His His His His Glu Glu Thr Pro Val Thr Pro Gln
1               5                   10                  15

Pro Pro Asp Ile Leu Leu Gly Pro Leu Phe Asn Asp Val Gln Asn Ala
            20                  25                  30

Lys Leu Phe Pro Asp Gln Lys Thr Phe Ala Asp Ala Val Pro Asn Ser
        35                  40                  45

Asp Pro Leu Met Ile Leu Ala Asp Tyr Arg Met Gln Gln Asn Gln Ser
    50                  55                  60

Gly Phe Asp Leu Arg His Phe Val Asn Val Asn Phe Thr Leu Pro Lys
65                  70                  75                  80

Glu Gly Glu Lys Tyr Val Pro Gly Ser Lys Thr Ile His Val Ser Val
                85                  90                  95

Val Thr Pro Asp Gly Pro Val Tyr Glu Asp Val Glu Met Val Ser
            100                 105                 110

Val Lys Ala Lys Ser Gly Glu Leu Gly Ile Leu Pro Gly His Ile Pro
            115                 120                 125

Leu Val Ala Pro Leu Glu Ile Ser Ala Ala Arg Leu Lys Lys Gly Gly
        130                 135                 140

Lys Thr Gln Tyr Ile Ala Val Ser Gly Gly Phe Leu Glu Val Arg Pro
145                 150                 155                 160

Asp Asn Val Thr Ile Leu Ala Gln Ala Ala Glu Arg Ala Glu Asp Ile
                165                 170                 175

Asp Val Leu Arg Ala Lys Ala Arg Lys Ser Gly Arg Thr Pro Leu Gln
            180                 185                 190

Ser Gln Gln Asp Asp Ile Asp Phe Lys Arg Ala Glu Leu Ala Leu Lys
        195                 200                 205

Arg Ala Met Asn Arg Leu Ser Val Ala Glu Met Lys
210                 215                 220

<210> SEQ ID NO 52
<211> LENGTH: 610
<212> TYPE: PRT
<213> ORGANISM: Artificial Sequence
<220> FEATURE:
<223> OTHER INFORMATION: HIS-TreAC-ATPase: N-terminally HIS-tagged C-
      terminal fragment of TreA C-terminally fused with the ATP synthase
      epsilon subunit of Geobacillus

<400> SEQUENCE: 52

Met Ala His His His His His His Asn Phe Thr Leu Pro Lys Glu Gly
1               5                   10                  15

Glu Lys Tyr Val Pro Pro Glu Gly Gln Ser Leu Arg Glu His Ile Asp
            20                  25                  30

Gly Leu Trp Pro Val Leu Thr Arg Ser Thr Glu Asn Thr Glu Lys Trp
        35                  40                  45

Asp Ser Leu Leu Pro Leu Pro Glu Pro Tyr Val Val Pro Gly Gly Arg
    50                  55                  60

Phe Arg Glu Val Tyr Tyr Trp Asp Ser Tyr Phe Thr Met Leu Gly Leu
65                  70                  75                  80

Ala Glu Ser Gly His Trp Asp Lys Val Ala Asp Met Val Ala Asn Phe
                85                  90                  95

Ala His Glu Ile Asp Thr Tyr Gly His Ile Pro Asn Gly Asn Arg Ser
            100                 105                 110

Tyr Tyr Leu Ser Arg Ser Gln Pro Pro Phe Phe Ala Leu Met Val Glu
        115                 120                 125

Leu Leu Ala Gln His Glu Gly Asp Ala Ala Leu Lys Gln Tyr Leu Pro
    130                 135                 140

Gln Met Gln Lys Glu Tyr Ala Tyr Trp Met Asp Gly Val Glu Asn Leu
145                 150                 155                 160

Gln Ala Gly Gln Gln Glu Lys Arg Val Val Lys Leu Gln Asp Gly Thr
                165                 170                 175

Leu Leu Asn Arg Tyr Trp Asp Asp Arg Asp Thr Pro Arg Pro Glu Ser
            180                 185                 190

Trp Val Glu Asp Ile Ala Thr Ala Lys Ser Asn Pro Asn Arg Pro Ala
        195                 200                 205

Thr Glu Ile Tyr Arg Asp Leu Arg Ser Ala Ala Ala Ser Gly Trp Asp

```
            210                 215                 220
Phe Ser Ser Arg Trp Met Asp Asn Pro Gln Gln Leu Asn Thr Leu Arg
225                 230                 235                 240

Thr Thr Ser Ile Val Pro Val Asp Leu Asn Ser Leu Met Phe Lys Met
            245                 250                 255

Glu Lys Ile Leu Ala Arg Ala Ser Lys Ala Ala Gly Asp Asn Ala Met
            260                 265                 270

Ala Asn Gln Tyr Glu Thr Leu Ala Asn Ala Arg Gln Lys Gly Ile Glu
            275                 280                 285

Lys Tyr Leu Trp Asn Asp Gln Gln Gly Trp Tyr Ala Asp Tyr Asp Leu
290                 295                 300

Lys Ser His Lys Val Arg Asn Gln Leu Thr Ala Ala Leu Phe Pro
305                 310                 315                 320

Leu Tyr Val Asn Ala Ala Lys Asp Arg Ala Asn Lys Met Ala Thr
                325                 330                 335

Ala Thr Lys Thr His Leu Leu Gln Pro Gly Gly Leu Asn Thr Thr Ser
            340                 345                 350

Val Lys Ser Gly Gln Gln Trp Asp Ala Pro Asn Gly Trp Ala Pro Leu
            355                 360                 365

Gln Trp Val Ala Thr Glu Gly Leu Gln Asn Tyr Gly Gln Lys Glu Val
            370                 375                 380

Ala Met Asp Ile Ser Trp His Phe Leu Thr Asn Val Gln His Thr Tyr
385                 390                 395                 400

Asp Arg Glu Lys Lys Leu Val Glu Lys Tyr Asp Val Ser Thr Thr Gly
                405                 410                 415

Thr Gly Gly Gly Gly Glu Tyr Pro Leu Gln Asp Gly Phe Gly Trp
            420                 425                 430

Thr Asn Gly Val Thr Leu Lys Met Leu Asp Leu Ile Cys Pro Lys Glu
            435                 440                 445

Gln Pro Cys Asp Asn Val Pro Ala Thr Arg Pro Thr Val Lys Ser Ala
            450                 455                 460

Thr Thr Gln Pro Ser Thr Lys Glu Ala Gln Pro Thr Pro Gly Ser Lys
465                 470                 475                 480

Thr Ile His Val Ser Val Val Thr Pro Asp Gly Pro Val Tyr Glu Asp
                485                 490                 495

Asp Val Glu Met Val Ser Val Lys Ala Lys Ser Gly Glu Leu Gly Ile
            500                 505                 510

Leu Pro Gly His Ile Pro Leu Val Ala Pro Leu Glu Ile Ser Ala Ala
            515                 520                 525

Arg Leu Lys Lys Gly Lys Thr Gln Tyr Ile Ala Val Ser Gly Gly
530                 535                 540

Phe Leu Glu Val Arg Pro Asp Asn Val Thr Ile Leu Ala Gln Ala Ala
545                 550                 555                 560

Glu Arg Ala Glu Asp Ile Asp Val Leu Arg Ala Lys Ala Arg Lys Ser
                565                 570                 575

Gly Arg Thr Pro Leu Gln Ser Gln Gln Asp Asp Ile Asp Phe Lys Arg
            580                 585                 590

Ala Glu Leu Ala Leu Lys Arg Ala Met Asn Arg Leu Ser Val Ala Glu
            595                 600                 605

Met Lys
610

<210> SEQ ID NO 53
```

```
<211> LENGTH: 121
<212> TYPE: PRT
<213> ORGANISM: Artificial Sequence
<220> FEATURE:
<223> OTHER INFORMATION: HIS-TreAN-KI: N-terminally HIS-tagged N-
      terminal fragment of TreA with C-terminal fusion with leucine
      zipper 1

<400> SEQUENCE: 53
```

| Met | Ala | His | His | His | His | His | Glu | Glu | Thr | Pro | Val | Thr | Pro | Gln |
|-----|-----|-----|-----|-----|-----|-----|-----|-----|-----|-----|-----|-----|-----|-----|
| 1   |     |     |     | 5   |     |     |     |     | 10  |     |     |     |     | 15  |

Pro Pro Asp Ile Leu Leu Gly Pro Leu Phe Asn Asp Val Gln Asn Ala
            20              25              30

Lys Leu Phe Pro Asp Gln Lys Thr Phe Ala Asp Ala Val Pro Asn Ser
        35              40              45

Asp Pro Leu Met Ile Leu Ala Asp Tyr Arg Met Gln Gln Asn Gln Ser
    50              55              60

Gly Phe Asp Leu Arg His Phe Val Asn Val Asn Phe Thr Leu Pro Lys
65              70              75              80

Glu Gly Glu Lys Tyr Val Pro Gly Ser Val Pro Gly Ser Lys Ile Ala
                85              90              95

Ala Leu Lys Glu Lys Ile Ala Ala Leu Lys Glu Lys Asn Ala Ala Leu
            100             105             110

Lys Trp Lys Ile Ala Ala Leu Lys Glu
        115             120

```
<210> SEQ ID NO 54
<211> LENGTH: 507
<212> TYPE: PRT
<213> ORGANISM: Artificial Sequence
<220> FEATURE:
<223> OTHER INFORMATION: HIS-TreAC-EI: N-terminally HIS-tagged N-
      terminal fragment of TreA with C-terminal fusion leucine zipper 2

<400> SEQUENCE: 54
```

Met Ala His His His His His Asn Phe Thr Leu Pro Lys Glu Gly
1               5               10              15

Glu Lys Tyr Val Pro Pro Glu Gly Gln Ser Leu Arg Glu His Ile Asp
            20              25              30

Gly Leu Trp Pro Val Leu Thr Arg Ser Thr Glu Asn Thr Glu Lys Trp
        35              40              45

Asp Ser Leu Leu Pro Leu Pro Glu Pro Tyr Val Val Pro Gly Gly Arg
    50              55              60

Phe Arg Glu Val Tyr Tyr Trp Asp Ser Tyr Phe Thr Met Leu Gly Leu
65              70              75              80

Ala Glu Ser Gly His Trp Asp Lys Val Ala Asp Met Val Ala Asn Phe
                85              90              95

Ala His Glu Ile Asp Thr Tyr Gly His Ile Pro Asn Gly Asn Arg Ser
            100             105             110

Tyr Tyr Leu Ser Arg Ser Gln Pro Pro Phe Phe Ala Leu Met Val Glu
        115             120             125

Leu Leu Ala Gln His Glu Gly Asp Ala Ala Leu Lys Gln Tyr Leu Pro
    130             135             140

Gln Met Gln Lys Glu Tyr Ala Tyr Trp Met Asp Gly Val Glu Asn Leu
145             150             155             160

Gln Ala Gly Gln Gln Glu Lys Arg Val Val Lys Leu Gln Asp Gly Thr
                165             170             175

Leu Leu Asn Arg Tyr Trp Asp Asp Arg Asp Thr Pro Arg Pro Glu Ser

```
                180              185              190
Trp Val Glu Asp Ile Ala Thr Ala Lys Ser Asn Pro Asn Arg Pro Ala
            195                  200              205
Thr Glu Ile Tyr Arg Asp Leu Arg Ser Ala Ala Ala Ser Gly Trp Asp
            210                  215              220
Phe Ser Ser Arg Trp Met Asp Asn Pro Gln Gln Leu Asn Thr Leu Arg
225                  230                  235                  240
Thr Thr Ser Ile Val Pro Val Asp Leu Asn Ser Leu Met Phe Lys Met
                245                  250                  255
Glu Lys Ile Leu Ala Arg Ala Ser Lys Ala Ala Gly Asp Asn Ala Met
            260                  265                  270
Ala Asn Gln Tyr Glu Thr Leu Ala Asn Ala Arg Gln Lys Gly Ile Glu
            275                  280                  285
Lys Tyr Leu Trp Asn Asp Gln Gln Gly Trp Tyr Ala Asp Tyr Asp Leu
            290                  295                  300
Lys Ser His Lys Val Arg Asn Gln Leu Thr Ala Ala Leu Phe Pro
305                  310                  315                  320
Leu Tyr Val Asn Ala Ala Lys Asp Arg Ala Asn Lys Met Ala Thr
            325                  330                  335
Ala Thr Lys Thr His Leu Leu Gln Pro Gly Gly Leu Asn Thr Thr Ser
            340                  345                  350
Val Lys Ser Gly Gln Gln Trp Asp Ala Pro Asn Gly Trp Ala Pro Leu
            355                  360                  365
Gln Trp Val Ala Thr Glu Gly Leu Gln Asn Tyr Gly Gln Lys Glu Val
            370                  375                  380
Ala Met Asp Ile Ser Trp His Phe Leu Thr Asn Val Gln His Thr Tyr
385                  390                  395                  400
Asp Arg Glu Lys Lys Leu Val Glu Lys Tyr Asp Val Ser Thr Thr Gly
                405                  410                  415
Thr Gly Gly Gly Gly Glu Tyr Pro Leu Gln Asp Gly Phe Gly Trp
            420                  425                  430
Thr Asn Gly Val Thr Leu Lys Met Leu Asp Leu Ile Cys Pro Lys Glu
            435                  440                  445
Gln Pro Cys Asp Asn Val Pro Ala Thr Arg Pro Thr Val Lys Ser Ala
            450                  455                  460
Thr Thr Gln Pro Ser Thr Lys Glu Ala Gln Pro Thr Pro Gly Ser Glu
465                  470                  475                  480
Ile Ala Ala Leu Glu Lys Glu Ile Ala Ala Leu Glu Lys Glu Asn Ala
                485                  490                  495
Ala Leu Glu Trp Glu Ile Ala Ala Leu Glu Lys
            500                  505
```

<210> SEQ ID NO 55
<211> LENGTH: 121
<212> TYPE: PRT
<213> ORGANISM: Artificial Sequence
<220> FEATURE:
<223> OTHER INFORMATION: HIS-TreAN-EI: N-terminally HIS-tagged N-
    terminal fragment of TreA with C-terminal fusion with leucine
    zipper 1

<400> SEQUENCE: 55

```
Met Ala His His His His His His Glu Glu Thr Pro Val Thr Pro Gln
1               5                   10                  15
Pro Pro Asp Ile Leu Leu Gly Pro Leu Phe Asn Asp Val Gln Asn Ala
            20                  25                  30
```

```
Lys Leu Phe Pro Asp Gln Lys Thr Phe Ala Asp Ala Val Pro Asn Ser
            35                  40                  45

Asp Pro Leu Met Ile Leu Ala Asp Tyr Arg Met Gln Gln Asn Gln Ser
         50                  55                  60

Gly Phe Asp Leu Arg His Phe Val Asn Val Asn Phe Thr Leu Pro Lys
 65                  70                  75                  80

Glu Gly Glu Lys Tyr Val Pro Gly Ser Val Pro Gly Ser Glu Ile Ala
                 85                  90                  95

Ala Leu Glu Lys Glu Ile Ala Ala Leu Glu Lys Glu Asn Ala Ala Leu
            100                 105                 110

Glu Trp Glu Ile Ala Ala Leu Glu Lys
            115                 120
```

<210> SEQ ID NO 56
<211> LENGTH: 507
<212> TYPE: PRT
<213> ORGANISM: Artificial Sequence
<220> FEATURE:
<223> OTHER INFORMATION: HIS-TreAC-KI: N-terminally HIS-tagged N-
      terminal fragment of TreA with C-terminal fusion leucine zipper 2

<400> SEQUENCE: 56

```
Met Ala His His His His His His Asn Phe Thr Leu Pro Lys Glu Gly
 1               5                  10                  15

Glu Lys Tyr Val Pro Pro Glu Gly Gln Ser Leu Arg Glu His Ile Asp
                 20                  25                  30

Gly Leu Trp Pro Val Leu Thr Arg Ser Thr Glu Asn Thr Glu Lys Trp
             35                  40                  45

Asp Ser Leu Leu Pro Leu Pro Glu Pro Tyr Val Val Pro Gly Gly Arg
         50                  55                  60

Phe Arg Glu Val Tyr Tyr Trp Asp Ser Tyr Phe Thr Met Leu Gly Leu
 65                  70                  75                  80

Ala Glu Ser Gly His Trp Asp Lys Val Ala Asp Met Val Ala Asn Phe
                 85                  90                  95

Ala His Glu Ile Asp Thr Tyr Gly His Ile Pro Asn Gly Asn Arg Ser
            100                 105                 110

Tyr Tyr Leu Ser Arg Ser Gln Pro Pro Phe Phe Ala Leu Met Val Glu
            115                 120                 125

Leu Leu Ala Gln His Glu Gly Asp Ala Ala Leu Lys Gln Tyr Leu Pro
        130                 135                 140

Gln Met Gln Lys Glu Tyr Ala Tyr Trp Met Asp Gly Val Glu Asn Leu
145                 150                 155                 160

Gln Ala Gly Gln Gln Glu Lys Arg Val Val Lys Leu Gln Asp Gly Thr
                165                 170                 175

Leu Leu Asn Arg Tyr Trp Asp Asp Arg Asp Thr Pro Arg Pro Glu Ser
            180                 185                 190

Trp Val Glu Asp Ile Ala Thr Ala Lys Ser Pro Asn Arg Pro Ala
            195                 200                 205

Thr Glu Ile Tyr Arg Asp Leu Arg Ser Ala Ala Ser Gly Trp Asp
        210                 215                 220

Phe Ser Ser Arg Trp Met Asp Asn Pro Gln Gln Leu Asn Thr Leu Arg
225                 230                 235                 240

Thr Thr Ser Ile Val Pro Val Asp Leu Asn Ser Leu Met Phe Lys Met
                245                 250                 255

Glu Lys Ile Leu Ala Arg Ala Ser Lys Ala Ala Gly Asp Asn Ala Met
```

```
            260                 265                 270
Ala Asn Gln Tyr Glu Thr Leu Ala Asn Ala Arg Gln Lys Gly Ile Glu
            275                 280                 285

Lys Tyr Leu Trp Asn Asp Gln Gln Gly Trp Tyr Ala Asp Tyr Asp Leu
            290                 295                 300

Lys Ser His Lys Val Arg Asn Gln Leu Thr Ala Ala Leu Phe Pro
305                 310                 315                 320

Leu Tyr Val Asn Ala Ala Ala Lys Asp Arg Ala Asn Lys Met Ala Thr
                    325                 330                 335

Ala Thr Lys Thr His Leu Leu Gln Pro Gly Gly Leu Asn Thr Thr Ser
                340                 345                 350

Val Lys Ser Gly Gln Gln Trp Asp Ala Pro Asn Gly Trp Ala Pro Leu
            355                 360                 365

Gln Trp Val Ala Thr Glu Gly Leu Gln Asn Tyr Gly Gln Lys Glu Val
            370                 375                 380

Ala Met Asp Ile Ser Trp His Phe Leu Thr Asn Val Gln His Thr Tyr
385                 390                 395                 400

Asp Arg Glu Lys Lys Leu Val Glu Lys Tyr Asp Val Ser Thr Thr Gly
                405                 410                 415

Thr Gly Gly Gly Gly Glu Tyr Pro Leu Gln Asp Gly Phe Gly Trp
                420                 425                 430

Thr Asn Gly Val Thr Leu Lys Met Leu Asp Leu Ile Cys Pro Lys Glu
                435                 440                 445

Gln Pro Cys Asp Asn Val Pro Ala Thr Arg Pro Thr Val Lys Ser Ala
            450                 455                 460

Thr Thr Gln Pro Ser Thr Lys Glu Ala Gln Pro Thr Pro Gly Ser Lys
465                 470                 475                 480

Ile Ala Ala Leu Lys Glu Lys Ile Ala Ala Leu Lys Glu Lys Asn Ala
                    485                 490                 495

Ala Leu Lys Trp Lys Ile Ala Ala Leu Lys Glu
                500                 505

<210> SEQ ID NO 57
<211> LENGTH: 507
<212> TYPE: PRT
<213> ORGANISM: Artificial Sequence
<220> FEATURE:
<223> OTHER INFORMATION: rPrP-TreA-HIS: C-terminally HIS-tagged TreA N-
      terminally fused with bank vole prion protein

<400> SEQUENCE: 57

Met Ala His His His His His His Asn Phe Thr Leu Pro Lys Glu Gly
1               5                   10                  15

Glu Lys Tyr Val Pro Pro Glu Gly Gln Ser Leu Arg Glu His Ile Asp
                20                  25                  30

Gly Leu Trp Pro Val Leu Thr Arg Ser Thr Glu Asn Thr Glu Lys Trp
            35                  40                  45

Asp Ser Leu Leu Pro Leu Pro Glu Pro Tyr Val Val Pro Gly Gly Arg
        50                  55                  60

Phe Arg Glu Val Tyr Tyr Trp Asp Ser Tyr Phe Thr Met Leu Gly Leu
65                  70                  75                  80

Ala Glu Ser Gly His Trp Asp Lys Val Ala Asp Met Val Ala Asn Phe
                85                  90                  95

Ala His Glu Ile Asp Thr Tyr Gly His Ile Pro Asn Gly Asn Arg Ser
            100                 105                 110
```

```
Tyr Tyr Leu Ser Arg Ser Gln Pro Phe Phe Ala Leu Met Val Glu
            115                 120                 125

Leu Leu Ala Gln His Glu Gly Asp Ala Ala Leu Lys Gln Tyr Leu Pro
130                 135                 140

Gln Met Gln Lys Glu Tyr Ala Tyr Trp Met Asp Gly Val Glu Asn Leu
145                 150                 155                 160

Gln Ala Gly Gln Gln Glu Lys Arg Val Val Lys Leu Gln Asp Gly Thr
                165                 170                 175

Leu Leu Asn Arg Tyr Trp Asp Asp Arg Asp Thr Pro Arg Pro Glu Ser
            180                 185                 190

Trp Val Glu Asp Ile Ala Thr Ala Lys Ser Asn Pro Asn Arg Pro Ala
        195                 200                 205

Thr Glu Ile Tyr Arg Asp Leu Arg Ser Ala Ala Ala Ser Gly Trp Asp
    210                 215                 220

Phe Ser Ser Arg Trp Met Asp Asn Pro Gln Gln Leu Asn Thr Leu Arg
225                 230                 235                 240

Thr Thr Ser Ile Val Pro Val Asp Leu Asn Ser Leu Met Phe Lys Met
                245                 250                 255

Glu Lys Ile Leu Ala Arg Ala Ser Lys Ala Ala Gly Asp Asn Ala Met
            260                 265                 270

Ala Asn Gln Tyr Glu Thr Leu Ala Asn Ala Arg Gln Lys Gly Ile Glu
        275                 280                 285

Lys Tyr Leu Trp Asn Asp Gln Gln Gly Trp Tyr Ala Asp Tyr Asp Leu
    290                 295                 300

Lys Ser His Lys Val Arg Asn Gln Leu Thr Ala Ala Leu Phe Pro
305                 310                 315                 320

Leu Tyr Val Asn Ala Ala Lys Asp Arg Ala Asn Lys Met Ala Thr
                325                 330                 335

Ala Thr Lys Thr His Leu Leu Gln Pro Gly Gly Leu Asn Thr Thr Ser
            340                 345                 350

Val Lys Ser Gly Gln Gln Trp Asp Ala Pro Asn Gly Trp Ala Pro Leu
        355                 360                 365

Gln Trp Val Ala Thr Glu Gly Leu Gln Asn Tyr Gly Gln Lys Glu Val
    370                 375                 380

Ala Met Asp Ile Ser Trp His Phe Leu Thr Asn Val Gln His Thr Tyr
385                 390                 395                 400

Asp Arg Glu Lys Lys Leu Val Glu Lys Tyr Asp Val Ser Thr Thr Gly
                405                 410                 415

Thr Gly Gly Gly Gly Glu Tyr Pro Leu Gln Asp Gly Phe Gly Trp
            420                 425                 430

Thr Asn Gly Val Thr Leu Lys Met Leu Asp Leu Ile Cys Pro Lys Glu
        435                 440                 445

Gln Pro Cys Asp Asn Val Pro Ala Thr Arg Pro Thr Val Lys Ser Ala
    450                 455                 460

Thr Thr Gln Pro Ser Thr Lys Glu Ala Gln Pro Thr Pro Gly Ser Lys
465                 470                 475                 480

Ile Ala Ala Leu Lys Glu Lys Ile Ala Ala Leu Lys Glu Lys Asn Ala
                485                 490                 495

Ala Leu Lys Trp Lys Ile Ala Ala Leu Lys Glu
            500                 505

<210> SEQ ID NO 58
<211> LENGTH: 308
<212> TYPE: PRT
```

<213> ORGANISM: Artificial Sequence
<220> FEATURE:
<223> OTHER INFORMATION: rPrP-TreAN-HIS: C-terminally HIS-tagged N-terminal fragment of TreA N-terminally fused with bank vole prion protein

<400> SEQUENCE: 58

```
Met Gly Lys Lys Arg Pro Lys Pro Gly Gly Trp Asn Thr Gly Gly Ser
1               5                   10                  15

Arg Tyr Pro Gly Gln Gly Ser Pro Gly Gly Asn Arg Tyr Pro Pro Gln
            20                  25                  30

```
Met Gly Lys Lys Arg Pro Lys Pro Gly Gly Trp Asn Thr Gly Gly Ser
1               5                   10                  15

Arg Tyr Pro Gly Gln Gly Ser Pro Gly Gly Asn Arg Tyr Pro Pro Gln
            20                  25                  30

Gly Gly Gly Thr Trp Gly Gln Pro His Gly Gly Gly Trp Gly Gln Pro
            35                  40                  45

His Gly Gly Gly Trp Gly Gln Pro His Gly Gly Gly Trp Gly Gln Pro
50                  55                  60

His Gly Gly Gly Trp Gly Gln Gly Gly Gly Thr His Asn Gln Trp Asn
65                  70                  75                  80

Lys Pro Ser Lys Pro Lys Thr Asn Met Lys His Val Ala Gly Ala Ala
                85                  90                  95

Ala Ala Gly Ala Val Val Gly Gly Leu Gly Gly Tyr Met Leu Gly Ser
                100                 105                 110

Ala Met Ser Arg Pro Met Ile His Phe Gly Asn Asp Trp Glu Asp Arg
            115                 120                 125

Tyr Tyr Arg Glu Asn Met Asn Arg Tyr Pro Asn Gln Val Tyr Tyr Arg
            130                 135                 140

Pro Val Asp Gln Tyr Asn Asn Gln Asn Asn Phe Val His Asp Cys Val
145                 150                 155                 160

Asn Ile Thr Ile Lys Gln His Thr Val Thr Thr Thr Thr Lys Gly Glu
                165                 170                 175

Asn Phe Thr Glu Thr Asp Val Lys Met Met Glu Arg Val Val Glu Gln
                180                 185                 190

Met Cys Val Thr Gln Tyr Gln Lys Glu Ser Gln Ala Tyr Tyr Glu Gly
            195                 200                 205

Arg Ser Val Asp Asn Phe Thr Leu Pro Lys Gly Glu Lys Tyr Val
210                 215                 220

Pro Pro Glu Gly Gln Ser Leu Arg Glu His Ile Asp Gly Leu Trp Pro
225                 230                 235                 240

Val Leu Thr Arg Ser Thr Glu Asn Thr Glu Lys Trp Asp Ser Leu Leu
            245                 250                 255

Pro Leu Pro Glu Pro Tyr Val Val Pro Gly Gly Arg Phe Arg Glu Val
            260                 265                 270

Tyr Tyr Trp Asp Ser Tyr Phe Thr Met Leu Gly Leu Ala Glu Ser Gly
            275                 280                 285

His Trp Asp Lys Val Ala Asp Met Val Ala Asn Phe Ala His Glu Ile
            290                 295                 300

Asp Thr Tyr Gly His Ile Pro Asn Gly Asn Arg Ser Tyr Tyr Leu Ser
305                 310                 315                 320

Arg Ser Gln Pro Pro Phe Phe Ala Leu Met Val Glu Leu Leu Ala Gln
                325                 330                 335

His Glu Gly Asp Ala Ala Leu Lys Gln Tyr Leu Pro Gln Met Gln Lys
            340                 345                 350

Glu Tyr Ala Tyr Trp Met Asp Gly Val Glu Asn Leu Gln Ala Gly Gln
            355                 360                 365

Gln Glu Lys Arg Val Val Lys Leu Gln Asp Gly Thr Leu Leu Asn Arg
            370                 375                 380

Tyr Trp Asp Asp Arg Asp Thr Pro Arg Pro Glu Ser Trp Val Glu Asp
385                 390                 395                 400

Ile Ala Thr Ala Lys Ser Asn Pro Asn Arg Pro Ala Thr Glu Ile Tyr
                405                 410                 415
```

-continued

```
Arg Asp Leu Arg Ser Ala Ala Ser Gly Trp Asp Phe Ser Ser Arg
            420                 425                 430

Trp Met Asp Asn Pro Gln Gln Leu Asn Thr Leu Arg Thr Ser Ile
435                 440                 445

Val Pro Val Asp Leu Asn Ser Leu Met Phe Lys Met Glu Lys Ile Leu
    450                 455                 460

Ala Arg Ala Ser Lys Ala Ala Gly Asp Asn Ala Met Ala Asn Gln Tyr
465                 470                 475                 480

Glu Thr Leu Ala Asn Ala Arg Gln Lys Gly Ile Glu Lys Tyr Leu Trp
                485                 490                 495

Asn Asp Gln Gln Gly Trp Tyr Ala Asp Tyr Asp Leu Lys Ser His Lys
            500                 505                 510

Val Arg Asn Gln Leu Thr Ala Ala Leu Phe Pro Leu Tyr Val Asn
            515                 520                 525

Ala Ala Ala Lys Asp Arg Ala Asn Lys Met Ala Thr Ala Thr Lys Thr
530                 535                 540

His Leu Leu Gln Pro Gly Gly Leu Asn Thr Thr Ser Val Lys Ser Gly
545                 550                 555                 560

Gln Gln Trp Asp Ala Pro Asn Gly Trp Ala Pro Leu Gln Trp Val Ala
                565                 570                 575

Thr Glu Gly Leu Gln Asn Tyr Gly Gln Lys Glu Val Ala Met Asp Ile
            580                 585                 590

Ser Trp His Phe Leu Thr Asn Val Gln His Thr Tyr Asp Arg Glu Lys
        595                 600                 605

Lys Leu Val Glu Lys Tyr Asp Val Ser Thr Thr Gly Thr Gly Gly
610                 615                 620

Gly Gly Glu Tyr Pro Leu Gln Asp Gly Phe Gly Trp Thr Asn Gly Val
625                 630                 635                 640

Thr Leu Lys Met Leu Asp Leu Ile Cys Pro Lys Gln Pro Cys Asp
                645                 650                 655

Asn Val Pro Ala Thr Arg Pro Thr Val Lys Ser Ala Thr Gln Pro
            660                 665                 670

Ser Thr Lys Glu Ala Gln Pro Thr Pro His His His His His
        675                 680                 685

<210> SEQ ID NO 60
<211> LENGTH: 544
<212> TYPE: PRT
<213> ORGANISM: Artificial Sequence
<220> FEATURE:
<223> OTHER INFORMATION: HIS-TreACWE: N-terminally HIS-tagged TreA with
      CWE scar in linker region

<400> SEQUENCE: 60

Met Ala His His His His His His Glu Glu Thr Pro Val Thr Pro Gln
1               5                   10                  15

Pro Pro Asp Ile Leu Leu Gly Pro Leu Phe Asn Asp Val Gln Asn Ala
            20                  25                  30

Lys Leu Phe Pro Asp Gln Lys Thr Phe Ala Asp Ala Val Pro Asn Ser
        35                  40                  45

Asp Pro Leu Met Ile Leu Ala Asp Tyr Arg Met Gln Gln Asn Gln Ser
    50                  55                  60

Gly Phe Asp Leu Arg His Phe Val Asn Val Asn Phe Thr Leu Pro Lys
65                  70                  75                  80

Glu Cys Trp Glu Lys Tyr Val Pro Pro Glu Gly Gln Ser Leu Arg Glu
                85                  90                  95
```

```
His Ile Asp Gly Leu Trp Pro Val Leu Thr Arg Ser Thr Glu Asn Thr
            100                 105                 110

Glu Lys Trp Asp Ser Leu Leu Pro Leu Pro Glu Pro Tyr Val Val Pro
        115                 120                 125

Gly Gly Arg Phe Arg Glu Val Tyr Tyr Trp Asp Ser Tyr Phe Thr Met
    130                 135                 140

Leu Gly Leu Ala Glu Ser Gly His Trp Asp Lys Val Ala Asp Met Val
145                 150                 155                 160

Ala Asn Phe Ala His Glu Ile Asp Thr Tyr Gly His Ile Pro Asn Gly
                165                 170                 175

Asn Arg Ser Tyr Tyr Leu Ser Arg Ser Gln Pro Pro Phe Phe Ala Leu
            180                 185                 190

Met Val Glu Leu Leu Ala Gln His Glu Gly Asp Ala Ala Leu Lys Gln
        195                 200                 205

Tyr Leu Pro Gln Met Gln Lys Glu Tyr Ala Tyr Trp Met Asp Gly Val
    210                 215                 220

Glu Asn Leu Gln Ala Gly Gln Gln Glu Lys Arg Val Val Lys Leu Gln
225                 230                 235                 240

Asp Gly Thr Leu Leu Asn Arg Tyr Trp Asp Asp Arg Asp Thr Pro Arg
                245                 250                 255

Pro Glu Ser Trp Val Glu Asp Ile Ala Thr Ala Lys Ser Asn Pro Asn
            260                 265                 270

Arg Pro Ala Thr Glu Ile Tyr Arg Asp Leu Arg Ser Ala Ala Ala Ser
        275                 280                 285

Gly Trp Asp Phe Ser Ser Arg Trp Met Asp Asn Pro Gln Gln Leu Asn
    290                 295                 300

Thr Leu Arg Thr Thr Ser Ile Val Pro Val Asp Leu Asn Ser Leu Met
305                 310                 315                 320

Phe Lys Met Glu Lys Ile Leu Ala Arg Ala Ser Lys Ala Ala Gly Asp
                325                 330                 335

Asn Ala Met Ala Asn Gln Tyr Glu Thr Leu Ala Asn Ala Arg Gln Lys
            340                 345                 350

Gly Ile Glu Lys Tyr Leu Trp Asn Asp Gln Gly Trp Tyr Ala Asp
        355                 360                 365

Tyr Asp Leu Lys Ser His Lys Val Arg Asn Gln Leu Thr Ala Ala Ala
    370                 375                 380

Leu Phe Pro Leu Tyr Val Asn Ala Ala Lys Asp Arg Ala Asn Lys
385                 390                 395                 400

Met Ala Thr Ala Thr Lys Thr His Leu Leu Gln Pro Gly Gly Leu Asn
                405                 410                 415

Thr Thr Ser Val Lys Ser Gly Gln Gln Trp Asp Ala Pro Asn Gly Trp
            420                 425                 430

Ala Pro Leu Gln Trp Val Ala Thr Glu Gly Leu Gln Asn Tyr Gly Gln
        435                 440                 445

Lys Glu Val Ala Met Asp Ile Ser Trp His Phe Leu Thr Asn Val Gln
    450                 455                 460

His Thr Tyr Asp Arg Glu Lys Lys Leu Val Glu Lys Tyr Asp Val Ser
465                 470                 475                 480

Thr Thr Gly Thr Gly Gly Gly Glu Tyr Pro Leu Gln Asp Gly
                485                 490                 495

Phe Gly Trp Thr Asn Gly Val Thr Leu Lys Met Leu Asp Leu Ile Cys
            500                 505                 510
```

```
Pro Lys Glu Gln Pro Cys Asp Asn Val Pro Ala Thr Arg Pro Thr Val
            515                 520                 525

Lys Ser Ala Thr Thr Gln Pro Ser Thr Lys Glu Ala Gln Pro Thr Pro
        530                 535                 540

<210> SEQ ID NO 61
<211> LENGTH: 189
<212> TYPE: PRT
<213> ORGANISM: Artificial Sequence
<220> FEATURE:
<223> OTHER INFORMATION: TreAN-IntN: N-terminally HIS-tagged N-terminal
      fragment of TreA N-terminally fused N-terminal fragment of the
      split intein DnaE of Nostoc punctiforme

<400> SEQUENCE: 61

Met Ala His His His His His His Glu Glu Thr Pro Val Thr Pro Gln
1               5                   10                  15

Pro Pro Asp Ile Leu Leu Gly Pro Leu Phe Asn Asp Val Gln Asn Ala
            20                  25                  30

Lys Leu Phe Pro Asp Gln Lys Thr Phe Ala Asp Ala Val Pro Asn Ser
        35                  40                  45

Asp Pro Leu Met Ile Leu Ala Asp Tyr Arg Met Gln Gln Asn Gln Ser
    50                  55                  60

Gly Phe Asp Leu Arg His Phe Val Asn Val Asn Phe Thr Leu Pro Lys
65                  70                  75                  80

Glu Cys Leu Ser Tyr Glu Thr Glu Ile Leu Thr Val Glu Tyr Gly Leu
                85                  90                  95

Leu Pro Ile Gly Lys Ile Val Glu Lys Arg Ile Glu Cys Thr Val Tyr
            100                 105                 110

Ser Val Asp Asn Asn Gly Asn Ile Tyr Thr Gln Pro Val Ala Gln Trp
        115                 120                 125

His Asp Arg Gly Glu Gln Glu Val Phe Glu Tyr Cys Leu Glu Asp Gly
    130                 135                 140

Ser Leu Ile Arg Ala Thr Lys Asp His Lys Phe Met Thr Val Asp Gly
145                 150                 155                 160

Gln Met Leu Pro Ile Asp Glu Ile Phe Glu Arg Glu Leu Asp Leu Met
                165                 170                 175

Arg Val Asp Asn Leu Pro Asn Gly Ser Gly Gly Lys Leu
            180                 185

<210> SEQ ID NO 62
<211> LENGTH: 512
<212> TYPE: PRT
<213> ORGANISM: Artificial Sequence
<220> FEATURE:
<223> OTHER INFORMATION: IntC-TreAC: C-terminally HIS-tagged C-terminal
      fragment of TreA N-terminally fused C-terminal fragment of the
      split intein DnaE of Nostoc punctiforme

<400> SEQUENCE: 62

Met Ala Ala Ser Gly Gly Thr Ser Ile Lys Ile Ala Thr Arg Lys Tyr
1               5                   10                  15

Leu Gly Lys Gln Asn Val Tyr Asp Ile Gly Val Glu Arg Asp His Asn
            20                  25                  30

Phe Ala Leu Lys Asn Gly Phe Ile Ala Ser Asn Cys Trp Glu Lys Tyr
        35                  40                  45

Val Pro Pro Glu Gly Gln Ser Leu Arg Glu His Ile Asp Gly Leu Trp
    50                  55                  60

Pro Val Leu Thr Arg Ser Thr Glu Asn Thr Glu Lys Trp Asp Ser Leu
```

```
                65                   70                  75                  80
Leu Pro Leu Pro Glu Pro Tyr Val Val Pro Gly Gly Arg Phe Arg Glu
                        85                  90                  95

Val Tyr Tyr Trp Asp Ser Tyr Phe Thr Met Leu Gly Leu Ala Glu Ser
                100                 105                 110

Gly His Trp Asp Lys Val Ala Asp Met Val Ala Asn Phe Ala His Glu
                115                 120                 125

Ile Asp Thr Tyr Gly His Ile Pro Asn Gly Asn Arg Ser Tyr Tyr Leu
    130                 135                 140

Ser Arg Ser Gln Pro Pro Phe Phe Ala Leu Met Val Glu Leu Leu Ala
145                 150                 155                 160

Gln His Glu Gly Asp Ala Ala Leu Lys Gln Tyr Leu Pro Gln Met Gln
                    165                 170                 175

Lys Glu Tyr Ala Tyr Trp Met Asp Gly Val Glu Asn Leu Gln Ala Gly
                180                 185                 190

Gln Gln Glu Lys Arg Val Val Lys Leu Gln Asp Gly Thr Leu Leu Asn
                195                 200                 205

Arg Tyr Trp Asp Asp Arg Asp Thr Pro Arg Pro Glu Ser Trp Val Glu
    210                 215                 220

Asp Ile Ala Thr Ala Lys Ser Asn Pro Asn Arg Pro Ala Thr Glu Ile
225                 230                 235                 240

Tyr Arg Asp Leu Arg Ser Ala Ala Ala Ser Gly Trp Asp Phe Ser Ser
                245                 250                 255

Arg Trp Met Asp Asn Pro Gln Gln Leu Asn Thr Leu Arg Thr Thr Ser
                260                 265                 270

Ile Val Pro Val Asp Leu Asn Ser Leu Met Phe Lys Met Glu Lys Ile
                275                 280                 285

Leu Ala Arg Ala Ser Lys Ala Ala Gly Asp Asn Ala Met Ala Asn Gln
                290                 295                 300

Tyr Glu Thr Leu Ala Asn Ala Arg Gln Lys Gly Ile Glu Lys Tyr Leu
305                 310                 315                 320

Trp Asn Asp Gln Gln Gly Trp Tyr Ala Asp Tyr Asp Leu Lys Ser His
                    325                 330                 335

Lys Val Arg Asn Gln Leu Thr Ala Ala Ala Leu Phe Pro Leu Tyr Val
                340                 345                 350

Asn Ala Ala Ala Lys Asp Arg Ala Asn Lys Met Ala Thr Ala Thr Lys
                355                 360                 365

Thr His Leu Leu Gln Pro Gly Gly Leu Asn Thr Thr Ser Val Lys Ser
    370                 375                 380

Gly Gln Gln Trp Asp Ala Pro Asn Gly Trp Ala Pro Leu Gln Trp Val
385                 390                 395                 400

Ala Thr Glu Gly Leu Gln Asn Tyr Gly Gln Lys Glu Val Ala Met Asp
                405                 410                 415

Ile Ser Trp His Phe Leu Thr Asn Val Gln His Thr Tyr Asp Arg Glu
                420                 425                 430

Lys Lys Leu Val Glu Lys Tyr Asp Val Ser Thr Thr Gly Thr Gly Gly
                435                 440                 445

Gly Gly Gly Glu Tyr Pro Leu Gln Asp Gly Phe Gly Trp Thr Asn Gly
                450                 455                 460

Val Thr Leu Lys Met Leu Asp Leu Ile Cys Pro Lys Glu Gln Pro Cys
465                 470                 475                 480

Asp Asn Val Pro Ala Thr Arg Pro Thr Val Lys Ser Ala Thr Thr Gln
                485                 490                 495
```

-continued

```
Pro Ser Thr Lys Glu Ala Gln Pro Thr Pro His His His His His
            500                 505                 510

<210> SEQ ID NO 63
<211> LENGTH: 327
<212> TYPE: PRT
<213> ORGANISM: Artificial Sequence
<220> FEATURE:
<223> OTHER INFORMATION: ER-TreAN-HIS: C-terminally HIS-tagged
      N-terminal fragment of TreA N-terminally fused with human
      estradiol receptor fragment

<400> SEQUENCE: 63

Met Gly Lys Arg Ser Lys Lys Asn Ser Leu Ala Leu Ser Leu Thr Ala
1               5                   10                  15

Asp Gln Met Val Ser Ala Leu Leu Asp Ala Glu Pro Pro Ile Leu Tyr
            20                  25                  30

Ser Glu Tyr Asp Pro Thr Arg Pro Phe Ser Glu Ala Ser Met Met Gly
        35                  40                  45

Leu Leu Thr Asn Leu Ala Asp Arg Glu Leu Val His Met Ile Asn Trp
    50                  55                  60

Ala Lys Arg Val Pro Gly Phe Val Asp Leu Thr Leu His Asp Gln Val
65                  70                  75                  80

His Leu Leu Glu Ser Ala Trp Leu Glu Ile Leu Met Ile Gly Leu Val
                85                  90                  95

Trp Arg Ser Met Glu His Pro Gly Lys Leu Leu Phe Ala Pro Asn Leu
            100                 105                 110

Leu Leu Asp Arg Asn Gln Gly Lys Ser Val Glu Gly Met Val Glu Ile
        115                 120                 125

Phe Asp Met Leu Leu Ala Thr Ser Ser Arg Phe Arg Met Met Asn Leu
    130                 135                 140

Gln Gly Glu Glu Phe Val Cys Leu Lys Ser Ile Ile Leu Leu Asn Ser
145                 150                 155                 160

Gly Val Tyr Thr Phe Leu Ser Ser Thr Leu Lys Ser Leu Glu Glu Lys
                165                 170                 175

Asp His Ile His Arg Val Leu Asp Lys Ile Thr Asp Thr Leu Ile His
            180                 185                 190

Leu Met Ala Lys Ala Gly Leu Thr Leu Gln Gln Gln His Gln Arg Leu
        195                 200                 205

Ala Gln Leu Leu Leu Ile Leu Ser His Ile Arg His Met Ser Asn Lys
    210                 215                 220

Gly Met Glu His Leu Tyr Ser Met Lys Ser Lys Asn Gly Gly Ser Gly
225                 230                 235                 240

Val Asp Glu Glu Thr Pro Val Thr Pro Gln Pro Pro Asp Ile Leu Leu
                245                 250                 255

Gly Pro Leu Phe Asn Asp Val Gln Asn Ala Lys Leu Phe Pro Asp Gln
            260                 265                 270

Lys Thr Phe Ala Asp Ala Val Pro Asn Ser Asp Pro Leu Met Ile Leu
        275                 280                 285

Ala Asp Tyr Arg Met Gln Gln Asn Gln Ser Gly Phe Asp Leu Arg His
    290                 295                 300

Phe Val Asn Val Asn Phe Thr Leu Pro Lys Glu Gly Glu Lys Tyr Val
305                 310                 315                 320

Pro His His His His His His
                325
```

-continued

```
<210> SEQ ID NO 64
<211> LENGTH: 717
<212> TYPE: PRT
<213> ORGANISM: Artificial Sequence
<220> FEATURE:
<223> OTHER INFORMATION: ER-TreAC-HIS: C-terminally HIS-tagged
      C-terminal fragment of TreA N-terminally fused with human
      estradiol receptor fragment

<400> SEQUENCE: 64
```

Met Gly Lys Arg Ser Lys Lys Asn Ser Leu Ala Leu Ser Leu Thr Ala
1               5                   10                  15

Asp Gln Met Val Ser Ala Leu Leu Asp Ala Glu Pro Pro Ile Leu Tyr
            20                  25                  30

Ser Glu Tyr Asp Pro Thr Arg Pro Phe Ser Glu Ala Ser Met Met Gly
        35                  40                  45

Leu Leu Thr Asn Leu Ala Asp Arg Glu Leu Val His Met Ile Asn Trp
    50                  55                  60

Ala Lys Arg Val Pro Gly Phe Val Asp Leu Thr Leu His Asp Gln Val
65                  70                  75                  80

His Leu Leu Glu Ser Ala Trp Leu Glu Ile Leu Met Ile Gly Leu Val
                85                  90                  95

Trp Arg Ser Met Glu His Pro Gly Lys Leu Leu Phe Ala Pro Asn Leu
            100                 105                 110

Leu Leu Asp Arg Asn Gln Gly Lys Ser Val Glu Gly Met Val Glu Ile
        115                 120                 125

Phe Asp Met Leu Leu Ala Thr Ser Ser Arg Phe Arg Met Met Asn Leu
    130                 135                 140

Gln Gly Glu Glu Phe Val Cys Leu Lys Ser Ile Ile Leu Leu Asn Ser
145                 150                 155                 160

Gly Val Tyr Thr Phe Leu Ser Ser Thr Leu Lys Ser Leu Glu Glu Lys
                165                 170                 175

Asp His Ile His Arg Val Leu Asp Lys Ile Thr Asp Thr Leu Ile His
            180                 185                 190

Leu Met Ala Lys Ala Gly Leu Thr Leu Gln Gln Gln His Gln Arg Leu
        195                 200                 205

Ala Gln Leu Leu Leu Ile Leu Ser His Ile Arg His Met Ser Asn Lys
    210                 215                 220

Gly Met Glu His Leu Tyr Ser Met Lys Ser Lys Asn Gly Gly Ser Gly
225                 230                 235                 240

Val Asp Asn Phe Thr Leu Pro Lys Glu Gly Glu Lys Tyr Val Pro Pro
                245                 250                 255

Glu Gly Gln Ser Leu Arg Glu His Ile Asp Gly Leu Trp Pro Val Leu
            260                 265                 270

Thr Arg Ser Thr Glu Asn Thr Glu Lys Trp Asp Ser Leu Leu Pro Leu
        275                 280                 285

Pro Glu Pro Tyr Val Val Pro Gly Gly Arg Phe Arg Glu Val Tyr Tyr
    290                 295                 300

Trp Asp Ser Tyr Phe Thr Met Leu Gly Leu Ala Glu Ser Gly His Trp
305                 310                 315                 320

Asp Lys Val Ala Asp Met Val Ala Asn Phe Ala His Glu Ile Asp Thr
                325                 330                 335

Tyr Gly His Ile Pro Asn Gly Asn Arg Ser Tyr Tyr Leu Ser Arg Ser
            340                 345                 350

Gln Pro Pro Phe Phe Ala Leu Met Val Glu Leu Leu Ala Gln His Glu

```
                 355                 360                 365
Gly Asp Ala Ala Leu Lys Gln Tyr Leu Pro Gln Met Gln Lys Glu Tyr
370                 375                 380

Ala Tyr Trp Met Asp Gly Val Glu Asn Leu Gln Ala Gly Gln Gln Glu
385                 390                 395                 400

Lys Arg Val Val Lys Leu Gln Asp Gly Thr Leu Leu Asn Arg Tyr Trp
                405                 410                 415

Asp Asp Arg Asp Thr Pro Arg Pro Glu Ser Trp Val Glu Asp Ile Ala
            420                 425                 430

Thr Ala Lys Ser Asn Pro Asn Arg Pro Ala Thr Glu Ile Tyr Arg Asp
        435                 440                 445

Leu Arg Ser Ala Ala Ala Ser Gly Trp Asp Phe Ser Ser Arg Trp Met
    450                 455                 460

Asp Asn Pro Gln Gln Leu Asn Thr Leu Arg Thr Thr Ser Ile Val Pro
465                 470                 475                 480

Val Asp Leu Asn Ser Leu Met Phe Lys Met Glu Lys Ile Leu Ala Arg
                485                 490                 495

Ala Ser Lys Ala Ala Gly Asp Asn Ala Met Ala Asn Gln Tyr Glu Thr
            500                 505                 510

Leu Ala Asn Ala Arg Gln Lys Gly Ile Glu Lys Tyr Leu Trp Asn Asp
        515                 520                 525

Gln Gln Gly Trp Tyr Ala Asp Tyr Asp Leu Lys Ser His Lys Val Arg
    530                 535                 540

Asn Gln Leu Thr Ala Ala Ala Leu Phe Pro Leu Tyr Val Asn Ala Ala
545                 550                 555                 560

Ala Lys Asp Arg Ala Asn Lys Met Ala Thr Ala Thr Lys Thr His Leu
                565                 570                 575

Leu Gln Pro Gly Gly Leu Asn Thr Thr Ser Val Lys Ser Gly Gln Gln
            580                 585                 590

Trp Asp Ala Pro Asn Gly Trp Ala Pro Leu Gln Trp Val Ala Thr Glu
        595                 600                 605

Gly Leu Gln Asn Tyr Gly Gln Lys Glu Val Ala Met Asp Ile Ser Trp
    610                 615                 620

His Phe Leu Thr Asn Val Gln His Thr Tyr Asp Arg Glu Lys Lys Leu
625                 630                 635                 640

Val Glu Lys Tyr Asp Val Ser Thr Thr Gly Thr Gly Gly Gly Gly Gly
                645                 650                 655

Glu Tyr Pro Leu Gln Asp Gly Phe Gly Trp Thr Asn Gly Val Thr Leu
            660                 665                 670

Lys Met Leu Asp Leu Ile Cys Pro Lys Glu Gln Pro Cys Asp Asn Val
        675                 680                 685

Pro Ala Thr Arg Pro Thr Val Lys Ser Ala Thr Thr Gln Pro Ser Thr
    690                 695                 700

Lys Glu Ala Gln Pro Thr Pro His His His His His
705                 710                 715

<210> SEQ ID NO 65
<211> LENGTH: 304
<212> TYPE: PRT
<213> ORGANISM: Artificial Sequence
<220> FEATURE:
<223> OTHER INFORMATION: IFNGRA-TreAN-HIS: C-terminally HIS-tagged
      N-terminal fragment of TreA N-terminally fused with bovine
      interferon-gamma receptor A fragment

<400> SEQUENCE: 65
```

```
Met Ala Ser Ala Ile Pro Gly Leu Ser Ser Val Pro Pro Thr Asn
1               5                   10                  15

Val Thr Ile Gln Ala Tyr Asn Leu Asn Thr Val Ile Phe Trp Asp Tyr
            20                  25                  30

Pro Val Ile Leu Gln Ser Pro Met Phe Thr Val Gln Val Met Asn Tyr
                35                  40                  45

Glu Asp Gly Lys Trp Ile Asp Ala Cys Asn Thr Ser Asp His Ser Cys
    50                  55                  60

Asn Ile Phe Ser Val Ile Asn Asp Pro Ser Ser Ser Val Trp Gly Arg
65                  70                  75                  80

Val Lys Val Arg Val Gly Gln Glu Glu Ser Val Tyr Ala Gln Ser Lys
                85                  90                  95

Glu Phe Ile Leu Cys Lys Glu Gly Lys Val Gly Pro Pro Lys Leu Gly
                100                 105                 110

Ile Arg Lys Lys Glu Asn Gln Ile Ile Val Asp Ile Phe His Pro Leu
                115                 120                 125

Ile Thr Val Asn Gly Lys Glu Pro Glu Ala Met Tyr Asp Asp Glu Asn
                130                 135                 140

Thr Cys Tyr Thr Phe Thr Tyr Ser Val Phe Val Ser Ile Asn Arg Ser
145                 150                 155                 160

Glu Thr Thr Asp Lys Met Tyr Thr Lys Glu Glu Asp Cys Asn Glu Thr
                165                 170                 175

Gln Cys Phe Leu Asn Ile Pro Val Ser Ser Leu Asn Ser Gln Tyr Cys
                180                 185                 190

Val Ser Ala Glu Gly Val Ser Glu Leu Trp Ala Val Thr Thr Glu Lys
                195                 200                 205

Ser Asp Glu Leu Cys Ile Thr Phe Ser Val Asp Glu Glu Thr Pro Val
                210                 215                 220

Thr Pro Gln Pro Pro Asp Ile Leu Leu Gly Pro Leu Phe Asn Asp Val
225                 230                 235                 240

Gln Asn Ala Lys Leu Phe Pro Asp Gln Lys Thr Phe Ala Asp Ala Val
                245                 250                 255

Pro Asn Ser Asp Pro Leu Met Ile Leu Ala Asp Tyr Arg Met Gln Gln
                260                 265                 270

Asn Gln Ser Gly Phe Asp Leu Arg His Phe Val Asn Val Asn Phe Thr
                275                 280                 285

Leu Pro Lys Glu Gly Glu Lys Tyr Val Pro His His His His His His
                290                 295                 300
```

<210> SEQ ID NO 66
<211> LENGTH: 694
<212> TYPE: PRT
<213> ORGANISM: Artificial Sequence
<220> FEATURE:
<223> OTHER INFORMATION: IFNGRA-TreAC-HIS: C-terminally HIS-tagged
      C-terminal fragment of TreA N-terminally fused with bovine
      interferon-gamma receptor A fragment

<400> SEQUENCE: 66

```
Met Ala Ser Ala Ile Pro Gly Leu Ser Ser Val Pro Pro Thr Asn
1               5                   10                  15

Val Thr Ile Gln Ala Tyr Asn Leu Asn Thr Val Ile Phe Trp Asp Tyr
            20                  25                  30

Pro Val Ile Leu Gln Ser Pro Met Phe Thr Val Gln Val Met Asn Tyr
                35                  40                  45
```

```
Glu Asp Gly Lys Trp Ile Asp Ala Cys Asn Thr Ser Asp His Ser Cys
 50                  55                  60

Asn Ile Phe Ser Val Ile Asn Asp Pro Ser Ser Val Trp Gly Arg
 65              70                  75                  80

Val Lys Val Arg Val Gly Gln Glu Ser Val Tyr Ala Gln Ser Lys
             85                  90                  95

Glu Phe Ile Leu Cys Lys Glu Gly Lys Val Gly Pro Pro Lys Leu Gly
                100                 105                 110

Ile Arg Lys Lys Glu Asn Gln Ile Val Asp Ile Phe His Pro Leu
        115                 120                 125

Ile Thr Val Asn Gly Lys Glu Pro Glu Ala Met Tyr Asp Asp Glu Asn
    130                 135                 140

Thr Cys Tyr Thr Phe Thr Tyr Ser Val Phe Val Ser Ile Asn Arg Ser
145                 150                 155                 160

Glu Thr Thr Asp Lys Met Tyr Thr Lys Glu Glu Asp Cys Asn Glu Thr
                165                 170                 175

Gln Cys Phe Leu Asn Ile Pro Val Ser Ser Leu Asn Ser Gln Tyr Cys
            180                 185                 190

Val Ser Ala Glu Gly Val Ser Glu Leu Trp Ala Val Thr Thr Glu Lys
        195                 200                 205

Ser Asp Glu Leu Cys Ile Thr Phe Ser Val Asp Asn Phe Thr Leu Pro
    210                 215                 220

Lys Glu Gly Glu Lys Tyr Val Pro Pro Glu Gly Gln Ser Leu Arg Glu
225                 230                 235                 240

His Ile Asp Gly Leu Trp Pro Val Leu Thr Arg Ser Thr Glu Asn Thr
                245                 250                 255

Glu Lys Trp Asp Ser Leu Leu Pro Leu Pro Glu Pro Tyr Val Val Pro
            260                 265                 270

Gly Gly Arg Phe Arg Glu Val Tyr Tyr Trp Asp Ser Tyr Phe Thr Met
        275                 280                 285

Leu Gly Leu Ala Glu Ser Gly His Trp Asp Lys Val Ala Asp Met Val
    290                 295                 300

Ala Asn Phe Ala His Glu Ile Asp Thr Tyr Gly His Ile Pro Asn Gly
305                 310                 315                 320

Asn Arg Ser Tyr Tyr Leu Ser Arg Ser Gln Pro Pro Phe Phe Ala Leu
                325                 330                 335

Met Val Glu Leu Leu Ala Gln His Glu Gly Asp Ala Ala Leu Lys Gln
            340                 345                 350

Tyr Leu Pro Gln Met Gln Lys Glu Tyr Ala Tyr Trp Met Asp Gly Val
        355                 360                 365

Glu Asn Leu Gln Ala Gly Gln Gln Glu Lys Arg Val Val Lys Leu Gln
    370                 375                 380

Asp Gly Thr Leu Leu Asn Arg Tyr Trp Asp Asp Arg Asp Thr Pro Arg
385                 390                 395                 400

Pro Glu Ser Trp Val Glu Asp Ile Ala Thr Ala Lys Ser Asn Pro Asn
                405                 410                 415

Arg Pro Ala Thr Glu Ile Tyr Arg Asp Leu Arg Ser Ala Ala Ser
            420                 425                 430

Gly Trp Asp Phe Ser Ser Arg Trp Met Asp Asn Pro Gln Gln Leu Asn
        435                 440                 445

Thr Leu Arg Thr Thr Ser Ile Val Pro Val Asp Leu Asn Ser Leu Met
    450                 455                 460

Phe Lys Met Glu Lys Ile Leu Ala Arg Ala Ser Lys Ala Ala Gly Asp
```

```
                465                 470                 475                 480
Asn Ala Met Ala Asn Gln Tyr Glu Thr Leu Ala Asn Ala Arg Gln Lys
                    485                 490                 495
Gly Ile Glu Lys Tyr Leu Trp Asn Asp Gln Gln Gly Trp Tyr Ala Asp
                500                 505                 510
Tyr Asp Leu Lys Ser His Lys Val Arg Asn Gln Leu Thr Ala Ala Ala
                515                 520                 525
Leu Phe Pro Leu Tyr Val Asn Ala Ala Lys Asp Arg Ala Asn Lys
                530                 535                 540
Met Ala Thr Ala Thr Lys Thr His Leu Leu Gln Pro Gly Gly Leu Asn
545                 550                 555                 560
Thr Thr Ser Val Lys Ser Gly Gln Gln Trp Asp Ala Pro Asn Gly Trp
                565                 570                 575
Ala Pro Leu Gln Trp Val Ala Thr Glu Gly Leu Gln Asn Tyr Gly Gln
                580                 585                 590
Lys Glu Val Ala Met Asp Ile Ser Trp His Phe Leu Thr Asn Val Gln
                595                 600                 605
His Thr Tyr Asp Arg Glu Lys Lys Leu Val Glu Lys Tyr Asp Val Ser
                610                 615                 620
Thr Thr Gly Thr Gly Gly Gly Gly Glu Tyr Pro Leu Gln Asp Gly
625                 630                 635                 640
Phe Gly Trp Thr Asn Gly Val Thr Leu Lys Met Leu Asp Leu Ile Cys
                645                 650                 655
Pro Lys Glu Gln Pro Cys Asp Asn Val Pro Ala Thr Arg Pro Thr Val
                660                 665                 670
Lys Ser Ala Thr Thr Gln Pro Ser Thr Lys Glu Ala Gln Pro Thr Pro
                675                 680                 685
His His His His His His
    690

<210> SEQ ID NO 67
<211> LENGTH: 596
<212> TYPE: PRT
<213> ORGANISM: Artificial Sequence
<220> FEATURE:
<223> OTHER INFORMATION: Ab-TreA-HIS: C-terminally HIS-tagged TreA with
      N-terminal fusion with Amyloid beta p42 peptide

<400> SEQUENCE: 67

Met Asp Ala Glu Phe Arg His Asp Ser Gly Tyr Glu Val His His Gln
1               5                   10                  15
Lys Leu Val Phe Phe Ala Glu Asp Val Gly Ser Asn Lys Gly Ala Ile
                20                  25                  30
Ile Gly Leu Met Val Gly Gly Val Val Ile Ala Val Asp Gly Gly
                35                  40                  45
Ser Gly Gly Gly Ser Gly Gly Gly Glu Thr Pro Val Thr Pro Gln Pro
    50                  55                  60
Pro Asp Ile Leu Leu Gly Pro Leu Phe Asn Asp Val Gln Asn Ala Lys
65                  70                  75                  80
Leu Phe Pro Asp Gln Lys Thr Phe Ala Asp Ala Val Pro Asn Ser Asp
                85                  90                  95
Pro Leu Met Ile Leu Ala Asp Tyr Arg Met Gln Gln Asn Gln Ser Gly
                100                 105                 110
Phe Asp Leu Arg His Phe Val Asn Val Asn Phe Thr Leu Pro Lys Glu
                115                 120                 125
```

-continued

```
Gly Glu Lys Tyr Val Pro Pro Glu Gly Gln Ser Leu Arg Glu His Ile
130                 135                 140

Asp Gly Leu Trp Pro Val Leu Thr Arg Ser Thr Glu Asn Thr Glu Lys
145                 150                 155                 160

Trp Asp Ser Leu Leu Pro Leu Pro Glu Pro Tyr Val Val Pro Gly Gly
            165                 170                 175

Arg Phe Arg Glu Val Tyr Tyr Trp Asp Ser Tyr Phe Thr Met Leu Gly
            180                 185                 190

Leu Ala Glu Ser Gly His Trp Asp Lys Val Ala Asp Met Val Ala Asn
        195                 200                 205

Phe Ala His Glu Ile Asp Thr Tyr Gly His Ile Pro Asn Gly Asn Arg
210                 215                 220

Ser Tyr Tyr Leu Ser Arg Ser Gln Pro Pro Phe Phe Ala Leu Met Val
225                 230                 235                 240

Glu Leu Leu Ala Gln His Gly Asp Ala Ala Leu Lys Gln Tyr Leu
            245                 250                 255

Pro Gln Met Gln Lys Glu Tyr Ala Tyr Trp Met Asp Gly Val Glu Asn
            260                 265                 270

Leu Gln Ala Gly Gln Gln Glu Lys Arg Val Val Lys Leu Gln Asp Gly
        275                 280                 285

Thr Leu Leu Asn Arg Tyr Trp Asp Asp Arg Asp Thr Pro Arg Pro Glu
290                 295                 300

Ser Trp Val Glu Asp Ile Ala Thr Ala Lys Ser Asn Pro Asn Arg Pro
305                 310                 315                 320

Ala Thr Glu Ile Tyr Arg Asp Leu Arg Ser Ala Ala Ser Gly Trp
            325                 330                 335

Asp Phe Ser Ser Arg Trp Met Asp Asn Pro Gln Gln Leu Asn Thr Leu
            340                 345                 350

Arg Thr Thr Ser Ile Val Pro Val Asp Leu Asn Ser Leu Met Phe Lys
            355                 360                 365

Met Glu Lys Ile Leu Ala Arg Ala Ser Lys Ala Ala Gly Asp Asn Ala
            370                 375                 380

Met Ala Asn Gln Tyr Glu Thr Leu Ala Asn Ala Arg Gln Lys Gly Ile
385                 390                 395                 400

Glu Lys Tyr Leu Trp Asn Asp Gln Gln Gly Trp Tyr Ala Asp Tyr Asp
            405                 410                 415

Leu Lys Ser His Lys Val Arg Asn Gln Leu Thr Ala Ala Leu Phe
            420                 425                 430

Pro Leu Tyr Val Asn Ala Ala Lys Asp Arg Ala Asn Lys Met Ala
            435                 440                 445

Thr Ala Thr Lys Thr His Leu Leu Gln Pro Gly Gly Leu Asn Thr Thr
450                 455                 460

Ser Val Lys Ser Gly Gln Gln Trp Asp Ala Pro Asn Gly Trp Ala Pro
465                 470                 475                 480

Leu Gln Trp Val Ala Thr Glu Gly Leu Gln Asn Tyr Gly Gln Lys Glu
            485                 490                 495

Val Ala Met Asp Ile Ser Trp His Phe Leu Thr Asn Val Gln His Thr
            500                 505                 510

Tyr Asp Arg Glu Lys Lys Leu Val Glu Lys Tyr Asp Val Ser Thr Thr
            515                 520                 525

Gly Thr Gly Gly Gly Gly Glu Tyr Pro Leu Gln Asp Gly Phe Gly
530                 535                 540

Trp Thr Asn Gly Val Thr Leu Lys Met Leu Asp Leu Ile Cys Pro Lys
```

```
                        545                 550                 555                 560
Glu Gln Pro Cys Asp Asn Val Pro Ala Thr Arg Pro Thr Val Lys Ser
                    565                 570                 575

Ala Thr Thr Gln Pro Ser Thr Lys Glu Ala Gln Pro Thr Pro His His
                580                 585                 590

His His His His
        595

<210> SEQ ID NO 68
<211> LENGTH: 130
<212> TYPE: PRT
<213> ORGANISM: Artificial Sequence
<220> FEATURE:
<223> OTHER INFORMATION: Ab-TreAN-HIS: C-terminally HIS-tagged
      N-terminal fragment of TreA with N-terminal fusion with Amyloid
      beta p42 peptide

<400> SEQUENCE: 68

Met Asp Ala Glu Phe Arg His Asp Ser Gly Tyr Glu Val His His Gln
1               5                   10                  15

Lys Leu Val Phe Phe Ala Glu Asp Val Gly Ser Asn Lys Gly Ala Ile
            20                  25                  30

Ile Gly Leu Met Val Gly Gly Val Val Ile Ala Val Asp Glu Glu Thr
        35                  40                  45

Pro Val Thr Pro Gln Pro Pro Asp Ile Leu Leu Gly Pro Leu Phe Asn
    50                  55                  60

Asp Val Gln Asn Ala Lys Leu Phe Pro Asp Gln Lys Thr Phe Ala Asp
65                  70                  75                  80

Ala Val Pro Asn Ser Asp Pro Leu Met Ile Leu Ala Asp Tyr Arg Met
                85                  90                  95

Gln Gln Asn Gln Ser Gly Phe Asp Leu Arg His Phe Val Asn Val Asn
            100                 105                 110

Phe Thr Leu Pro Lys Glu Gly Glu Lys Tyr Val Pro His His His His
        115                 120                 125

His His
    130

<210> SEQ ID NO 69
<211> LENGTH: 520
<212> TYPE: PRT
<213> ORGANISM: Artificial Sequence
<220> FEATURE:
<223> OTHER INFORMATION: Ab-TreAC-HIS: C-terminally HIS-tagged
      C-terminal fragment of TreA with N-terminal fusion with Amyloid
      beta p42 peptide

<400> SEQUENCE: 69

Met Asp Ala Glu Phe Arg His Asp Ser Gly Tyr Glu Val His His Gln
1               5                   10                  15

Lys Leu Val Phe Phe Ala Glu Asp Val Gly Ser Asn Lys Gly Ala Ile
            20                  25                  30

Ile Gly Leu Met Val Gly Gly Val Val Ile Ala Val Asp Asn Phe Thr
        35                  40                  45

Leu Pro Lys Glu Gly Glu Lys Tyr Val Pro Pro Glu Gly Gln Ser Leu
    50                  55                  60

Arg Glu His Ile Asp Gly Leu Trp Pro Val Leu Thr Arg Ser Thr Glu
65                  70                  75                  80

Asn Thr Glu Lys Trp Asp Ser Leu Leu Pro Leu Pro Glu Pro Tyr Val
                85                  90                  95
```

```
Val Pro Gly Gly Arg Phe Arg Glu Val Tyr Tyr Trp Asp Ser Tyr Phe
            100                 105                 110
Thr Met Leu Gly Leu Ala Glu Ser Gly His Trp Asp Lys Val Ala Asp
            115                 120                 125
Met Val Ala Asn Phe Ala His Glu Ile Asp Thr Tyr Gly His Ile Pro
130                 135                 140
Asn Gly Asn Arg Ser Tyr Tyr Leu Ser Arg Ser Gln Pro Pro Phe Phe
145                 150                 155                 160
Ala Leu Met Val Glu Leu Leu Ala Gln His Glu Gly Asp Ala Ala Leu
            165                 170                 175
Lys Gln Tyr Leu Pro Gln Met Gln Lys Glu Tyr Ala Tyr Trp Met Asp
            180                 185                 190
Gly Val Glu Asn Leu Gln Ala Gly Gln Gln Glu Lys Arg Val Val Lys
            195                 200                 205
Leu Gln Asp Gly Thr Leu Leu Asn Arg Tyr Trp Asp Asp Arg Asp Thr
            210                 215                 220
Pro Arg Pro Glu Ser Trp Val Glu Asp Ile Ala Thr Ala Lys Ser Asn
225                 230                 235                 240
Pro Asn Arg Pro Ala Thr Glu Ile Tyr Arg Asp Leu Arg Ser Ala Ala
            245                 250                 255
Ala Ser Gly Trp Asp Phe Ser Ser Arg Trp Met Asp Asn Pro Gln Gln
            260                 265                 270
Leu Asn Thr Leu Arg Thr Thr Ser Ile Val Pro Val Asp Leu Asn Ser
            275                 280                 285
Leu Met Phe Lys Met Glu Lys Ile Leu Ala Arg Ala Ser Lys Ala Ala
            290                 295                 300
Gly Asp Asn Ala Met Ala Asn Gln Tyr Glu Thr Leu Ala Asn Ala Arg
305                 310                 315                 320
Gln Lys Gly Ile Glu Lys Tyr Leu Trp Asn Asp Gln Gln Gly Trp Tyr
            325                 330                 335
Ala Asp Tyr Asp Leu Lys Ser His Lys Val Arg Asn Gln Leu Thr Ala
            340                 345                 350
Ala Ala Leu Phe Pro Leu Tyr Val Asn Ala Ala Lys Asp Arg Ala
            355                 360                 365
Asn Lys Met Ala Thr Ala Thr Lys Thr His Leu Leu Gln Pro Gly Gly
            370                 375                 380
Leu Asn Thr Thr Ser Val Lys Ser Gly Gln Gln Trp Asp Ala Pro Asn
385                 390                 395                 400
Gly Trp Ala Pro Leu Gln Trp Val Ala Thr Glu Gly Leu Gln Asn Tyr
            405                 410                 415
Gly Gln Lys Glu Val Ala Met Asp Ile Ser Trp His Phe Leu Thr Asn
            420                 425                 430
Val Gln His Thr Tyr Asp Arg Glu Lys Lys Leu Val Glu Lys Tyr Asp
            435                 440                 445
Val Ser Thr Thr Gly Thr Gly Gly Gly Gly Glu Tyr Pro Leu Gln
            450                 455                 460
Asp Gly Phe Gly Trp Thr Asn Gly Val Thr Leu Lys Met Leu Asp Leu
465                 470                 475                 480
Ile Cys Pro Lys Glu Gln Pro Cys Asp Asn Val Pro Ala Thr Arg Pro
            485                 490                 495
Thr Val Lys Ser Ala Thr Thr Gln Pro Ser Thr Lys Glu Ala Gln Pro
            500                 505                 510
```

-continued

Thr Pro His His His His His His
        515                 520

<210> SEQ ID NO 70
<211> LENGTH: 1032
<212> TYPE: PRT
<213> ORGANISM: Artificial Sequence
<220> FEATURE:
<223> OTHER INFORMATION: GDH-HIS-TreA: Glucose dehydrogenase
      N-terminally fused to the TreA (w/o signal peptide) with flexible
      linker and HIS-tag in between GDH and TreA

<400> SEQUENCE: 70

Met Ala Gly Lys Tyr Leu Leu Pro Thr Ala Ala Gly Leu Leu Leu
1               5                   10                  15

Leu Ala Ala Gln Pro Ala Met Ala Asp Val Pro Leu Thr Pro Ser Gln
            20                  25                  30

Phe Ala Lys Ala Lys Ser Glu Asn Phe Asp Lys Lys Val Ile Leu Ser
        35                  40                  45

Asn Leu Asn Lys Pro His Ala Leu Leu Trp Gly Pro Asp Asn Gln Ile
    50                  55                  60

Trp Leu Thr Glu Arg Ala Thr Gly Lys Ile Leu Arg Val Asn Pro Glu
65                  70                  75                  80

Ser Gly Ser Val Lys Thr Val Phe Gln Val Pro Glu Ile Val Asn Asp
                85                  90                  95

Ala Asp Gly Gln Asn Gly Leu Leu Gly Phe Ala Phe His Pro Arg Phe
            100                 105                 110

Lys Asn Asn Pro Tyr Ile Tyr Ile Ser Gly Thr Phe Lys Asn Pro Lys
        115                 120                 125

Ser Thr Asp Lys Glu Leu Pro Asn Gln Thr Ile Ile Arg Arg Tyr Thr
    130                 135                 140

Tyr Lys Lys Lys Thr Asp Thr Leu Glu Lys Pro Val Asp Leu Leu Ala
145                 150                 155                 160

Gly Leu Pro Ser Ser Lys Asp His Gln Gly Gly Arg Leu Val Ile Gly
                165                 170                 175

Pro Asp Gln Lys Ile Tyr Tyr Thr Ile Gly Asp Gln Gly Arg Asn Gln
            180                 185                 190

Phe Ala Gly Leu Phe Leu Pro Asn Gln Ala Gln His Thr Pro Thr Gln
        195                 200                 205

Gln Glu Leu Asn Gly Lys Asp Tyr His Thr Tyr Met Gly Lys Val Leu
    210                 215                 220

Arg Leu Asn Leu Asp Gly Ser Ile Pro Lys Asp Asn Pro Ser Phe Asn
225                 230                 235                 240

Gly Val Val Ser His Ile Tyr Thr Leu Gly His Arg Asn Pro Gln Gly
                245                 250                 255

Leu Ala Phe Thr Pro Asn Gly Lys Leu Leu Gln Ser Asp His Gly Pro
            260                 265                 270

Asn Ser Asp Asp Glu Ile Asn Leu Ile Val Lys Gly Gly Asn Tyr Gly
        275                 280                 285

Trp Pro Asn Val Ala Gly Tyr Lys Asp Asp Ser Gly Tyr Ala Tyr Ala
    290                 295                 300

Asn Tyr Ser Ala Ala Ala Asn Lys Ser Ile Lys Asp Leu Ala Gln Asn
305                 310                 315                 320

Gly Leu Lys Val Ala Ala Gly Val Pro Val Thr Lys Glu Ser Glu Trp
                325                 330                 335

Thr Gly Lys Asn Phe Val Pro Pro Leu Lys Thr Leu Tyr Thr Val Gln

-continued

```
            340                 345                 350
Asp Thr Tyr Asn Tyr Asn Asp Pro Thr Cys Gly Glu Val Thr Tyr Ile
                355                 360                 365
Cys Trp Pro Ser Val Ala Pro Ser Ala Tyr Val Tyr Lys Gly Gly
        370                 375                 380
Lys Lys Ala Ile Thr Gly Trp Glu Asn Thr Leu Leu Val Pro Ser Leu
385                 390                 395                 400
Lys Arg Gly Val Ile Phe Arg Ile Lys Phe Asp Pro Thr Tyr Ser Thr
                405                 410                 415
Thr Tyr Asp Asp Ala Val Pro Met Phe Lys Ser Asn Asn Arg Tyr Arg
                420                 425                 430
Asp Val Ile Ala Ser Pro Asp Gly Asn Val Leu Tyr Val Leu Thr Asp
                435                 440                 445
Thr Ala Gly Asn Pro Val Gln Lys Asp Asp Gly Ser Pro Thr Asn Thr
        450                 455                 460
Leu Glu Asn Pro Gly Ser Leu Ile Lys Phe Thr Tyr Lys Ala Lys Gly
465                 470                 475                 480
Gly Lys Gly Gly Ser Gly Gly Ser Ser Tyr Ala His His His His
                485                 490                 495
His Glu Glu Thr Pro Val Thr Pro Gln Pro Pro Asp Ile Leu Leu Gly
        500                 505                 510
Pro Leu Phe Asn Asp Val Gln Asn Ala Lys Leu Phe Pro Asp Gln Lys
        515                 520                 525
Thr Phe Ala Asp Ala Val Pro Asn Ser Asp Pro Leu Met Ile Leu Ala
        530                 535                 540
Asp Tyr Arg Met Gln Gln Asn Gln Ser Gly Phe Asp Leu Arg His Phe
545                 550                 555                 560
Val Asn Val Asn Phe Thr Leu Pro Lys Glu Gly Glu Lys Tyr Val Pro
                565                 570                 575
Pro Glu Gly Gln Ser Leu Arg Glu His Ile Asp Gly Leu Trp Pro Val
        580                 585                 590
Leu Thr Arg Ser Thr Glu Asn Thr Glu Lys Trp Asp Ser Leu Leu Pro
        595                 600                 605
Leu Pro Glu Pro Tyr Val Val Pro Gly Gly Arg Phe Arg Glu Val Tyr
        610                 615                 620
Tyr Trp Asp Ser Tyr Phe Thr Met Leu Gly Leu Ala Glu Ser Gly His
625                 630                 635                 640
Trp Asp Lys Val Ala Asp Met Val Ala Asn Phe Ala His Glu Ile Asp
                645                 650                 655
Thr Tyr Gly His Ile Pro Asn Gly Asn Arg Ser Tyr Tyr Leu Ser Arg
                660                 665                 670
Ser Gln Pro Pro Phe Phe Ala Leu Met Val Glu Leu Leu Ala Gln His
        675                 680                 685
Glu Gly Asp Ala Ala Leu Lys Gln Tyr Leu Pro Gln Met Gln Lys Glu
        690                 695                 700
Tyr Ala Tyr Trp Met Asp Gly Val Glu Asn Leu Gln Ala Gly Gln Gln
705                 710                 715                 720
Glu Lys Arg Val Val Lys Leu Gln Asp Gly Thr Leu Leu Asn Arg Tyr
                725                 730                 735
Trp Asp Asp Arg Asp Thr Pro Arg Pro Glu Ser Trp Val Glu Asp Ile
                740                 745                 750
Ala Thr Ala Lys Ser Asn Pro Asn Arg Pro Ala Thr Glu Ile Tyr Arg
        755                 760                 765
```

```
Asp Leu Arg Ser Ala Ala Ser Gly Trp Asp Phe Ser Arg Trp
    770                 775                 780

Met Asp Asn Pro Gln Gln Leu Asn Thr Leu Arg Thr Thr Ser Ile Val
785                 790                 795                 800

Pro Val Asp Leu Asn Ser Leu Met Phe Lys Met Glu Lys Ile Leu Ala
                805                 810                 815

Arg Ala Ser Lys Ala Ala Gly Asp Asn Ala Met Ala Asn Gln Tyr Glu
            820                 825                 830

Thr Leu Ala Asn Ala Arg Gln Lys Gly Ile Glu Lys Tyr Leu Trp Asn
        835                 840                 845

Asp Gln Gln Gly Trp Tyr Ala Asp Tyr Asp Leu Lys Ser His Lys Val
    850                 855                 860

Arg Asn Gln Leu Thr Ala Ala Leu Phe Pro Leu Tyr Val Asn Ala
865                 870                 875                 880

Ala Ala Lys Asp Arg Ala Asn Lys Met Ala Thr Ala Thr Lys Thr His
                885                 890                 895

Leu Leu Gln Pro Gly Gly Leu Asn Thr Thr Ser Val Lys Ser Gly Gln
            900                 905                 910

Gln Trp Asp Ala Pro Asn Gly Trp Ala Pro Leu Gln Trp Val Ala Thr
        915                 920                 925

Glu Gly Leu Gln Asn Tyr Gly Gln Lys Glu Val Ala Met Asp Ile Ser
    930                 935                 940

Trp His Phe Leu Thr Asn Val Gln His Thr Tyr Asp Arg Glu Lys Lys
945                 950                 955                 960

Leu Val Glu Lys Tyr Asp Val Ser Thr Thr Gly Thr Gly Gly Gly Gly
                965                 970                 975

Gly Glu Tyr Pro Leu Gln Asp Gly Phe Gly Trp Thr Asn Gly Val Thr
            980                 985                 990

Leu Lys Met Leu Asp Leu Ile Cys Pro Lys Glu Gln Pro Cys Asp Asn
        995                 1000                1005

Val Pro Ala Thr Arg Pro Thr Val Lys Ser Ala Thr Thr Gln Pro
    1010                1015                1020

Ser Thr Lys Glu Ala Gln Pro Thr Pro
1025                1030

<210> SEQ ID NO 71
<211> LENGTH: 606
<212> TYPE: PRT
<213> ORGANISM: Artificial Sequence
<220> FEATURE:
<223> OTHER INFORMATION: GDH-HIS-TreAN-EI: Glucose dehydrogenase
      N-terminally, and leucine zipper peptide EI C-terminally fused to
      the N-terminal fragment of TreAN (w/o signal peptide), which with
      flexible linker and HIS-tag in between GDH and TreAN

<400> SEQUENCE: 71

Met Ala Gly Lys Tyr Leu Leu Pro Thr Ala Ala Gly Leu Leu Leu
1               5                   10                  15

Leu Ala Ala Gln Pro Ala Met Ala Asp Val Pro Leu Thr Pro Ser Gln
            20                  25                  30

Phe Ala Lys Ala Lys Ser Glu Asn Phe Asp Lys Val Ile Leu Ser
        35                  40                  45

Asn Leu Asn Lys Pro His Ala Leu Leu Trp Gly Pro Asp Asn Gln Ile
    50                  55                  60

Trp Leu Thr Glu Arg Ala Thr Gly Lys Ile Leu Arg Val Asn Pro Glu
65                  70                  75                  80
```

-continued

```
Ser Gly Ser Val Lys Thr Val Phe Gln Val Pro Glu Ile Val Asn Asp
                85                  90                  95
Ala Asp Gly Gln Asn Gly Leu Leu Gly Phe Ala Phe His Pro Arg Phe
            100                 105                 110
Lys Asn Asn Pro Tyr Ile Tyr Ile Ser Gly Thr Phe Lys Asn Pro Lys
        115                 120                 125
Ser Thr Asp Lys Glu Leu Pro Asn Gln Thr Ile Ile Arg Arg Tyr Thr
130                 135                 140
Tyr Lys Lys Lys Thr Asp Thr Leu Glu Lys Pro Val Asp Leu Leu Ala
145                 150                 155                 160
Gly Leu Pro Ser Ser Lys Asp His Gln Gly Gly Arg Leu Val Ile Gly
                165                 170                 175
Pro Asp Gln Lys Ile Tyr Tyr Thr Ile Gly Asp Gln Gly Arg Asn Gln
            180                 185                 190
Phe Ala Gly Leu Phe Leu Pro Asn Gln Ala Gln His Thr Pro Thr Gln
        195                 200                 205
Gln Glu Leu Asn Gly Lys Asp Tyr His Thr Tyr Met Gly Lys Val Leu
210                 215                 220
Arg Leu Asn Leu Asp Gly Ser Ile Pro Lys Asp Asn Pro Ser Phe Asn
225                 230                 235                 240
Gly Val Val Ser His Ile Tyr Thr Leu Gly His Arg Asn Pro Gln Gly
                245                 250                 255
Leu Ala Phe Thr Pro Asn Gly Lys Leu Leu Gln Ser Asp His Gly Pro
            260                 265                 270
Asn Ser Asp Asp Glu Ile Asn Leu Ile Val Lys Gly Gly Asn Tyr Gly
        275                 280                 285
Trp Pro Asn Val Ala Gly Tyr Lys Asp Asp Ser Gly Tyr Ala Tyr Ala
290                 295                 300
Asn Tyr Ser Ala Ala Ala Asn Lys Ser Ile Lys Asp Leu Ala Gln Asn
305                 310                 315                 320
Gly Leu Lys Val Ala Ala Gly Val Pro Val Thr Lys Glu Ser Glu Trp
                325                 330                 335
Thr Gly Lys Asn Phe Val Pro Pro Leu Lys Thr Leu Tyr Thr Val Gln
            340                 345                 350
Asp Thr Tyr Asn Tyr Asn Asp Pro Thr Cys Gly Glu Val Thr Tyr Ile
        355                 360                 365
Cys Trp Pro Ser Val Ala Pro Ser Ser Ala Tyr Val Tyr Lys Gly Gly
370                 375                 380
Lys Lys Ala Ile Thr Gly Trp Glu Asn Thr Leu Leu Val Pro Ser Leu
385                 390                 395                 400
Lys Arg Gly Val Ile Phe Arg Ile Lys Phe Asp Pro Thr Tyr Ser Thr
                405                 410                 415
Thr Tyr Asp Asp Ala Val Pro Met Phe Lys Ser Asn Asn Arg Tyr Arg
            420                 425                 430
Asp Val Ile Ala Ser Pro Asp Gly Asn Val Leu Tyr Val Leu Thr Asp
        435                 440                 445
Thr Ala Gly Asn Pro Val Gln Lys Asp Asp Gly Ser Pro Thr Asn Thr
450                 455                 460
Leu Glu Asn Pro Gly Ser Leu Ile Lys Phe Thr Tyr Lys Ala Lys Gly
465                 470                 475                 480
Gly Lys Gly Gly Ser Gly Gly Ser Ser Tyr Ala His His His His
                485                 490                 495
```

-continued

```
His Glu Glu Thr Pro Val Thr Pro Gln Pro Asp Ile Leu Leu Gly
                500                 505                 510

Pro Leu Phe Asn Asp Val Gln Asn Ala Lys Leu Phe Pro Asp Gln Lys
        515                 520                 525

Thr Phe Ala Asp Ala Val Pro Asn Ser Asp Pro Leu Met Ile Leu Ala
    530                 535                 540

Asp Tyr Arg Met Gln Gln Asn Gln Ser Gly Phe Asp Leu Arg His Phe
545                 550                 555                 560

Val Asn Val Asn Phe Thr Leu Pro Lys Glu Gly Glu Lys Tyr Val Pro
                565                 570                 575

Gly Ser Glu Ile Ala Ala Leu Glu Lys Glu Ile Ala Ala Leu Glu Lys
        580                 585                 590

Glu Asn Ala Ala Leu Glu Trp Glu Ile Ala Ala Leu Glu Lys
        595                 600                 605

<210> SEQ ID NO 72
<211> LENGTH: 606
<212> TYPE: PRT
<213> ORGANISM: Artificial Sequence
<220> FEATURE:
<223> OTHER INFORMATION: GDH-HIS-TreAN-KI: Glucose dehydrogenase
      N-terminally, and leucine zipper peptide KI C-terminally fused to
      the N-terminal fragment of TreAN (w/o signal peptide), which with
      flexible linker and HIS-tag in between GDH and TreAN

<400> SEQUENCE: 72

Met Ala Gly Lys Tyr Leu Leu Pro Thr Ala Ala Ala Gly Leu Leu Leu
1               5                   10                  15

Leu Ala Ala Gln Pro Ala Met Ala Asp Val Pro Leu Thr Pro Ser Gln
                20                  25                  30

Phe Ala Lys Ala Lys Ser Glu Asn Phe Asp Lys Lys Val Ile Leu Ser
        35                  40                  45

Asn Leu Asn Lys Pro His Ala Leu Leu Trp Gly Pro Asp Asn Gln Ile
    50                  55                  60

Trp Leu Thr Glu Arg Ala Thr Gly Lys Ile Leu Arg Val Asn Pro Glu
65                  70                  75                  80

Ser Gly Ser Val Lys Thr Val Phe Gln Val Pro Glu Ile Val Asn Asp
                85                  90                  95

Ala Asp Gly Gln Asn Gly Leu Leu Gly Phe Ala Phe His Pro Arg Phe
            100                 105                 110

Lys Asn Asn Pro Tyr Ile Tyr Ile Ser Gly Thr Phe Lys Asn Pro Lys
        115                 120                 125

Ser Thr Asp Lys Glu Leu Pro Asn Gln Thr Ile Ile Arg Arg Tyr Thr
    130                 135                 140

Tyr Lys Lys Lys Thr Asp Thr Leu Glu Lys Pro Val Asp Leu Leu Ala
145                 150                 155                 160

Gly Leu Pro Ser Ser Lys Asp His Gln Gly Gly Arg Leu Val Ile Gly
                165                 170                 175

Pro Asp Gln Lys Ile Tyr Tyr Thr Ile Gly Asp Gln Gly Arg Asn Gln
            180                 185                 190

Phe Ala Gly Leu Phe Leu Pro Asn Gln Ala Gln His Thr Pro Thr Gln
        195                 200                 205

Gln Glu Leu Asn Gly Lys Asp Tyr His Thr Tyr Met Gly Lys Val Leu
    210                 215                 220

Arg Leu Asn Leu Asp Gly Ser Ile Pro Lys Asp Asn Pro Ser Phe Asn
225                 230                 235                 240
```

Gly Val Val Ser His Ile Tyr Thr Leu Gly His Arg Asn Pro Gln Gly
            245                 250                 255

Leu Ala Phe Thr Pro Asn Gly Lys Leu Leu Gln Ser Asp His Gly Pro
            260                 265                 270

Asn Ser Asp Asp Glu Ile Asn Leu Ile Val Lys Gly Gly Asn Tyr Gly
            275                 280                 285

Trp Pro Asn Val Ala Gly Tyr Lys Asp Asp Ser Gly Tyr Ala Tyr Ala
            290                 295                 300

Asn Tyr Ser Ala Ala Asn Lys Ser Ile Lys Asp Leu Ala Gln Asn
305                 310                 315                 320

Gly Leu Lys Val Ala Ala Gly Val Pro Val Thr Lys Glu Ser Glu Trp
            325                 330                 335

Thr Gly Lys Asn Phe Val Pro Pro Leu Lys Thr Leu Tyr Thr Val Gln
            340                 345                 350

Asp Thr Tyr Asn Tyr Asn Asp Pro Thr Cys Gly Glu Val Thr Tyr Ile
            355                 360                 365

Cys Trp Pro Ser Val Ala Pro Ser Ser Ala Tyr Val Tyr Lys Gly Gly
            370                 375                 380

Lys Lys Ala Ile Thr Gly Trp Glu Asn Thr Leu Leu Val Pro Ser Leu
385                 390                 395                 400

Lys Arg Gly Val Ile Phe Arg Ile Lys Phe Asp Pro Thr Tyr Ser Thr
            405                 410                 415

Thr Tyr Asp Asp Ala Val Pro Met Phe Lys Ser Asn Asn Arg Tyr Arg
            420                 425                 430

Asp Val Ile Ala Ser Pro Asp Gly Asn Val Leu Tyr Val Leu Thr Asp
            435                 440                 445

Thr Ala Gly Asn Pro Val Gln Lys Asp Asp Gly Ser Pro Thr Asn Thr
450                 455                 460

Leu Glu Asn Pro Gly Ser Leu Ile Lys Phe Thr Tyr Lys Ala Lys Gly
465                 470                 475                 480

Gly Lys Gly Gly Ser Gly Gly Ser Ser Tyr Ala His His His His
            485                 490                 495

His Glu Glu Thr Pro Val Thr Pro Gln Pro Pro Asp Ile Leu Leu Gly
            500                 505                 510

Pro Leu Phe Asn Asp Val Gln Asn Ala Lys Leu Phe Pro Asp Gln Lys
            515                 520                 525

Thr Phe Ala Asp Ala Val Pro Asn Ser Asp Pro Leu Met Ile Leu Ala
            530                 535                 540

Asp Tyr Arg Met Gln Gln Asn Gln Ser Gly Phe Asp Leu Arg His Phe
545                 550                 555                 560

Val Asn Val Asn Phe Thr Leu Pro Lys Glu Gly Glu Lys Tyr Val Pro
            565                 570                 575

Gly Ser Lys Ile Ala Ala Leu Lys Glu Lys Ile Ala Ala Leu Lys Glu
            580                 585                 590

Lys Asn Ala Ala Leu Lys Trp Lys Ile Ala Ala Leu Lys Glu
            595                 600                 605

<210> SEQ ID NO 73
<211> LENGTH: 633
<212> TYPE: PRT
<213> ORGANISM: Artificial Sequence
<220> FEATURE:
<223> OTHER INFORMATION: GDH-HIS-TreAN-pG: Glucose dehydrogenase
      N-terminally, and the immunoglobulin binding domain Domain B1 of
      protein G C-terminally fused to the N-terminal fragment of TreAN
      (w/o signal peptide), which with flexible linker and HIS-tag in between GDH and TreAN

<400> SEQUENCE: 73

```
Met Ala Gly Lys Tyr Leu Leu Pro Thr Ala Ala Gly Leu Leu Leu
1               5                   10                  15

Leu Ala Ala Gln Pro Ala Met Ala Asp Val Pro Leu Thr Pro Ser Gln
            20                  25                  30

Phe Ala Lys Ala Lys Ser Glu Asn Phe Asp Lys Lys Val Ile Leu Ser
            35                  40                  45

Asn Leu Asn Lys Pro His Ala Leu Leu Trp Gly Pro Asp Asn Gln Ile
    50                  55                  60

Trp Leu Thr Glu Arg Ala Thr Gly Lys Ile Leu Arg Val Asn Pro Glu
65                  70                  75                  80

Ser Gly Ser Val Lys Thr Val Phe Gln Val Pro Glu Ile Val Asn Asp
                85                  90                  95

Ala Asp Gly Gln Asn Gly Leu Leu Gly Phe Ala Phe His Pro Arg Phe
            100                 105                 110

Lys Asn Asn Pro Tyr Ile Tyr Ile Ser Gly Thr Phe Lys Asn Pro Lys
            115                 120                 125

Ser Thr Asp Lys Glu Leu Pro Asn Gln Thr Ile Ile Arg Arg Tyr Thr
    130                 135                 140

Tyr Lys Lys Lys Thr Asp Thr Leu Glu Lys Pro Val Asp Leu Leu Ala
145                 150                 155                 160

Gly Leu Pro Ser Ser Lys Asp His Gln Gly Gly Arg Leu Val Ile Gly
                165                 170                 175

Pro Asp Gln Lys Ile Tyr Tyr Thr Ile Gly Asp Gln Gly Arg Asn Gln
            180                 185                 190

Phe Ala Gly Leu Phe Leu Pro Asn Gln Ala Gln His Thr Pro Thr Gln
            195                 200                 205

Gln Glu Leu Asn Gly Lys Asp Tyr His Thr Tyr Met Gly Lys Val Leu
    210                 215                 220

Arg Leu Asn Leu Asp Gly Ser Ile Pro Lys Asp Asn Pro Ser Phe Asn
225                 230                 235                 240

Gly Val Val Ser His Ile Tyr Thr Leu Gly His Arg Asn Pro Gln Gly
                245                 250                 255

Leu Ala Phe Thr Pro Asn Gly Lys Leu Leu Gln Ser Asp His Gly Pro
            260                 265                 270

Asn Ser Asp Asp Glu Ile Asn Leu Ile Val Lys Gly Gly Asn Tyr Gly
    275                 280                 285

Trp Pro Asn Val Ala Gly Tyr Lys Asp Asp Ser Gly Tyr Ala Tyr Ala
290                 295                 300

Asn Tyr Ser Ala Ala Asn Lys Ser Ile Lys Asp Leu Ala Gln Asn
305                 310                 315                 320

Gly Leu Lys Val Ala Ala Gly Val Pro Val Thr Lys Glu Ser Glu Trp
                325                 330                 335

Thr Gly Lys Asn Phe Val Pro Pro Leu Lys Thr Leu Tyr Thr Val Gln
            340                 345                 350

Asp Thr Tyr Asn Tyr Asn Asp Pro Thr Cys Gly Glu Val Thr Tyr Ile
            355                 360                 365

Cys Trp Pro Ser Val Ala Pro Ser Ser Ala Tyr Val Tyr Lys Gly Gly
    370                 375                 380

Lys Lys Ala Ile Thr Gly Trp Glu Asn Thr Leu Leu Val Pro Ser Leu
385                 390                 395                 400
```

Lys Arg Gly Val Ile Phe Arg Ile Lys Phe Asp Pro Thr Tyr Ser Thr
                405                 410                 415

Thr Tyr Asp Asp Ala Val Pro Met Phe Lys Ser Asn Asn Arg Tyr Arg
            420                 425                 430

Asp Val Ile Ala Ser Pro Asp Gly Asn Val Leu Tyr Val Leu Thr Asp
            435                 440                 445

Thr Ala Gly Asn Pro Val Gln Lys Asp Asp Gly Ser Pro Thr Asn Thr
        450                 455                 460

Leu Glu Asn Pro Gly Ser Leu Ile Lys Phe Thr Tyr Lys Ala Lys Gly
465                 470                 475                 480

Gly Lys Gly Gly Ser Gly Gly Ser Ser Tyr Ala His His His His
                485                 490                 495

His Glu Glu Thr Pro Val Thr Pro Gln Pro Pro Asp Ile Leu Leu Gly
            500                 505                 510

Pro Leu Phe Asn Asp Val Gln Asn Ala Lys Leu Phe Pro Asp Gln Lys
        515                 520                 525

Thr Phe Ala Asp Ala Val Pro Asn Ser Asp Pro Leu Met Ile Leu Ala
        530                 535                 540

Asp Tyr Arg Met Gln Gln Asn Gln Ser Gly Phe Asp Leu Arg His Phe
545                 550                 555                 560

Val Asn Val Asn Phe Thr Leu Pro Lys Glu Gly Glu Lys Tyr Val Pro
                565                 570                 575

Gly Ser Thr Tyr Lys Leu Ile Leu Asn Gly Lys Thr Leu Lys Gly Glu
                580                 585                 590

Thr Thr Thr Glu Ala Val Asp Ala Ala Thr Ala Glu Lys Val Phe Lys
                595                 600                 605

Gln Tyr Ala Asn Asp Asn Gly Val Asp Gly Glu Trp Thr Tyr Asp Ala
        610                 615                 620

Ala Thr Lys Thr Phe Thr Val Thr Glu
625                 630

<210> SEQ ID NO 74
<211> LENGTH: 616
<212> TYPE: PRT
<213> ORGANISM: Artificial Sequence
<220> FEATURE:
<223> OTHER INFORMATION: GDH-HIS-TreAN-pA: Glucose dehydrogenase
    N-terminally, and the immunoglobulin binding domain Domain B1 of
    protein G C-terminally fused to the N-terminal fragment of TreAN
    (w/o signal peptide), which with flexible linker and HIS-tag in
    between GDH and TreAN

<400> SEQUENCE: 74

Met Ala Asp Val Pro Leu Thr Pro Ser Gln Phe Ala Lys Ala Lys Ser
1               5                   10                  15

Glu Asn Phe Asp Lys Lys Val Ile Leu Ser Asn Leu Asn Lys Pro His
                20                  25                  30

Ala Leu Leu Trp Gly Pro Asp Asn Gln Ile Trp Leu Thr Glu Arg Ala
            35                  40                  45

Thr Gly Lys Ile Leu Arg Val Asn Pro Glu Ser Gly Ser Val Lys Thr
        50                  55                  60

Val Phe Gln Val Pro Glu Ile Val Asn Asp Ala Asp Gly Gln Asn Gly
65                  70                  75                  80

Leu Leu Gly Phe Ala Phe His Pro Arg Phe Lys Asn Asn Pro Tyr Ile
                85                  90                  95

Tyr Ile Ser Gly Thr Phe Lys Asn Pro Lys Ser Thr Asp Lys Glu Leu
                100                 105                 110

-continued

```
Pro Asn Gln Thr Ile Ile Arg Arg Tyr Thr Tyr Lys Lys Lys Thr Asp
        115                 120                 125

Thr Leu Glu Lys Pro Val Asp Leu Leu Ala Gly Leu Pro Ser Ser Lys
    130                 135                 140

Asp His Gln Gly Gly Arg Leu Val Ile Gly Pro Asp Gln Lys Ile Tyr
145                 150                 155                 160

Tyr Thr Ile Gly Asp Gln Gly Arg Asn Gln Phe Ala Gly Leu Phe Leu
                165                 170                 175

Pro Asn Gln Ala Gln His Thr Pro Thr Gln Gln Glu Leu Asn Gly Lys
            180                 185                 190

Asp Tyr His Thr Tyr Met Gly Lys Val Leu Arg Leu Asn Leu Asp Gly
        195                 200                 205

Ser Ile Pro Lys Asp Asn Pro Ser Phe Asn Gly Val Val Ser His Ile
    210                 215                 220

Tyr Thr Leu Gly His Arg Asn Pro Gln Gly Leu Ala Phe Thr Pro Asn
225                 230                 235                 240

Gly Lys Leu Leu Gln Ser Asp His Gly Pro Asn Ser Asp Asp Glu Ile
                245                 250                 255

Asn Leu Ile Val Lys Gly Gly Asn Tyr Gly Trp Pro Asn Val Ala Gly
            260                 265                 270

Tyr Lys Asp Asp Ser Gly Tyr Ala Tyr Ala Asn Tyr Ser Ala Ala Ala
        275                 280                 285

Asn Lys Ser Ile Lys Asp Leu Ala Gln Asn Gly Leu Lys Val Ala Ala
    290                 295                 300

Gly Val Pro Val Thr Lys Glu Ser Glu Trp Thr Gly Lys Asn Phe Val
305                 310                 315                 320

Pro Pro Leu Lys Thr Leu Tyr Thr Val Gln Asp Thr Tyr Asn Tyr Asn
                325                 330                 335

Asp Pro Thr Cys Gly Glu Val Thr Tyr Ile Cys Trp Pro Ser Val Ala
            340                 345                 350

Pro Ser Ser Ala Tyr Val Tyr Lys Gly Gly Lys Lys Ala Ile Thr Gly
        355                 360                 365

Trp Glu Asn Thr Leu Leu Val Pro Ser Leu Lys Arg Gly Val Ile Phe
    370                 375                 380

Arg Ile Lys Phe Asp Pro Thr Tyr Ser Thr Thr Tyr Asp Asp Ala Val
385                 390                 395                 400

Pro Met Phe Lys Ser Asn Asn Arg Tyr Arg Asp Val Ile Ala Ser Pro
                405                 410                 415

Asp Gly Asn Val Leu Tyr Val Leu Thr Asp Thr Ala Gly Asn Pro Val
            420                 425                 430

Gln Lys Asp Asp Gly Ser Pro Thr Asn Thr Leu Glu Asn Pro Gly Ser
        435                 440                 445

Leu Ile Lys Phe Thr Tyr Lys Ala Lys Gly Lys Gly Lys Gly Ser Gly
    450                 455                 460

Gly Ser Ser Tyr Ala His His His His His His Glu Glu Thr Pro Val
465                 470                 475                 480

Thr Pro Gln Pro Pro Asp Ile Leu Leu Gly Pro Leu Phe Asn Asp Val
                485                 490                 495

Gln Asn Ala Lys Leu Phe Pro Asp Gln Lys Thr Phe Ala Asp Ala Val
            500                 505                 510

Pro Asn Ser Asp Pro Leu Met Ile Leu Ala Asp Tyr Arg Met Gln Gln
        515                 520                 525
```

```
Asn Gln Ser Gly Phe Asp Leu Arg His Phe Val Asn Val Asn Phe Thr
    530                 535                 540

Leu Pro Lys Glu Gly Lys Tyr Val Pro Gly Ser Thr Ala Asp Asn
545                 550                 555                 560

Lys Phe Asn Lys Glu Gln Gln Asn Ala Phe Tyr Glu Ile Leu His Leu
                565                 570                 575

Pro Asn Leu Asn Glu Glu Gln Arg Asn Gly Phe Ile Gln Ser Leu Lys
                580                 585                 590

Asp Asp Pro Ser Gln Ser Ala Asn Leu Leu Ala Glu Ala Lys Lys Leu
                595                 600                 605

Asn Asp Ala Gln Ala Pro Lys Ala
    610                 615

<210> SEQ ID NO 75
<211> LENGTH: 643
<212> TYPE: PRT
<213> ORGANISM: Artificial Sequence
<220> FEATURE:
<223> OTHER INFORMATION: GDH-HIS-TreAN-pL: Glucose dehydrogenase
      N-terminally, and the immunoglobulin binding domain B1 of protein
      G C-terminally fused to the N-terminal fragment of TreAN (w/o
      signal peptide), which with flexible linker and HIS-tag in between
      GDH and TreAN

<400> SEQUENCE: 75

Met Ala Gly Lys Tyr Leu Leu Pro Thr Ala Ala Gly Leu Leu Leu
1               5                   10                  15

Leu Ala Ala Gln Pro Ala Met Ala Asp Val Pro Leu Thr Pro Ser Gln
                20                  25                  30

Phe Ala Lys Ala Lys Ser Glu Asn Phe Asp Lys Lys Val Ile Leu Ser
                35                  40                  45

Asn Leu Asn Lys Pro His Ala Leu Leu Trp Gly Pro Asp Asn Gln Ile
    50                  55                  60

Trp Leu Thr Glu Arg Ala Thr Gly Lys Ile Leu Arg Val Asn Pro Glu
65                  70                  75                  80

Ser Gly Ser Val Lys Thr Val Phe Gln Val Pro Glu Ile Val Asn Asp
                85                  90                  95

Ala Asp Gly Gln Asn Gly Leu Leu Gly Phe Ala Phe His Pro Arg Phe
                100                 105                 110

Lys Asn Asn Pro Tyr Ile Tyr Ile Ser Gly Thr Phe Lys Asn Pro Lys
                115                 120                 125

Ser Thr Asp Lys Glu Leu Pro Asn Gln Thr Ile Ile Arg Arg Tyr Thr
    130                 135                 140

Tyr Lys Lys Lys Thr Asp Thr Leu Glu Lys Pro Val Asp Leu Leu Ala
145                 150                 155                 160

Gly Leu Pro Ser Ser Lys Asp His Gln Gly Gly Arg Leu Val Ile Gly
                165                 170                 175

Pro Asp Gln Lys Ile Tyr Tyr Thr Ile Gly Asp Gln Gly Arg Asn Gln
                180                 185                 190

Phe Ala Gly Leu Phe Leu Pro Asn Gln Ala Gln His Thr Pro Thr Gln
                195                 200                 205

Gln Glu Leu Asn Gly Lys Asp Tyr His Thr Tyr Met Gly Lys Val Leu
    210                 215                 220

Arg Leu Asn Leu Asp Gly Ser Ile Pro Lys Asp Asn Pro Ser Phe Asn
225                 230                 235                 240

Gly Val Val Ser His Ile Tyr Thr Leu Gly His Arg Asn Pro Gln Gly
                245                 250                 255
```

Leu Ala Phe Thr Pro Asn Gly Lys Leu Leu Gln Ser Asp His Gly Pro
            260                 265                 270

Asn Ser Asp Asp Glu Ile Asn Leu Ile Val Lys Gly Gly Asn Tyr Gly
            275                 280                 285

Trp Pro Asn Val Ala Gly Tyr Lys Asp Ser Gly Tyr Ala Tyr Ala
            290                 295                 300

Asn Tyr Ser Ala Ala Asn Lys Ser Ile Lys Asp Leu Ala Gln Asn
305                 310                 315                 320

Gly Leu Lys Val Ala Ala Gly Val Pro Val Thr Lys Glu Ser Glu Trp
            325                 330                 335

Thr Gly Lys Asn Phe Val Pro Pro Leu Lys Thr Leu Tyr Thr Val Gln
            340                 345                 350

Asp Thr Tyr Asn Tyr Asn Asp Pro Thr Cys Gly Glu Val Thr Tyr Ile
            355                 360                 365

Cys Trp Pro Ser Val Ala Pro Ser Ser Ala Tyr Val Tyr Lys Gly Gly
            370                 375                 380

Lys Lys Ala Ile Thr Gly Trp Glu Asn Thr Leu Leu Val Pro Ser Leu
385                 390                 395                 400

Lys Arg Gly Val Ile Phe Arg Ile Lys Phe Asp Pro Thr Tyr Ser Thr
            405                 410                 415

Thr Tyr Asp Asp Ala Val Pro Met Phe Lys Ser Asn Asn Arg Tyr Arg
            420                 425                 430

Asp Val Ile Ala Ser Pro Asp Gly Asn Val Leu Tyr Val Leu Thr Asp
            435                 440                 445

Thr Ala Gly Asn Pro Val Gln Lys Asp Gly Ser Pro Thr Asn Thr
450                 455                 460

Leu Glu Asn Pro Gly Ser Leu Ile Lys Phe Thr Tyr Lys Ala Lys Gly
465                 470                 475                 480

Gly Lys Gly Gly Ser Gly Gly Ser Ser Tyr Ala His His His His
            485                 490                 495

His Glu Glu Thr Pro Val Thr Pro Gln Pro Pro Asp Ile Leu Leu Gly
            500                 505                 510

Pro Leu Phe Asn Asp Val Gln Asn Ala Lys Leu Phe Pro Asp Gln Lys
            515                 520                 525

Thr Phe Ala Asp Ala Val Pro Asn Ser Asp Pro Leu Met Ile Leu Ala
            530                 535                 540

Asp Tyr Arg Met Gln Gln Asn Gln Ser Gly Phe Asp Leu Arg His Phe
545                 550                 555                 560

Val Asn Val Asn Phe Thr Leu Pro Lys Glu Gly Lys Tyr Val Pro
            565                 570                 575

Gly Ser Ala Met Glu Glu Val Thr Ile Lys Ala Asn Leu Ile Phe Ala
            580                 585                 590

Asn Gly Ser Thr Gln Thr Ala Glu Phe Lys Gly Thr Phe Glu Lys Ala
            595                 600                 605

Thr Ser Glu Ala Tyr Ala Tyr Ala Asp Thr Leu Lys Lys Asp Asn Gly
            610                 615                 620

Glu Trp Thr Val Asp Val Ala Asp Lys Gly Tyr Thr Leu Asn Ile Lys
625                 630                 635                 640

Phe Ala Gly

<210> SEQ ID NO 76
<211> LENGTH: 472
<212> TYPE: PRT

<213> ORGANISM: Artificial Sequence
<220> FEATURE:
<223> OTHER INFORMATION: HIS-TreAC-TreAN-HA: N-terminally HIS-tagged,
    C-terminally HA-tagged fusion of the N-terminal and C-terminal
    fragments of TreA in alternative frame folded format

<400> SEQUENCE: 76

```
Met Ala His His His His His Asn Phe Thr Leu Pro Lys Glu Gly
1               5                   10                  15

Glu Lys Tyr Val Pro Pro Glu Gly Gln Ser Leu Arg Glu His Ile Asp
            20                  25                  30

Gly Ser Tyr Phe Thr Met Leu Gly Leu Ala Glu Ser Gly His Trp Asp
            35                  40                  45

Lys Val Ala Asp Met Val Ala Asn Phe Ala His Glu Ile Asp Thr Tyr
            50                  55                  60

Gly His Ile Pro Asn Gly Asn Arg Ser Tyr Tyr Leu Ser Arg Ser Gln
65                  70                  75                  80

Pro Pro Phe Phe Ala Leu Met Val Glu Leu Leu Ala Gln His Glu Gly
                85                  90                  95

Asp Ala Ala Leu Lys Gln Tyr Leu Pro Gln Met Gln Lys Glu Tyr Ala
                100                 105                 110

Tyr Trp Met Asp Gly Val Arg Pro Glu Ser Trp Val Glu Asp Ile Ala
            115                 120                 125

Thr Ala Lys Ser Asn Pro Asn Arg Pro Ala Thr Glu Ile Tyr Arg Asp
            130                 135                 140

Leu Arg Ser Ala Ala Ser Gly Trp Asp Phe Ser Ser Arg Trp Met
145                 150                 155                 160

Asp Asn Pro Gln Gln Leu Asn Thr Leu Arg Thr Thr Ser Ile Val Pro
                165                 170                 175

Val Asp Leu Asn Ser Leu Met Phe Lys Met Glu Lys Ile Leu Ala Arg
            180                 185                 190

Ala Ser Lys Ala Ala Gly Asp Asn Ala Met Ala Asn Gln Tyr Glu Thr
            195                 200                 205

Leu Ala Asn Ala Arg Gln Lys Gly Ile Glu Lys Tyr Leu Trp Asn Asp
210                 215                 220

Gln Gln Gly Trp Tyr Ala Asp Tyr Asp Leu Lys Ser His Lys Val Arg
225                 230                 235                 240

Asn Gln Leu Thr Ala Ala Leu Phe Pro Leu Tyr Val Asn Ala Ala
                245                 250                 255

Ala Lys Asp Arg Ala Asn Lys Met Ala Thr Ala Thr Lys Thr His Leu
            260                 265                 270

Leu Gln Pro Gly Gly Leu Asn Thr Thr Ser Val Lys Ser Gly Gln Gln
            275                 280                 285

Trp Asp Ala Pro Asn Gly Trp Ala Pro Leu Gln Trp Val Ala Thr Glu
            290                 295                 300

Gly Leu Gln Asn Tyr Gly Gln Lys Glu Val Ala Met Asp Ile Ser Trp
305                 310                 315                 320

His Phe Leu Thr Asn Val Gln His Thr Tyr Asp Arg Glu Lys Lys Leu
                325                 330                 335

Val Glu Lys Tyr Asp Val Ser Thr Thr Gly Thr Gly Gly Gly Gly
            340                 345                 350

Glu Tyr Pro Leu Gln Asp Gly Phe Gly Trp Thr Asn Gly Val Thr Leu
            355                 360                 365

Lys Met Leu Asp Leu Ile Cys Pro Lys Glu Gln Pro Glu Phe Glu Glu
            370                 375                 380
```

```
Thr Pro Val Thr Pro Gln Pro Pro Asp Ile Leu Leu Gly Pro Leu Phe
385                 390                 395                 400

Asn Asp Val Gln Asn Ala Lys Leu Phe Pro Asp Gln Lys Thr Phe Ala
            405                 410                 415

Asp Ala Val Pro Asn Ser Asp Pro Leu Met Ile Leu Ala Asp Tyr Arg
        420                 425                 430

Met Gln Gln Asn Gln Ser Gly Phe Asp Leu Arg His Phe Val Asn Val
    435                 440                 445

Asn Phe Thr Leu Pro Lys Glu Gly Glu Lys Tyr Val Pro Gly Ser Tyr
450                 455                 460

Pro Tyr Asp Val Pro Asp Tyr Ala
465                 470

<210> SEQ ID NO 77
<211> LENGTH: 542
<212> TYPE: PRT
<213> ORGANISM: Artificial Sequence
<220> FEATURE:
<223> OTHER INFORMATION: HA-TreAC-TreAN-HIS: N-terminally HA-tagged,
      C-terminally HIS-tagged fusion of the N-terminal and C-terminal
      fragments of TreA in alternative frame folded format

<400> SEQUENCE: 77

Met Ala Tyr Pro Tyr Asp Val Pro Asp Tyr Ala Val Asp Asn Phe Thr
1               5                   10                  15

Leu Pro Lys Glu Gly Glu Lys Tyr Val Pro Glu Gly Gln Ser Leu
            20                  25                  30

Arg Glu His Ile Asp Gly Leu Trp Pro Val Leu Thr Arg Ser Thr Glu
        35                  40                  45

Asn Thr Glu Lys Trp Asp Ser Leu Leu Pro Leu Pro Glu Pro Tyr Val
    50                  55                  60

Val Pro Gly Gly Arg Phe Arg Glu Val Tyr Tyr Trp Asp Ser Tyr Phe
65                  70                  75                  80

Thr Met Leu Gly Leu Ala Glu Ser Gly His Trp Asp Lys Val Ala Asp
            85                  90                  95

Met Val Ala Asn Phe Ala His Glu Ile Asp Thr Tyr Gly His Ile Pro
            100                 105                 110

Asn Gly Asn Arg Ser Tyr Tyr Leu Ser Arg Ser Gln Pro Pro Phe Phe
            115                 120                 125

Ala Leu Met Val Glu Leu Leu Ala Gln His Glu Gly Asp Ala Ala Leu
130                 135                 140

Lys Gln Tyr Leu Pro Gln Met Gln Lys Glu Tyr Ala Tyr Trp Met Asp
145                 150                 155                 160

Gly Val Glu Asn Leu Gln Ala Gly Gln Gln Lys Arg Val Val Lys
            165                 170                 175

Leu Gln Asp Gly Thr Leu Leu Asn Arg Tyr Trp Asp Asp Arg Asp Thr
            180                 185                 190

Pro Arg Pro Glu Ser Trp Val Glu Asp Ile Ala Thr Ala Lys Ser Asn
            195                 200                 205

Pro Asn Arg Pro Ala Thr Glu Ile Tyr Arg Asp Leu Arg Ser Ala Ala
        210                 215                 220

Ala Ser Gly Trp Asp Phe Ser Ser Arg Trp Met Asp Asn Pro Gln Gln
225                 230                 235                 240

Leu Asn Thr Leu Arg Thr Thr Ser Ile Val Pro Val Asp Leu Asn Ser
                245                 250                 255
```

```
Leu Met Phe Lys Met Glu Lys Ile Leu Ala Arg Ala Ser Lys Ala Ala
            260                 265                 270

Gly Asp Asn Ala Met Ala Asn Gln Tyr Glu Thr Leu Ala Asn Ala Arg
            275                 280                 285

Gln Lys Gly Ile Glu Lys Tyr Leu Trp Asn Asp Gln Gln Gly Trp Tyr
        290                 295                 300

Ala Asp Tyr Asp Leu Lys Ser His Lys Val Arg Asn Gln Leu Thr Ala
305                 310                 315                 320

Ala Ala Leu Phe Pro Leu Tyr Val Asn Ala Ala Lys Asp Arg Ala
            325                 330                 335

Asn Lys Met Ala Thr Ala Thr Lys Thr His Leu Leu Gln Pro Gly Gly
            340                 345                 350

Leu Asn Thr Thr Ser Val Lys Ser Gly Gln Gln Trp Asp Ala Pro Asn
            355                 360                 365

Gly Trp Ala Pro Leu Gln Trp Val Ala Thr Glu Gly Leu Gln Asn Tyr
        370                 375                 380

Gly Gln Lys Glu Val Ala Met Asp Ile Ser Trp His Phe Leu Thr Asn
385                 390                 395                 400

Val Gln His Thr Tyr Asp Arg Glu Lys Lys Leu Val Glu Lys Tyr Asp
            405                 410                 415

Val Ser Thr Thr Gly Thr Gly Gly Gly Gly Glu Tyr Pro Leu Gln
            420                 425                 430

Asp Gly Phe Gly Trp Thr Asn Gly Val Thr Leu Lys Met Leu Asp Leu
            435                 440                 445

Ile Cys Pro Lys Glu Gln Pro Glu Phe Glu Thr Pro Val Thr Pro
450                 455                 460

Gln Pro Pro Asp Ile Leu Leu Gly Pro Leu Phe Asn Asp Val Gln Asn
465                 470                 475                 480

Ala Lys Leu Phe Pro Asp Gln Lys Thr Phe Ala Asp Ala Val Pro Asn
            485                 490                 495

Ser Asp Pro Leu Met Ile Leu Ala Asp Tyr Arg Met Gln Gln Asn Gln
            500                 505                 510

Ser Gly Phe Asp Leu Arg His Phe Val Asn Val Asn Phe Thr Leu Pro
            515                 520                 525

Lys Glu Gly Glu Lys Tyr Val Pro His His His His His
            530                 535                 540
```

<210> SEQ ID NO 78
<211> LENGTH: 561
<212> TYPE: PRT
<213> ORGANISM: Artificial Sequence
<220> FEATURE:
<223> OTHER INFORMATION: SA-TreAC-HIS-TreAN-SA: N-terminal and
      C-terminal fragments of TreA in alternative frame folded format
      with N-terminal and C-terminal fusion with S. aureus binding
      peptide aptamer and a HIS-tag between both fragments

<400> SEQUENCE: 78

```
Met Val Pro His Asn Pro Gly Leu Ile Ser Leu Gln Gly Val Asp Asn
1               5                   10                  15

Phe Thr Leu Pro Lys Glu Gly Glu Lys Tyr Val Pro Pro Glu Gly Gln
            20                  25                  30

Ser Leu Arg Glu His Ile Asp Gly Leu Trp Pro Val Leu Thr Arg Ser
            35                  40                  45

Thr Glu Asn Thr Glu Lys Trp Asp Ser Leu Leu Pro Leu Pro Glu Pro
        50                  55                  60
```

-continued

Tyr Val Val Pro Gly Gly Arg Phe Arg Glu Val Tyr Tyr Trp Asp Ser
65                  70                  75                  80

Tyr Phe Thr Met Leu Gly Leu Ala Glu Ser Gly His Trp Asp Lys Val
            85                  90                  95

Ala Asp Met Val Ala Asn Phe Ala His Glu Ile Asp Thr Tyr Gly His
            100                 105                 110

Ile Pro Asn Gly Asn Arg Ser Tyr Tyr Leu Ser Arg Ser Gln Pro Pro
            115                 120                 125

Phe Phe Ala Leu Met Val Glu Leu Leu Ala Gln His Glu Gly Asp Ala
130                 135                 140

Ala Leu Lys Gln Tyr Leu Pro Gln Met Gln Lys Glu Tyr Ala Tyr Trp
145                 150                 155                 160

Met Asp Gly Val Glu Asn Leu Gln Ala Gly Gln Gln Glu Lys Arg Val
            165                 170                 175

Val Lys Leu Gln Asp Gly Thr Leu Leu Asn Arg Tyr Trp Asp Asp Arg
            180                 185                 190

Asp Thr Pro Arg Pro Glu Ser Trp Val Glu Asp Ile Ala Thr Ala Lys
            195                 200                 205

Ser Asn Pro Asn Arg Pro Ala Thr Glu Ile Tyr Arg Asp Leu Arg Ser
210                 215                 220

Ala Ala Ala Ser Gly Trp Asp Phe Ser Ser Arg Trp Met Asp Asn Pro
225                 230                 235                 240

Gln Gln Leu Asn Thr Leu Arg Thr Thr Ser Ile Val Pro Val Asp Leu
            245                 250                 255

Asn Ser Leu Met Phe Lys Met Glu Lys Ile Leu Ala Arg Ala Ser Lys
            260                 265                 270

Ala Ala Gly Asp Asn Ala Met Ala Asn Gln Tyr Glu Thr Leu Ala Asn
            275                 280                 285

Ala Arg Gln Lys Gly Ile Glu Lys Tyr Leu Trp Asn Asp Gln Gln Gly
            290                 295                 300

Trp Tyr Ala Asp Tyr Asp Leu Lys Ser His Lys Val Arg Asn Gln Leu
305                 310                 315                 320

Thr Ala Ala Ala Leu Phe Pro Leu Tyr Val Asn Ala Ala Ala Lys Asp
            325                 330                 335

Arg Ala Asn Lys Met Ala Thr Ala Thr Lys Thr His Leu Leu Gln Pro
            340                 345                 350

Gly Gly Leu Asn Thr Thr Ser Val Lys Ser Gly Gln Gln Trp Asp Ala
            355                 360                 365

Pro Asn Gly Trp Ala Pro Leu Gln Trp Val Ala Thr Glu Gly Leu Gln
            370                 375                 380

Asn Tyr Gly Gln Lys Glu Val Ala Met Asp Ile Ser Trp His Phe Leu
385                 390                 395                 400

Thr Asn Val Gln His Thr Tyr Asp Arg Glu Lys Lys Leu Val Glu Lys
            405                 410                 415

Tyr Asp Val Ser Thr Gly Thr Gly Gly Gly Gly Glu Tyr Pro
            420                 425                 430

Leu Gln Asp Gly Phe Gly Trp Thr Asn Gly Val Thr Leu Lys Met Leu
            435                 440                 445

Asp Leu Ile Cys Pro His His His His His Glu Phe Glu Glu Thr
            450                 455                 460

Pro Val Thr Pro Glu Glu Thr Pro Val Thr Pro Gln Pro Pro Asp Ile
465                 470                 475                 480

Leu Leu Gly Pro Leu Phe Asn Asp Val Gln Asn Ala Lys Leu Phe Pro

```
                        485                 490                 495
Asp Gln Lys Thr Phe Ala Asp Ala Val Pro Asn Ser Asp Pro Leu Met
            500                 505                 510

Ile Leu Ala Asp Tyr Arg Met Gln Gln Asn Gln Ser Gly Phe Asp Leu
            515                 520                 525

Arg His Phe Val Asn Val Asn Phe Thr Leu Pro Lys Glu Gly Glu Lys
            530                 535                 540

Tyr Val Pro Gly Ser Val Pro His Asn Pro Gly Leu Ile Ser Leu Gln
545                 550                 555                 560

Gly

<210> SEQ ID NO 79
<211> LENGTH: 712
<212> TYPE: PRT
<213> ORGANISM: Artificial Sequence
<220> FEATURE:
<223> OTHER INFORMATION: GOx-HIS-TreAN-HA: Signal Peptide of Aspergillus
      oryzae fused to glucose oxidase of Aspergillus niger with linker
      containing HIS-tag to fused to N-terminal fragment of TreA fused
      to the HA tag

<400> SEQUENCE: 79

Met Met Val Ala Trp Trp Ser Leu Phe Leu Tyr Gly Leu Gln Val Ala
1               5                   10                  15

Ala Pro Ala Leu Ala Ser Asn Gly Ile Glu Ala Ser Leu Leu Thr Asp
            20                  25                  30

Pro Arg Asp Val Ser Gly Arg Thr Val Asp Tyr Ile Ile Ala Gly Gly
            35                  40                  45

Gly Leu Thr Gly Leu Thr Thr Ala Ala Arg Leu Thr Glu Asn Pro Asn
        50                  55                  60

Ile Ser Val Leu Val Ile Glu Ser Gly Ser Tyr Glu Ser Asp Arg Gly
65                  70                  75                  80

Pro Ile Ile Glu Asp Leu Asn Ala Tyr Gly Asp Ile Phe Gly Ser Ser
                85                  90                  95

Val Asp His Ala Tyr Glu Thr Val Glu Leu Ala Thr Asn Asn Gln Thr
            100                 105                 110

Ala Leu Ile Arg Ser Gly Asn Gly Leu Gly Gly Ser Thr Leu Val Asn
            115                 120                 125

Gly Gly Thr Trp Thr Arg Pro His Lys Ala Gln Val Asp Ser Trp Glu
        130                 135                 140

Thr Val Phe Gly Asn Glu Gly Trp Asn Trp Asp Asn Val Ala Ala Tyr
145                 150                 155                 160

Ser Leu Gln Ala Glu Arg Ala Arg Ala Pro Asn Ala Lys Gln Ile Ala
                165                 170                 175

Ala Gly His Tyr Phe Asn Ala Ser Cys His Gly Val Asn Gly Thr Val
            180                 185                 190

His Ala Gly Pro Arg Asp Thr Gly Asp Asp Tyr Ser Pro Ile Val Lys
            195                 200                 205

Ala Leu Met Ser Ala Val Glu Asp Arg Gly Val Pro Thr Lys Lys Asp
        210                 215                 220

Phe Gly Cys Gly Asp Pro His Gly Val Ser Met Phe Pro Asn Thr Leu
225                 230                 235                 240

His Glu Asp Gln Val Arg Ser Asp Ala Ala Arg Glu Trp Leu Leu Pro
                245                 250                 255

Asn Tyr Gln Arg Pro Asn Leu Gln Val Leu Thr Gly Gln Tyr Val Gly
            260                 265                 270
```

-continued

```
Lys Val Leu Leu Ser Gln Asn Gly Thr Thr Pro Arg Ala Gly Val
            275                 280                 285

Glu Phe Gly Thr His Lys Gly Asn Thr His Asn Val Tyr Ala Lys His
    290                 295                 300

Glu Val Leu Leu Ala Ala Gly Ser Ala Val Ser Pro Thr Ile Leu Glu
305                 310                 315                 320

Tyr Ser Gly Ile Gly Met Lys Ser Ile Leu Glu Pro Leu Gly Ile Asp
                325                 330                 335

Thr Val Val Asp Leu Pro Val Gly Leu Asn Leu Gln Asp Gln Thr Thr
            340                 345                 350

Ala Thr Val Arg Ser Arg Ile Thr Ser Ala Gly Ala Gly Gln Gly Gln
            355                 360                 365

Ala Ala Trp Phe Ala Thr Phe Asn Glu Thr Phe Gly Asp Tyr Ser Glu
            370                 375                 380

Lys Ala His Glu Leu Leu Asn Thr Lys Leu Glu Gln Trp Ala Glu Glu
385                 390                 395                 400

Ala Val Ala Arg Gly Gly Phe His Asn Thr Thr Ala Leu Leu Ile Gln
                405                 410                 415

Tyr Glu Asn Tyr Arg Asp Trp Ile Val Asn His Asn Val Ala Tyr Ser
            420                 425                 430

Glu Leu Phe Leu Asp Thr Ala Gly Val Ala Ser Phe Asp Val Trp Asp
            435                 440                 445

Leu Leu Pro Phe Thr Arg Gly Tyr Val His Ile Leu Asp Lys Asp Pro
            450                 455                 460

Tyr Leu His His Phe Ala Tyr Asp Pro Gln Tyr Phe Leu Asn Glu Leu
465                 470                 475                 480

Asp Leu Leu Gly Gln Ala Ala Thr Gln Leu Ala Arg Asn Ile Ser
                485                 490                 495

Asn Ser Gly Ala Met Gln Thr Tyr Phe Ala Gly Glu Thr Ile Pro Gly
            500                 505                 510

Asp Asn Leu Ala Tyr Asp Ala Asp Leu Ser Ala Trp Thr Glu Tyr Ile
            515                 520                 525

Pro Tyr His Phe Arg Pro Asn Tyr His Gly Val Gly Thr Cys Ser Met
            530                 535                 540

Met Pro Lys Glu Met Gly Gly Val Val Asp Asn Ala Ala Arg Val Tyr
545                 550                 555                 560

Gly Val Gln Gly Leu Arg Val Ile Asp Gly Ser Ile Pro Pro Thr Gln
                565                 570                 575

Met Ser Ser His Val Met Thr Val Phe Tyr Ala Met Ala Leu Lys Ile
            580                 585                 590

Ser Asp Ala Ile Leu Glu Asp Tyr Ala Ser Met Gln Lys Gly Lys Gly
            595                 600                 605

Gly Ser Gly Gly Ser Ser Tyr Ala His His His His His His Glu Glu
            610                 615                 620

Thr Pro Val Thr Pro Gln Pro Pro Asp Ile Leu Leu Gly Pro Leu Phe
625                 630                 635                 640

Asn Asp Val Gln Asn Ala Lys Leu Phe Pro Asp Gln Lys Thr Phe Ala
                645                 650                 655

Asp Ala Val Pro Asn Ser Asp Pro Leu Met Ile Leu Ala Asp Tyr Arg
            660                 665                 670

Met Gln Gln Asn Gln Ser Gly Phe Asp Leu Arg His Phe Val Asn Val
            675                 680                 685
```

```
Asn Phe Thr Leu Pro Lys Glu Gly Glu Lys Tyr Val Pro Gly Ser Tyr
    690             695             700

Pro Tyr Asp Val Pro Asp Tyr Ala
705             710
```

The invention claimed is:

1. A composition for use to detect an analyte in a biological sample, said composition comprising:
   a first component consisting of a TreAN fragment of a trehalase enzyme split into two fragments, said TreAN fragment consisting of an amino acid sequence set forth in anyone of SEQ ID Nos: 20 and 25, said amino acid sequence excluding the HIS-tag, said TreAN fragment fused to a first complexing domain wherein the first complexing domain is a first conserved stable protein sequence selected for fusion with said TreAN fragment; and
   a second component consisting of a TreAC fragment of the split trehalase enzyme, said TreAC fragment consisting of an amino acid sequence set forth in anyone of SEQ ID NOs. 22 and 23, said amino acid sequence excluding the HIS-tag, said TreAC fragment fused to a second complexing domain wherein the second complexing domain is a second conserved stable protein sequence selected for fusion with said TreAC;
   wherein the first component and second component are mixed with the biological sample and a trehalose substrate;
   whereby a presence of the analyte in the biological sample will fuse the first component and the second component to thereby provide a trehalase-catalyzed generation of glucose moieties from the trehalose substrate, said generated glucose moieties detectable and/or measurable by a glucose-detecting technology selected from an electrochemical assay, a colorimetric assay, a fluorometric assay, and a luminescent assay; and
   whereby a lack of presence of the analyte in the biological sample will not generate said glucose moieties.

2. The composition according to claim 1, wherein the first component or the second component additionally comprises a glucose oxidase enzyme or a glucose dehydrogenase enzyme fused to the first complexing domain and/or the second complexing domain.

3. The composition according to claim 1, additionally comprising:
   a third component comprising one of a glucose oxidase enzyme preparation and a glucose dehydrogenase enzyme preparation;
   wherein the third component is mixed with a mixture of the first component, the second component, and the biological sample whereby if the biological sample comprises one or more analytes capable of complexing the first component and the second component, trehalase-catalyzed generation of glucose moieties from the trehalose substrate will occur, said generated glucose moieties measurable by a glucose-detection assay selected from an electrochemical assay, a colorimetric assay, a fluorometric assay, and a luminescent assay.

4. The composition according to claim 1, additionally comprising:
   a third component consisting of a glucose oxidase enzyme preparation or a glucose dehydrogenase enzyme preparation;
   a fourth component consisting of peroxidase enzyme preparation; and
   a fifth component consisting of a substrate for the peroxidase enzyme preparation,
   wherein the third component, fourth component, and fifth component are mixed with a mixture of the first component, the second component, and the biological sample whereby if the biological sample comprises one or more analytes capable of complexing the first component and the second component, trehalase-catalyzed generation of glucose moieties from the trehalose substrate will occur, said generated glucose moieties measurable by a glucose-detection assay selected from an electrochemical assay, a colorimetric assay, a fluorometric assay, and a luminescent assay.

5. A biosensor for detecting an analyte in a biological sample, the biosensor comprising:
   a test strip or a test chip communicable with a test strip reader;
   a first component engaged with a surface of the test strip or the test chip, wherein the first component consists of a TreAN fragment of a trehalase enzyme, said TreAN fragment consisting of an amino acid sequence set forth in anyone of SEQ ID NOs. 20 and 25, said amino acid sequence excluding the HIS-tag, said TreAN fragment fused to a first complexing domain wherein the first complexing domain is a first conserved stable protein sequence selected for fusion with said TreAN fragment; and
   a second component engaged with the surface of the test strip or the test chip, wherein the second component consists of a TreAC fragment of the trehalase enzyme, said TreAC fragment consisting of an amino acid sequence set forth in anyone of SEQ ID Nos: 22 and 23, said amino acid sequence excluding the HIS-tag, said TreAC fragment fused to a second complexing domain wherein the second complexing domain is a second conserved stable protein sequence selected for fusion with said TreAC fragment;
   wherein the test strip or the test chip is contactable with the biological sample and with a trehalose substrate whereby a presence of the analyte in the biological sample will complex the first component and the second component to thereby produce a trehalase-catalyzed generation of glucose moieties from the trehalose substrate, said generated glucose moieties detectable and/or measurable by a glucose-detecting technology selected from one of an electrochemical assay, a colorimetricassay, a fluorometricassay, and a luminescent assay; and whereby a lack of presence of the analyte in the biological sample will not produce said glucose moieties.

6. A kit for detecting an analyte in a biological sample, said kit comprising:
- a biosensor according to claim 5; and
- a trehalose substrate preparation,
- wherein said trehalose substrate preparation is applicable to said test strip or test chip after a biological sample has been applied to the test strip or the test chip to thereby produce a signal measurable by one of an electrochemical assay, a colorimetric assay, a fluorometric assay, and a luminescent assay if the biological sample comprises the analyte acting as a linking element to fuse the first component and the second component.

7. The kit according to claim 6, additionally comprising a third component consisting of a glucose oxidase enzyme preparation or a glucose dehydrogenase enzyme preparation, said third component applicable to the test strip after application of the biological sample.

8. The kit according to claim 6, additionally comprising:
- a third component consisting of a glucose oxidase enzyme preparation or a glucose dehydrogenase enzyme preparation;
- a fourth component consisting of a peroxidase enzyme preparation; and
- a fifth component consisting of a substrate for the peroxidase enzyme preparation,
- wherein the third component, fourth, and fifth component are mixed together and applied to said test strip after the biological sample has been applied to the test strip.

* * * * *